United States Patent
Barlow et al.

(10) Patent No.: US 10,238,822 B2
(45) Date of Patent: Mar. 26, 2019

(54) PAP SYSTEM

(71) Applicant: ResMed Limited, Bella Vista, New South Wales (AU)

(72) Inventors: Adam Francis Barlow, Sydney (AU); Clementine Le Loc'h, Sydney (AU); Dmitri Anatolievich Doudkine, Sydney (AU); Craig Edward Harris, Sydney (AU); Robert Edward Henry, Sydney (AU)

(73) Assignee: ResMed Limited, Bella Vista (AU)

( * ) Notice: Subject to any disclaimer, the term of this patent is extended or adjusted under 35 U.S.C. 154(b) by 767 days.

(21) Appl. No.: 14/804,515

(22) Filed: Jul. 21, 2015

(65) Prior Publication Data

US 2015/0320960 A1 Nov. 12, 2015

Related U.S. Application Data

(63) Continuation of application No. 13/393,187, filed as application No. PCT/AU2010/001106 on Aug. 27, 2010, now Pat. No. 9,132,252.

(Continued)

(30) Foreign Application Priority Data

Jan. 22, 2010 (AU) ................................ 2010900237
Jan. 27, 2010 (AU) ................................ 2010900304

(Continued)

(51) Int. Cl.
*A61M 16/00* (2006.01)
*A61M 16/06* (2006.01)
(Continued)

(52) U.S. Cl.
CPC ........ *A61M 16/00* (2013.01); *A61M 16/0003* (2014.02); *A61M 16/0066* (2013.01);
(Continued)

(58) Field of Classification Search
CPC .............. A61M 16/00; A61M 16/0003; A61M 16/0622
See application file for complete search history.

(56) References Cited

U.S. PATENT DOCUMENTS 3,164,840 A 1/1965 Reynolds
3,394,260 A 7/1968 Phipps
(Continued)

FOREIGN PATENT DOCUMENTS

CN 1859940 A 11/2006
CN 101272706 9/2008
(Continued)

OTHER PUBLICATIONS

First Examination Report dated Sep. 8, 2016 issued in New Zealand Application No. 723778 (2 pages).
(Continued)

*Primary Examiner* — Valerie L Woodward
(74) *Attorney, Agent, or Firm* — Nixon & Vanderhye P.C.

(57) ABSTRACT

A PAP system is adapted for treatment of respiratory disease or sleep disordered breathing. The PAP system includes headgear, a patient interface and a flow generator. The flow generator includes a blower adapted to provide pressurized breathable gas to a patient through the patient interface. The blower is at least partially vibrationally isolated from the patient's head by at least one foam layer mounted within the flow generator to secure the blower. The at least one foam layer is adapted to reduce the amount of transmitted vibration received by the patient. The flow generator further includes a mounting structure limiting an extent of a com- (Continued)

pression of the at least one foam layer due to the weight of the blower. The mounting structure includes at least one protrusion extending from an interior surface of the flow generator toward the blower.

30 Claims, 173 Drawing Sheets

Related U.S. Application Data

(60) Provisional application No. 61/272,919, filed on Nov. 19, 2009, provisional application No. 61/272,188, filed on Aug. 28, 2009.

(30) Foreign Application Priority Data

Feb. 5, 2010 (AU) .............................. 2010900455
Feb. 18, 2010 (AU) .............................. 2010900647

(51) Int. Cl.
   *A61M 16/08* (2006.01)
   *A61M 16/10* (2006.01)

(52) U.S. Cl.
   CPC .... *A61M 16/0622* (2014.02); *A61M 16/0666* (2013.01); *A61M 16/0683* (2013.01); *A61M 16/0816* (2013.01); *A61M 16/107* (2014.02); *A61M 2016/003* (2013.01); *A61M 2205/3334* (2013.01); *A61M 2205/50* (2013.01); *A61M 2205/587* (2013.01); *A61M 2205/8206* (2013.01); *A61M 2205/8262* (2013.01); *A61M 2209/086* (2013.01); *A61M 2209/088* (2013.01); *A61M 2210/06* (2013.01); *A61M 2210/083* (2013.01)

(56) References Cited

U.S. PATENT DOCUMENTS

| | | | |
|---|---|---|---|
| 4,233,972 A | 11/1980 | Hauff et al. | |
| 4,297,999 A | 11/1981 | Kitrell | |
| 4,430,995 A | 2/1984 | Hilton | |
| 4,590,951 A | 5/1986 | O'Conner | |
| 5,303,701 A | 4/1994 | Heins et al. | |
| 5,318,020 A | 6/1994 | Schegerin | |
| 5,372,130 A | 12/1994 | Stern et al. | |
| 5,503,146 A | 4/1996 | Froehlich et al. | |
| 5,570,476 A | 11/1996 | Olive | |
| 5,673,692 A | 10/1997 | Schulze et al. | |
| 5,786,785 A | 7/1998 | Gindrup et al. | |
| RE36,242 E | 6/1999 | Apisdorf | |
| 5,968,854 A | 10/1999 | Akopian et al. | |
| 6,266,824 B1 | 7/2001 | Giansanti | |
| 6,435,184 B1 | 8/2002 | Ho | |
| 6,513,526 B2 | 2/2003 | Kwok et al. | |
| 6,561,190 B1 | 5/2003 | Kwok | |
| 6,561,191 B1 | 5/2003 | Kwok | |
| 6,772,760 B2 | 8/2004 | Frater et al. | |
| 6,772,762 B2 | 8/2004 | Piesinger | |
| 6,895,962 B2 | 5/2005 | Kullik et al. | |
| D589,136 S | 3/2009 | Kenyon | |
| D589,137 S | 3/2009 | Kenyon | |
| D589,138 S | 3/2009 | Kenyon | |
| 7,748,381 B2 | 7/2010 | Croll et al. | |
| 7,866,944 B2 | 1/2011 | Kenyon et al. | |
| 7,913,692 B2 | 3/2011 | Kwok | |
| 7,975,688 B1* | 7/2011 | Truitt ................ | A61M 16/0066 128/200.24 |
| 8,517,017 B2* | 8/2013 | Bowditch ............ | A61M 16/00 128/204.23 |
| 9,132,252 B2 | 9/2015 | Barlow et al. | |
| 2002/0029777 A1 | 3/2002 | Zimprich et al. | |
| 2002/0077012 A1 | 6/2002 | Lu | |
| 2002/0119044 A1 | 8/2002 | O'Conner | |
| 2003/0062045 A1 | 4/2003 | Woodring et al. | |
| 2003/0172930 A1 | 9/2003 | Kullik et al. | |
| 2004/0065330 A1 | 4/2004 | Landis | |
| 2004/0079373 A1 | 4/2004 | Mukaiyama et al. | |
| 2004/0226562 A1 | 11/2004 | Bordewick | |
| 2004/0255364 A1 | 12/2004 | Feher | |
| 2005/0034724 A1 | 2/2005 | O'Dea | |
| 2005/0103339 A1 | 5/2005 | Daly et al. | |
| 2005/0217673 A1 | 10/2005 | Daly et al. | |
| 2006/0096596 A1 | 5/2006 | Occhialini et al. | |
| 2006/0150973 A1 | 7/2006 | Chalvignac | |
| 2006/0213523 A1* | 9/2006 | VanDerWoude .... | A41D 13/0025 128/863 |
| 2006/0237013 A1* | 10/2006 | Kwok ................. | A61M 16/06 128/204.23 |
| 2007/0000493 A1 | 1/2007 | Cox | |
| 2007/0048159 A1* | 3/2007 | DiMatteo .......... | A61M 16/0066 417/423.14 |
| 2007/0089221 A1 | 4/2007 | Manzella et al. | |
| 2007/0144525 A1 | 6/2007 | Davidson et al. | |
| 2007/0247009 A1* | 10/2007 | Hoffman ............ | F04D 25/0606 310/51 |
| 2007/0251527 A1* | 11/2007 | Sleeper ............. | A61M 16/0057 128/204.21 |
| 2007/0277819 A1 | 12/2007 | Osborne et al. | |
| 2007/0277827 A1* | 12/2007 | Bordewick .......... | A61M 16/00 128/205.25 |
| 2008/0000474 A1 | 1/2008 | Jochle et al. | |
| 2008/0060649 A1 | 3/2008 | Veliss et al. | |
| 2008/0216831 A1 | 9/2008 | McGinnis et al. | |
| 2008/0216833 A1 | 9/2008 | Pujol et al. | |
| 2008/0304986 A1 | 12/2008 | Kenyon et al. | |
| 2009/0112299 A1 | 4/2009 | Chapman | |
| 2009/0136241 A1 | 5/2009 | Kenyon | |
| 2009/0194101 A1* | 8/2009 | Kenyon ............. | A61M 16/0057 128/201.22 |
| 2009/0246013 A1* | 10/2009 | Kenyon ............. | A61M 16/0057 415/208.2 |
| 2009/0301485 A1* | 12/2009 | Kenyon ............. | A61M 16/0057 128/204.18 |
| 2010/0132711 A1 | 6/2010 | Kenyon | |
| 2010/0170513 A1* | 7/2010 | Bowditch ............ | A61M 16/00 128/204.23 |
| 2012/0138058 A1* | 6/2012 | Fu ..................... | A61M 16/0066 128/204.23 |
| 2012/0152255 A1 | 6/2012 | Barlow et al. | |

FOREIGN PATENT DOCUMENTS

| | | |
|---|---|---|
| CN | 101466429 A | 6/2009 |
| CN | 101502690 A | 8/2009 |
| DE | 102 61 602 A1 | 7/2000 |
| EP | 0 164 946 | 9/1989 |
| EP | 0 330 740 | 9/1989 |
| EP | 1 318 307 | 6/2003 |
| EP | 1655052 | 5/2006 |
| EP | 2 000 675 | 12/2008 |
| EP | 2 215 216 A | 8/2009 |
| EP | 2085106 | 8/2009 |
| GB | 2 209 474 A | 5/1989 |
| GB | 2 388 536 | 11/2003 |
| WO | WO 99/13931 | 3/1999 |
| WO | 2005/028009 A1 | 3/2005 |
| WO | WO 2006/138416 | 12/2006 |
| WO | WO 2007/117716 | 10/2007 |
| WO | 2007/150003 | 12/2007 |
| WO | WO 2008/028247 | 3/2008 |

OTHER PUBLICATIONS

International Preliminary Report on Patentability dated Feb. 28, 2012 issued in International Application No. PCT/AU2010/001106 (1 pages).
Further Examination Report dated Aug. 16, 2017 issued in New Zealand Application No. 723778 (4 pages).

(56) References Cited

OTHER PUBLICATIONS

Notification of the Fourth Office Action dated Sep. 2, 2015 issued in Chinese Application No. 201080049302.8 with English translation (15 pages).
Decision of Rejection dated Mar. 2, 2016 issued in Chinese Application No. 201080049302.8 with English translation (21 pages).
Notification of the Third Office Action in Chinese Application No. 201080049302.8 with English translation (17 pages).
Further Examination Report dated Oct. 28, 2014 issued in New Zealand Application No. 613721 (2 pages).
International Search Report for PCT/AU2010/001106, dated Dec. 6, 2010.
Chinese Office Action dated Mar. 4, 2014 in Chinese Application No. 201080049302.8, with English translation (14 pages).
Notification of Second Office Action dated Sep. 3, 2014 issued in Chinese Application No. 201080049302.8 with English translation (16 pages).
Notice of Opposition to Grant of Patent dated Jun. 27, 2014 filed in New Zealand Application No. 598152 (3 pages).
Amended Notice of Opposition to Grant of Patent dated Aug. 28, 2014 filed in New Zealand Application No. 598152 (2 pages).
Statement of Case dated Aug. 28, 2014 filed in New Zealand Application No. 598152 (7 pages).
World Health Organization—Electromagnetic Fields and Public Health, Mar. 2006, http://www.who.int/peh-emf/publications/facts/fs299/en (2 pages).
World Health Organization—Framewor for Developing Health-based EMF Standards, 2006, http://www.who.int/peh-emf/standards/EMF_standards_framework%5b1%5d.pdf (42 pages).
International Commission on Non-Ionizing Radiation Protection—ICNIRP Guidelines for Limiting Exposure to Time-Varying Electric, Magnetic and Electromagnetic Fields (Up to 300 GHZ), Health Physics 74(4), pp. 494-522., 1998.
Examination Report in related New Zealand patent application No. 598152 dated Oct. 23, 2012.
Further Examination Report dated Sep. 12, 2014 issued in New Zealand Application No. 613721 (2 pages).
First Examination Report dated Aug. 14, 2014 in New Zealand Application No. 628624 (1 page).
Further Examination Report dated Aug. 13, 2014 issued in New Zealand Application No. 613721 (2 pages).
Extended European Search Report dated Aug. 25, 2014 issued in European Application No. 10811028.9 (8 pages).
Further Examination Report dated Jun. 11, 2015 issued in New Zealand Application No. 628624 (2 pages).
Office Action dated Oct. 14, 2016 issued in European Application No. 10811028.9 (4 pages).
Notification of the First Office Action dated Feb. 27, 2018 issued in Chinese Application No. 2016104403227 with English translation (22 pages).
First Examination Report dated Mar. 1, 2018 issued in New Zealand Application No. 739854 (2 pages).
Extended European Search Report dated Aug. 22, 2018 issued in European Application No. 18175918.4 (9 pages).

\* cited by examiner

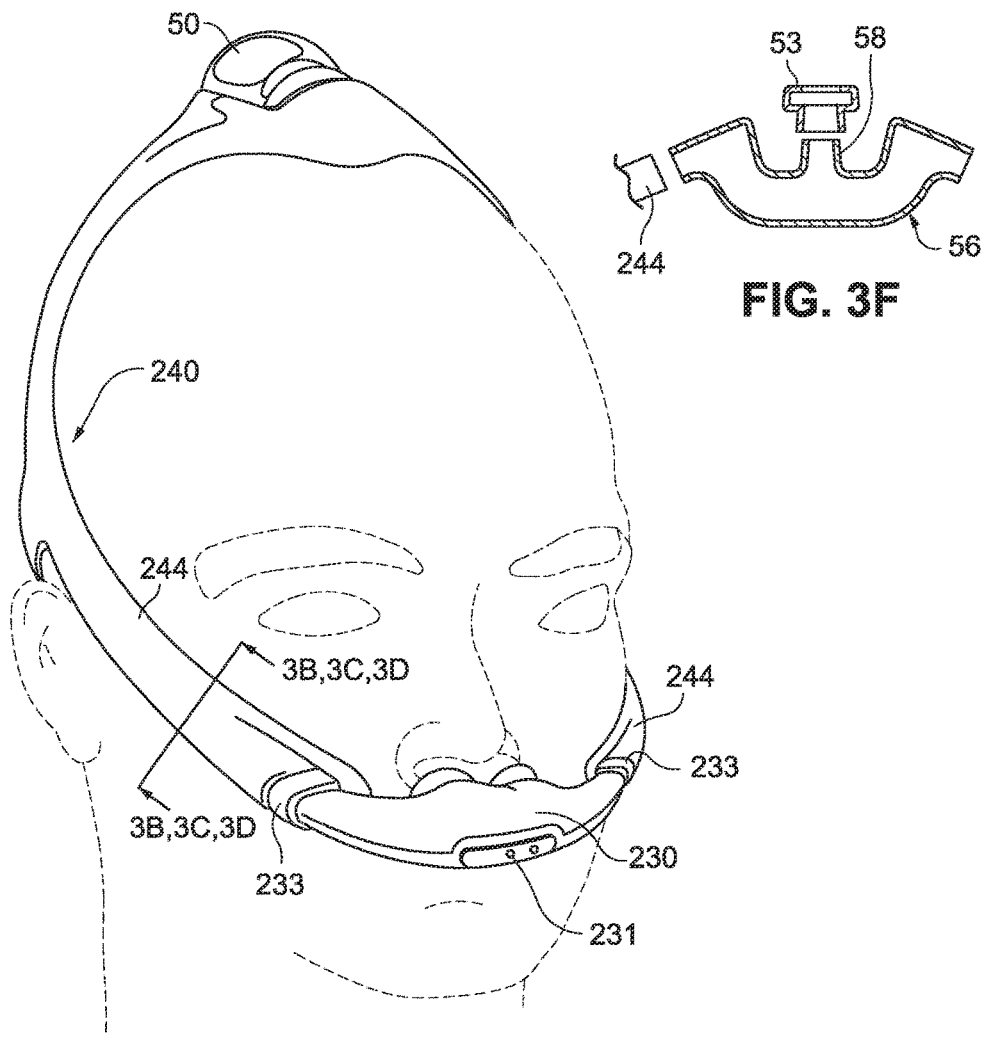
FIG. 3A
FIG. 3F
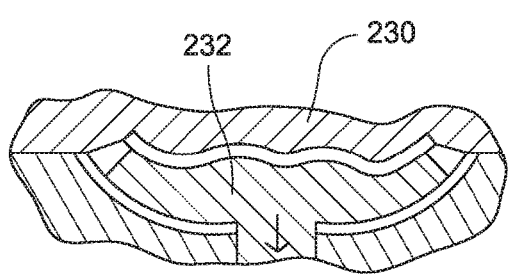
FIG. 3E
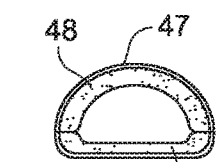
FIG. 3B
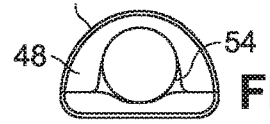
FIG. 3C
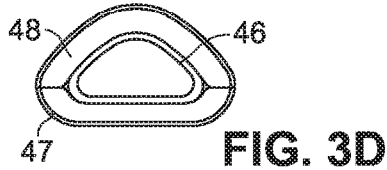
FIG. 3D

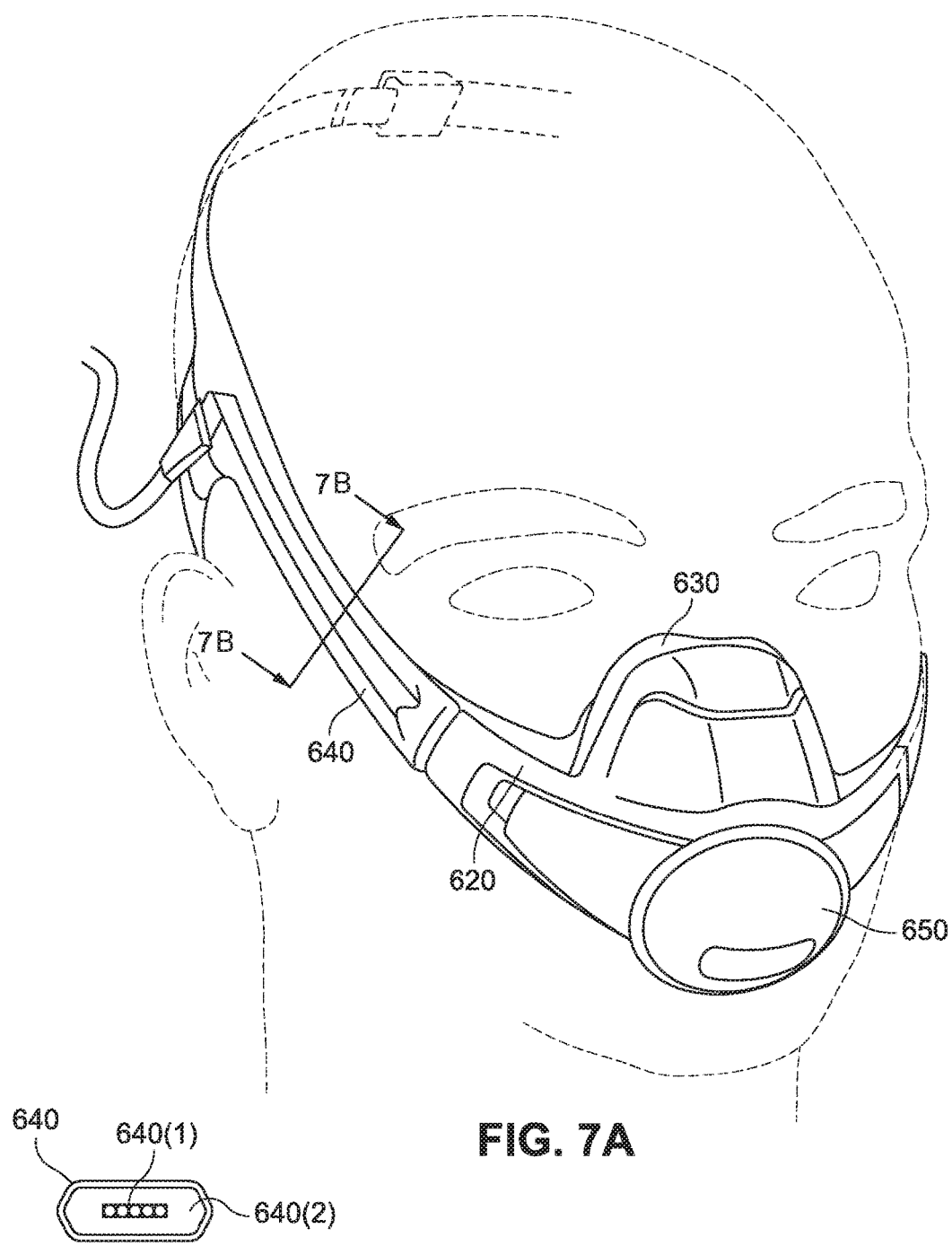

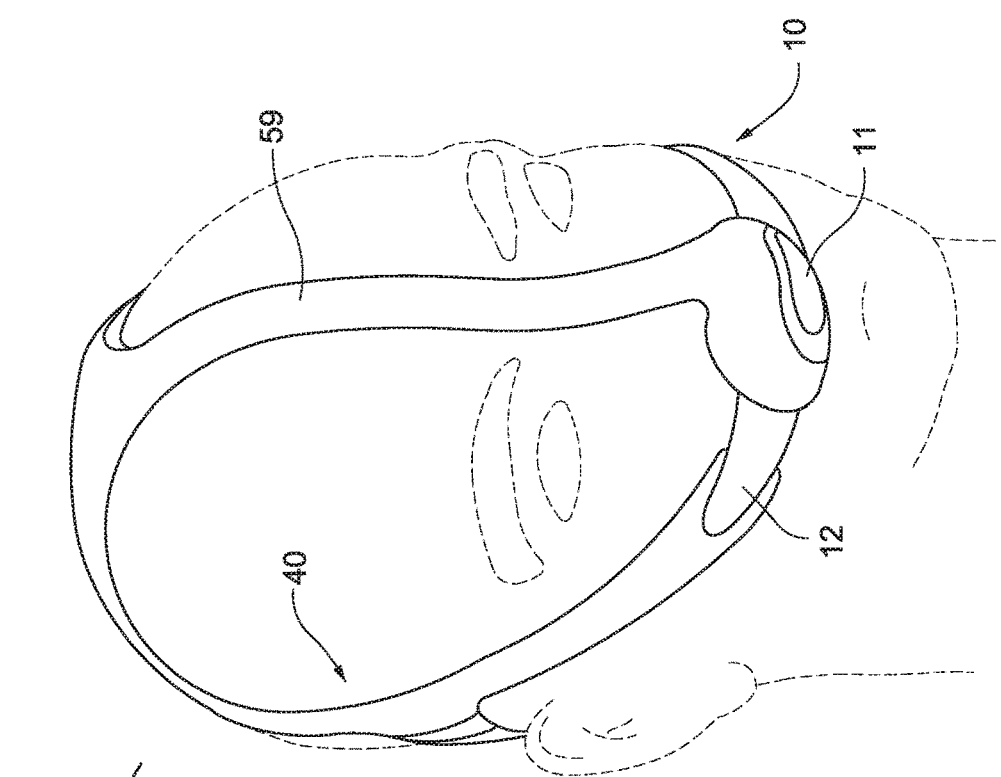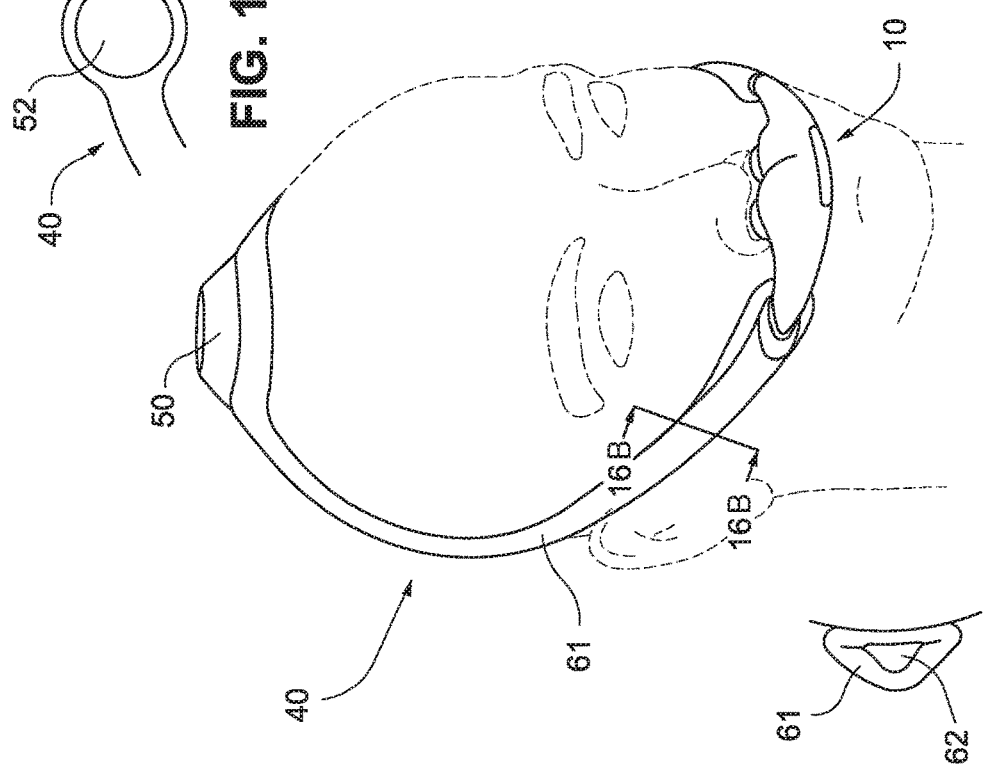

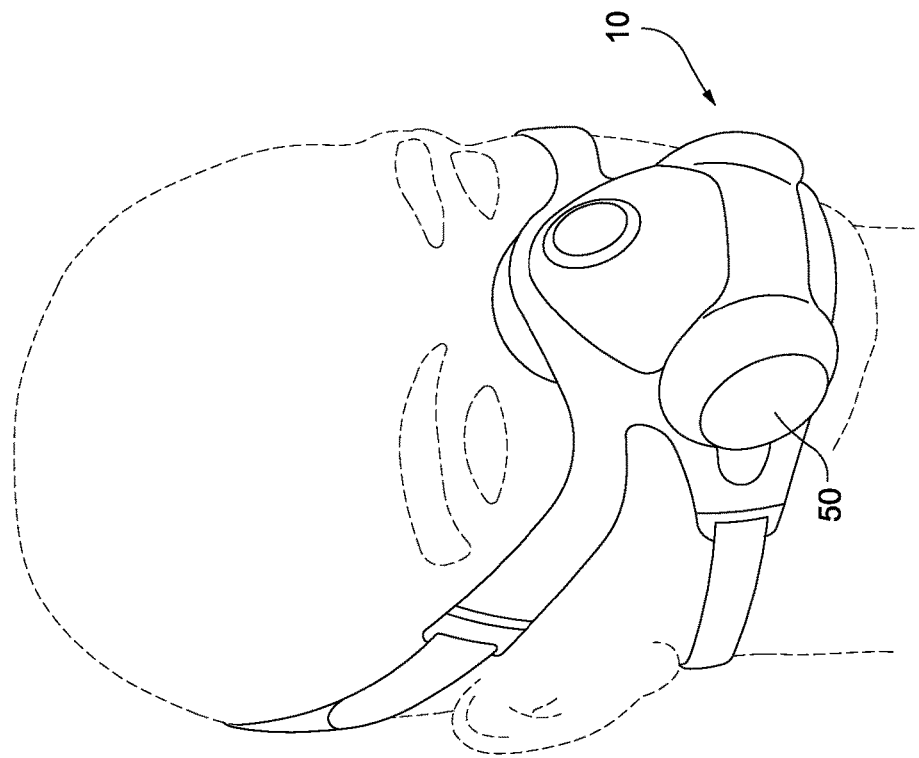
FIG. 25
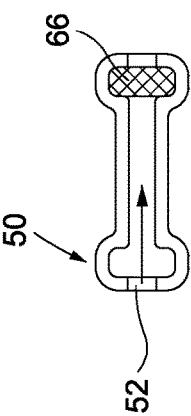
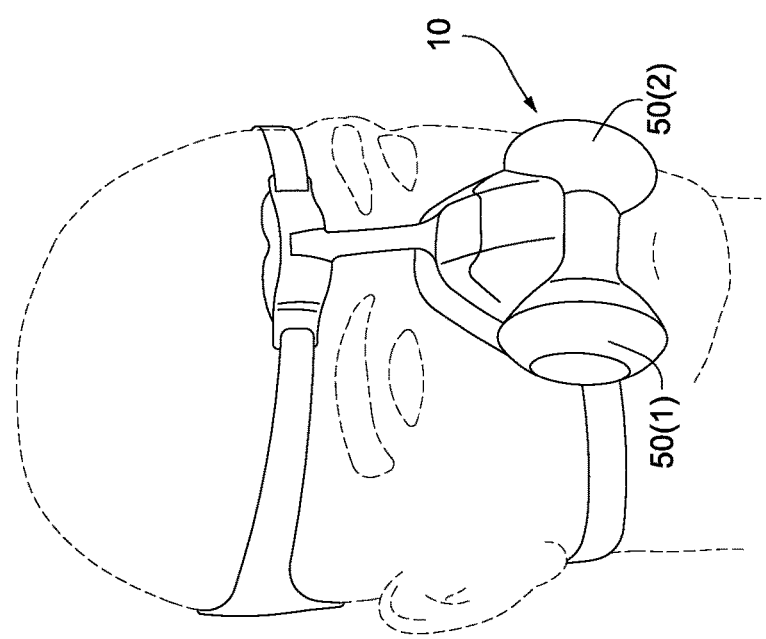
FIG. 24

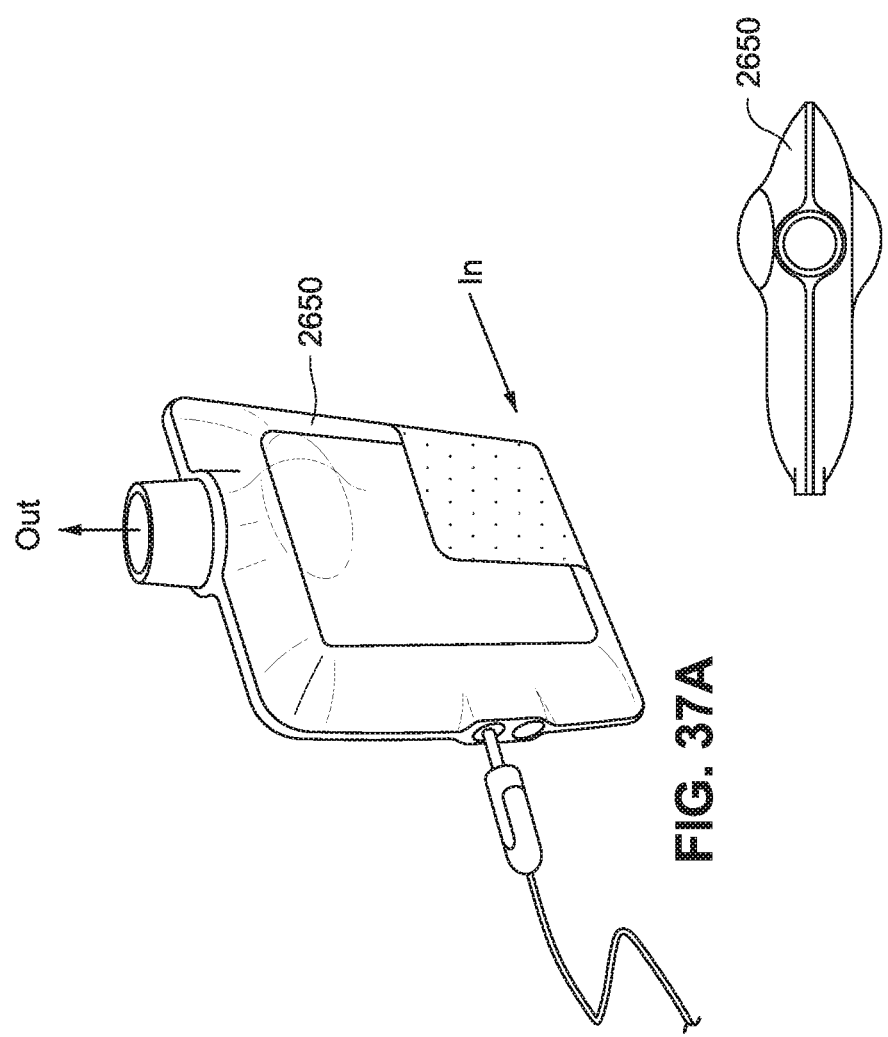

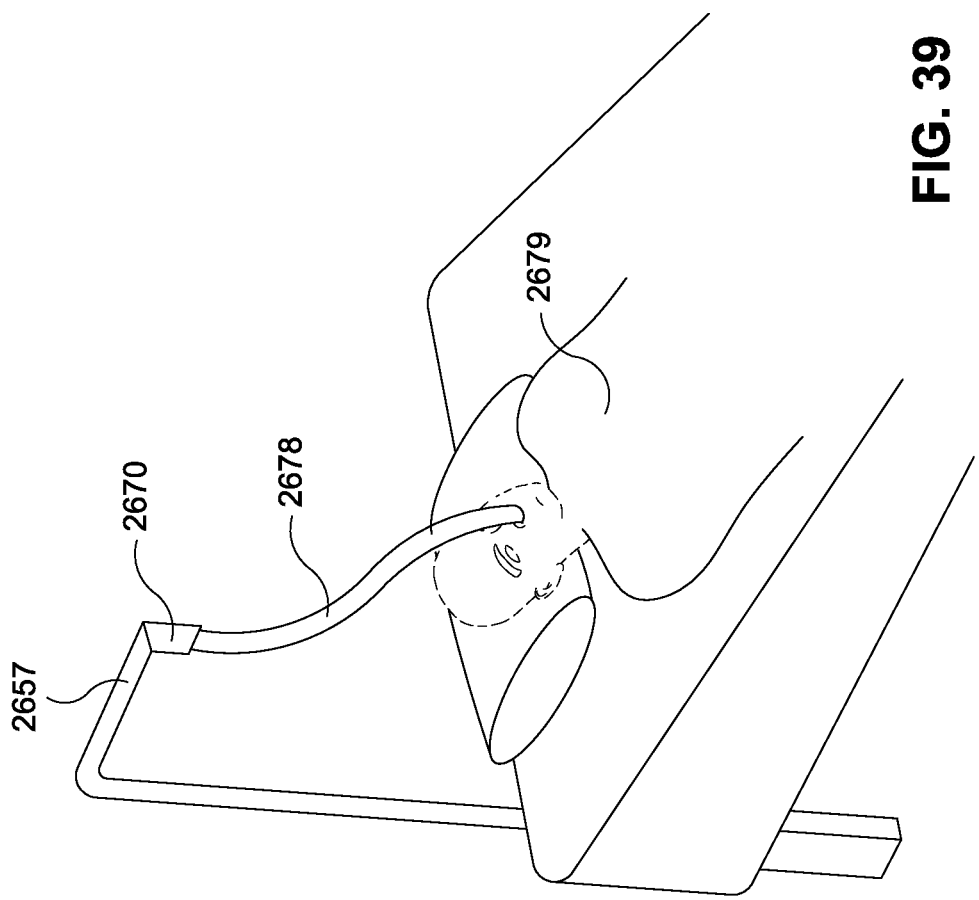

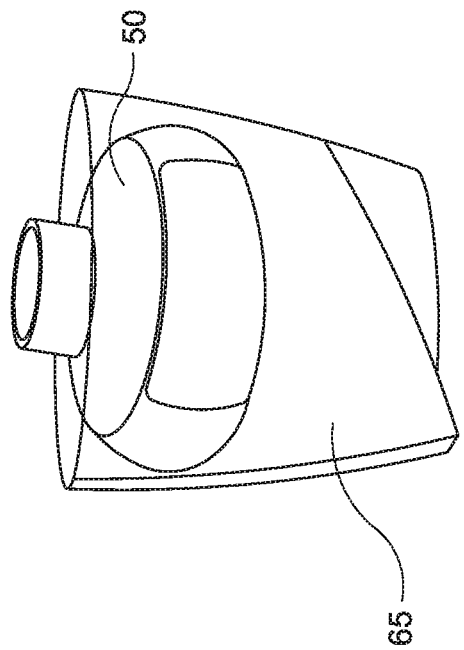
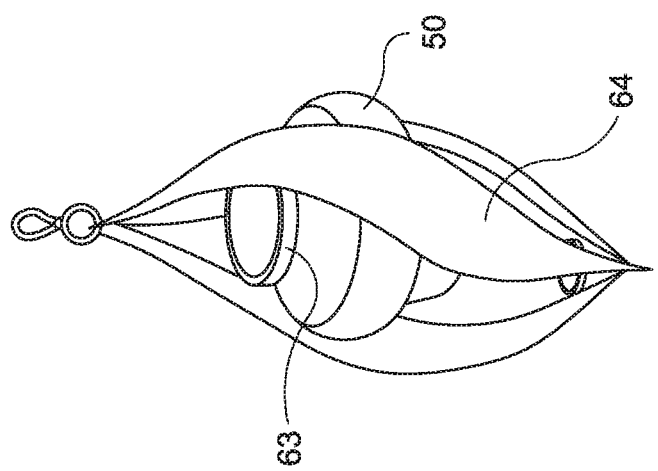
FIG. 41B
FIG. 41A

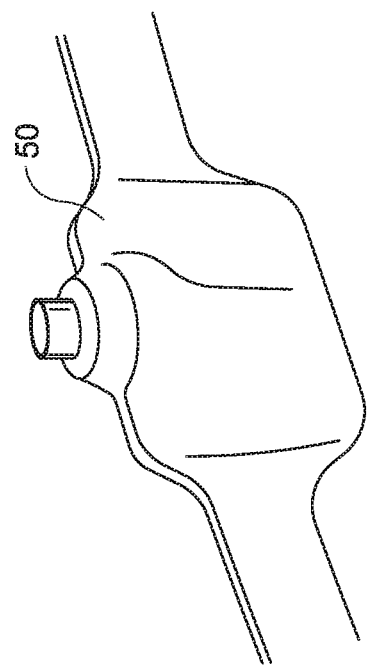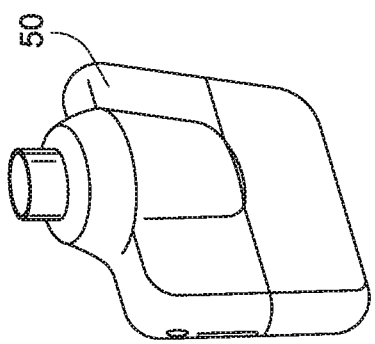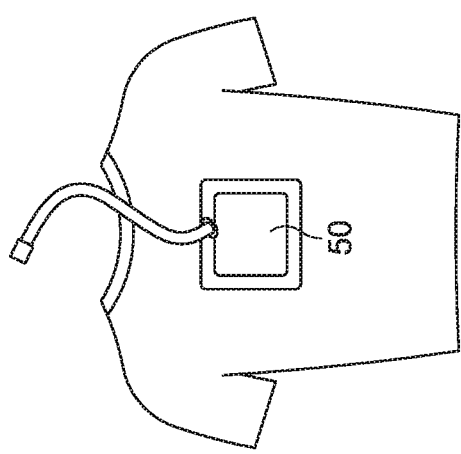

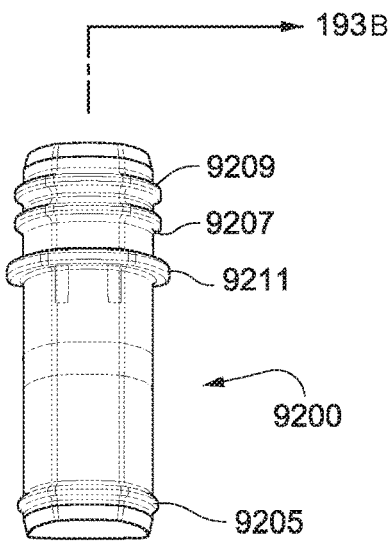
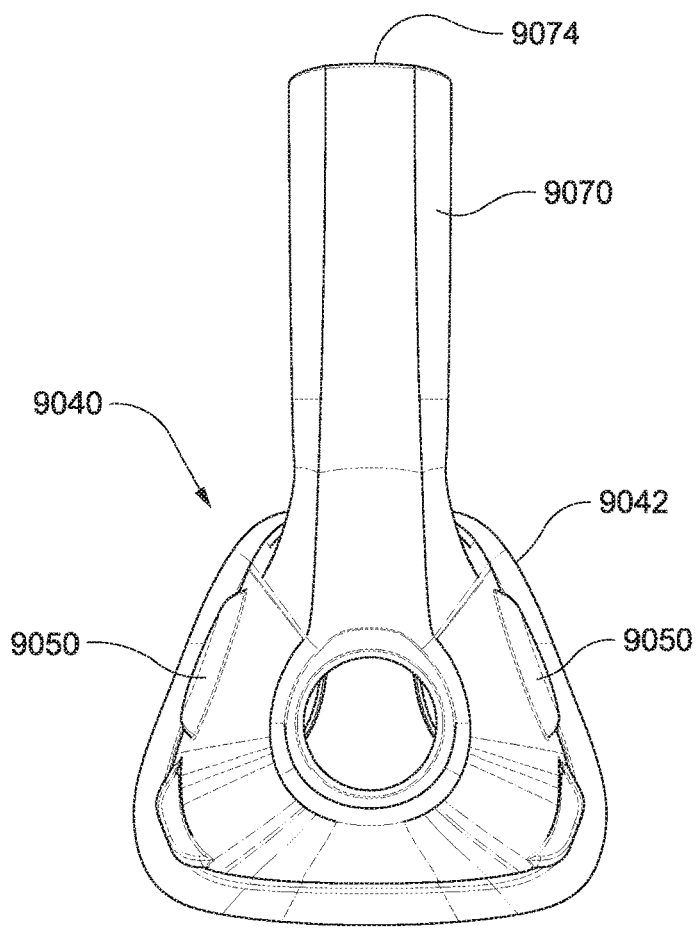
FIG. 193A

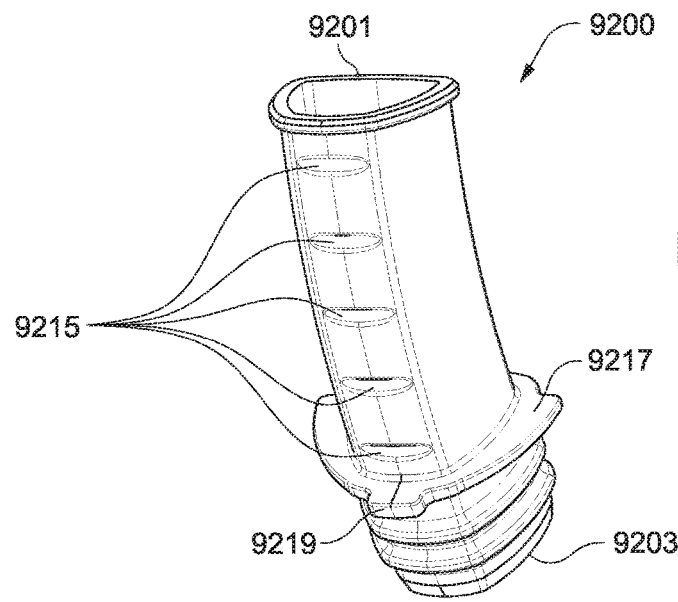
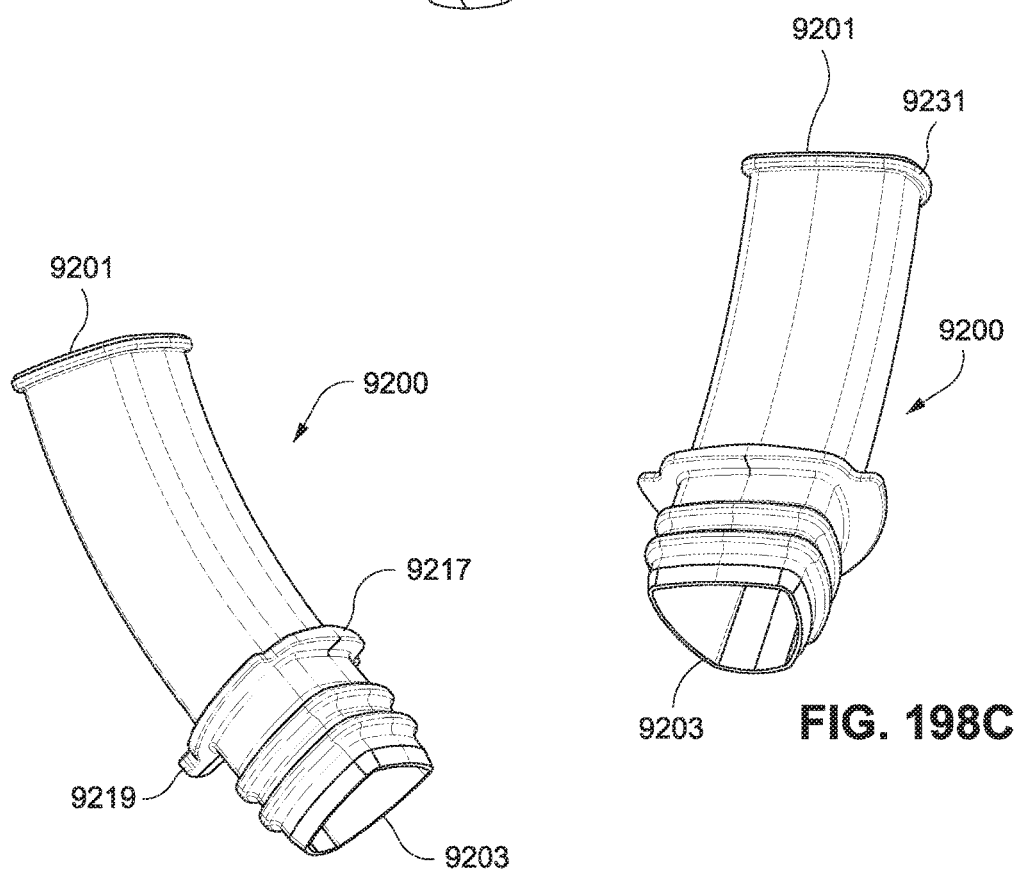
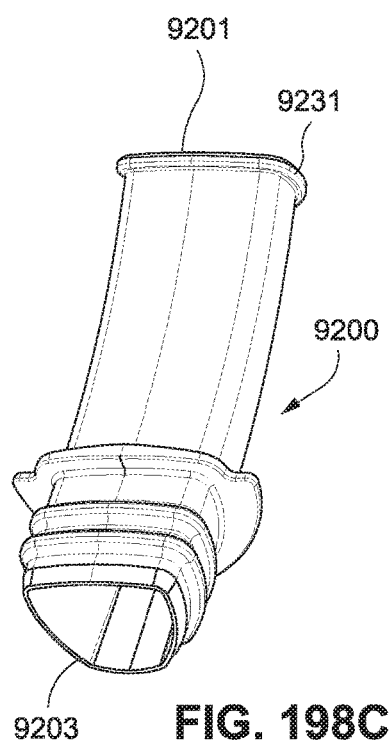

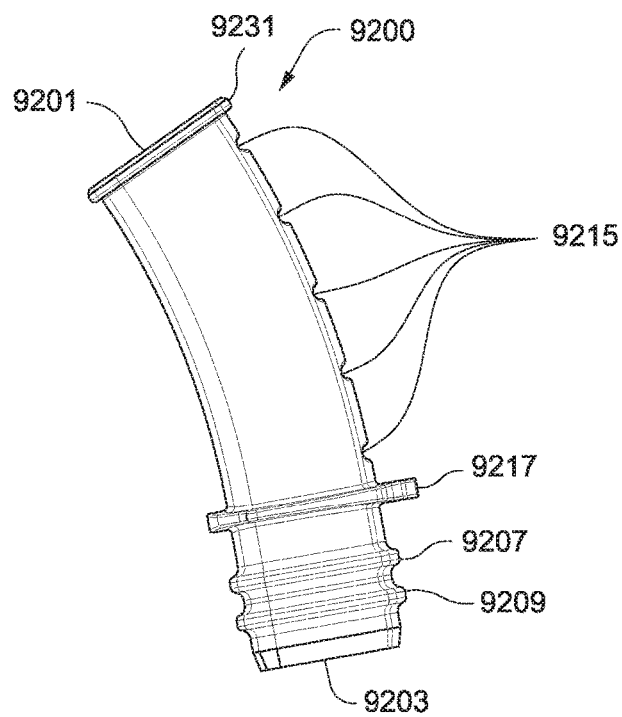
FIG. 198D
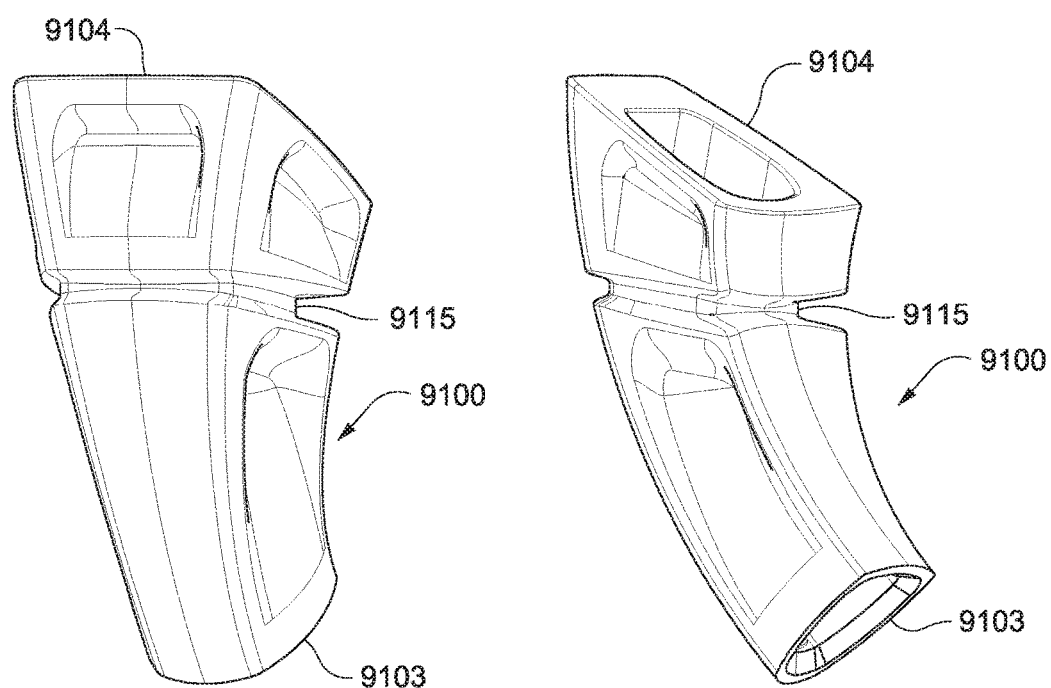
FIG.199A
FIG. 199B

PAP SYSTEM

CROSS-REFERENCE TO RELATED APPLICATIONS

This application is a continuation of U.S. Ser. No. 13/393,187, filed Feb. 29, 2012, now allowed, which is the U.S. National Phase of International Application No. PCT/AU2010/001106, filed Aug. 27, 2010, which designed the U.S. and claims the benefit of U.S. Provisional Applications 61/272,188, filed Aug. 28, 2009, and 61/272,919, filed Nov. 19, 2009, and Australian Provisional Applications AU 2010900237, filed Jan. 22, 2010, 2010900304, filed Jan. 27, 2010, 2010900455, filed Feb. 5, 2010, and 2010900647, filed Feb. 18, 2010, the entire contents of each being incorporated herein by reference in their entirety.

U.S. Provisional Applications 61/213,326, filed May 29, 2009, 61/222,711, filed Jul. 2, 2009, 61/272,043, filed Aug. 11, 2009, 61/272,162, filed Aug. 25, 2009, and 61/272,250, filed Sep. 4, 2009, are each incorporated herein by reference in their entirety. International Application PCTAU2010/001031, filed Aug. 11, 2010, is incorporated herein by reference in its entirety.

FIELD

The present technology relates to Positive Airway Pressure (PAP) systems and/or methods of use for treatment, e.g., of Sleep Disordered Breathing (SDB) with Continuous Positive Airway Pressure (CPAP) or Non-Invasive Positive Pressure Ventilation (NIPPV).

BACKGROUND

Examples of head mounted blowers, wearable CPAP, or portable CPAP are known in the art. For example, see U.S. Patent Application Publications 2006/0237013 A1 and 2009/0320842 A1, each incorporated herein by reference, and the BreatheX™ system.

SUMMARY

Certain embodiments relate to minimalistic CPAP systems, methods of use and devices structured to at least reduce impact on the patient.

Certain embodiments relate to patient interfaces that incorporates a relatively small or miniature blower.

Certain embodiments relate to CPAP systems, methods of use and devices structured to at least reduce size and bulk, reduce vibrations, reduce generated noise or combinations thereof.

Certain embodiments relate to small CPAP devices configured to supply pressurized breathable gas (e.g., air) in a manner suitable for treatment of sleep apneas.

Certain embodiments relate to PAP systems including a patient interface including sealing arrangement adapted to form a seal with the patient's nose and/or mouth and headgear to support the sealing arrangement in position on the patient's head. A blower is structured to generate a supply of pressurized air. The blower is supported by the patient interface on the patient's head (e.g., within or formed as part of the headgear or cushion (e.g., integrated with nozzles) and in communication with the patient interface. The headgear may form one or more ducts to communicate pressurized air from the blower to a breathing cavity defined by the sealing arrangement. Alternatively, a separate tube may be provided to communicate pressurized air from the blower to the sealing arrangement.

Certain embodiments relate to PAP devices including a portable blower structured to generate a supply of pressurized air and a blower dock structured to retain, charge, and/or download diagnostics from the blower.

Certain embodiments relate to PAP systems and methods of use that include a patient interface, a portable blower structured to generate a supply of pressurized air, and a blower support structure structured to support the portable blower on the patient's body.

Certain embodiments relate to PAP systems and methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head and dampen vibrations and/or noise from the blower in use. The blower support includes an inflatable cushion including an inflatable chamber adapted to be inflated by pressurized air from the blower.

Certain embodiments relate to headgears including a plurality of straps, wherein one or more selected portions of the straps include a bladder or pocket. In certain embodiments, the one or more selected portions of the straps include a bladder or pocket of vibration damping material to dampen vibrations.

Certain embodiments relate to PAP systems and methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower includes at least one inlet oriented at angles between normal to parallel to the plane of the patient's face. In certain embodiments, the blower includes at least one inlet oriented at angles between substantially normal to substantially parallel to the plane of the patient's face.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower includes at least one inlet which is attached to a snorkel arrangement.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower includes at least dual inlets. In certain embodiments, at least one of the inlets may be substantially cylinder shaped.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower may be decoupled, or substantially decoupled, from the headgear and/or the patient's head to reduce vibration transmission. The blower may be decoupled, or substantially decoupled, with the housing by the use of shock and/or vibration absorbing housing mounts.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. In certain embodiments, the blower is at least partially encapsulated in a polymer, such as an elastic polymer (or other suitable material) which is mounted in a housing and the outer surface of the encapsulation includes at least one vibration absorbing protrusion.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower is mounted in a housing wherein the motor and electronics are mounted in the housing away or remote from the patient's head, e.g., relative to other components of the blower.

Certain embodiments relate to PAP systems or methods of use that include a patient interface including sealing arrangement adapted to form a seal with the patient's nose and/or mouth and headgear to support the sealing arrangement in position on the patient's head, a blower structured to generate a supply of pressurized air, the blower supported by the patient interface on the patient's head and in communication with the patient interface, and a blower support structured to support the blower on the patient's head. The blower is mounted in a housing and the housing is substantially configured to match the surface of the crown or front portion of a patient's head. In certain embodiments, the housing has at least in part a rounded configuration.

Certain embodiments may include PAP devices or systems adapted to be worn or carried. The PAP systems may include a flow generator adapted to be positioned on the crown of a patient's head using headgear. In certain embodiments, the flow generator may be adapted to be mounted on the front portion of a patient's head using headgear. The headgear may include a combination of straps, rigidisers, EMF shielding or combinations thereof. In certain embodiments the headgear is adapted to minimize or limit movement of the flow generator on the patient's head and also secure a patient interface to the patient's face. In certain embodiments the headgear is adapted to substantially minimize or substantially limit movement of the flow generator on the patient's head and also secure a patient interface to the patient's face.

In certain embodiments, the flow generator may also include features to minimize or isolate noise and vibration transmission, when in use. These features may include: foam mounting of the blower within a housing of the flow generator, and/or inlets being directed away from the patient's face and ears.

In certain embodiments, the flow generator may also include various features to improve comfort and/or fit of the device including a curved lower surface.

In certain embodiments, the present technology may include a PAP device or system adapted to be worn or carried by a patient. The PAP system may include a flow generator adapted to be mounted on the crown of a patient's head using headgear. In certain embodiments, the flow generator may be positioned on the front portion of a patient's head using headgear. The headgear may include a combination of straps, rigidisers, EMF shielding or combinations thereof.

The headgear may be adapted to minimize or limit movement of the flow generator on the patient's head and also secure a patient interface to the patient's face.

Certain embodiments provide a mask system that is simple and/or unobtrusive configuration. Certain embodiments provide mask systems that can accommodate a wide range of different facial shapes. Certain embodiments provide mask systems with a wide fit range.

Certain embodiments provide a cushion that is adapted to form a seal around a nose of a patient including a seal in a nasal bridge region of a patient. The nasal bridge region is a region of greater variability between different patients than other regions of a nose. Another region of potential variability between faces is an angle of the forehead with respect to a plane of the face.

In order to accommodate a wide range of face shapes, a series of masks of different sizes and shapes may be constructed. However this may be expensive. In accordance with certain embodiments, a cushion angle adjustment mechanism for mask systems may be provided to facilitate rotation of the cushion with respect to the plane of the face. In this way, a given mask system is able to accommodate a wider fit range of patients.

The cushion size and shape may be structured to accommodate a wide range of different facial shapes.

Certain embodiments relate to mask systems including a frame adapted to attach to headgear, a sealing arrangement releasably connectable to the frame, and an elbow provided to the sealing arrangement and adapted to be connected to an air delivery tube that delivers breathable gas to the patient. The sealing arrangement defines a breathing chamber and is adapted to form a seal with at least a portion of the patient's face. The sealing arrangement includes structure to establish a positive connection with the frame and with the elbow.

Certain embodiments relate to mask systems including a frame and a sealing arrangement provided to the frame. The sealing arrangement includes a silicone cushion and a foam cushion provided to the silicone cushion. The silicone cushion defines a breathing chamber and the foam cushion is supported by the silicone cushion such that the foam cushion is not in communication with the breathing chamber. The foam cushion supports the sealing arrangement on the frame. In certain embodiments, the silicone cushion defines a breathing chamber and the foam cushion is supported by the silicone cushion such that the foam cushion is substantially not in communication with the breathing chamber.

Certain embodiments relate to mask systems including a frame adapted to attach headgear and a sealing arrangement releasably connectable to the frame. The sealing arrangement defines a breathing chamber and is adapted to form a seal with the patient's face. The sealing arrangement includes one or more protrusions adapted to interlock with respective openings provided to the frame. In certain embodiments, the sealing arrangement includes one or more protrusions adapted to interlock with respective openings provided to the frame and provide visual reinforcement that the connection has been established.

Certain embodiments relate to a sealing arrangement for mask systems including a side wall defining a breathing chamber, an undercushion curving outwards from the side wall and away from the breathing cavity, and a membrane that at least partially covers the undercushion. The membrane extends from the undercushion and curves inwards into the breathing cavity.

Certain embodiments relate to mask systems including a frame, a sealing arrangement releasably connectable to the frame, an elbow provided to the sealing arrangement and adapted to be connected to an air delivery tube that delivers breathable gas to the patient, and a forehead support provided to the frame. The sealing arrangement defines a breathing chamber and is adapted to form a seal with the patient's face. The forehead support includes an elongated arm adapted to extend from the frame and an upper headgear connector adapted to attach upper headgear straps. In certain aspects, at least a portion of the arm is constructed from metal.

Certain embodiments may relates to mask systems including a frame, a sealing arrangement releasably connectable to the frame, an inlet tube provided to the sealing arrangement and adapted to be connected to an air delivery tube that delivers breathable gas to the patient, and a forehead support provided to the frame. Where the sealing arrangement may be integrally, or substantially integrally, joined to an inlet tube extending in a vertically direction from the sealing arrangement, when worn. The inlet tube may be releasably retained by frame. The sealing arrangement may include a vent.

In certain embodiments, the mask system may be adapted for use with a travel PAP device wherein the mask system is secured in place on a patient by headgear and headgear also secures a flow generator delivering pressurized breathable gas to the mask system.

Other embodiments, aspects, features, and/or advantages of this technology will become apparent from the following detailed description when taken in conjunction with the accompanying drawings, which are a part of this disclosure and which illustrate, by way of example, principles of e s disclosed technology. In certain embodiments, PAP systems are disclosed that may be configured to provide a minimal visual footprint in use. The flow generator of such PAP systems comprises at least one blower and/or at least one blower housing and are in air communication with a patient interface. In addition, these PAP systems may include other structural elements (for example, but not limited, to headgear, shoulder-type harnesses, pendant-type arrangements, articles of clothing, straps or band arrangements or combinations thereof) resulting in PAP systems that may be portable, carried by the patient, used for travel, mask mounted, head mounted or combinations thereof.

In certain embodiments, the height of the flow generator may be, for example, less than 100 mm, less than 80 mm, less than 60 mm, less than 40 mm, or less than 20 mm. The volume of the flow generator may be, for example, less than 400 cm$^3$, less than 350 cm$^3$, less than 300 cm$^3$ less than 250 cm$^3$, less than 200 cm$^3$, less than 150 cm$^3$, less than 125 cm$^3$, less than 100 cm$^3$, less than 75 cm$^3$, or less than 50 cm$^3$. The flow generator excluding the weight of batteries may weigh, for example, less than 500 g, less than 400 g, less than 300 g, less than 250 g, less than 200 g, less than 150 g or less than 100 g. The noise output by the flow generator may be, for example, less than 70 dBA, less than 60 dBA, less than 50 dBA, less than 46 dBA, or less than 40 dBA, or less than 35 dBA.

In addition, certain embodiments of the flow generator may be configured such that the flow generator may be positioned at a range of angles and positions through the night as the patient rolls around in their sleep and still suitably function. Certain flow generators may suitably function at multiple axes of orientation. In certain embodiments, at least one blower may be a single stage axial blower.

In certain embodiments, the PAP system may include at least one damping structure to reduce the vibrations perceived by the user of the PAP system. In certain embodiments, the PAP system may comprise at least one damping structure that reduces the vibration perceived by the user by at least 20%, 30%, 40%, 50%, 60%, 70% or 80%. In certain embodiments, the PAP system may comprise at least two damping structures that reduce the vibration perceived by the user by at least 20%, 30%, 40%, 50%, 60%, 70% or 80%. In certain embodiments, the PAP system may comprise at least three damping structures that reduce the vibration perceived by the user by at least 20%, 30%, 40%, 50%, 60%, 70% or 80%. In certain embodiments, the PAP system may comprise at least one damping structure that reduces the vibration perceived by the user from the flow generator by at least 20%, 30%, 40%, 50%, 60%, 70% or 80%.

In certain embodiments, the PAP system may comprise at least two damping structures that reduce the vibration perceived by the user from the flow generator by at least 20%, 30%, 40%, 50%, 60%, 70% or 80%. In certain embodiments, the PAP system may comprise at least three damping structures that reduce the vibration perceived by the user from the flow generator by at least 20%, 30%, 40%, 50%, 60%, 70% or 80%. In certain embodiments, the vibration and/or noise output of the flow generator (in dBA), the height of the flow generator (in mm), the volume of the flow generator (in cm3), the weight of the flow generator excluding batteries (in grams), may be combined in various combinations to provide PAP systems with a minimal visual footprint in use and reduced noise and/or vibration output in use.

BRIEF DESCRIPTION OF THE DRAWINGS

The accompanying drawings facilitate an understanding of the various embodiments of this technology. In such drawings:

FIGS. 3A to 3F show a headworn PAP system according to certain embodiments;

FIGS. 7A and 7B show a patient interface with a built-in blower according to certain embodiments;

FIGS. 16A to 16C show a headworn PAP system according to certain embodiments;

FIG. 17 shows a headworn PAP system according to certain embodiments;

FIG. 24 shows a patient interface with a built-in blower according to certain embodiments;

FIG. 25 shows a patient interface with built-in blowers according to certain embodiments;

FIGS. 37A and 37B show a portable blower according to certain embodiments;

FIG. 39 shows light-up tubing according to certain embodiments;

FIGS. 41A and 41B show a wearable and/or portable blower according to certain embodiments;

FIGS. 42A to 42C shows a wearable blower according to certain embodiments;

FIGS. 153 and 154 show perspective views of FIG. 152;
FIG. 155 shows a front view of a portion of FIG. 152.

FIG. 156 shows a perspective view of certain embodiments of a PAP system;

FIG. 157 shows a perspective view of certain embodiments of a PAP system;

FIG. 158 shows a cross-sectional view of a portion of FIG. 157;

FIG. 159 shows an exploded view of a portion FIG. 157;

FIG. 160 shows a schematic view of a diagram depicting power supply arrangements for the embodiment of FIG. 157;

FIGS. 161 and 162 are perspective views of a sealing arrangement, or cushion assembly, according to certain embodiments;

FIG. 163 is a side view of the cushion assembly of FIG. 161;

FIG. 164 is a front view of the cushion assembly of FIG. 161;

FIG. 165 is a side view of the cushion assembly of FIG. 161;

FIG. 166 is a rear view of the cushion assembly of FIG. 161;

FIG. 167 is a bottom view of the cushion assembly of FIG. 161;

Figure 161:
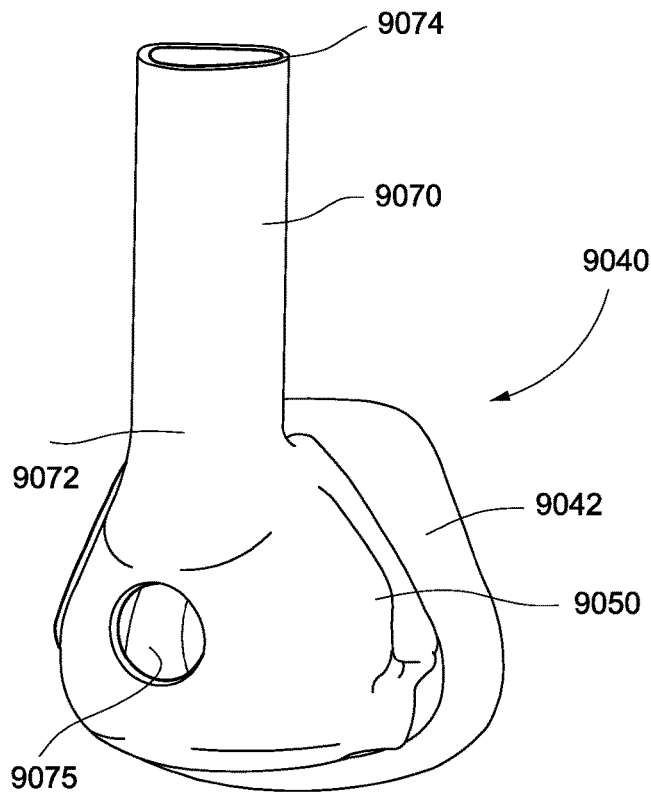
Figure 162:
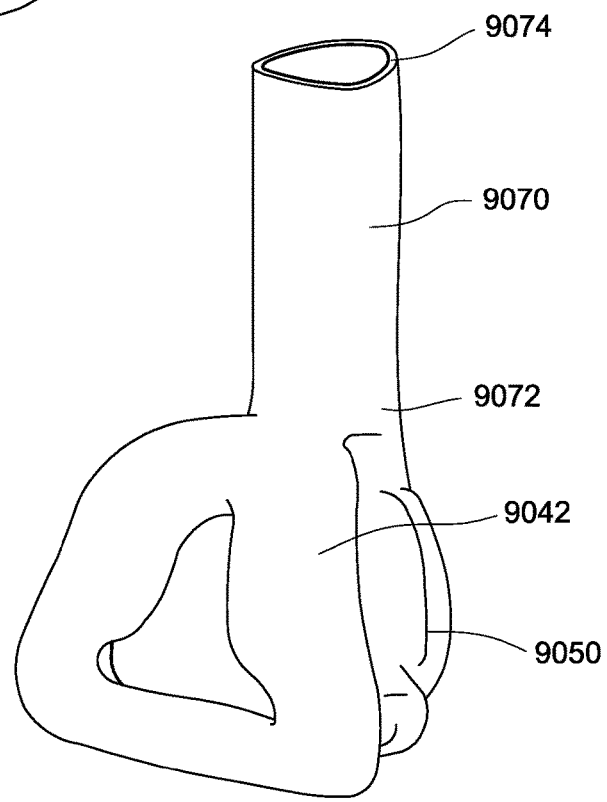
Figure 163:
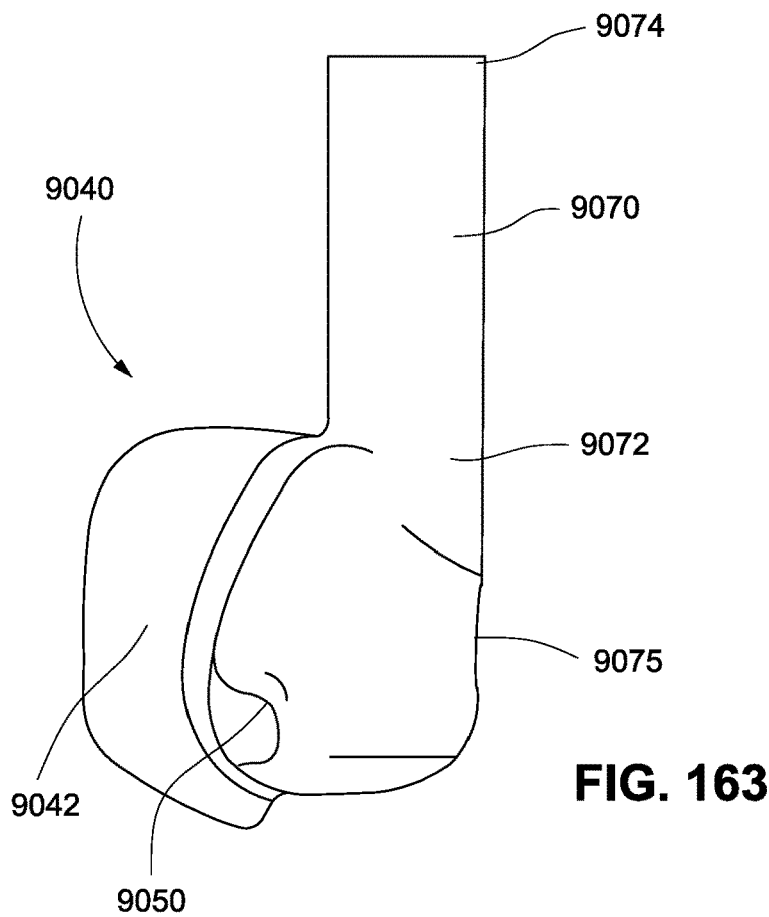
Figure 164:
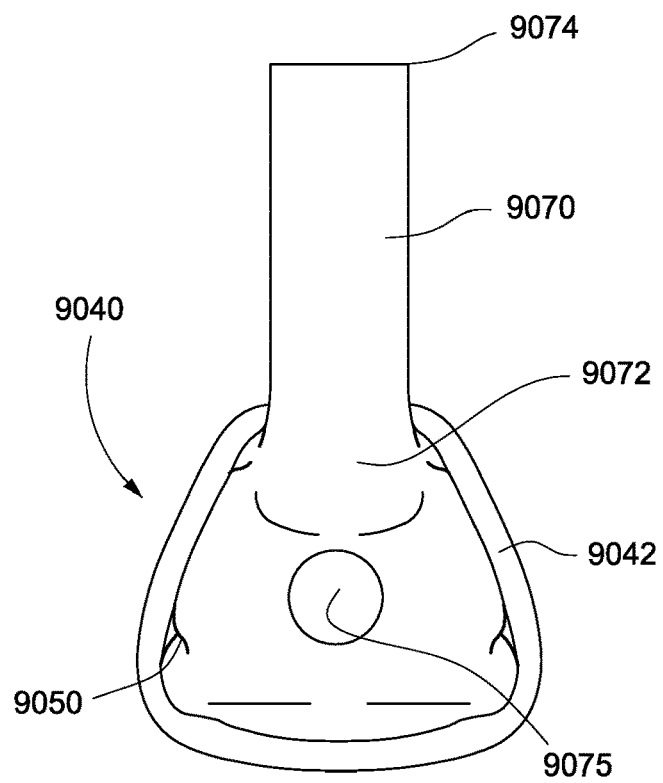
Figure 165:
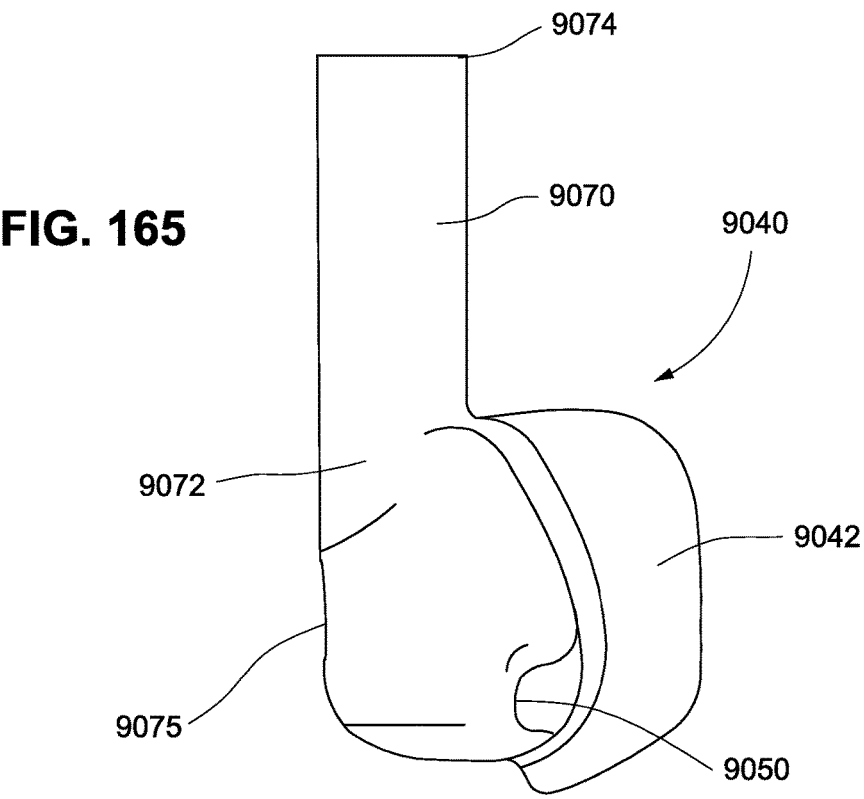
Figure 166:
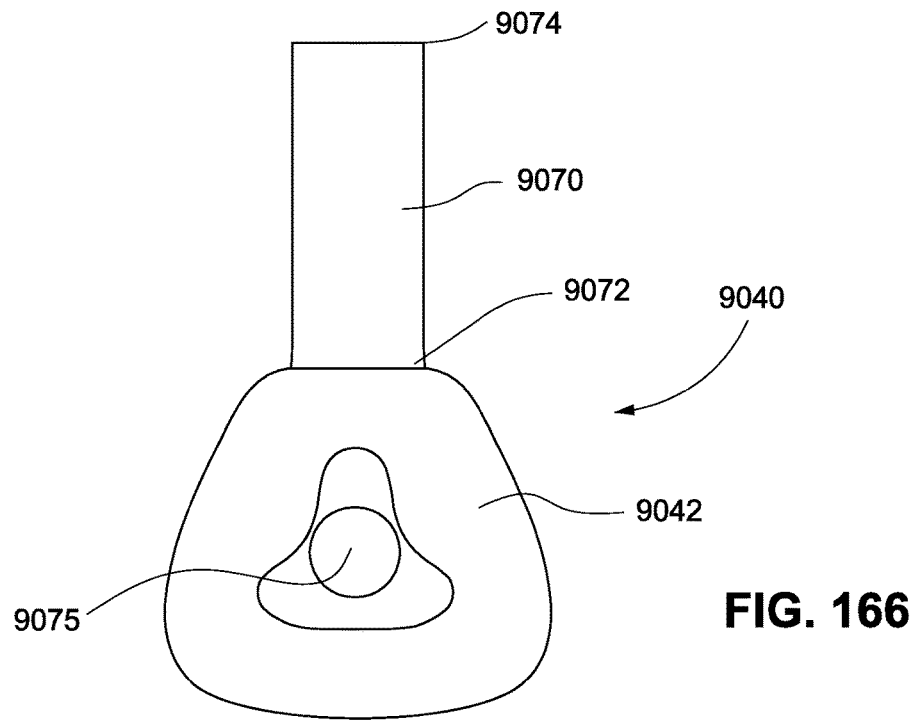
Figure 167:
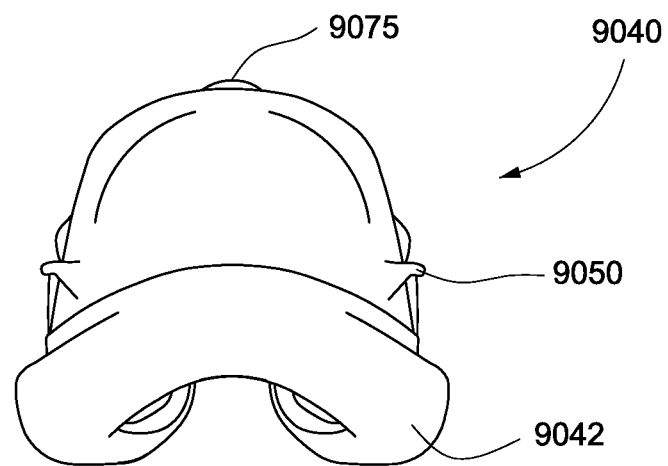
Figure 168:
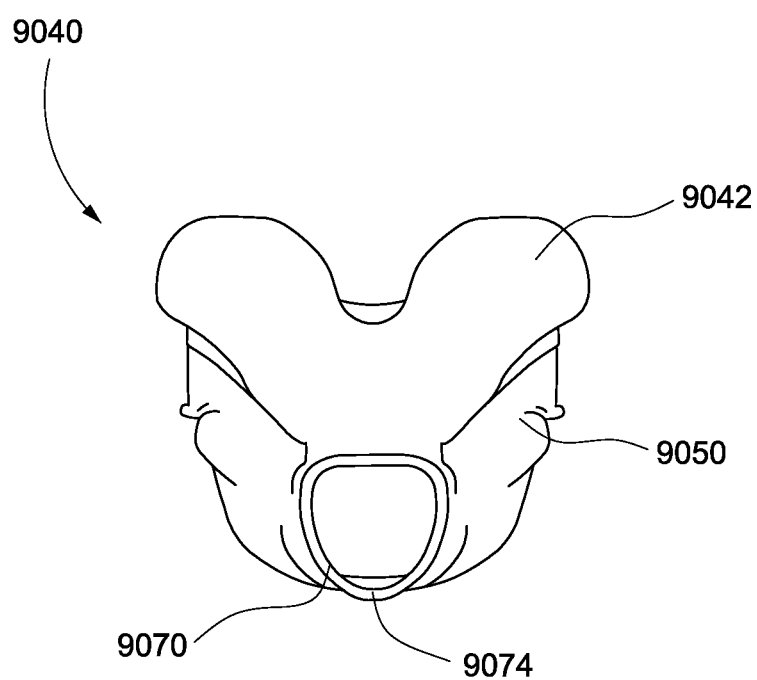
Figure 169:
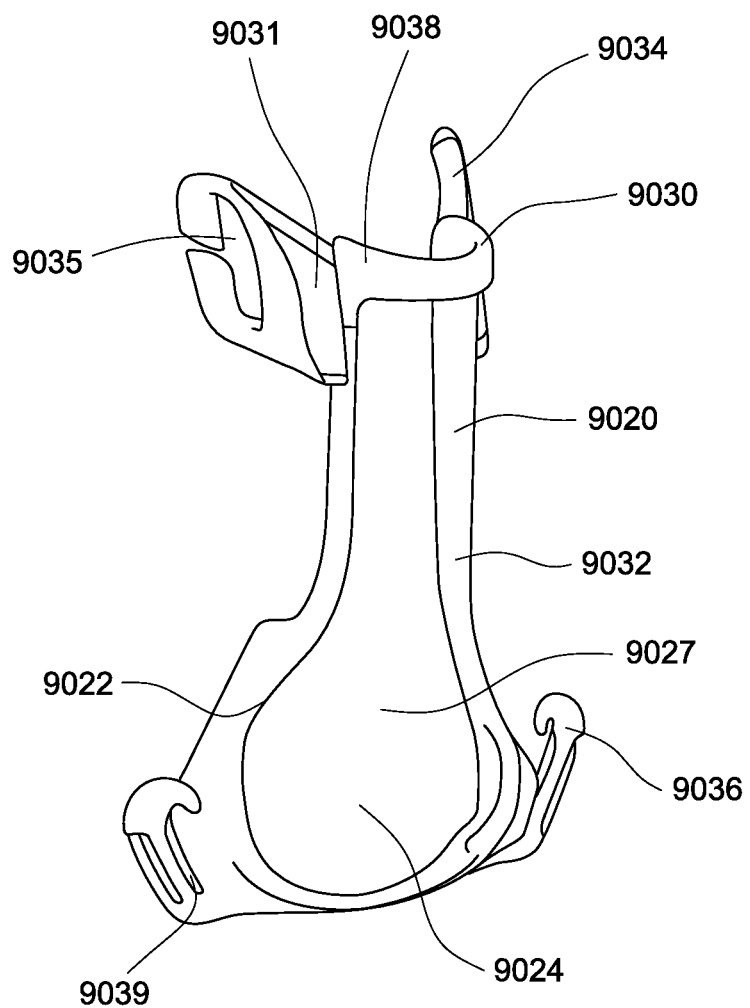
Figure 170:
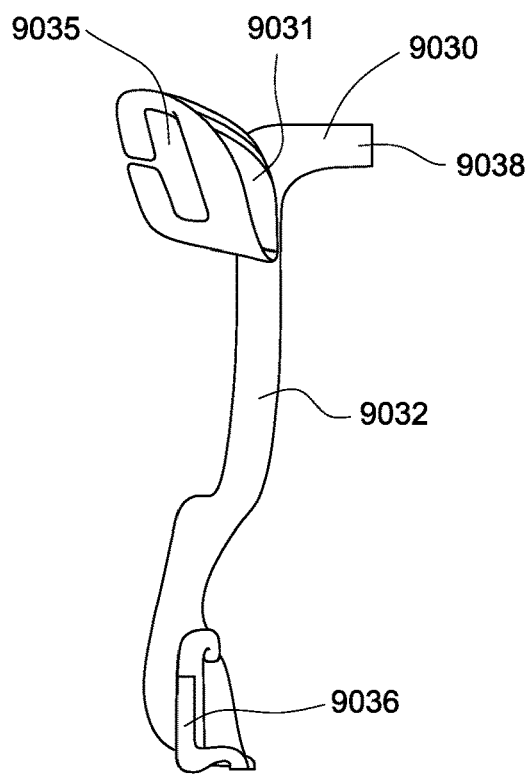
Figure 171:
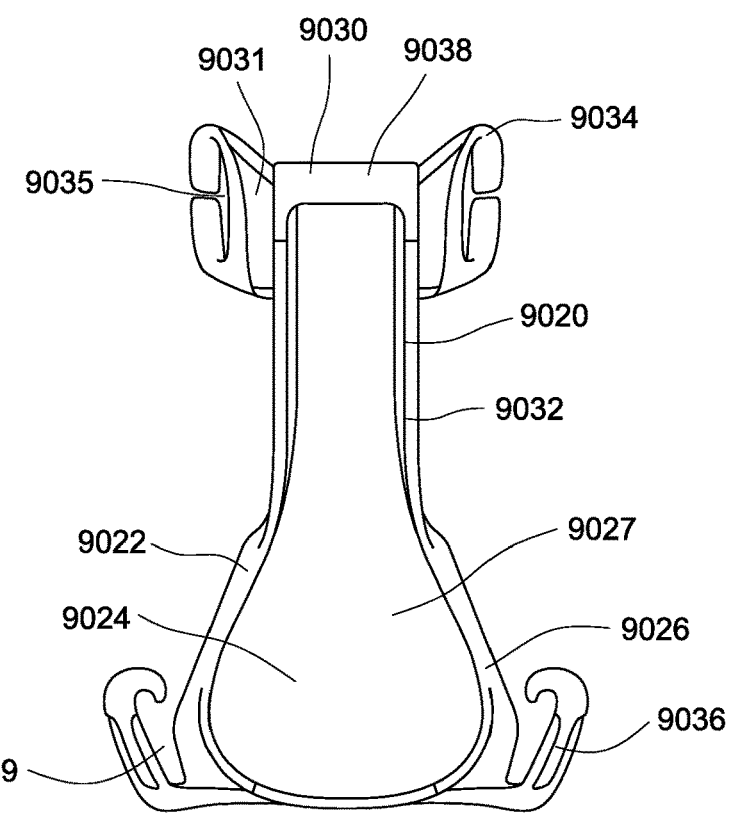
Figure 172:
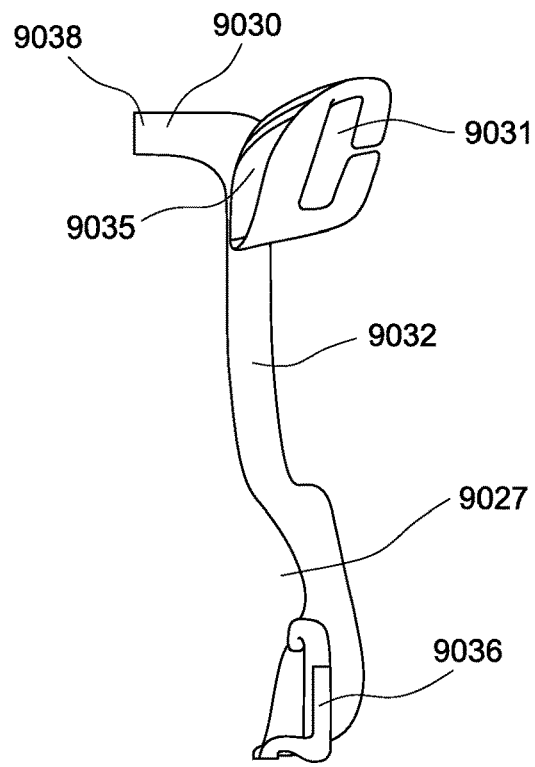
Figure 173:
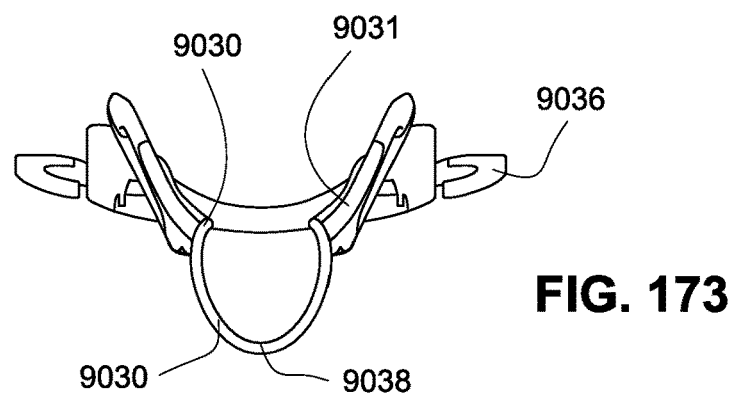
Figure 174:
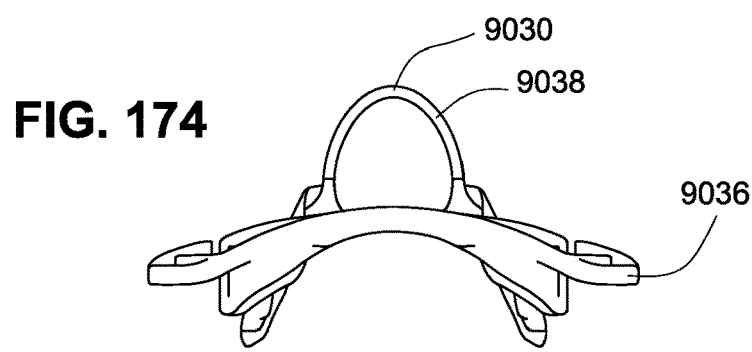
Figures 175, 176:
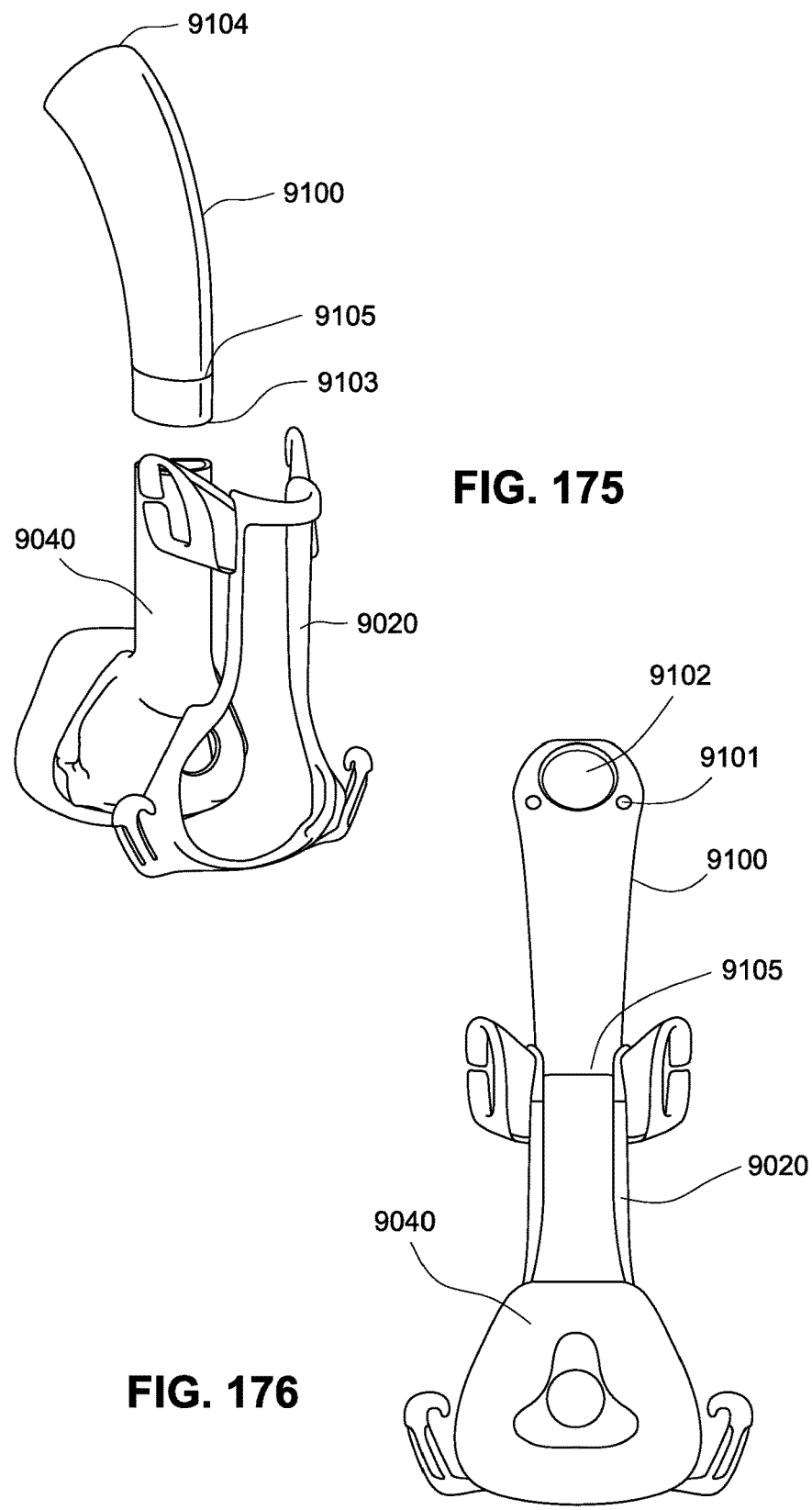
Figure 177:
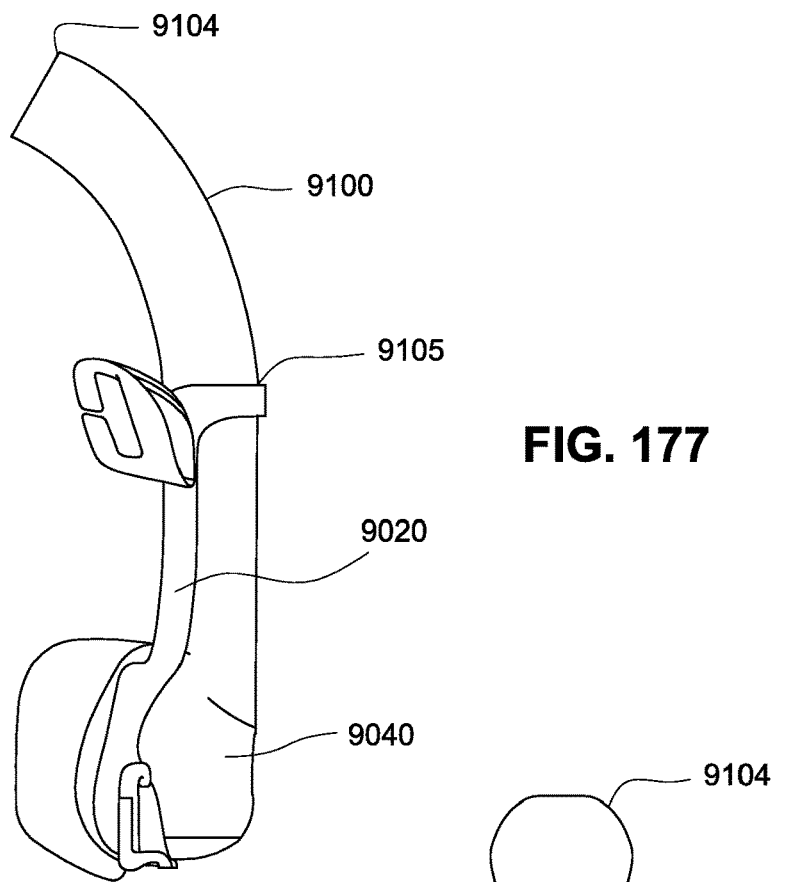
Figure 178:
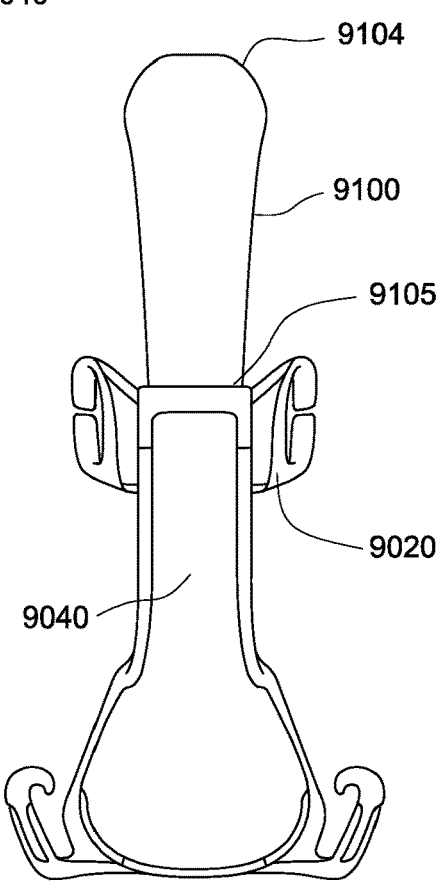
Figure 179:
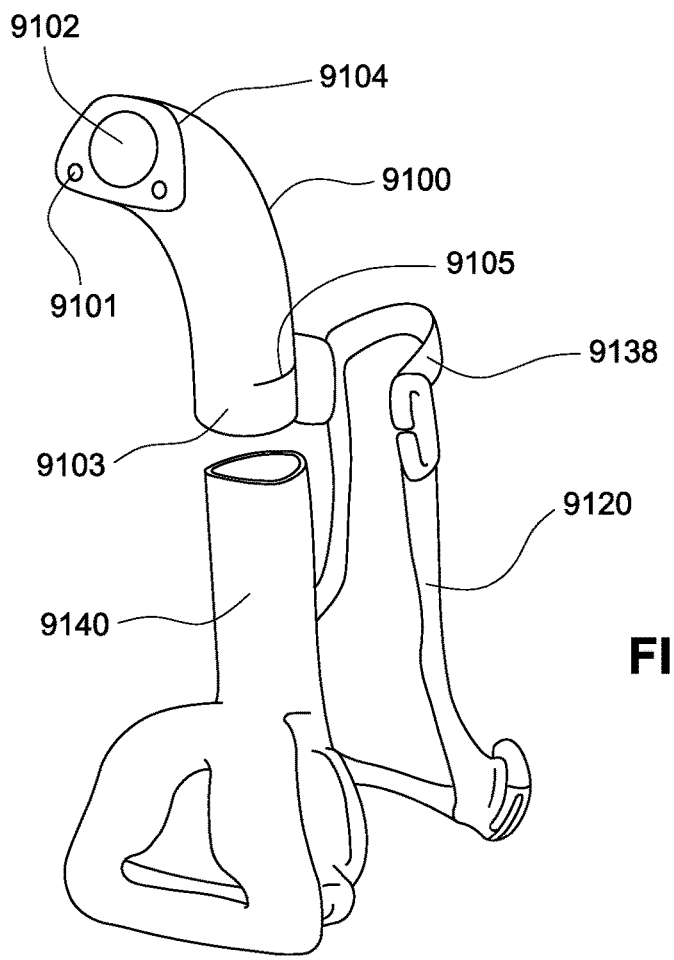
Figure 180:
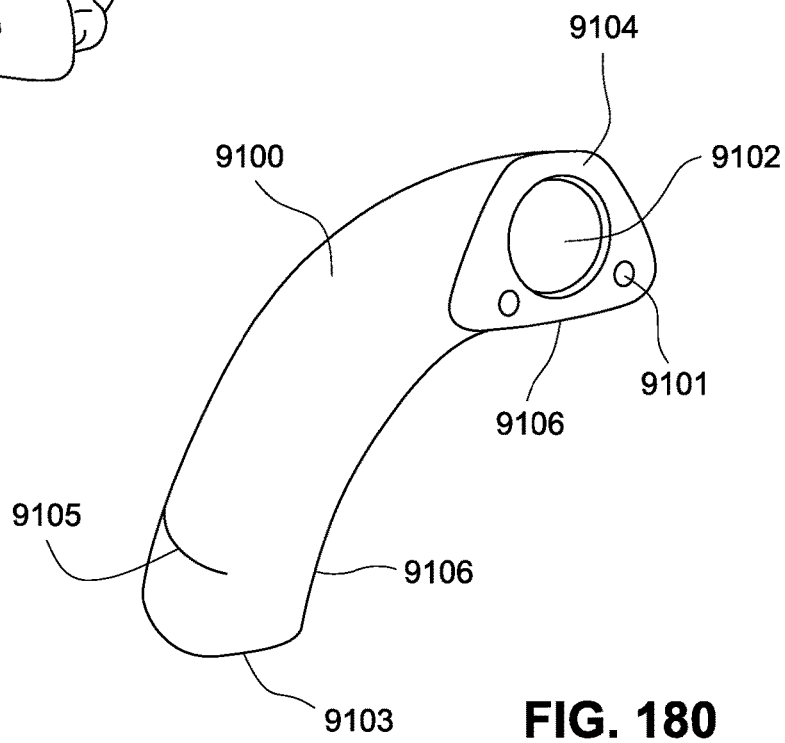
Figure 181:
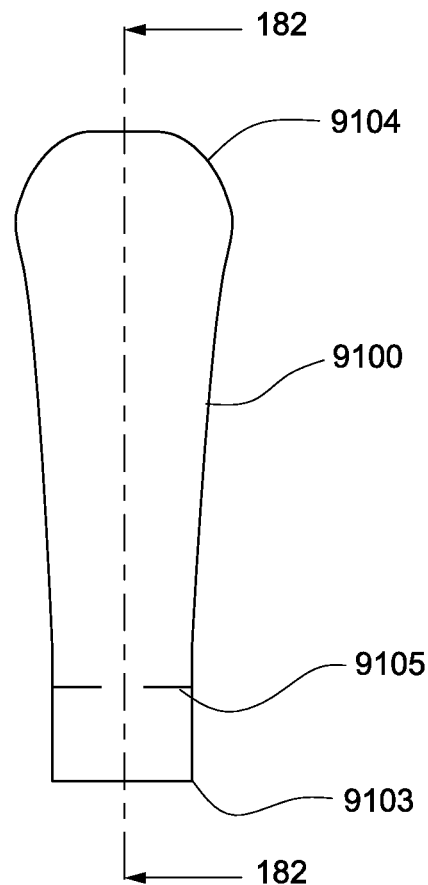
Figure 182:
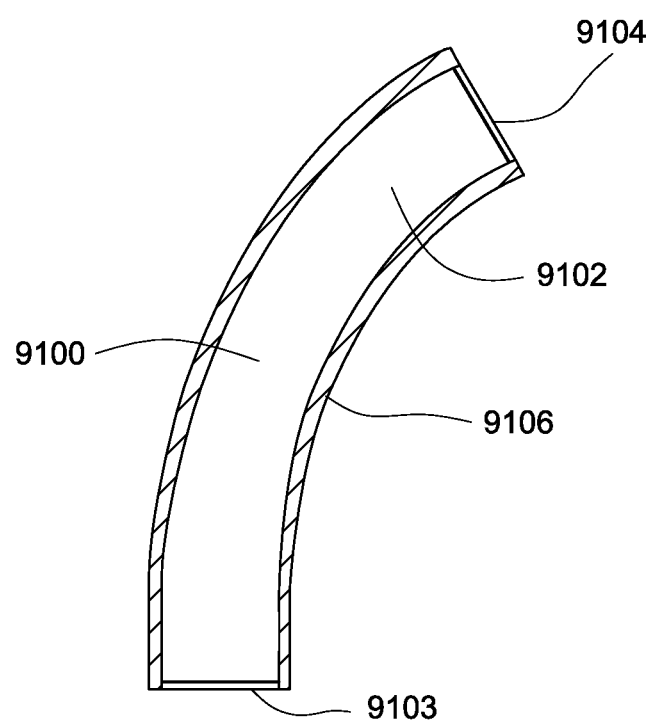
Figure 190:
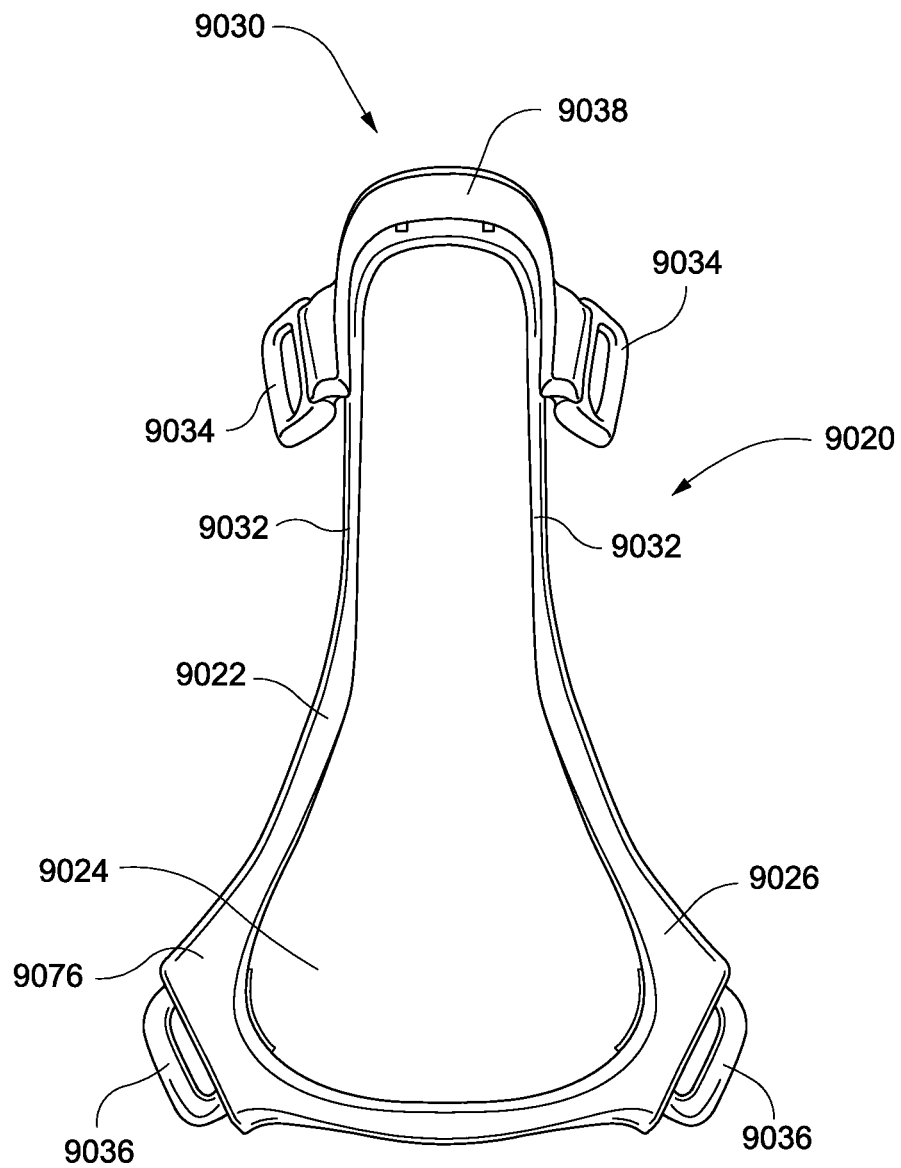
Figure 191:
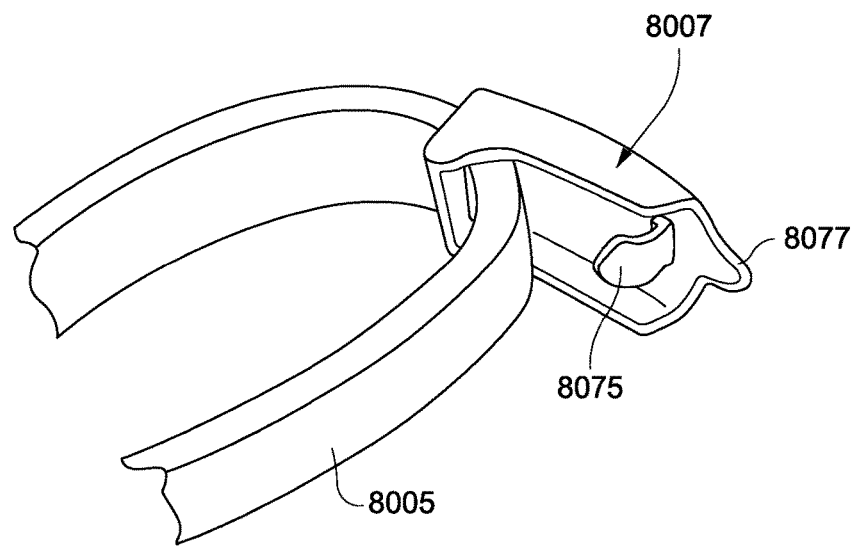
Figure 192:
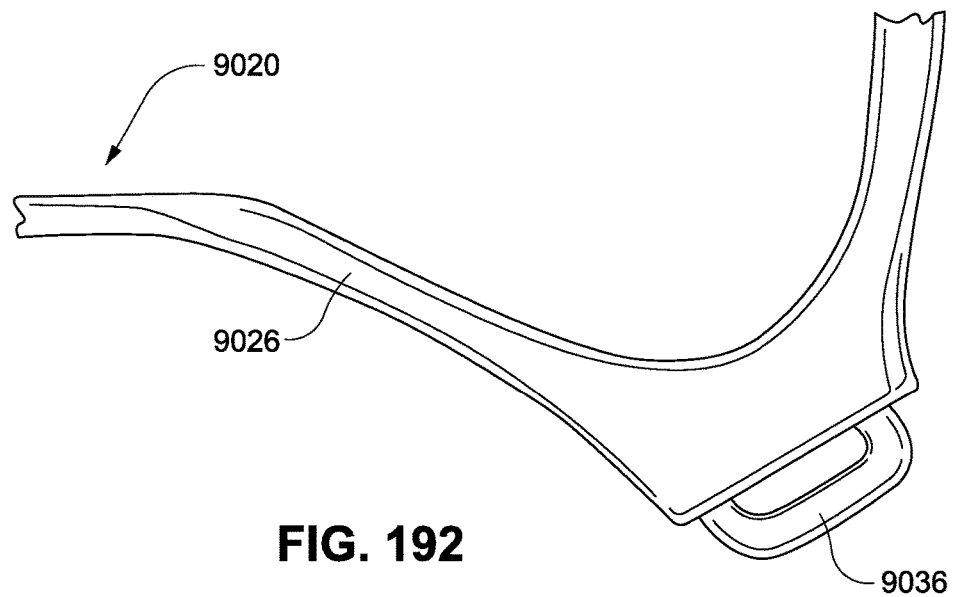
Figure 193B:
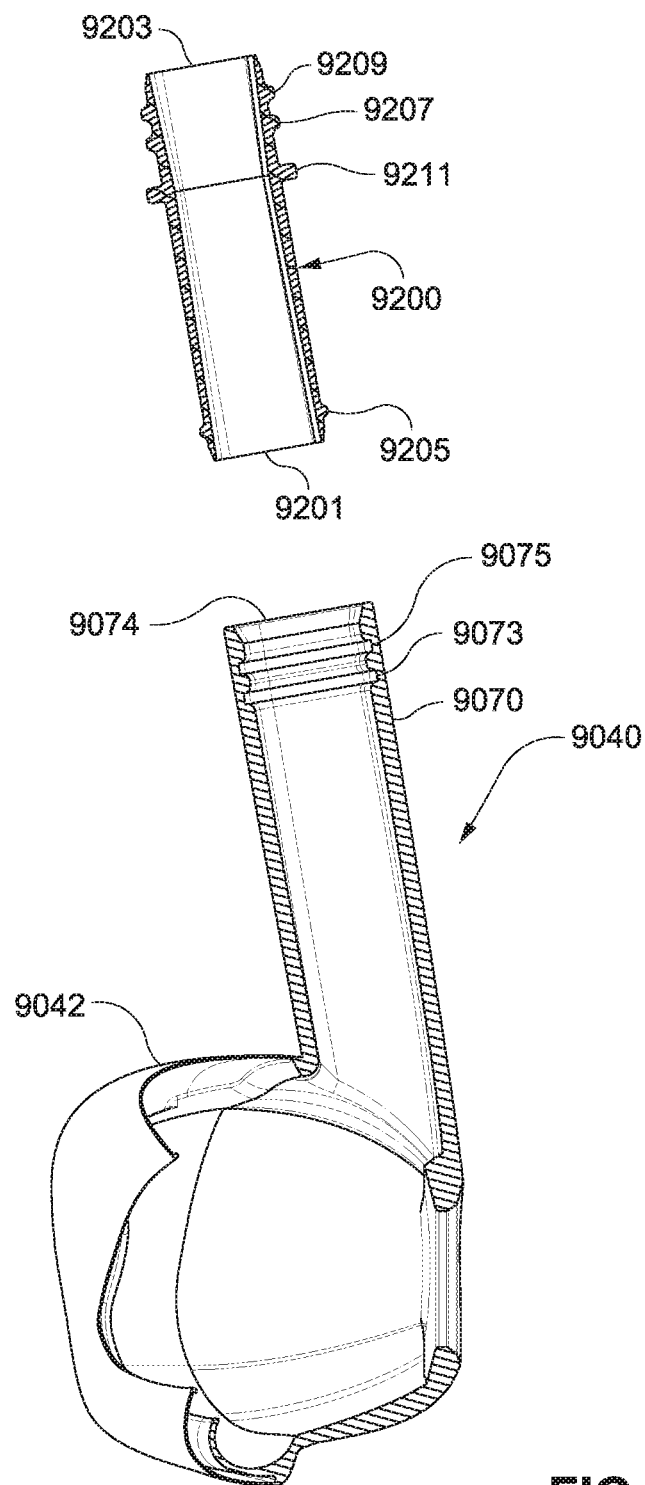
Figure 194A:
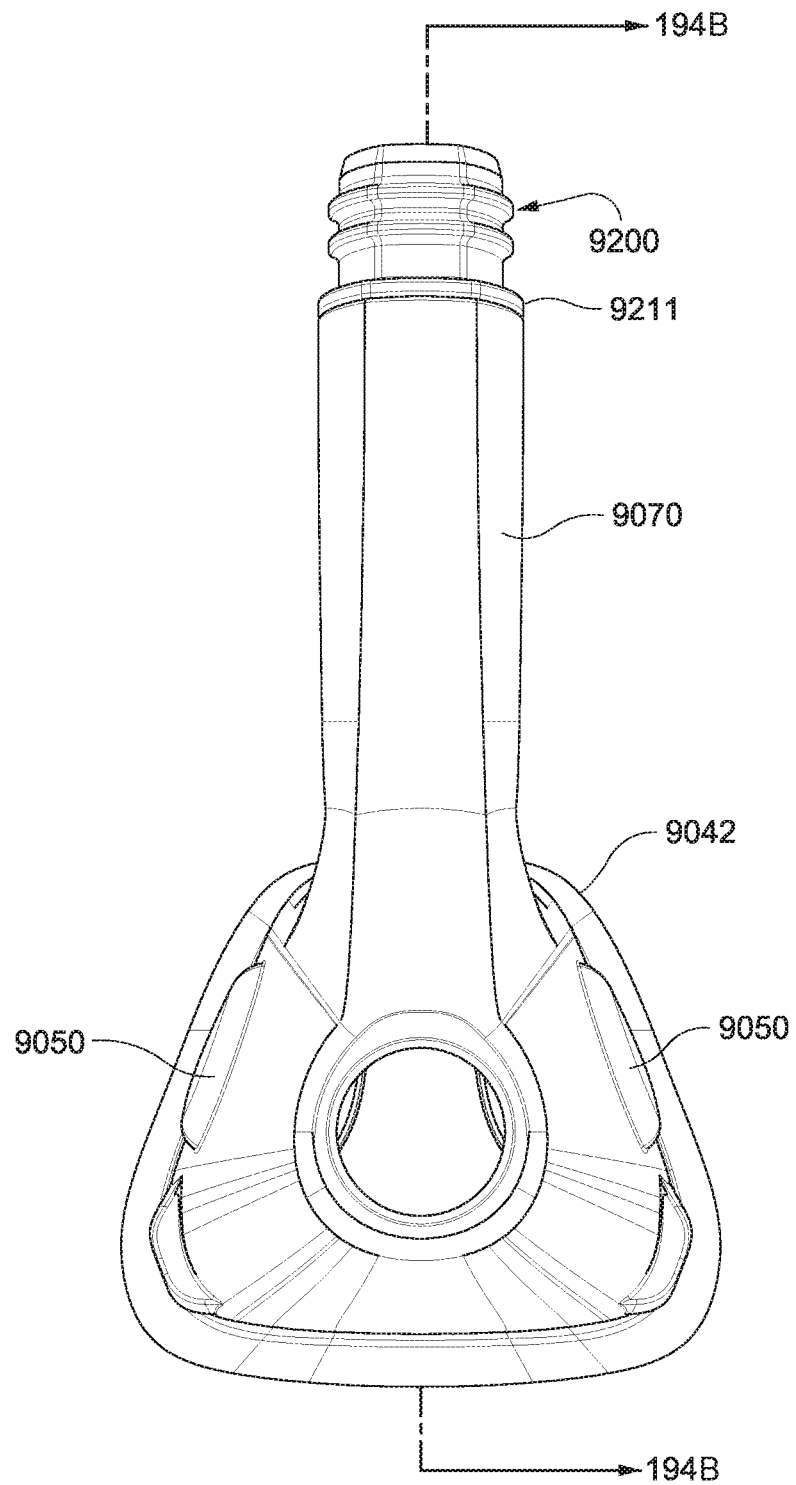
Figure 194B:
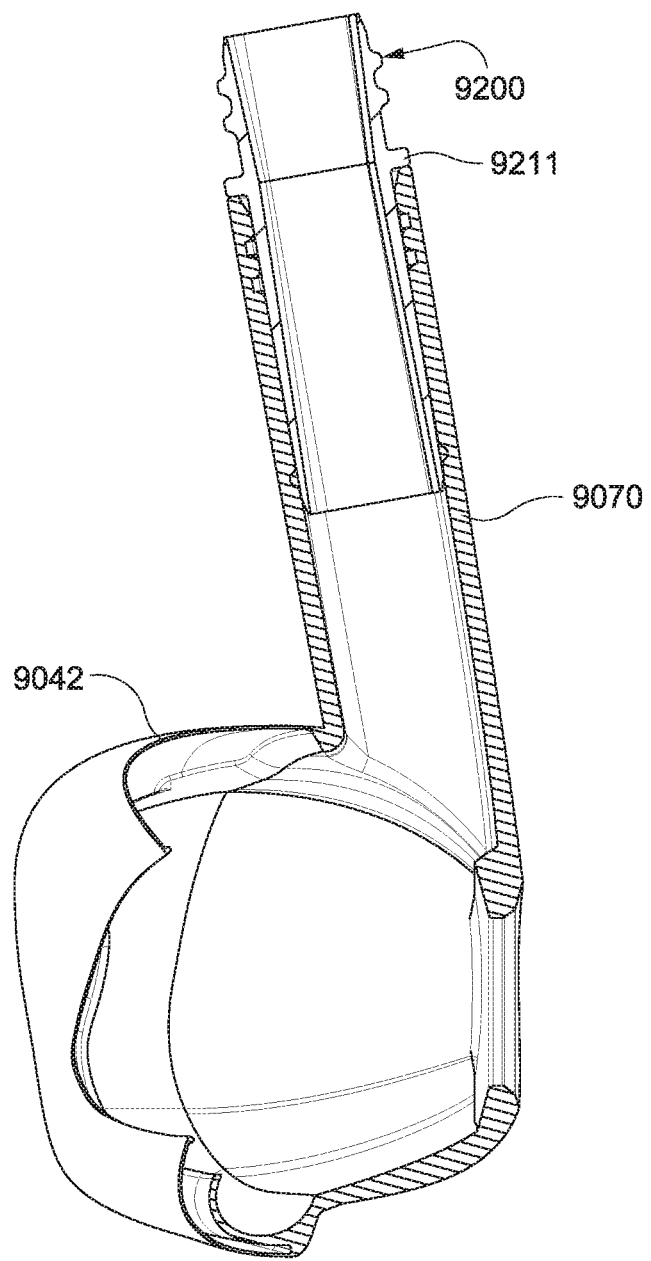
Figure 195A:
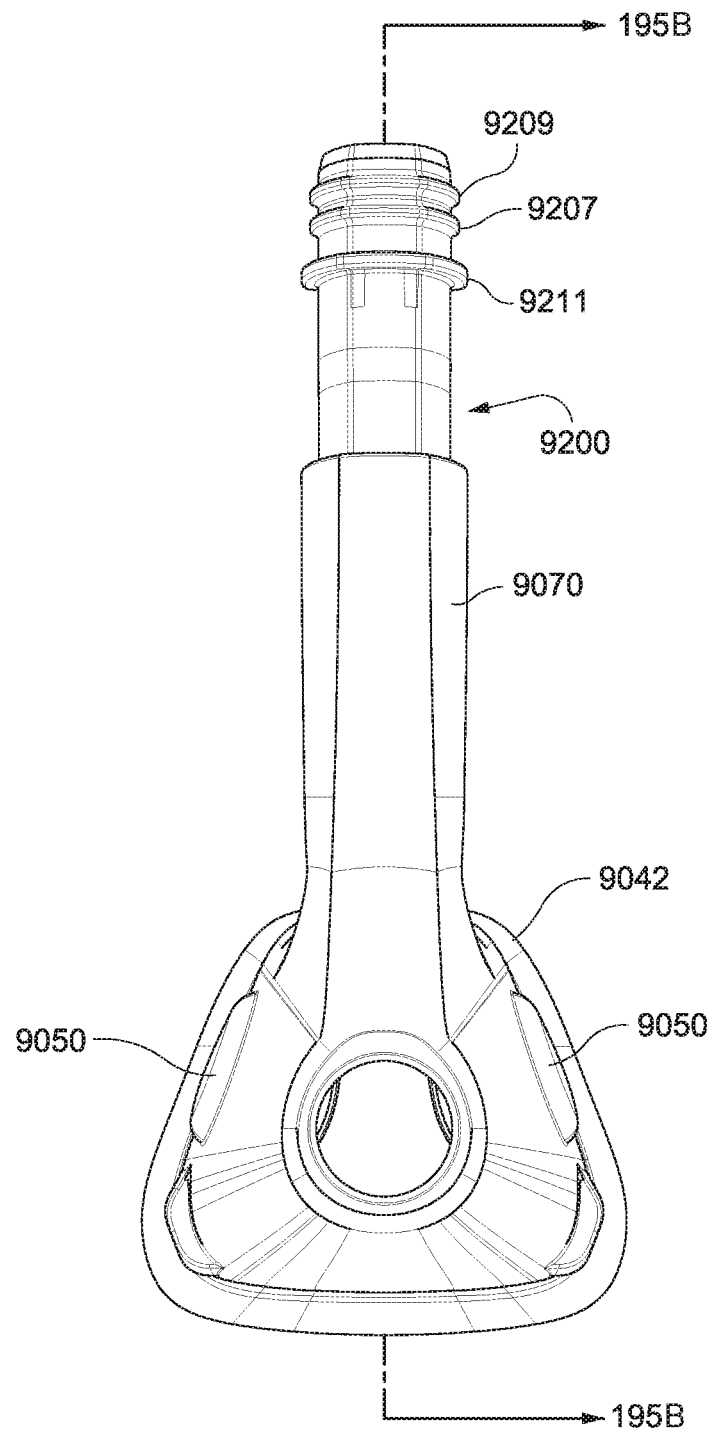
Figure 195B:
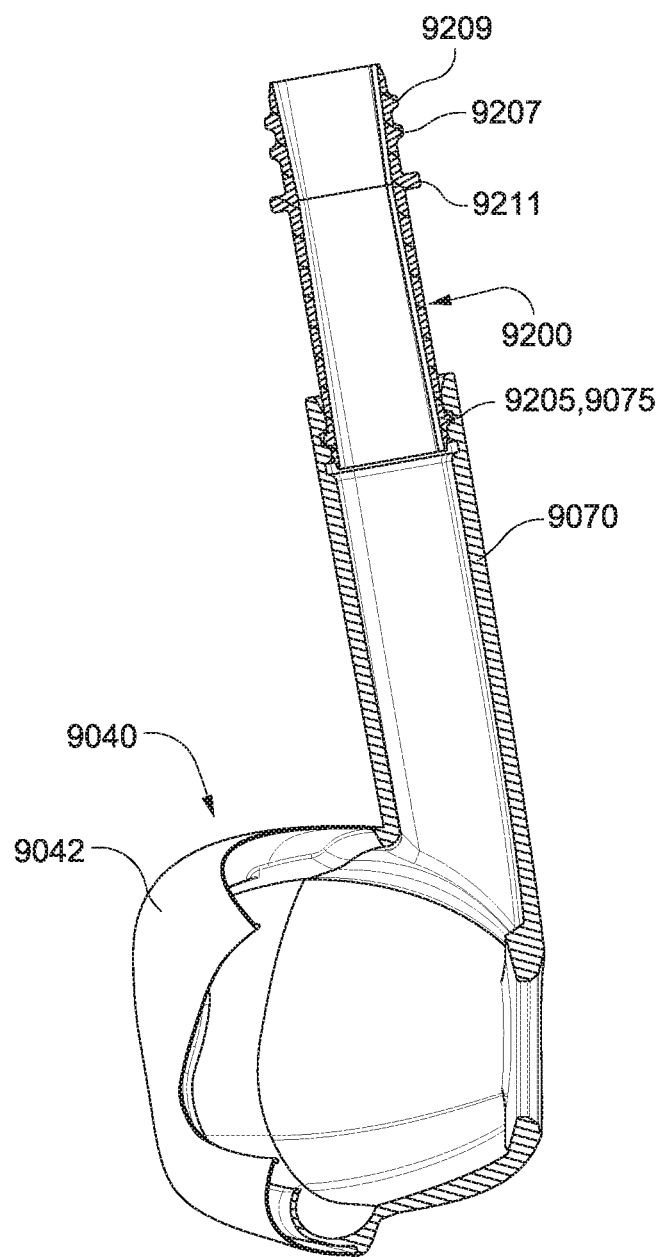
Figure 196A:
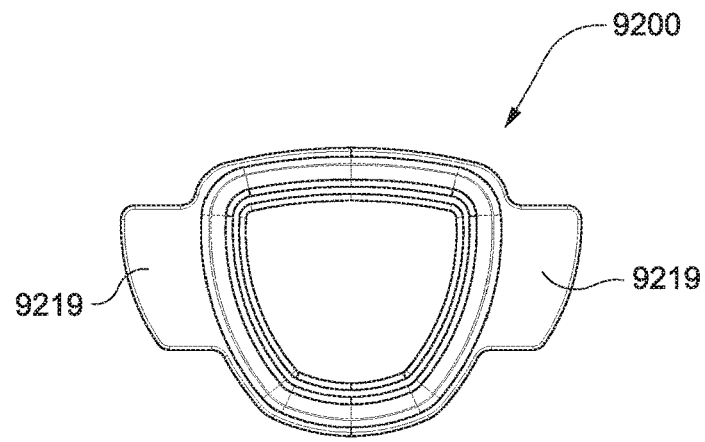
Figure 196B:
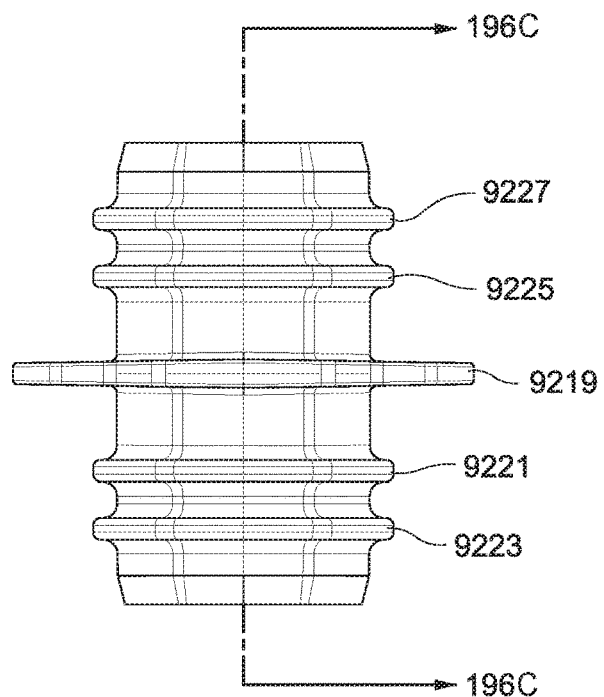
Figure 196C:
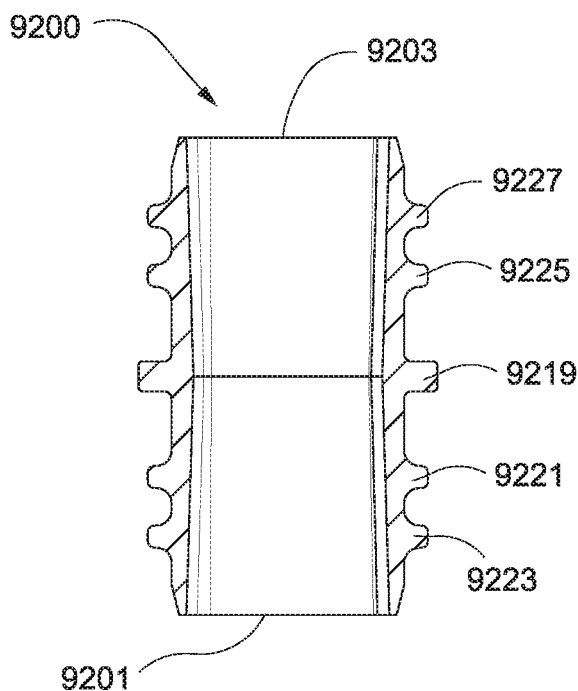
Figure 196D:
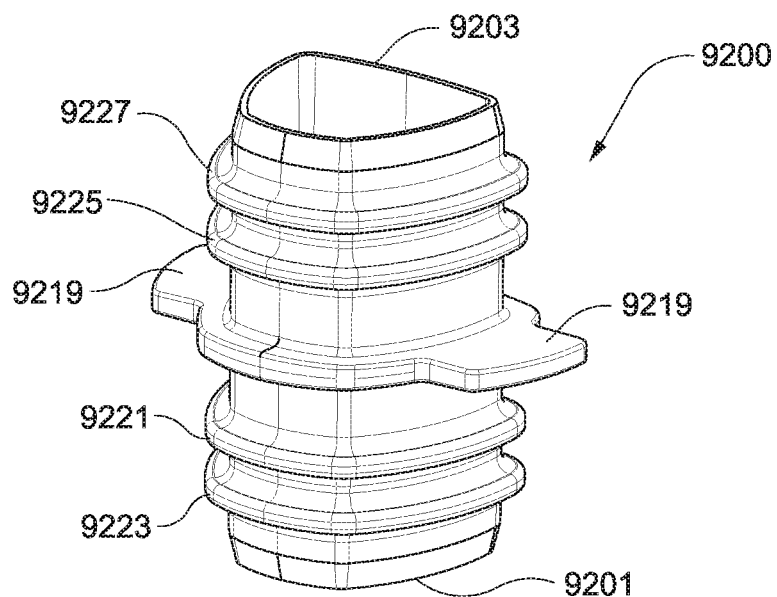
Figure 197A:
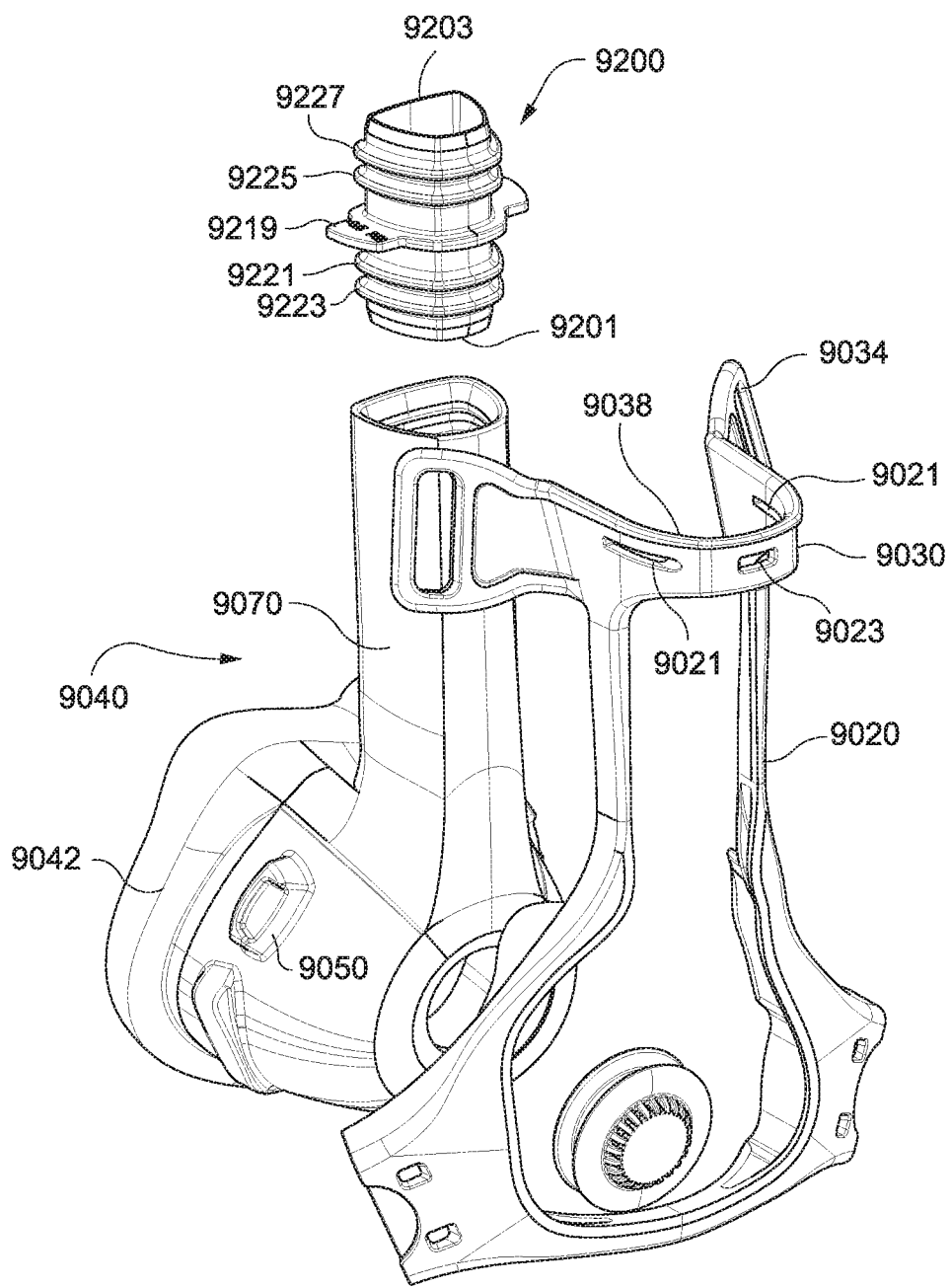
Figure 197B:
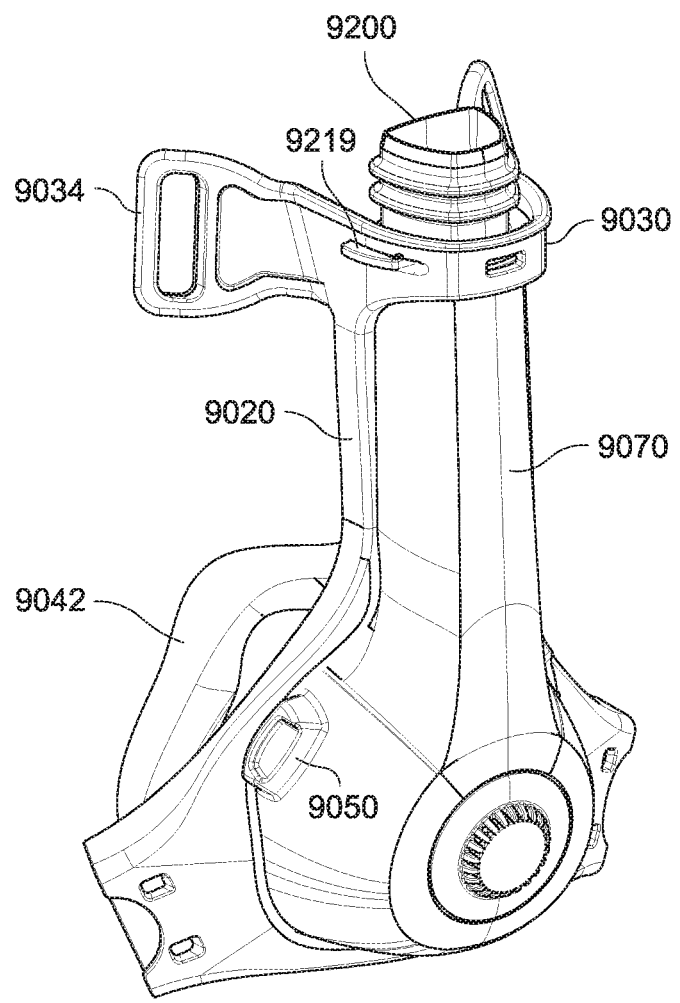
Figure 197C:
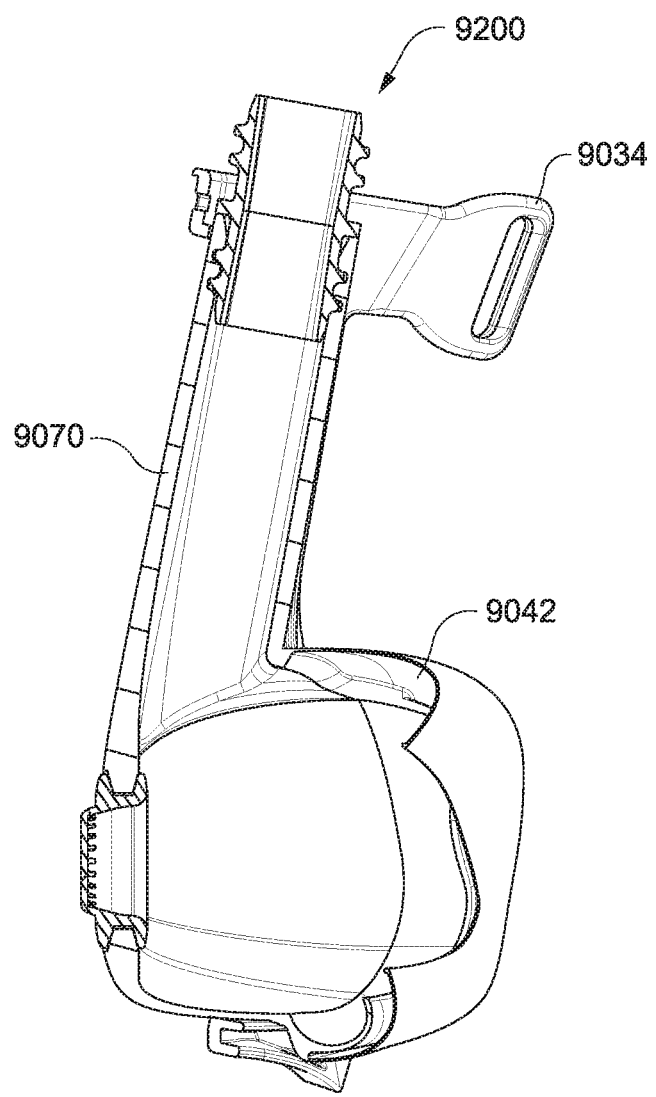
Figure 199C:
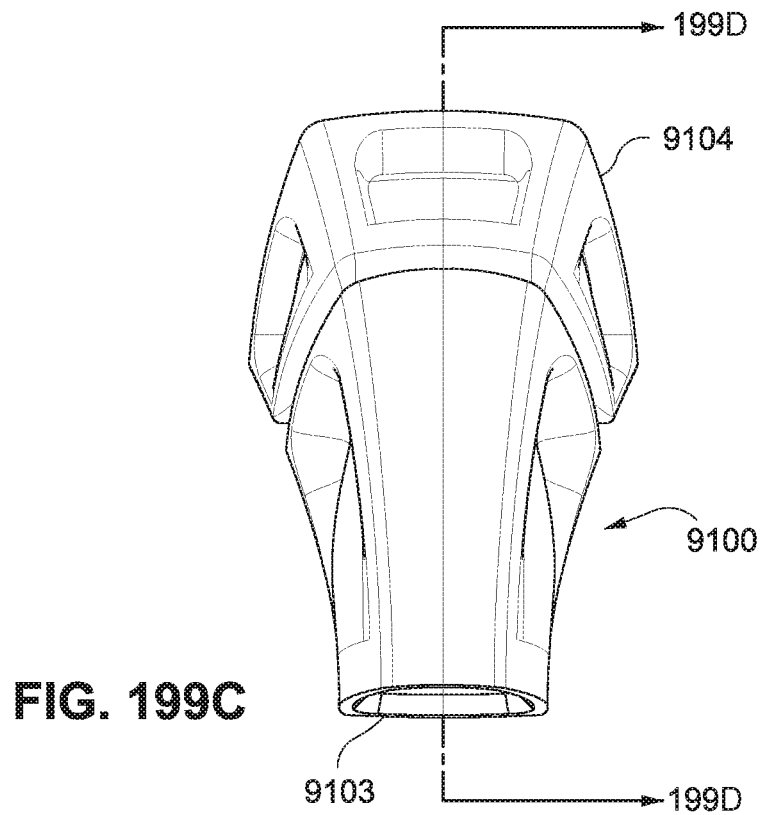
Figure 199D:
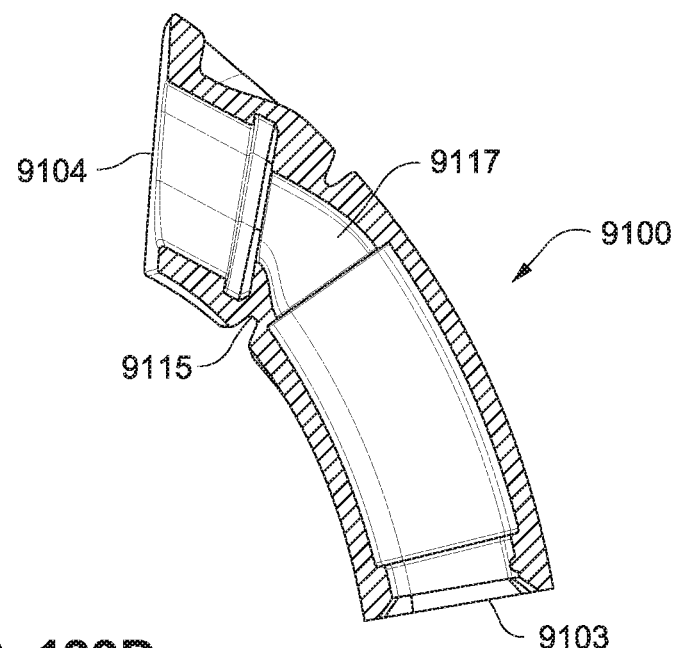
Figure 200A:
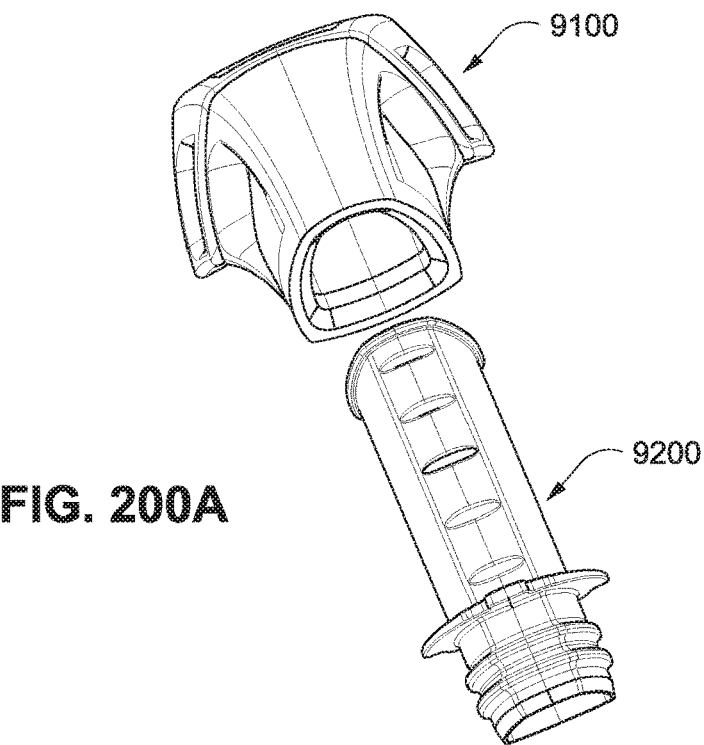
Figure 200B:
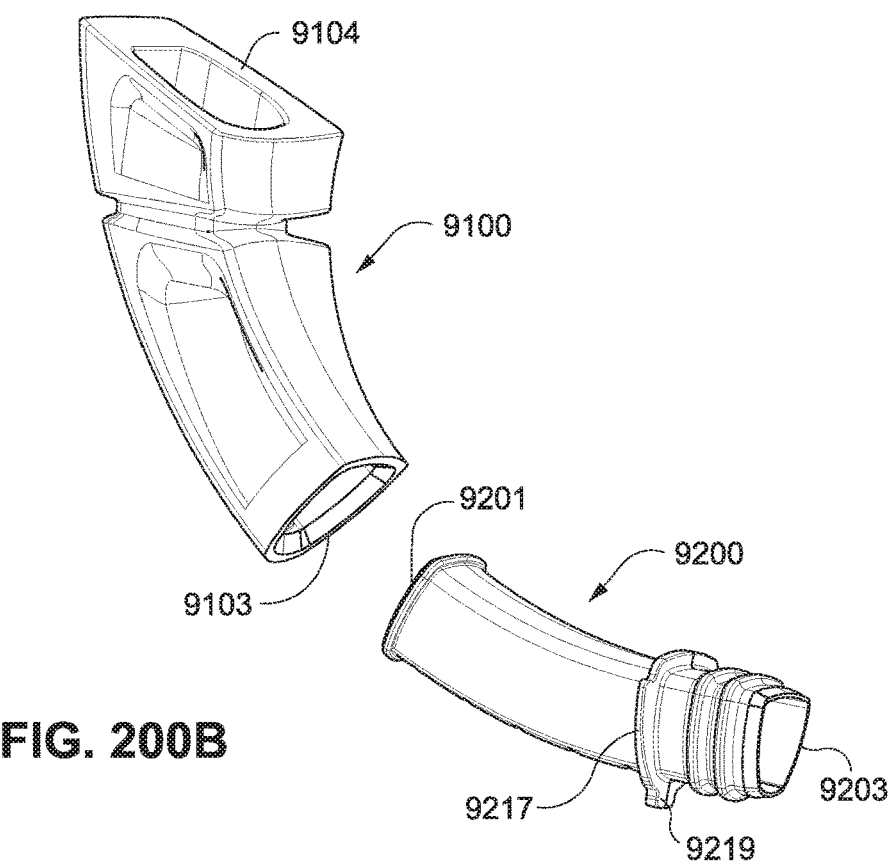
Figures 200C, 200D:
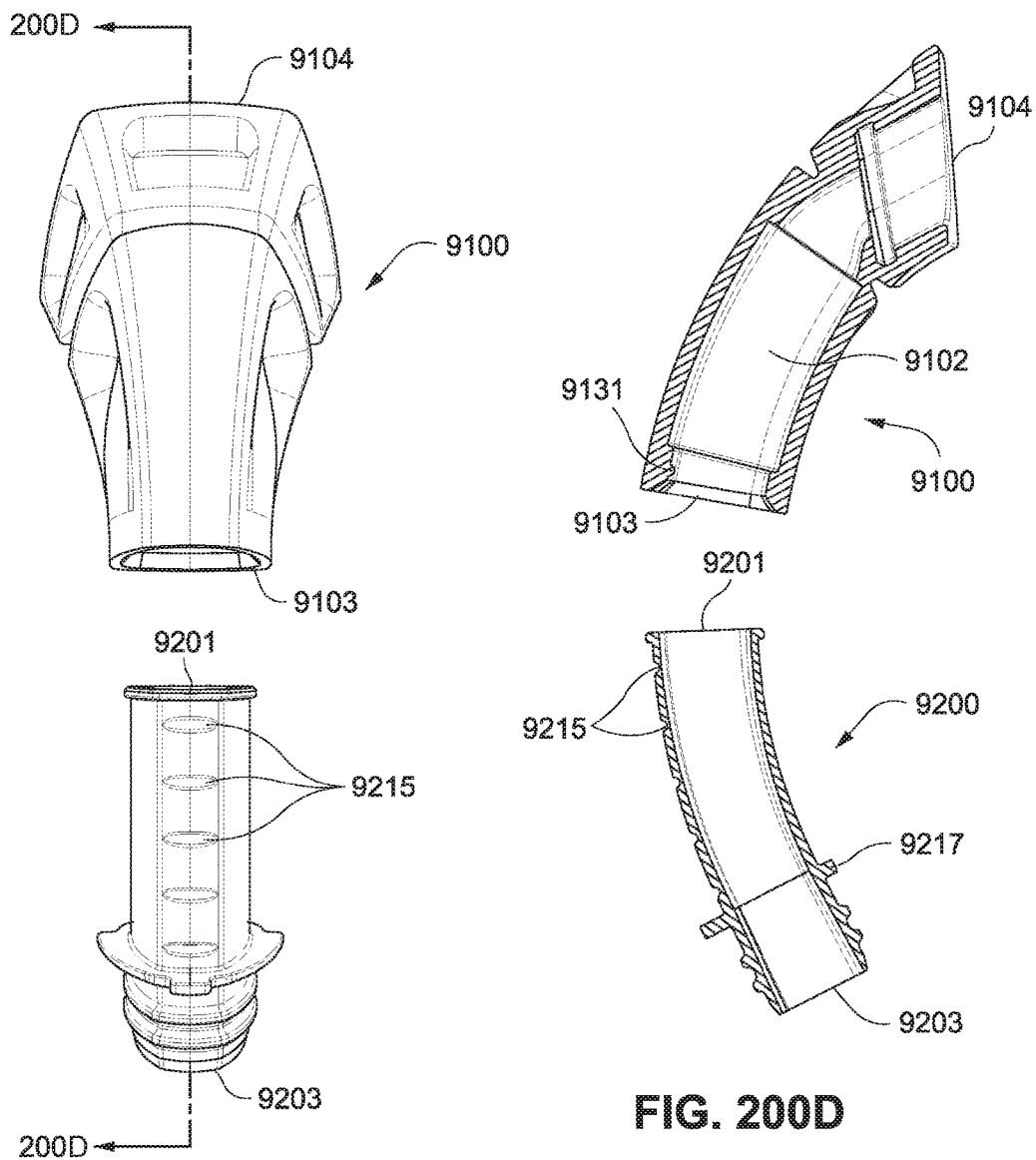
Figure 204A:
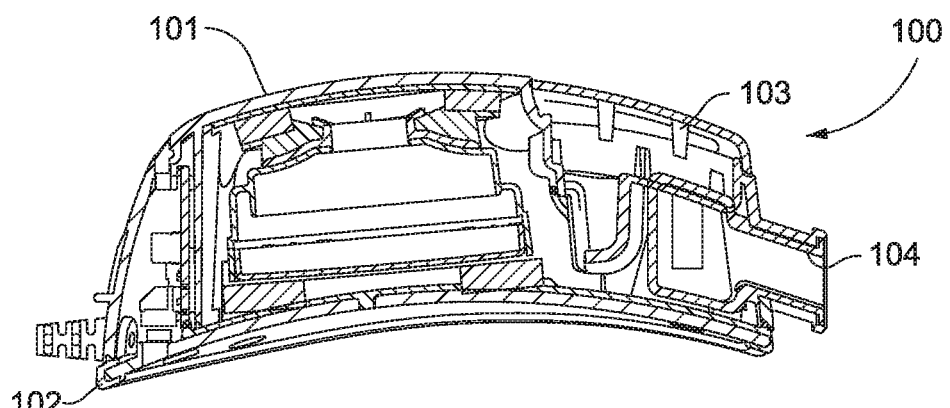
Figure 204B:
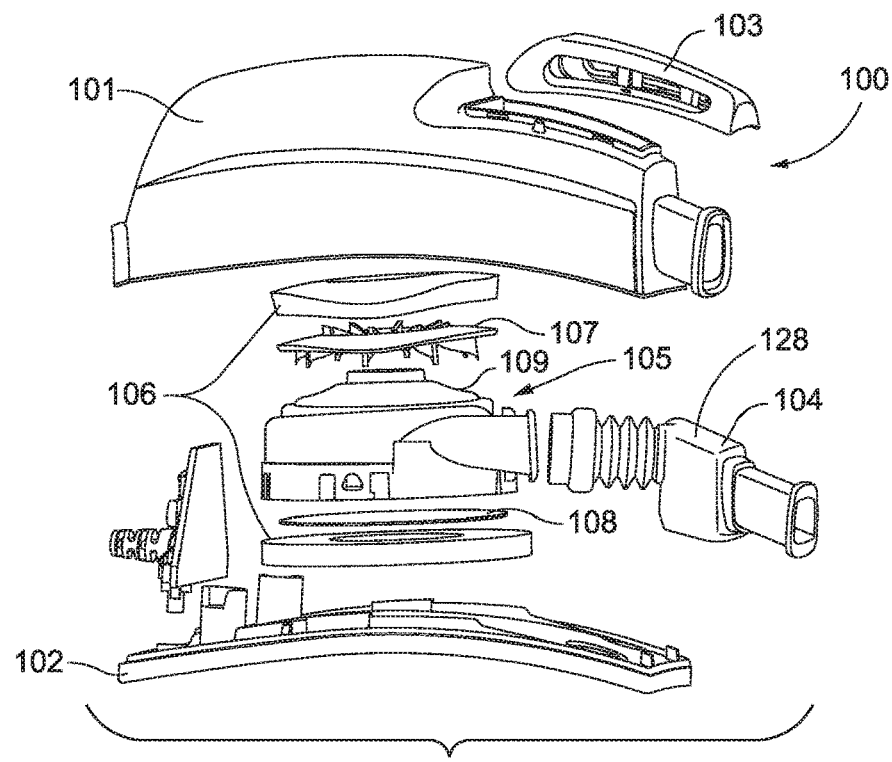
Figure 204C:
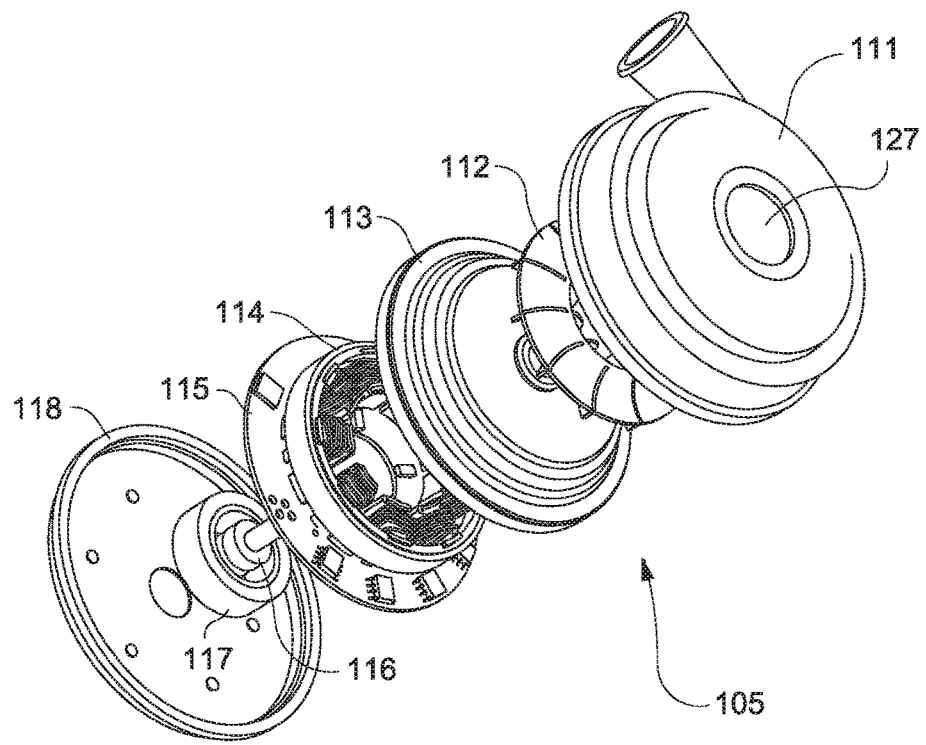
Figure 204D:
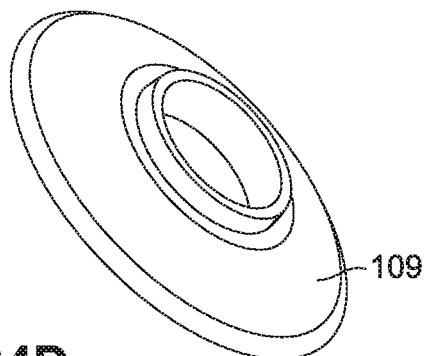
Figure 204E:
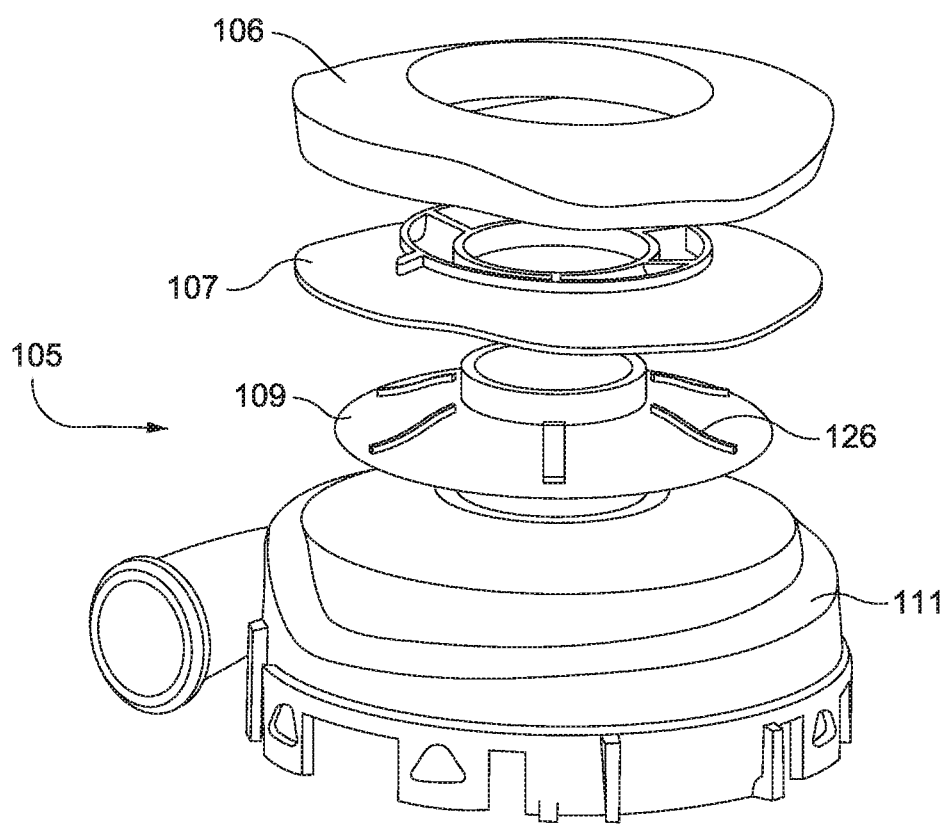
Figure 204F:
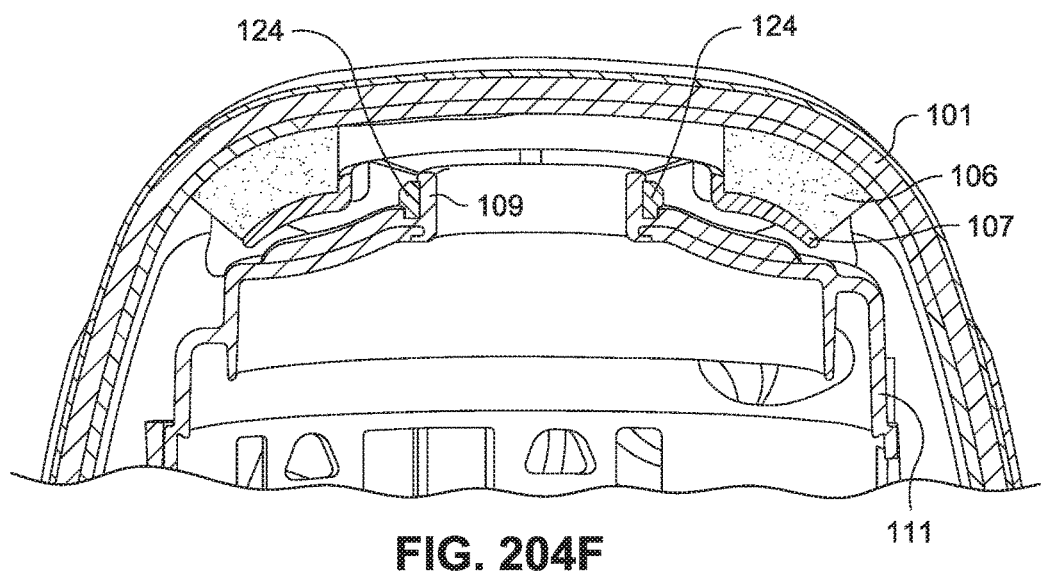
Figure 204G:
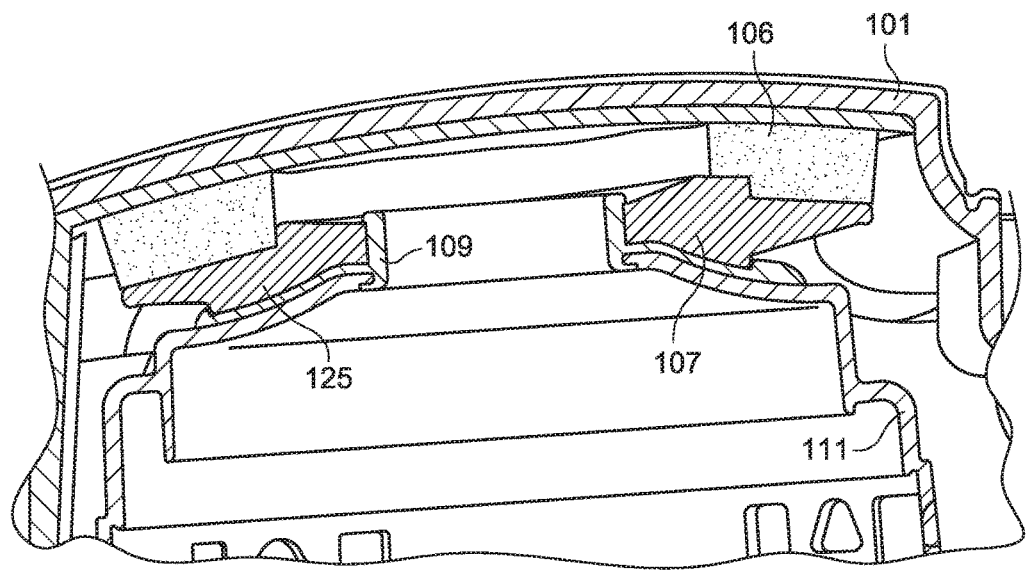
Figure 204H:
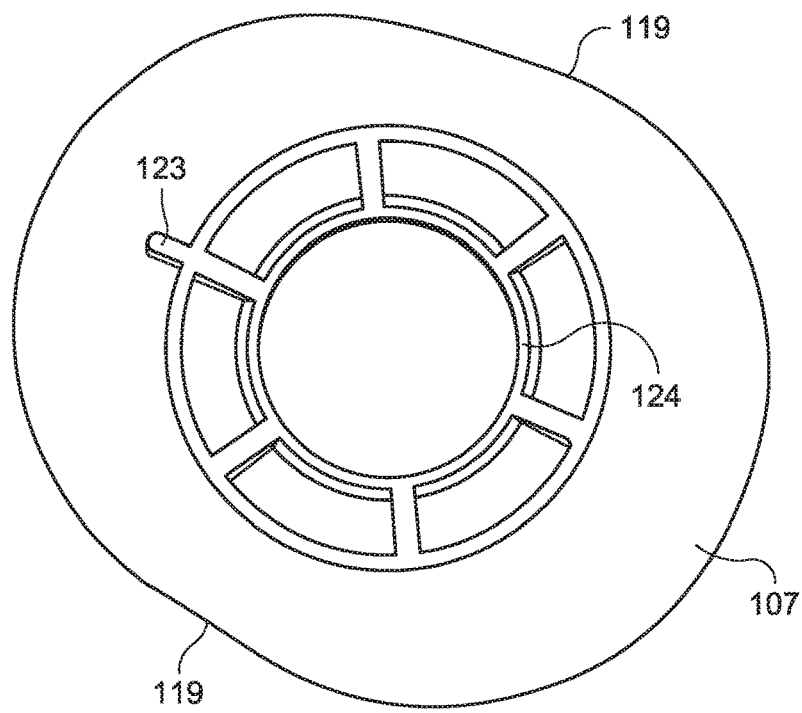
Figure 204I:
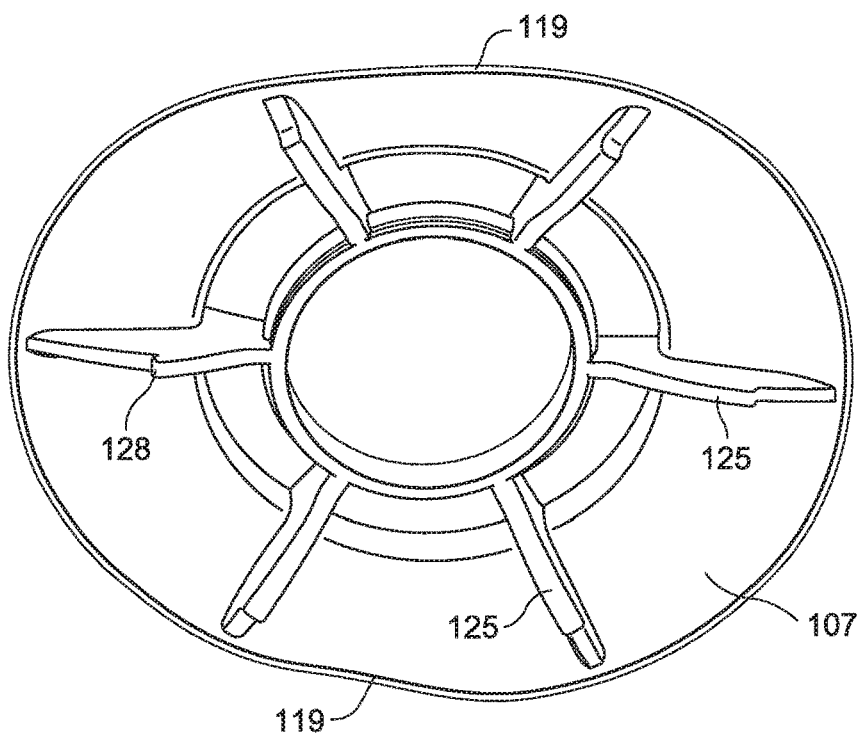
Figure 204J:
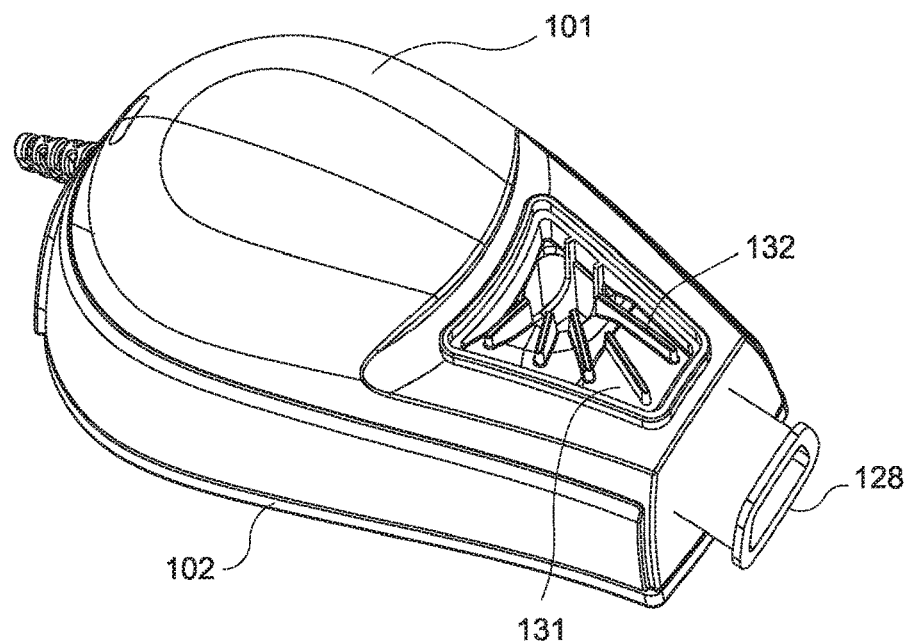
Figure 204K:
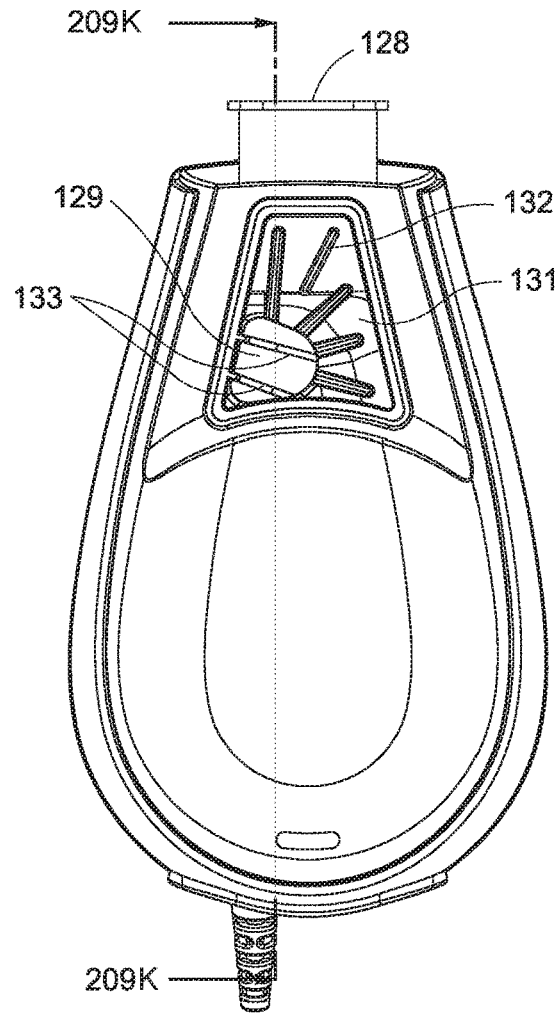
Figure 204L:
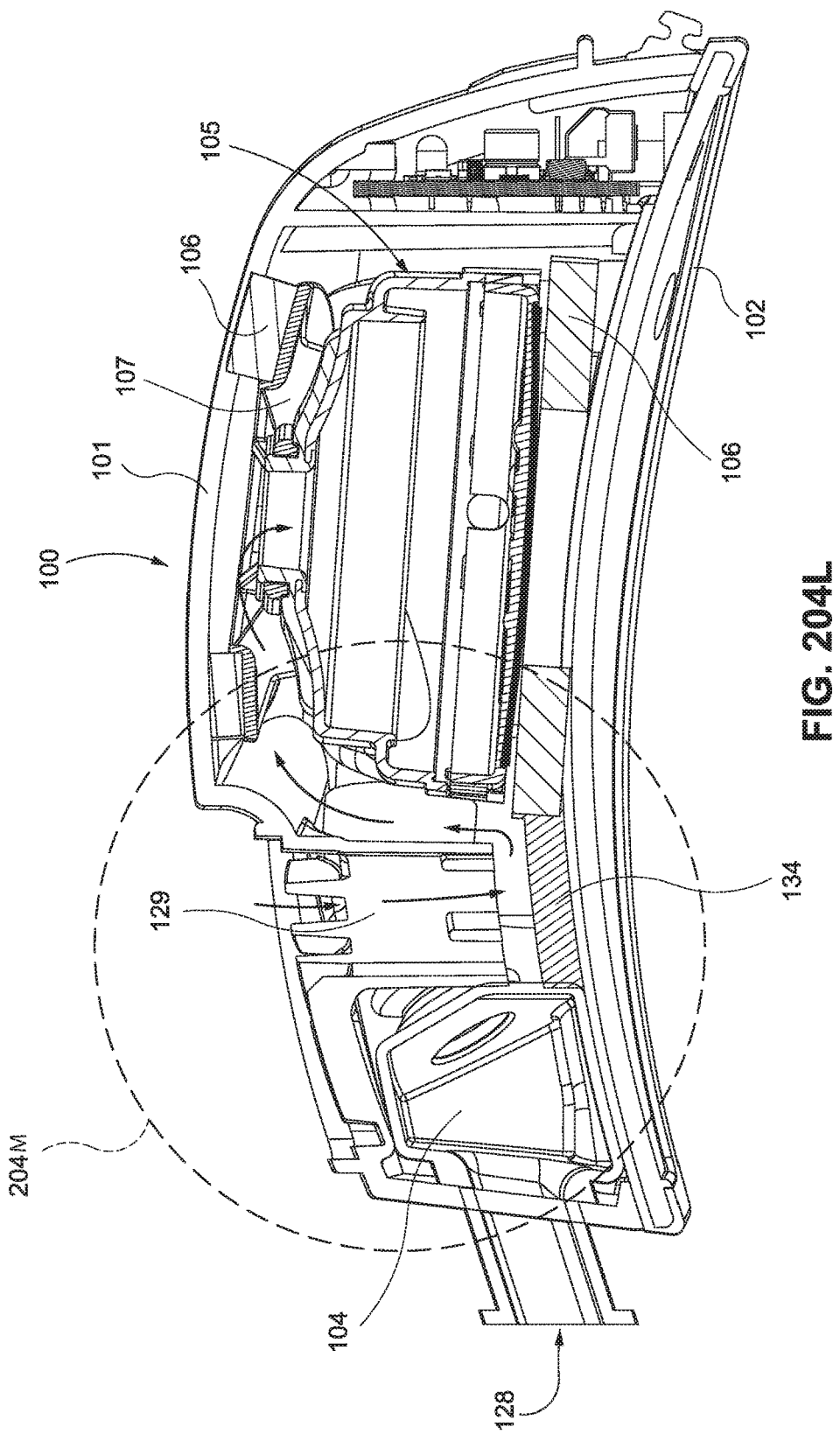
Figure 204M:
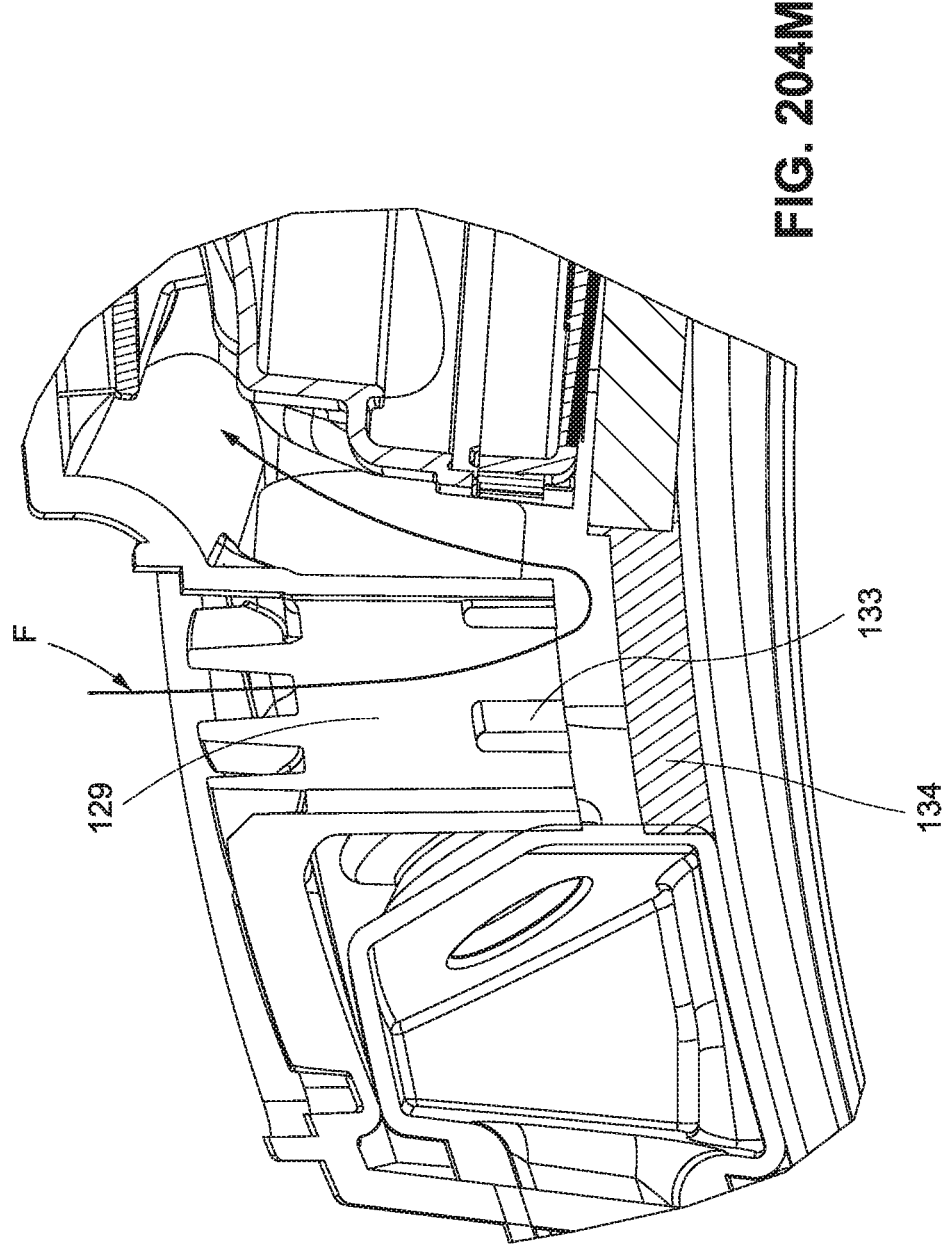
Figure 205A:
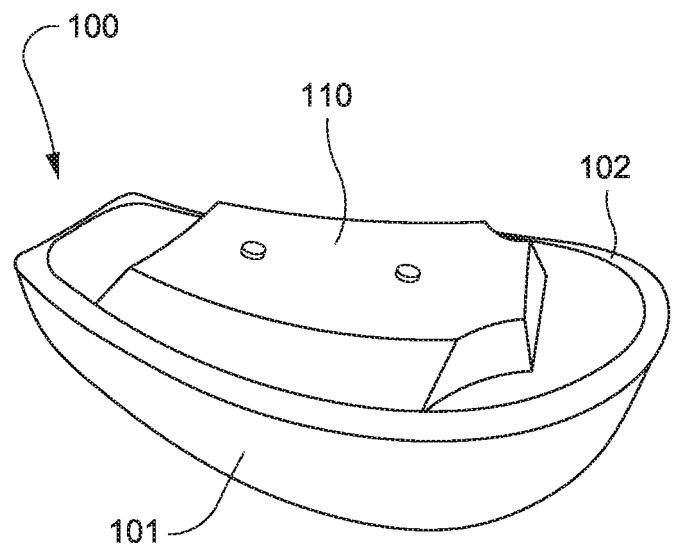
Figure 205B:
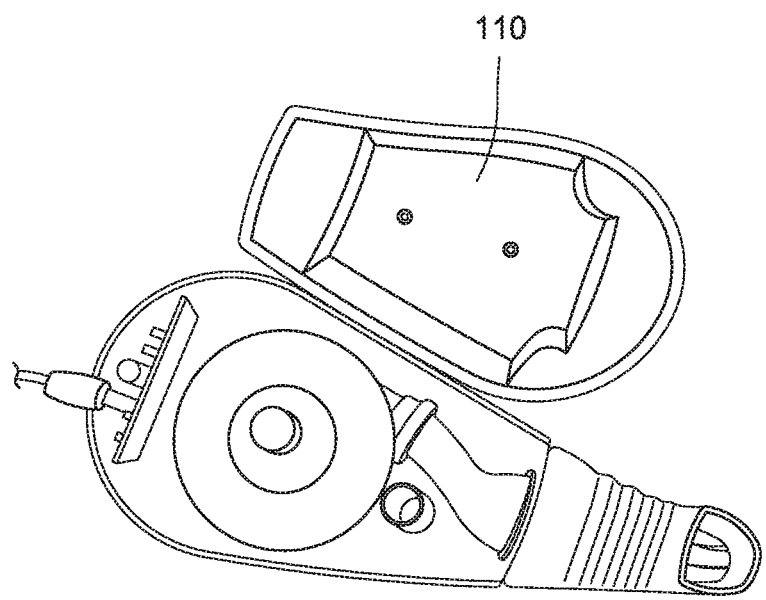

FIG. 168 is a top view of the cushion assembly of FIG. 161;

FIG. 169 is a perspective view of a frame of a patient interface according to certain embodiments;

FIG. 170 is a side view of the frame of FIG. 169;

FIG. 171 is a front view of the frame of FIG. 169;

FIG. 172 is a side view of the frame of FIG. 169;

FIG. 173 is a front view of the frame of FIG. 169;

FIG. 174 is a bottom view of the frame of FIG. 169;

FIG. 175 is an exploded front perspective view of a patient interface, or mask, system according to certain embodiments;

FIG. 176 is a back assembly view of FIG. 175;

FIG. 177 is a side assembly view of FIG. 175;

FIG. 178 is a front assembly view of FIG. 175;

FIG. 179 is an exploded back perspective view of FIG. 175;

FIG. 180 is a perspective view of tubing to adapted to connect to the cushion assembly of FIG. 161;

FIG. 181 is a front view of the tubing shown in FIG. 180;

FIG. 182 is a cross sectional view of FIG. 181;

FIGS. 183-188 show a PAP system according to certain embodiments;

FIGS. 189A to 189H show a flexible short outlet tube according to certain embodiments;

FIGS. 190-192 show a patient interface frame and headgear strap connector connectable to the frame according to certain embodiments;

FIGS. 193A and 193B show an exploded view of a sealing arrangement, including a cushion, and a connector tube according to certain embodiments;

FIGS. 194A and 194B show the sealing arrangement and connector tube of FIGS. 193A and 193B in a connected state;

FIGS. 195A and 195B show the sealing arrangement and connector tube of FIGS. 194A and 194B in an extended state;

FIGS. 196A to 196D show a connector tube according to certain embodiments;

FIGS. 197A to 197C show a headworn PAP system according to certain embodiments;

FIGS. 198A to 198D show a connector tube according to certain embodiments;

FIGS. 199A to 199D show a short outlet tube according to certain embodiments;

FIGS. 200A to 200D show exploded views of the connector tube of FIGS. 198A to 198D and the short outlet tube of FIGS. 199A to 199D;

FIGS. 201A to 201D show the connector tube and short outlet tube of FIGS. 200A to 200D in a connected, extended state;

FIGS. 202A to 202D show the connector tube and short outlet tube of FIGS. 200A to 200D in a connected, unextended state;

FIGS. 203A to 203E show a short outlet tube according to certain embodiments;

FIGS. 204A to 204M show a PAP device, or flow generator assembly, according to certain embodiments; and FIGS. 205A and 205B show a PAP device, or flow generator assembly, according to certain embodiments.

DETAILED DESCRIPTION

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The subject headings used in the detailed description are included only for the ease of reference of the reader and should not be used to limit the subject matter found throughout the disclosure or the claims. The subject headings should not be used in construing the scope of the claims or the claim limitations.

1. PAP System

A PAP system (e.g., CPAP system) typically includes a PAP device (including a blower for generating air at positive pressure), an air delivery conduit (also referred to as a tube or tubing), and a patient interface. In use, the PAP device generates a supply of pressurized air (e.g. 2-30 cm H2O) that is delivered to the patient interface via the air delivery conduit. The patient interface or mask may have suitable configurations as is known in the art, e.g., full-face mask, nasal mask, oro-nasal mask, mouth mask, nasal prongs, etc. Also, headgear may be utilized to comfortably support the patient interface in a desired position on the patient's face.

Certain embodiments relate to PAP systems in which the PAP device or blower is adapted to be worn on the patient's head, is built into or incorporated into the patient interface or mask, is wearable or carried by the patient, is portable, is reduced in size or combinations thereof. In certain embodiments, the blower may be of the types described in International Application PCT/AU2010/001031, filed Aug. 11, 2010, entitled "Single Stage, Axial Symmetric Blower and Portable Ventilator," which is incorporated herein by reference in its entirety.

1.1 Certain Embodiments of Headworn PAP Systems

Certain embodiments relate to PAP systems that may be entirely headworn. In certain embodiments, the blower may be mounted on the patient's head (e.g., on the crown of the patient's head or on the front portion of a patient's head).

In certain embodiments, the elbow and external tubing may be removed as the tubing may run through, or substantially through, the headgear.

In certain embodiments, the blower may be mounted on a cushion comprising foam to prevent and/or limit transmission of vibration and/or noise. The foam cushion may include multiple layers of foam of differential hardnesses or densities.

In certain embodiments, the blower may be positioned at various locations on the patient's head including, but not limited to, the top region of the patient's head, the side regions of the patient head, nose region of the patient's nose, underneath the patient's chin region. In some embodiments, the blower may be positioned on a portion of the patient's head between the back of the patient's head and the patient's nose, (e.g., on the top of the patient's head, on the patient's forehead, in an area between the top and the forehead, on the back of the patient's head, in an area between the top and the back of the patient's head). In addition, in certain embodiments, the blower may be positioned symmetrically between the left and right halves of the patient's head or may be positioned asymmetrically between the left and right halves of the patient's head In certain embodiments, the blower, or blowers, may be positioned at various location on the patient's head including, but not limited to, the top region of the patient's head, the side regions of the patient head, nose region of the patient's nose, underneath the patient's chin region, between the back of the patient's head and the patient's nose, on the top of the patient's head, on the patient's forehead, in an area between the top and the forehead of the patient's head, on the back of the patient's head, in an area between the top and the back of the patient's head, symmetrically between the left and right halves of the patient's head, be positioned asymmetrically between the left and right halves of the patient's head or combinations thereof.

In certain embodiments, the blower may be mounted on a front portion of a patient's head between the crown and the forehead, preferably closer to the patient's forehead.

In certain embodiments, the headgear may include an air channel with no or limited turns in the air path and a 90° turn may be avoided.

Additionally, in certain embodiments, one or more headgear straps (e.g., constructed of fabric) may be adapted to function as a vent for the system.

FIGS. 1A-1C, 2, 3A-3D and 12-23 show headworn PAP systems according to certain illustrative embodiments.

Figures 1A, 1B, 1C:
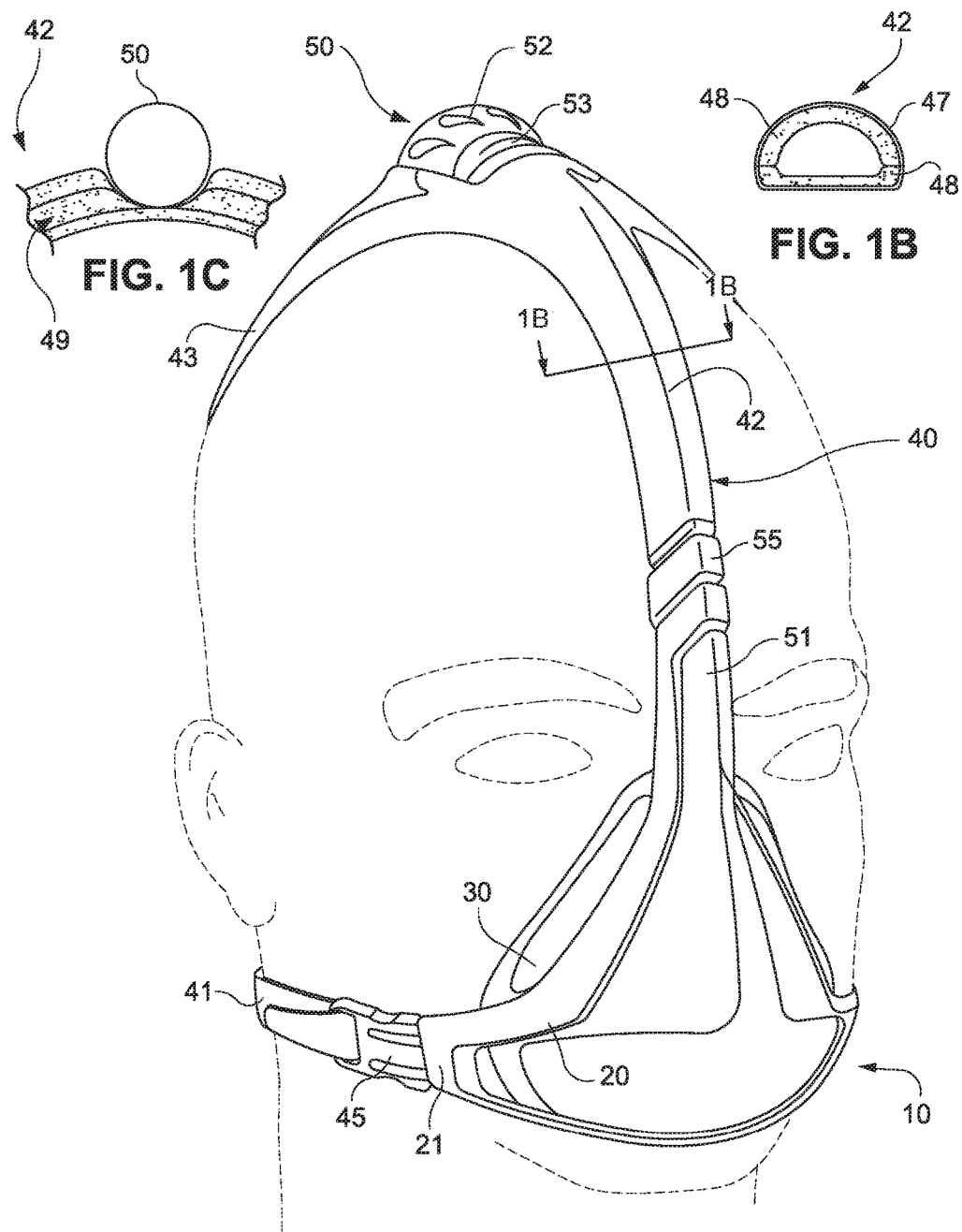
FIGS. 1A to 1C show a headworn PAP system according to certain embodiments.

In FIG. 1A, the patient interface, or mask, system 10 includes a frame 20, a cushion 30 provided to the frame and adapted to form a seal with the patient nose and mouth, and headgear 40 to support the mask in position on the patient's head. The headgear 40 includes side straps 41, 43 and an over-the-head strap 42 that passes between the patient's eyes towards the top of the patient's head. As illustrated, the headgear 40 supports a blower 50 in position on the crown of the patient's head. The over-the-head strap 42 forms a duct to communicate pressurized air from the blower to the breathing chamber defined by the cushion. In addition, the headgear includes multi layer foam and/or damping material 49 to support the blower 50 and limit vibration/noise. In certain embodiments, the mask may include one or more aspects as described in International Application PCT/AU2009/000241, filed Feb. 27, 2009, which is incorporated herein by reference in its entirety.

Frame 20 is arranged such that it connects with cushion 30 adjacent its perimeter or outer most edge. This is so that the appearance of the mask is less obtrusive as the visual impact of the mask will be reduced. It also enables a clear line of sight to the patient's nares and/or mouth when viewed from the front. A short (flexible) tube 51 is coupled with the cushion 30 to deliver the pressurized air from the blower 50 via the over-the-head strap 42 to the cushion 30. The short (flexible) tube 51 may be integrally moulded with the cushion. The short tube 51 may be made from a sealing material, such as silicone. Frame 20 may include headgear connection portions 21 for interfacing with headgear straps 41. As shown in FIG. 1A, headgear is connected to the frame using clips 45. Alternative connection means are possible, such as hooks or slots for receiving headgear straps, push fit, hook and loop connections, magnets, other connecting means or combinations thereof. Headgear may also be provided with a cuff, or interfacing means, 55 that is able to be push fit or otherwise connect with the frame 20. As shown in FIG. 1A, over-the head-strap 42 is provided with a cuff 55, the cuff being stitched, glued, ultrasonically welded, radio frequency welded, connected by other means or combinations thereof, to the end or connecting portion of over-the-head strap 42. This interfacing means then connects to the frame.

The flexible tubing 51 may be moulded within the over-the-head strap 42 and interfacing means to connect with the mask. The flexible tubing 51 may alternatively be moulded with the mask, for example as one part with the cushion, and inserted within the cuff 55 and over-the-head strap 42. The flexible tubing 51 may be formed of, for example, silicone, and integrally moulded with the cushion.

Over-the-head strap 42 may be constructed of more than one layer of material. The outer most layer 47 may be a fabric, textile, other soft material or combinations thereof for providing comfort when in contact with the patient's skin. An inner layer 48 may be foam, gel, 3D woven fabric, other damping material or combinations thereof to absorb noise from the air delivery tube. Another inner layer may be a polymer sheet or film 46 (FIG. 3D) to seal the inner portion of the duct so as to prevent air leakage. The polymer sheet may be polyurethane, polyvinyl, another suitable polymer or combinations thereof. Alternatively, the inner portion may be sealed using silicone spraying or a separately attachable duct 54 (FIG. 3C). In a further alternative, skinned foam may be inserted within the outer layer. The portion of the over-the-head strap contacting the user's face may include additional layers or thicker regions of the damping layer so as to absorb more vibration and noise.

At the blower connecting end of the over-the-head strap 42, a second cuff or connecting means 53 may be provided to connect the blower outlet to the headgear 40. The cuff 53 may be formed of a polymer that may be a thermoplastic elastomer, thermoplastic urethane, polyester, polypropylene, other suitable materials or combinations thereof. The cuff 53 may be glued or integrally formed with the over-the-head strap 42.

The blower mounting portion of the headgear may include a cradle or positioning means to capture the blower, stabilize it in position, and preferably absorb noise and/or vibration. The blower mounting portion of the headgear may include additional layers of damping materials 49 such as foam, silicone, gel, 3D textiles, other suitable damping materials or combinations thereof.

The blower may have an air intake or inlet portion 52 positioned parallel to the top portion of the patient's head (as shown in FIG. 1A). Alternatively, the inlet may be positioned normal or perpendicular to the top portion of the patient's head. Alternatively, the inlet may be positioned at other angles between normal and perpendicular to the top portion of the patient's head.

Figure 2:
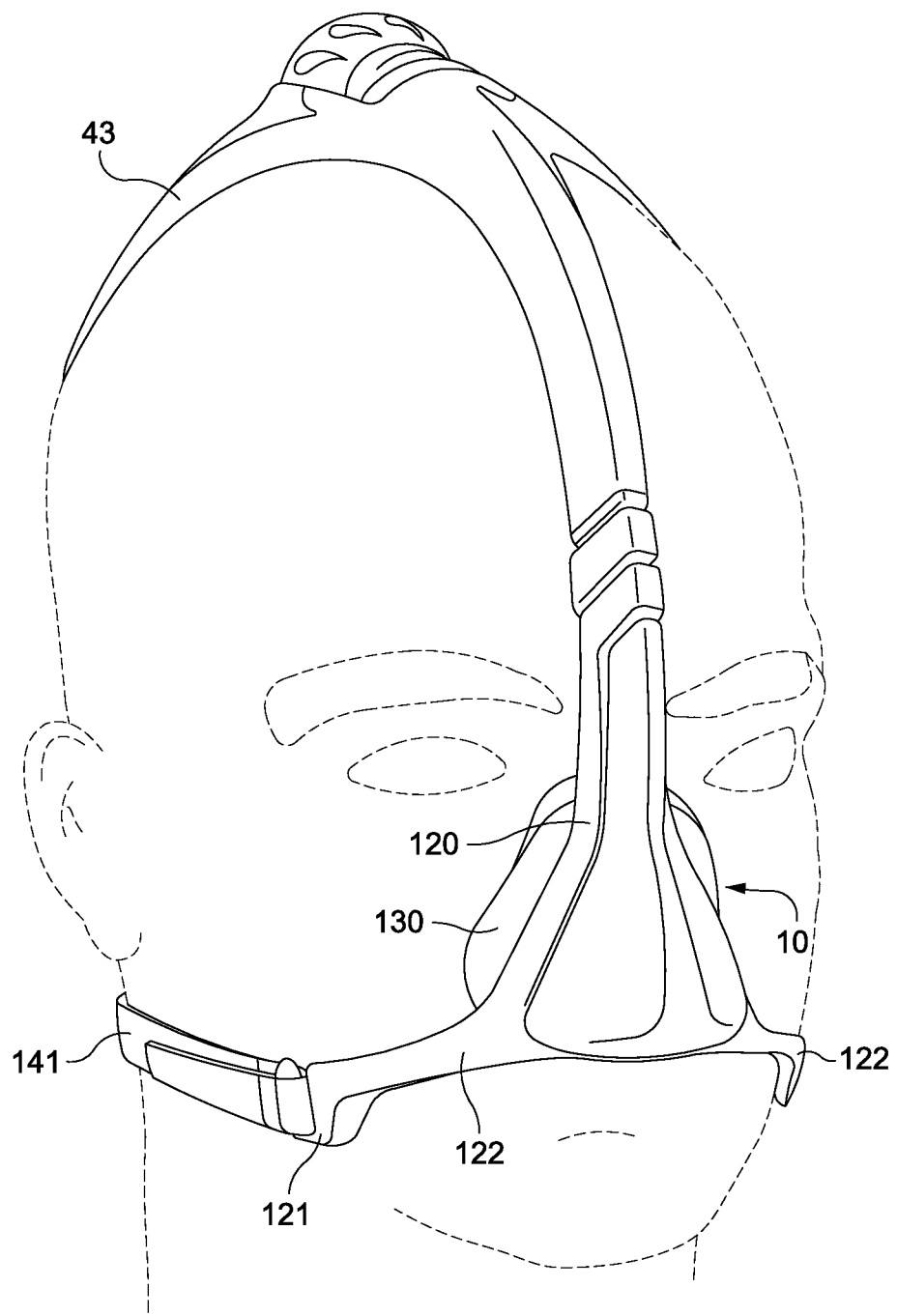
FIG. 2 shows a headworn PAP system according to certain embodiments.

FIG. 2 shows a mask according to certain embodiments. Here, the patient interface of FIG. 2 includes a nasal cushion 130 and the frame 120 includes an alternative configuration for attaching lower headgear straps 141, as compared to that shown in FIG. 1A.

Lower headgear connectors 121 may be slots or loops to receive loops of headgear straps 141. Slots may be connected to arms or wings 122 that may move the connection point of the headgear to the frame 120 away from the patient's line of sight.

In FIGS. 3A to F, the patient interface includes a nasal prong or pillow arrangement 230 adapted to form a seal with the patient's nares. The headgear 240 includes side straps 244 that form ducts to communicate pressurized air from the blower to the nasal prong arrangement. In certain embodiments, the headgear and/or mask may include one or more aspects as described in WO 2009/052560 A1, U.S. Patent Application Publication 2009/0044808 A1, and/or U.S. Pat. No. 7,318,437, each of which is incorporated herein by reference in its entirety.

Cushion 230 may include a plug or vent clip 231 to seal the cushion. In order to manufacture the pillows on cushion 230, the core 232 may be removed through the aperture as shown in FIG. 3E. Alternatively, the plug 231 may include vent holes to provide venting to the mask arrangement. FIG. 3E shows the cushion 230 with the floating core 232 and the aperture from which the core has been removed as indicated by the arrow.

Headgear straps 244 may be attachable to the cushion 230. Headgear straps 244 may be ducted or hollowed to enable the passage of gas through the straps. The cushion connecting ends of the headgear straps 244 may include cuffs, or connecting means, 233 to enable removal of the cushion from the headgear. The cuffs may be moulded, glued, radio frequency welded, ultrasonically welded or otherwise attached to the cushion connecting ends of the headgear straps 244.

The headgear straps 244 may include more than one layer. The outer most layer 47 may include a soft, comfortable material such as fabric, foam, frosted polymers, other suitable materials or combinations thereof. An inner layer 48 may comprise a damping material such as foam, gel, silicone, 3D textiles, other suitable materials or combinations thereof. The headgear straps 244 may be constructed using ultrasonic welding, thermoforming or combinations thereof. An inner most portion of the headgear straps 244 may include a sealed, ducted portion 54 for transmitting gases from the blower to the cushion. This may be constructed from an extruded silicone tube, a helical tube, a polyurethane tube or a combination thereof.

The top portion of the headgear may include a transition portion, or connecting portion, 56 for joining the headgear straps 244 to the blower. Transition portion 56 may include a substantially W-shaped portion as shown in FIG. 3F, wherein there are two outer portions for connecting with the side straps or ducts within headgear straps 244, and a central connecting portion 58 for connecting with the blower via cuff 53. This transition portion may be integrally formed with the headgear, for example by thermoforming, ultrasonic welding, gluing, other connecting means or combinations thereof. In alternative embodiments, the transition portion may be positioned within or on the headgear without permanent fixation. The transition portion may be made of suitable sealed materials, for example silicone, TPE, TPU, polypropylene, polycarbonate, or other suitable materials. The transition portion may sealingly engage with headgear ducts and the blower. The transition portion and headgear ducts may sealingly engage by interference fit. Alternatively, they may be formed in one piece. The transition portion and blower may sealingly engage by interference fit, such as push fit.

FIGS. 12-23 show alternative configurations for communicating pressurized air from the blower to the mask, alternative frame configurations for attaching headgear, alternative headgear arrangements, and/or alternative cushion or sealing arrangements, according to certain embodiments.

Figure 12:
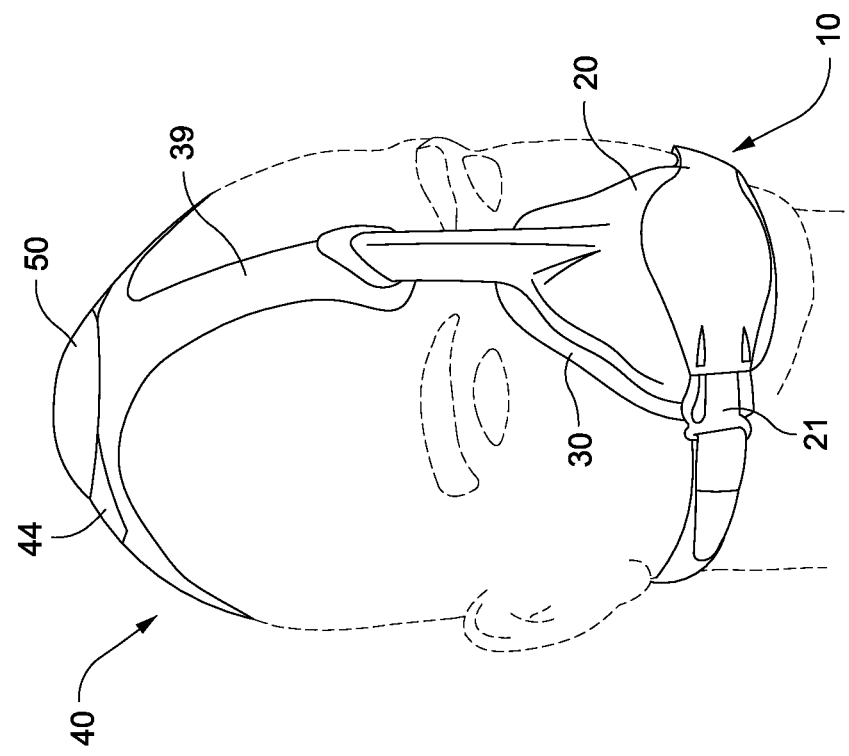
FIG. 12 shows a headworn PAP system according to certain embodiments.

FIG. 12 shows a blower 50 positioned on the top or at the apex of the patient's head that is substantially held in position by a headgear 40. The headgear may include a securing portion 44 for maintaining the blower in position on the headgear. The securing portion may include a formed region that holds the blower in compression to substantially maintain it in position. Alternatively, the securing portion may include a sock, clip, wrap, other suitable structure, or combinations thereof to maintain the blower in position. The headgear may further include a channel, or hollow region, 39 to pass a tube from the blower outlet to the mask. The channel or hollow region may extend along the length of the tube or a portion thereof. The channel may maintain the heat within the tube. The channel may also make the system appear more streamlined. The channel may further dampen and/or prevent the flow of noise from the blower to the mask 10. The mask 10 may include a cushion 30 and a frame 20. The mask may further include lower headgear connection points 21. The lower headgear connection points may include clips, loops or other headgear connection mechanism.

Figure 13:
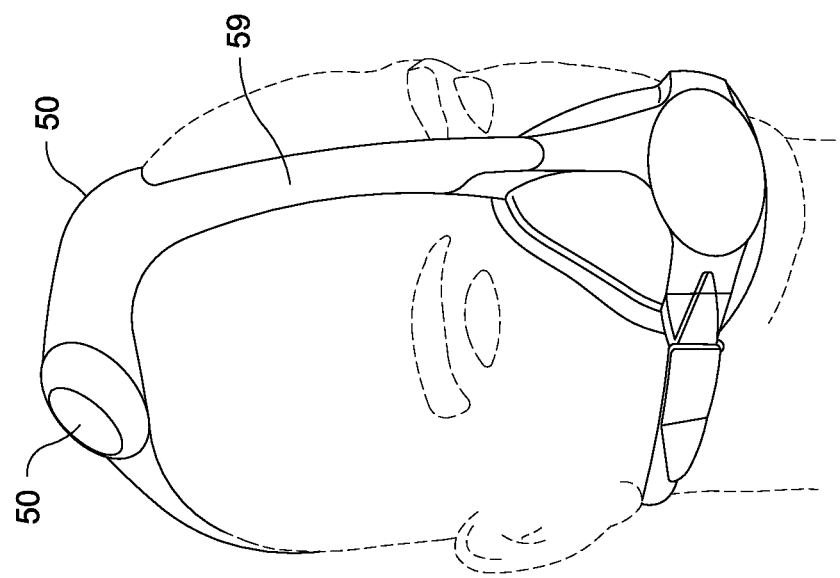
FIG. 13 shows a headworn PAP system according to certain embodiments.

FIG. 13 further demonstrates an arrangement for mask and blower system, where there are at least two blowers positioned at the top or apex region of the patient's head. Each blower may connect to a tube 59, where the tube then connects to the mask system. Preferably, the tubes connecting the blowers and the mask are positioned under or encapsulated within the headgear straps. The embodiment shows two blowers, however it is possible for more than two blowers to be positioned on the headgear.

Figure 14:
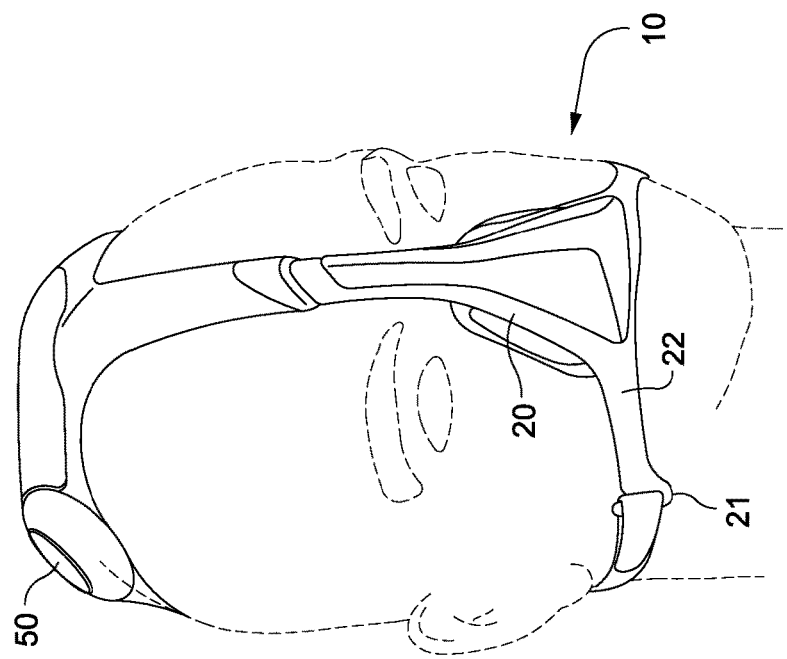
FIG. 14 shows a headworn PAP system according to certain embodiments.

FIG. 14 shows an alternative arrangement to the embodiment shown in FIG. 13. FIG. 13 shows a full face mask or mask that seals around at least the nose and mouth of a patient. The embodiment shown in FIG. 14 shows a mask 10 that seals around a nose region of a patient. In addition, the mask includes a frame 20, where the frame may be a skeleton frame or a frame that surrounds the perimeter of the mask without shrouding or covering the central portion of the mask. This may make it easier to see the patient's nares when the system is in use. Such an arrangement may be beneficial in a clinical setting where a view to the patient's nares is desirable. In addition, the frame includes outriggers, or slender extensions, 22 from the frame to the headgear connecting portions 21 to reduce the visual bulk of the mask. In addition, the outriggers may also enable greater flexibility at the headgear connecting portions. Such flexibility may be desirable to enable greater sealing engagement of the mask with the patient.

Figure 15:
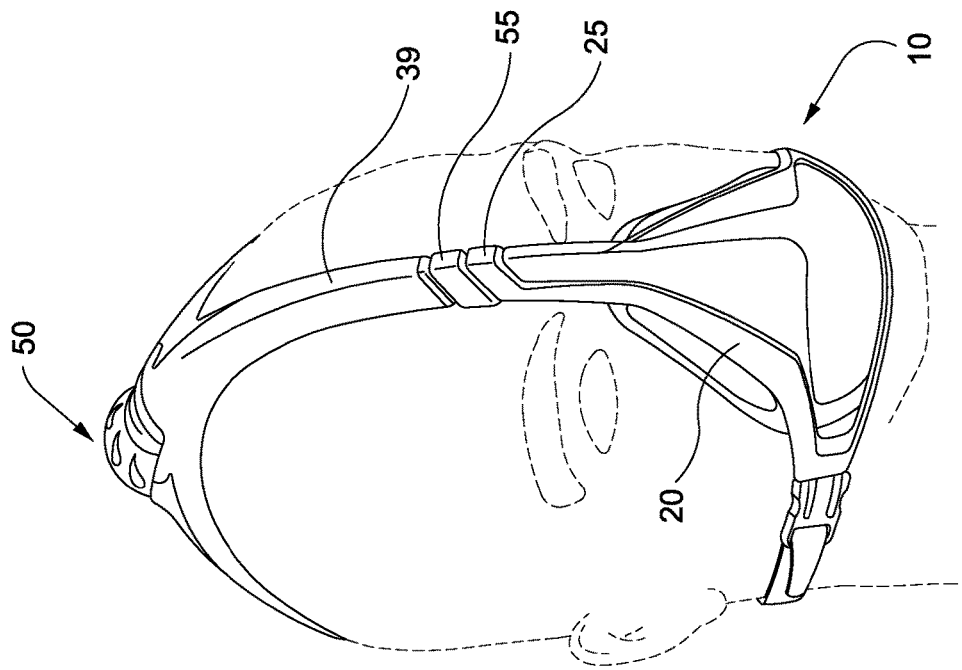
FIG. 15 shows a headworn PAP system according to certain embodiments.

FIG. 15 shows a full-face mask according to certain embodiments. The blower 50 is positioned at the top or apex of the patient's head. The intake of the blower housing is rearward facing, that is, facing in a horizontal direction away from the patient's face. It may also be possible for the intake of the blower housing to be positioned in alternative orientations, such as directly vertical. The headgear may include a channel or hollow region 39 for positioning of a tube, the tube being attached to the outlet of the blower housing and the mask 10. The headgear channel 39 may terminate at a cuff, or connecting means, 55 where the mask frame 20 has an opposition cuff, or connection means, 25 for engagement with the headgear channel. The connection may be a mechanical connection such as a snap fit, a taper lock, a permanent chemical connection, moulded in one piece or combinations thereof. The frame may be of a skeleton or perimeter arrangement similar to that shown in FIG. 14.

FIGS. 16A to 16C show an alternative arrangement, where the patient interface 10 is a pillows or prongs type mask. The patient interface is fluidly connected or a part of a tube arrangement 61, where the tubes are routed or positioned on each of the patient's cheeks and between the patient's eyes and ears. The tubes terminate or connect to a blower or blower housing, positioned at the top or apex of the patient's head. The headgear 40 may encapsulate or otherwise surround the tubes as shown in FIG. 16C. The headgear may be formed with the tubes or may be retrospectively fit or placed around the tubes. As shown in FIG. 16B, the tubes may be radio frequency welded within a thermoformed fabric, for example.

FIG. 17 shows an alternative pillows or prongs type mask 10, where the tube 59 is routed directly vertical or upwards of the patient's head. That is, the tube is positioned in use between the patient's eyes. The mask 10 may connect to the headgear 40 on its lateral sides by push fit tabs, hook and loop, or any other engagement mechanism 12. The mask 10 may have an orifice 11 for venting on its lower portion, directly opposite the position or attachment points of the prongs or pillows. This may be to facilitate: manufacture.

Figure 18:
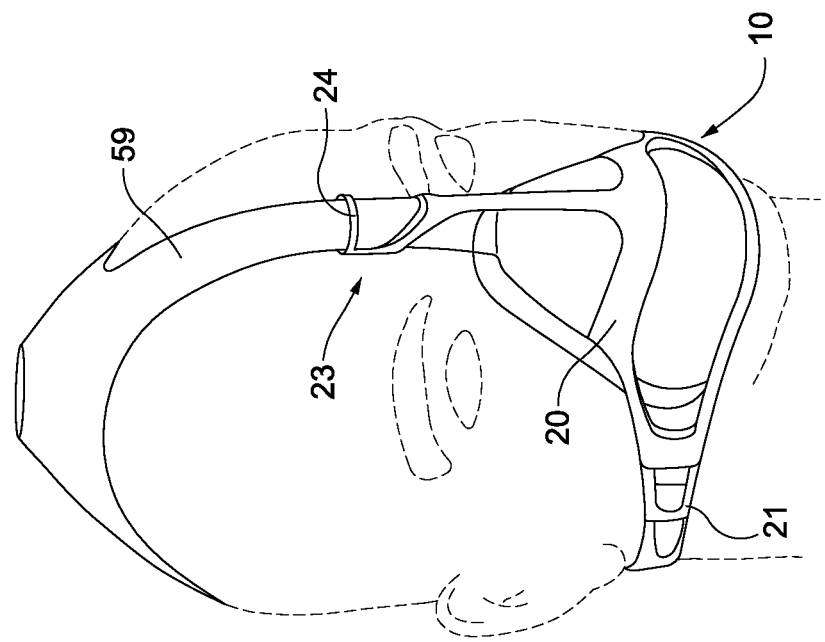
FIG. 18 shows a headworn PAP system according to certain embodiments.

FIG. 18 shows further embodiments where by allowing the core to be removed from the pillow or prong mask as described in relation to FIGS. 3A to 3D, then the hollow air path within the pillow or prongs is produced. This embodiment includes many attributes of the system described in FIG. 15. The skeleton or minimized frame 20 in this embodiment has a top portion 23 that is generally upside down T-shaped. The upper stem 24 of the T-shaped portion 23 loops or wraps around the tube 59. Lower headgear connectors 21 are positioned on the lower portion of the minimized frame.

Figure 19:
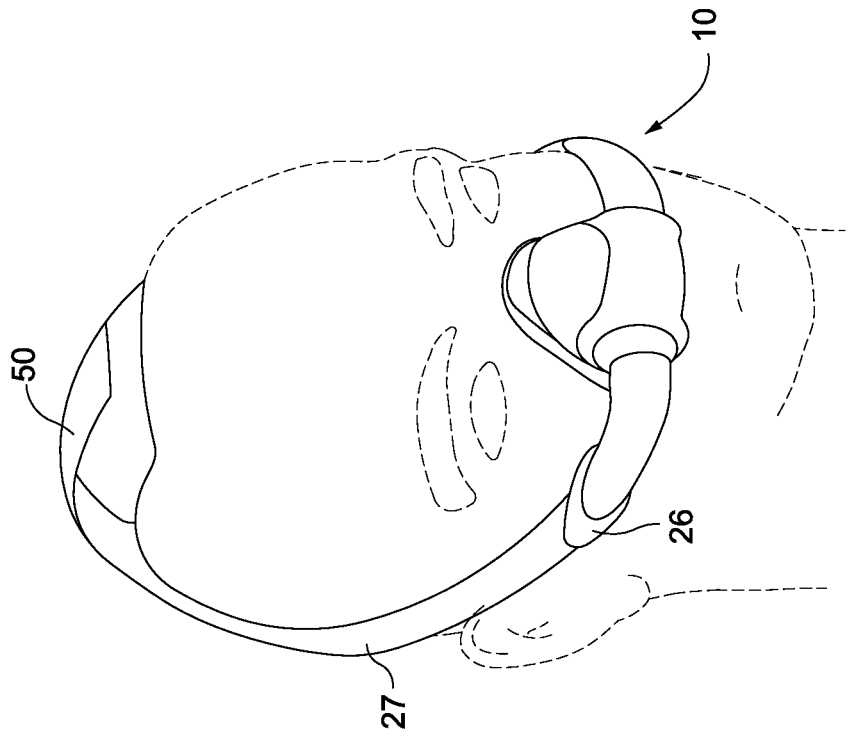
FIG. 19 shows a headworn PAP system according to certain embodiments.

FIG. 19 shows alternative embodiments. The mask 10 may have side connectors 26 to a tube, or tubes, where the tubes 27 are directed or positioned along the patient's cheeks and between the patient's eyes and ears. The tubes 27 terminate or connect at the blower 50, and connect to the rear or inferior side of the blower or blower housing. The rear or inferior side of the blower is generally opposite the side of the blower facing the same direction as the face of the patient. This may enhance the stability of the system by cupping or embracing the rear of the patient's head in use.

Figure 20:
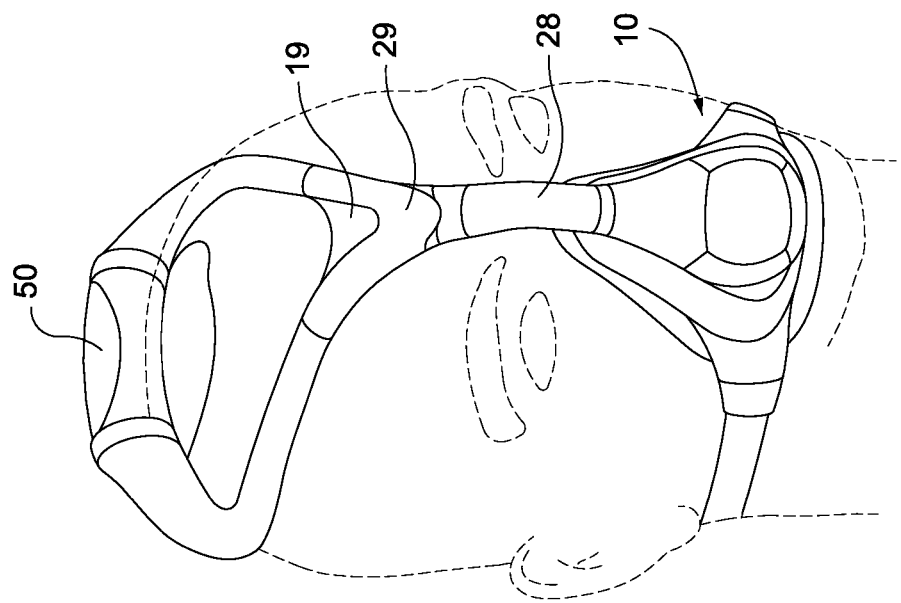
FIG. 20 shows a headworn PAP system according to certain embodiments.

FIG. 20 shows further alternative embodiments. The mask 10 may have a tube connecting portion 28 at the top or apex of the mask. The tube 29 may bifurcate at the forehead region of the patient. There may be a webbing, or mesh, 19 at the junction or separation point of the tube 29 to prevent the bifurcated tube from splaying to far outward. The bifurcated tubes may then enter or connect to the outlet of the blower 50 or blower housing.

Figure 21:
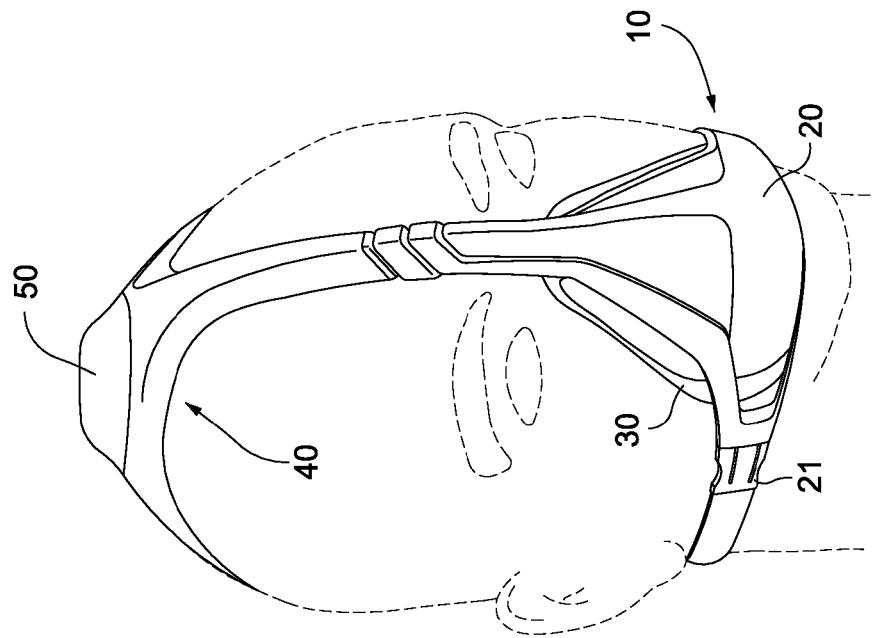
FIG. 21 shows a headworn PAP system according to certain embodiments.

FIG. 21 shows further alternative embodiments. The mask 10 is a full face mask having an alternative configuration for attaching lower headgear straps.

Figure 22:
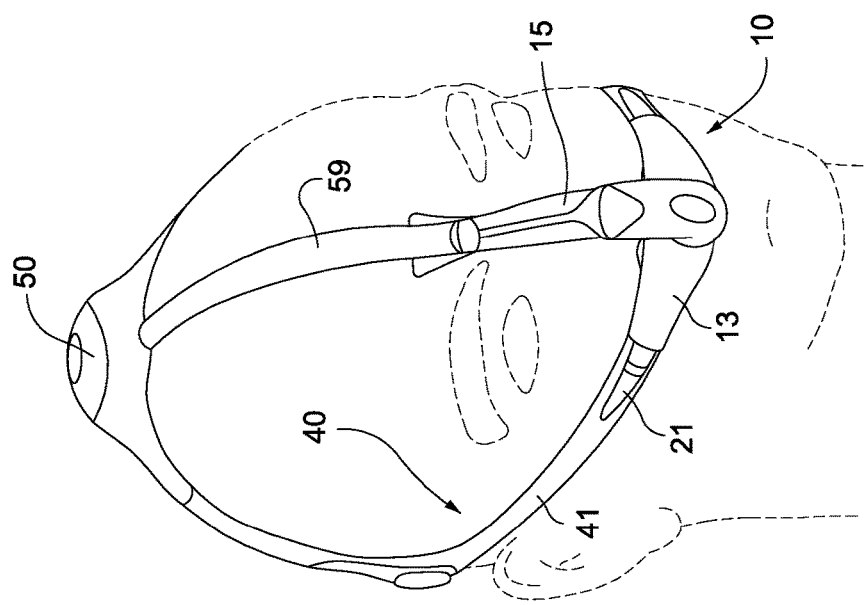
FIG. 22 shows a headworn PAP system according to certain embodiments.

FIG. 22 shows further embodiments. An alternative patient interface 10, being a nasal cradle 13, may have a tube connecting portion at the front of the nasal cradle cushion 13 that delivers the pressurized air from the blower 50 directly into the front of the nasal cushion. A tube 59 is routed directly vertical or upwards of the patient's head from tube connecting portion 15 to the blower 50 positioned on the patient's head. That is, the tube is positioned in use between the patient's eyes. Headgear side straps 41 support the positioning of the nasal cradle on the patient's nares.

Figure 23:
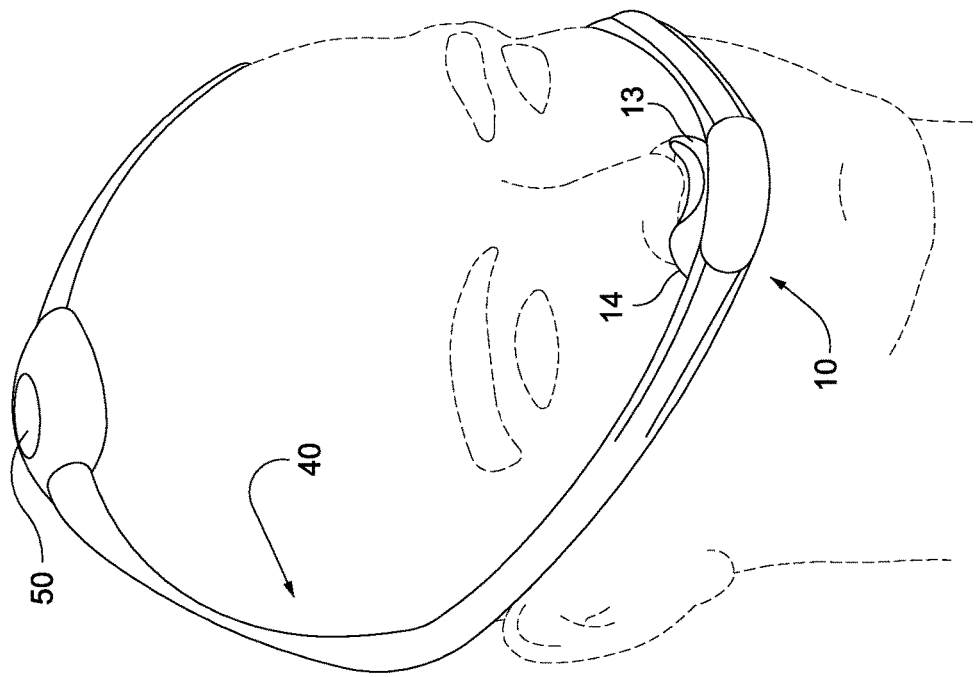
FIG. 23 shows a headworn PAP system according to certain embodiments.

FIG. 23 shows an alternative patient interface 10, being a nasal cradle 13. The nasal cradle 13 may include a single orifice to deliver breathable gas to both nares of the patient, with the outer walls 14 engaging an outer region of the nose of the patient.

FIGS. 56-67 show headworn PAP systems according to certain embodiments. In each embodiment, the blower 50 is supported by one or more headgear straps 43 on top of the patient's head, and communicated with the patient interface 10 via an over-the-head (e.g., see FIGS. 56-59) or top to side of head (e.g., see FIGS. 60 and 61) air delivery tube 65.

The blower and its housing utilized in these embodiments have a wider range of usage requirements than typical blowers. For example, the blower may be headworn so it may therefore be positioned at various angles through the night as the patient rolls around in their sleep. Therefore, the blower may need to function at multiple axes of orientation. The blower may suffer from gyroscopic effects. The life of the components may be affected by the additional movement and therefore loading of the parts. In addition, when directly coupled to the head, the blower may vibrate which may not only be uncomfortable to the patient but may also have physiological effects. Accordingly, certain embodiments may have a wider range of usage requirements than typical blowers. Certain embodiments may be configured such that the blower may be positioned at various angles through the night as the patient rolls around in their sleep and still suitably function. Certain blowers may suitably function at multiple axes of orientation. Certain blowers may suitably function such that effective life of the components may be obtained. Certain embodiments may be configured such that the effects of vibration and/or noise are suitable dampened and the patient is comfortable and does not suffer from physiological effects in use.

In FIGS. 56-61, the blower is supported in spaced relation from the patient's head by a pedestal or support structure 185, which may decouple or isolate the blower from the patient's head in use, e.g., to dampen vibrations as discussed below. In FIGS. 62-67, at least portions of the blower and air delivery tubing are enclosed or covered by a sheathing material 195, which may dampen noise and vibrations from the blower in use.

In certain embodiments, the blower housing may be adapted to include "wings" on either side of blower housing. The wings would not impinge on the aesthetic size or bulk of the device from the wearer's perspective, but may greatly increase the volume of the muffling body of the blower housing. For example, FIGS. 123A-129 illustrate alternative examples of a blower housing or flow generator having a front outlet and side air intake filters. In certain embodiments, headgear may be attached to the sides of the flow generator or blower housing to support the flow generator in position. The headgear may be attached to the flow generator using connection structures (e.g., slots) for attaching headgear straps.

Figure 123A:
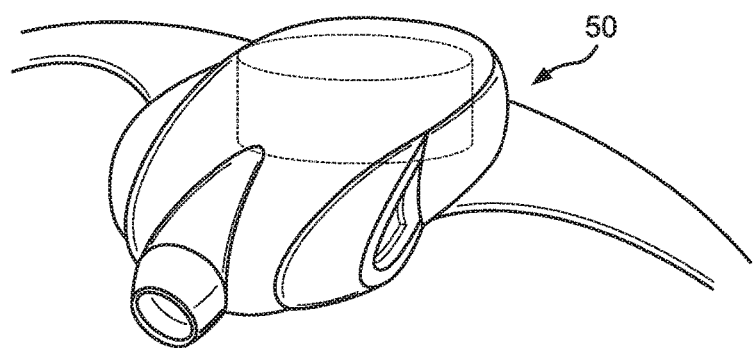
FIGS. 123A to 129 show alternative examples of a blower housing including wings or outwardly flared portions according to certain embodiments.
Figure 123B:
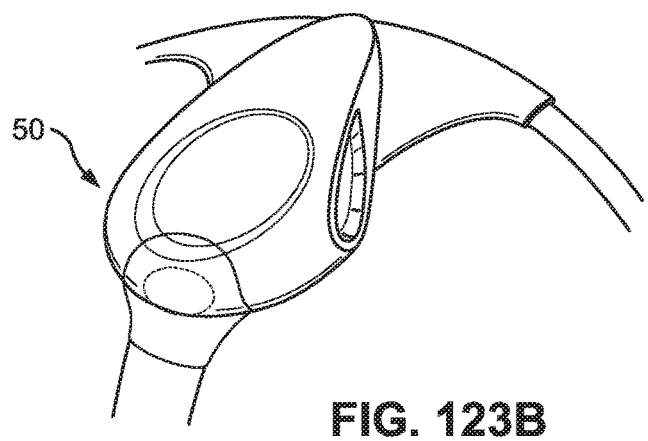

FIG. 123A shows an embodiment where the flow generator includes side intake filters positioned near the front the flow generator and a front facing outlet tube, the headgear straps extend from each side of the flow generator. FIG. 123B is an alternative embodiment showing side intake filters in a more central location along the side of the flow generator. A front outlet tube and back headgear attachment is provided. The tapered design provides a blending from the back of the flow generator to a low point towards the back of the head to remove visual bulk.

Figure 124:
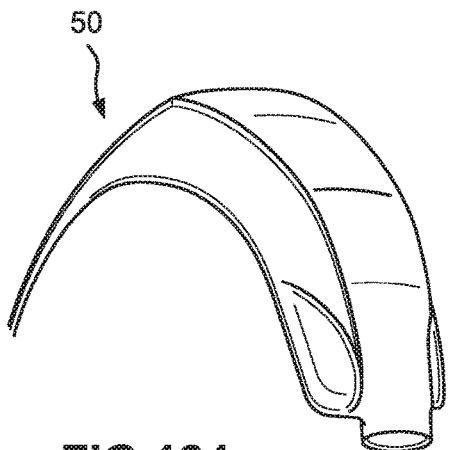
Figure 126:
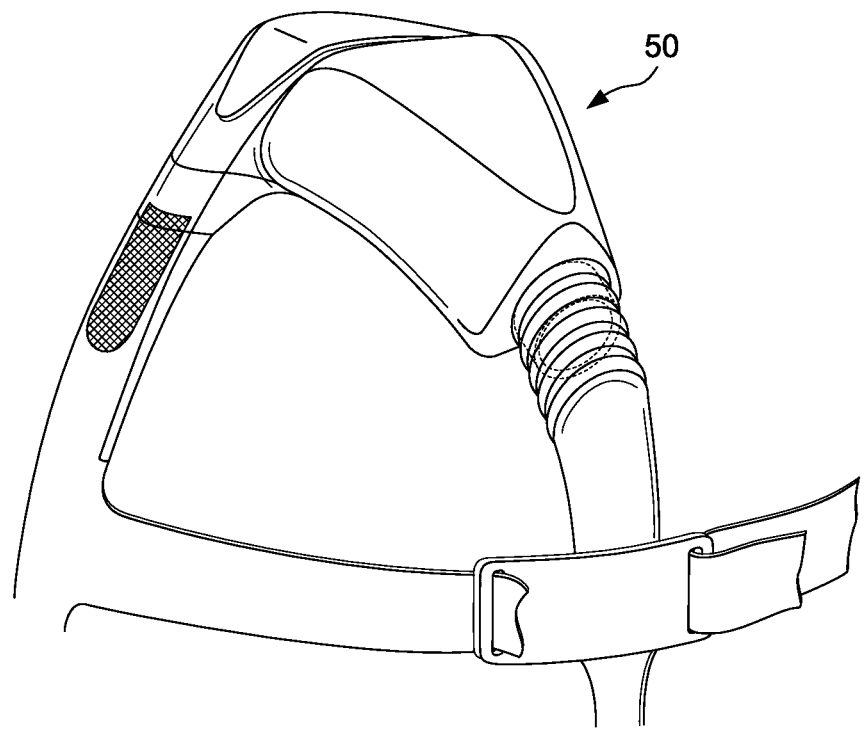

FIGS. 124 and 126 is a flow generator embodiment showing headgear attachment blending up to the flow generator or blower housing to soften the height of the blower. The tapered sides of the flow generator reduce the visual bulk of the housing by angling down and rounding the top edges. The headgear strap extends from the back of the flow generator or blower housing.

Figure 125:
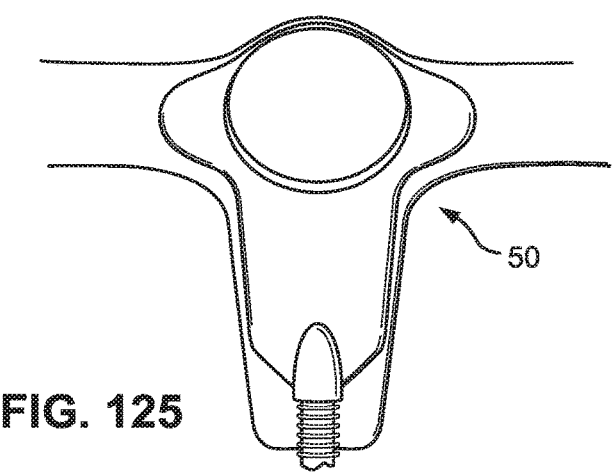
Figure 127:
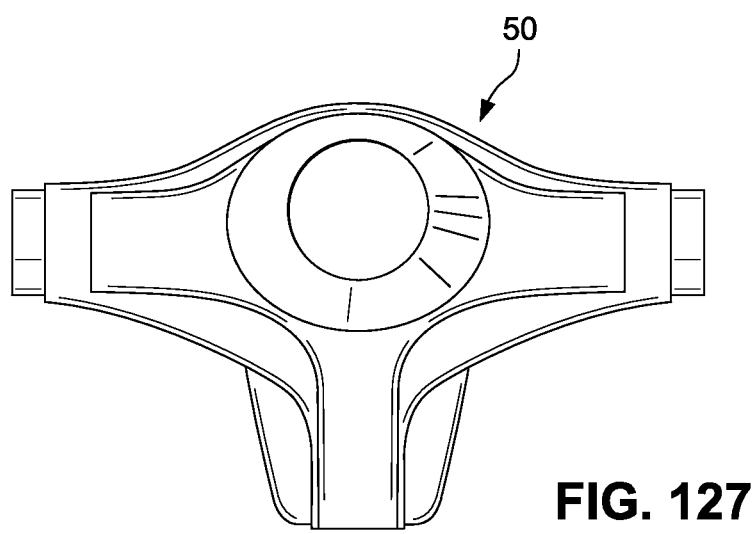
Figure 128:
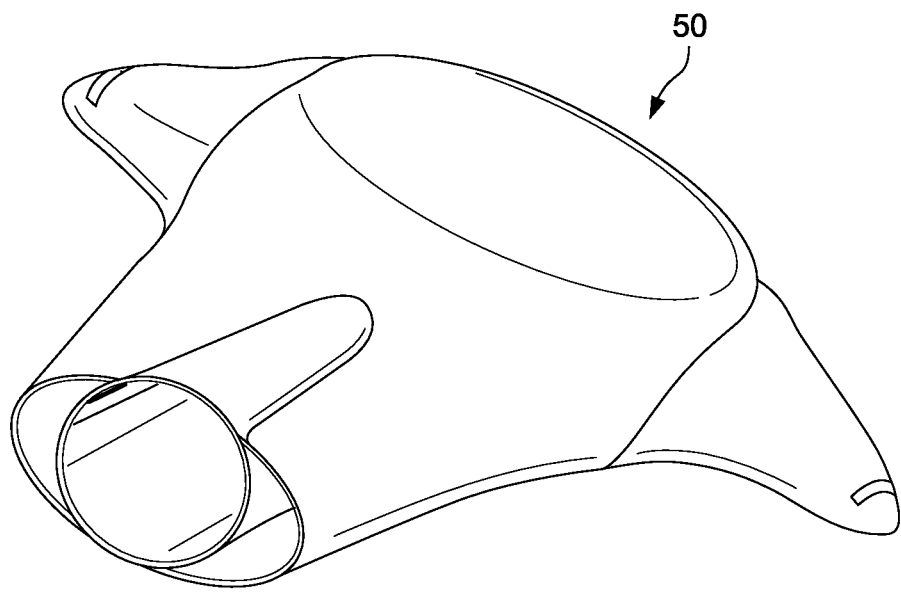

FIGS. 125 and 127 are top views of embodiments of an assembly comprising a flow generator mounted on to a headgear. The blower is central and shown as a circle. The horizontal portions directly adjacent the blower are muffling volume. These extend on to the crown strap of the headgear. The vertical portion has an inner tube that is the outlet portion, and two adjacent portions that are the inlet FIG. 128 is an isometric view of the assembly shown in FIG. 127. The muffling volumes resemble wings extending from the central blower. The wings include slots for receiving the headgear straps. Alternatively, the blower housing could be coupled directly to the headgear so these slots would not be necessary. The outlet is the round tube, having the inlet portions immediately adjacent and on the sides of the outlet. This is a streamlined, visually unobtrusive design.

Figure 129:
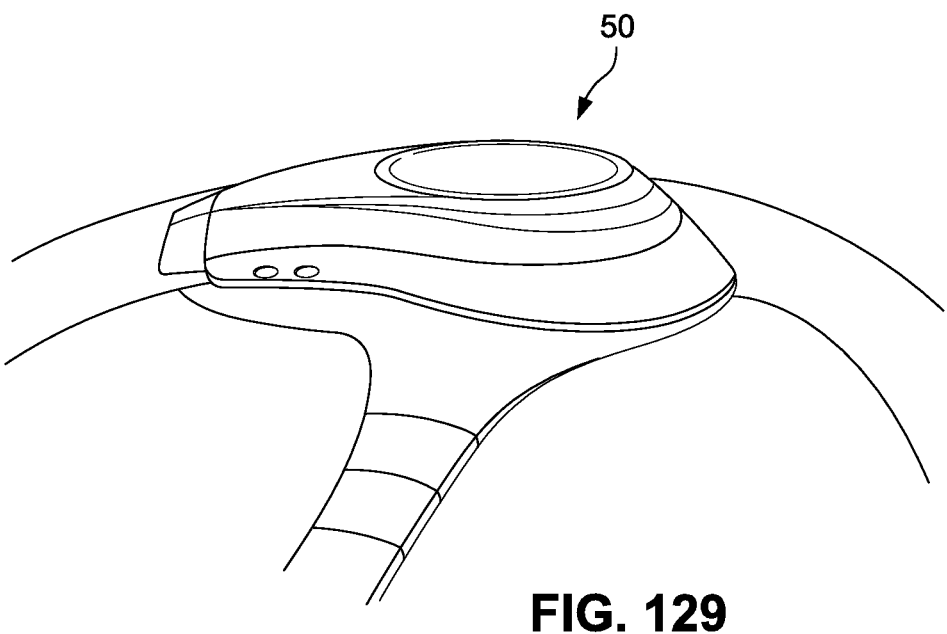

FIG. 129 is an embodiment showing tapered sides blending into headgear straps and back of the patient's head to reduce the step change or height difference. An intake filter may also be located on the top front section (not shown).

1.1.1 Certain Embodiments of the Blower Isolation

As noted above, mounting the blower on the patient's head (e.g., on the patient's crown) may allow vibration noise to be transmitted directly to the skull of the patient. Also, the headgear straps may transmit noise to the patient's skull in use. The following provides alternative examples of a blower support structured to decouple or isolate the blower from the patient's skull so as to dampen vibrations in use.

In certain embodiments, it may be desirable that the blower not radiate heat to a level that the patient cannot tolerate or is dangerous. In certain applications, the blower may not produce sustained temperatures over 60° C. In certain applications, the blower may not produce sustained temperatures over 30° C. In certain embodiments, the blower may produce sustained temperatures under at least 60° C., 50° C., 40° C., 35° C. or 30° C.

1.1.1.1 Certain Embodiments of the Blower Inflatable Cushion

Figure 68A:
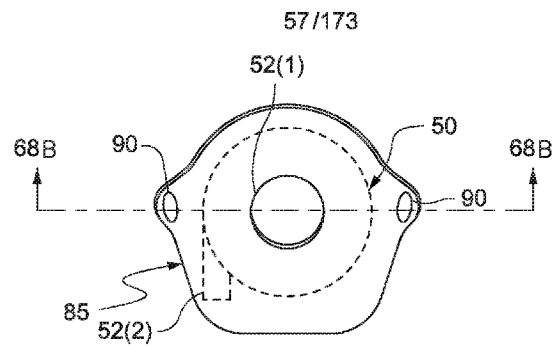
FIG. 68A shows a blower support for a blower according to certain embodiments.
Figure 68B:
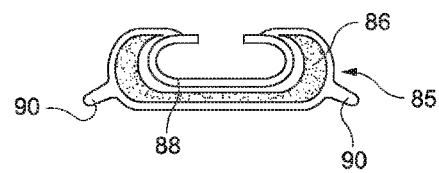
FIG. 68B is a cross-sectional view of the blower support of FIG. 68A.

FIGS. 68A and 68B illustrate a blower support in the form of an inflatable cushion 85 (e.g., constructed of silicone or TPE) adapted to support a blower 50 on the patient's head in use. The blower is communicated with an inflatable chamber 86 of the cushion so that pressurized air from the blower is directed into the chamber to inflate the cushion 85, and thereby lift the blower from the patient's head. Air from the blower may flow through the cushion 85 and into the air delivery conduit in communication with the patient interface, or air from the blower may be ported to the inflatable chamber. The inflated cushion isolates (e.g., vibration isolation) the blower from its surroundings (i.e., patient's head, headgear, and air column in the air delivery tube). The inflated cushion may also act as a volume muffler. In certain embodiments, the inflated cushion may isolate vibration from the blower from its surroundings and may also act as a volume muffler to reduce noise. In certain embodiments, the inflated cushion may isolate vibration from the blower from the patient's head, headgear, air column in the air delivery tube or combinations thereof and may also act as a volume muffler to reduce noise.

In addition, the cushion 85 may provide headgear connectors 90 on respective sides thereof that are adapted to attach to respective headgear straps for supporting the blower on top of the patient's head in use.

As illustrated, the cushion 85 defines a recess or nest 88 adapted to receive the blower. The nest may be turned inside out to facilitate assembly of the blower into the cushion. When assembled, the silicone or TPE cushion 85 forms seals along the inlet 52(1) and outlet 52(2) of the blower. A sealing lip may be added to the blower to assist sealing.

1.1.1.2 Certain Embodiments of the Web Arrangement

Figure 69:
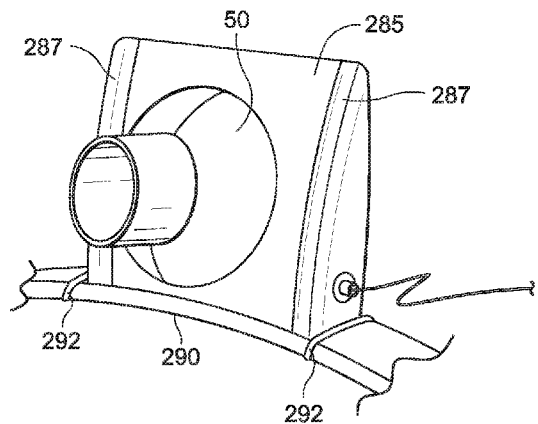
FIG. 69 shows a blower support for a blower according to certain embodiments.

FIG. 69 illustrates a blower support. The blower support may include a gel or silicone skin 285 adapted to support a blower 50 on the patient's head in use. The gel or silicone skin decouples the blower from its surroundings, e.g., skin acts as a web to support the blower in spaced relation from the patient's head.

As illustrated, the blower support includes a headgear connector 290 adapted to attach to respective headgear straps, spaced-apart arms 287 extending upwardly from the headgear connector, and the skin 285 which is supported by the arms 287. The skin includes an opening adapted to receive and retain the blower 50 therewithin. Also, the headgear connector may include one or more moulded hinges 292 (e.g., constructed of silicone, rubber, TPE) to prevent vibration transmission along the headgear connector and to the headgear straps.

Figure 70:
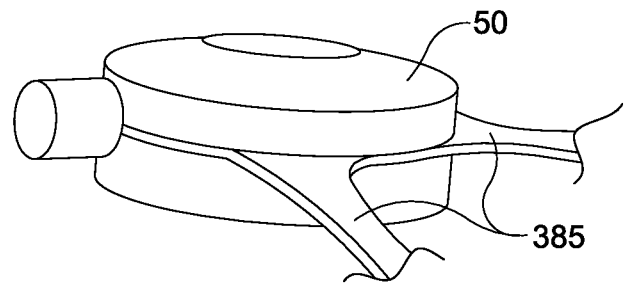
FIGS. 70, 71, and 72 are various views of a blower support for a blower according to certain embodiments.
Figure 71:
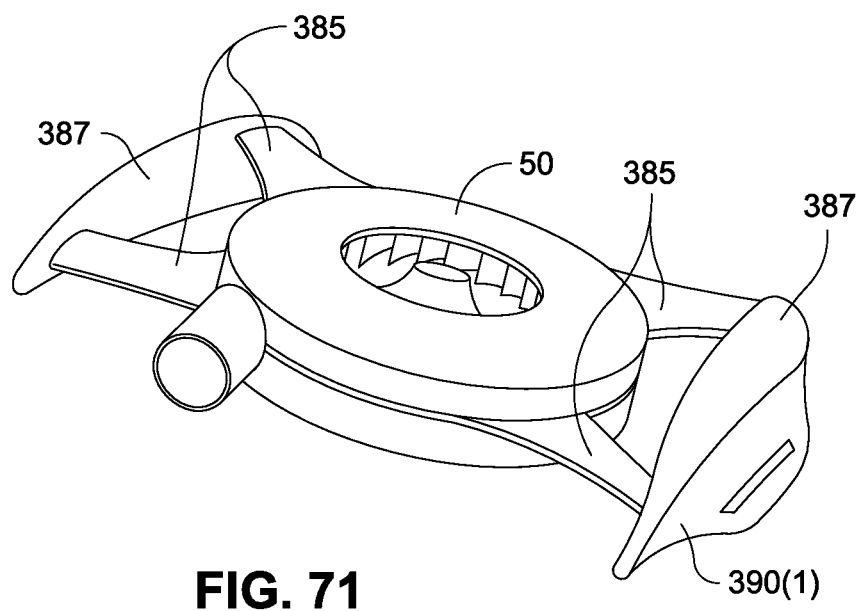
Figure 72:
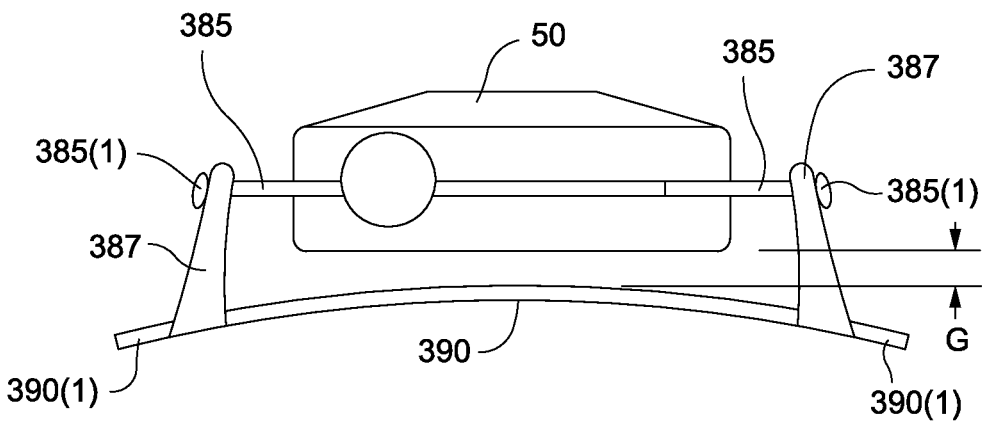

FIGS. 70-72 illustrate a blower support including a web-like or trampoline-like arrangement 385 adapted to support the blower in spaced relation from the patient's head in use.

As illustrated, the blower support 385 includes a headgear connector 390 adapted to attach to respective headgear straps, spaced-apart arms 387 extending upwardly from the headgear connector, and a plurality of support members 385 to interconnect the arms with the blower 50 so as to support the blower in spaced relation from the headgear connector (e.g., blower spaced from the headgear connector by a gap G).

The support members 385 are constructed of a resilient material (e.g., silicone, rubber, TPE) to dampen vibrations and form a web or trampoline-like arrangement that allows the blower 50 to oscillate within the gap and hence dampen and isolate vibrations from the patient's head in use. The support members 385 may be formed as separate parts and attached between the blower 50 and arms 387. Alternatively, the support members may be moulded onto the blower 50 (e.g., co-moulded, two-shot transfer) and then attached to the arms 387 (e.g., end of each support member 385 includes a head 385(1) structured to retain the support member within a respective slot or opening formed in the arm 387 as shown in FIG. 72).

Also, the wings or end portions 390(1) of the headgear connector (i.e., including slot for engagement with respective headgear strap) may be constructed of a resilient material (e.g., silicone, rubber, TPE) to prevent vibration transmission along the headgear connector and to the headgear straps.

The web arrangements may also include combinations of materials.

1.1.1.3 Certain Embodiments of the Damping Support Structure

Figure 73:
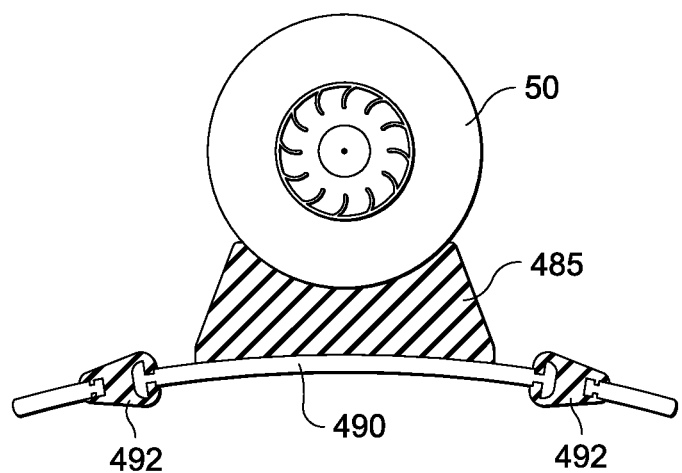
FIGS. 73 and 74 are various views of a blower support for a blower according to certain embodiments.
Figure 74:
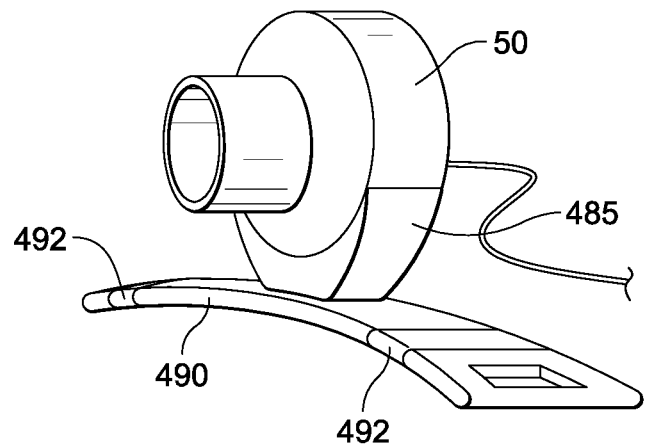

FIGS. 73 and 74 illustrate a blower support including a damping structure 485 adapted to support a blower 50 on the patient's head in use. The damping structure 485 is constructed of a vibration damping material (e.g., silicone, gel, foam, air cushion or bladder, spacer fabric, etc.) structured to dampen vibrations from the blower in use. The damping structure may also be constructed of combinations of vibration damping materials.

As illustrated, the blower support includes a headgear connector 490 adapted to attach to respective headgear strap and the damping structure 485 to support the blower 50. The headgear connector may include sections 492 constructed of vibration damping material to prevent vibration transmission along the headgear connector and to the headgear straps. In addition, further vibration damping material may be positioned along the underside of the headgear connector, e.g., along the side adapted to contact the patient's head in use.

1.1.1.4 Certain Embodiments of the Damping Headgear

Figure 75:
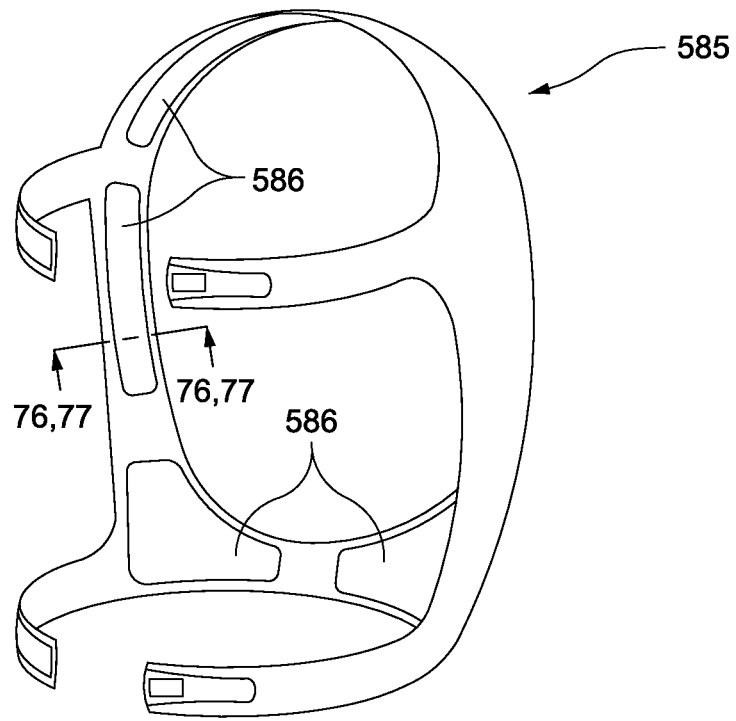
FIG. 75 shows headgear according to certain embodiments.

FIG. 75 illustrates headgear 585 adapted to support a blower on the patient's head in use. The headgear includes one or more portions constructed of a vibration damping material (e.g., gel, TPE, foam, air cushion or bladder, liquid, silicone, rubber, etc.) to dampen vibrations form the blower in use. The headgear may also include combinations of vibration damping materials.

In the illustrated embodiment, the headgear 585 includes a plurality of straps, i.e., upper side straps, lower side straps, top strap, rear strap. As illustrated, one or more selected portions of the straps include a bladder or pocket of vibration damping material 586. For example, spaced apart bladders may be provided along the top and rear headgear straps. However, the headgear may include other suitable bladder arrangements.

Figure 76:
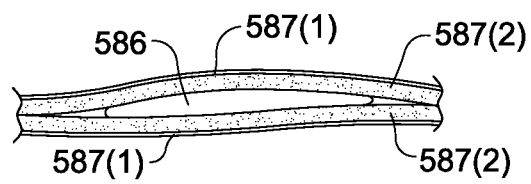
FIGS. 76 and 77 show exemplary cross-sections through the headgear of FIG. 75.
Figure 77:
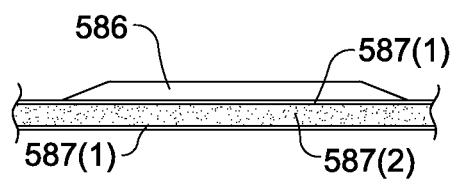

Each strap may be constructed of a multi-layered, composite material (e.g., such as Breathe-0-Prene™) including outer fabric layers 587(1) and an inner foam layer 587(2), e.g., see FIGS. 76 and 77. As shown in FIG. 76, the bladder 586 may be inserted into a pocket or recess formed in the foam layer 587(2). Alternatively, as shown in FIG. 77, the bladder 586 may be attached (e.g., adhered, welded, etc.) to the fabric layer 587(1) oriented towards the patient's skin in use.

1.1.1.5 Certain Embodiments of the Damping Support Structure within Blower

Figure 78:
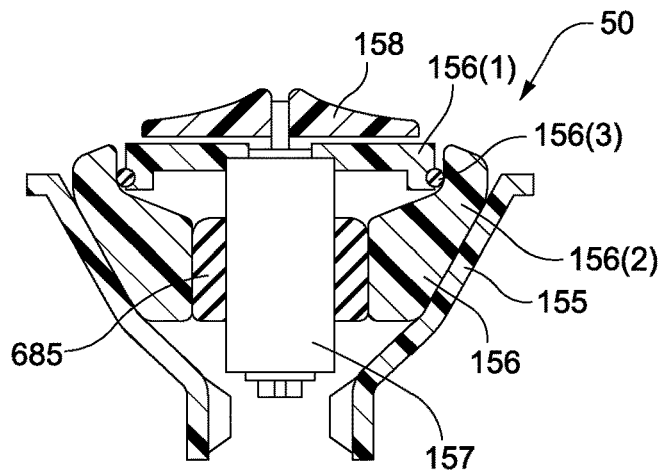
FIG. 78 shows a blower including a damping structure according to certain embodiments.
Figure 79:
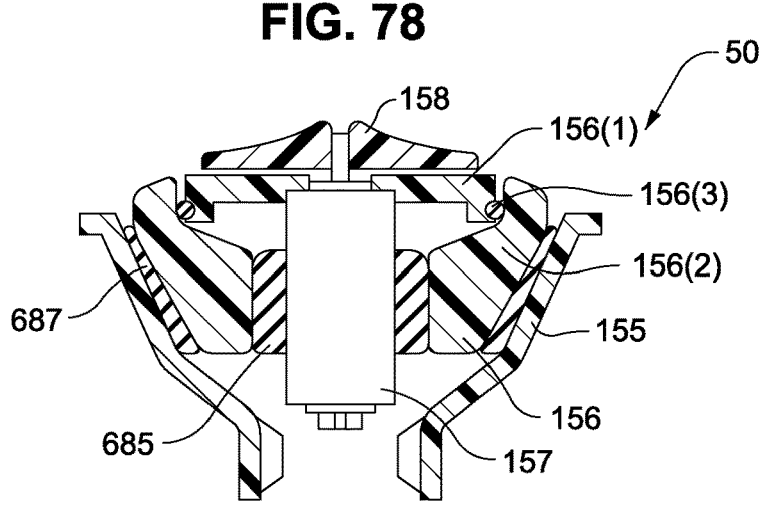
FIG. 79 shows a blower including a damping structure according to certain embodiments.
Figure 80:
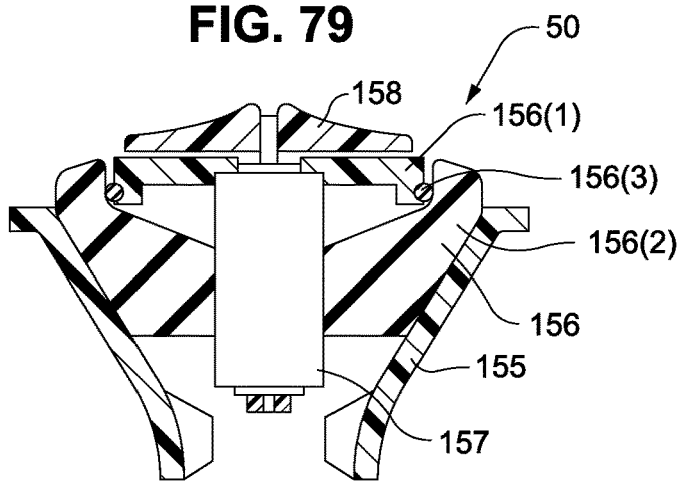
FIG. 80 shows a blower including a damping structure according to certain embodiments.

FIGS. 78-80 illustrate alternative examples of a blower including a damping structure (e.g., constructed of a vibration damping material such as silicone, gel, TPE, rubber, etc.) adapted to dampen vibration transmission from the motor to the outer casing or housing. The support structure within the blower may also include combinations of vibration damping materials. As illustrated, each blower 50 includes an outer casing or housing 155, a stator component 156 positioned within and supported by the outer casing, and a motor 157 positioned within the stator component and adapted to drive an impeller 158. The stator component 156 includes first and second parts 156(1), 156(2) coupled to one another by an O-ring 156(3), which decouples the first and second parts to dampen vibrations from the first part to the second part.

In FIG. 78, the damping structure is in the form of a jacket 685 positioned between the motor 157 and the second part 156(2) of the stator component. In use, the jacket is structured to prevent vibrations from be transmitted to the stator component and on to the outer casing.

FIG. 79 shows a similar arrangement to FIG. 78. In contrast, a second damping structure 687 is provided between the second part 156(2) of the stator component and the outer casing 155 to enhance the damping effect. In certain embodiments, the second damping structure may be overmoulded onto either the stator component or the outer casing.

In FIG. 80, the second part 156(2) of the stator component is constructed of a vibration damping material (e.g., TPE, silicone, rubber, or other suitable rubberized vibration isolating material). Such arrangement provides a relatively "soft" stator component to dampen vibration transmission from the motor 157 to the outer casing 155 in use.

1.1.1.6 Certain Embodiments of the Damping Support Structure Encasing Blower

FIGS. 81-85 illustrate alternative examples of a blower including a damping structure configured to encase or enclose the blower, thereby damping vibrations and muffling noise from the blower in use. In certain embodiments, a blower may include a damping structure configured to at least partially encase or enclose the blower, thereby damping vibrations and muffling noise from the blower in use. The support structure encasing the blower may also include combinations of damping materials.

Figure 81:
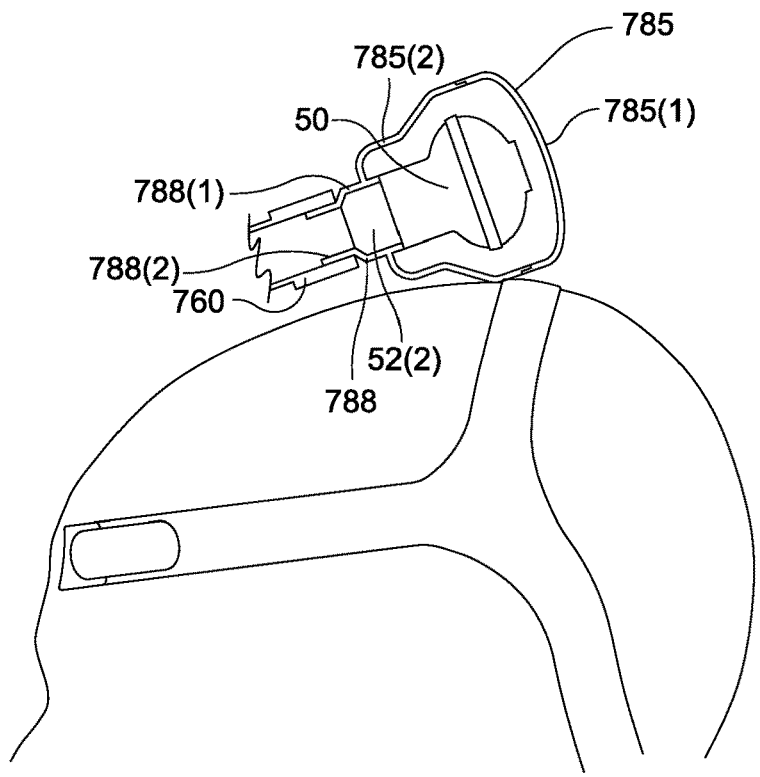
FIGS. 81 and 82 show a blower including a damping structure according to certain embodiments.
Figure 82:
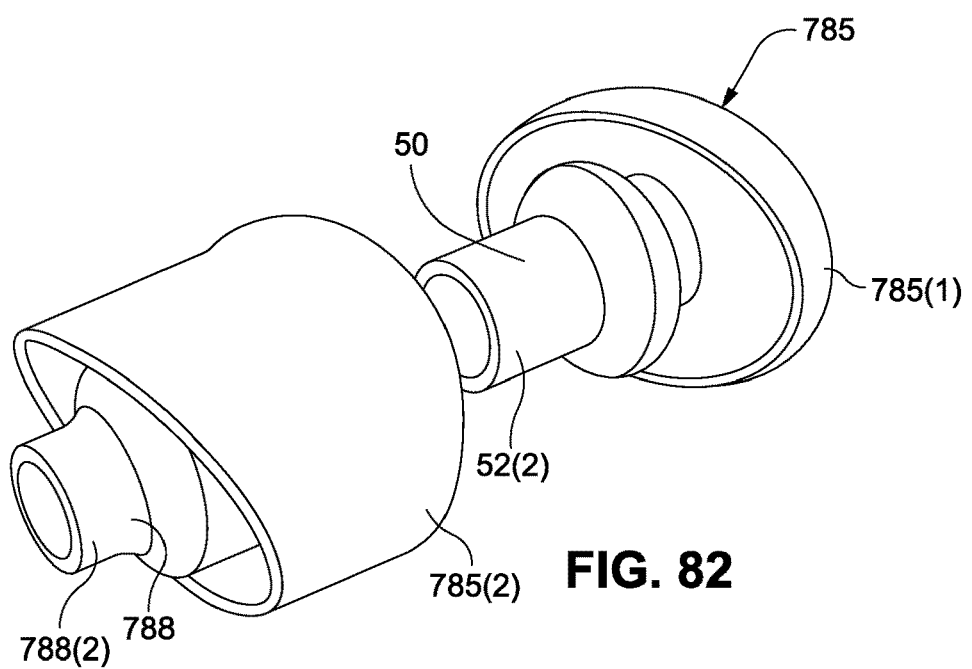

In FIGS. 81 and 82, the damping structure is in the form of an outer housing 785 including first and second housing parts 785(1), 785(2) coupled to one another, e.g., by a joint. As illustrated, the base of the second housing part 785(2) includes a cuff 788. The cuff includes a first portion 788(1) adapted to engage the outlet 52(2) of the blower 50 so as to support the blower within the housing interior. The second portion 788(2) of the cuff is adapted to engage the air delivery tube 760 structured to deliver pressurized gas from the blower to the patient interface. The damping structure is constructed of a vibration damping material adapted to dampen vibrations and/or muffle noise from the blower in use.

Figure 83:
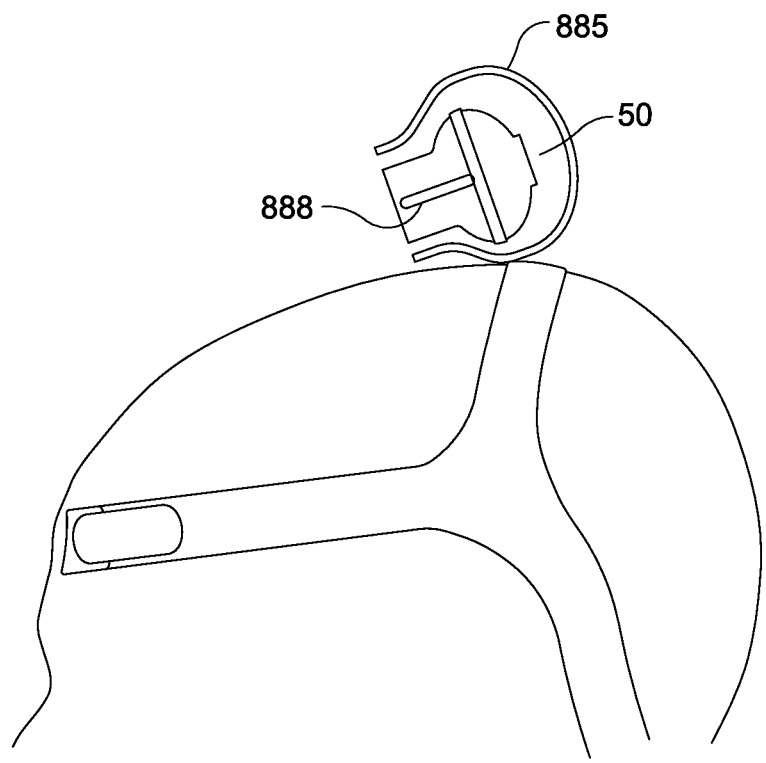
FIGS. 83 and 84 show a blower including a damping structure according to certain embodiments.
Figure 84:
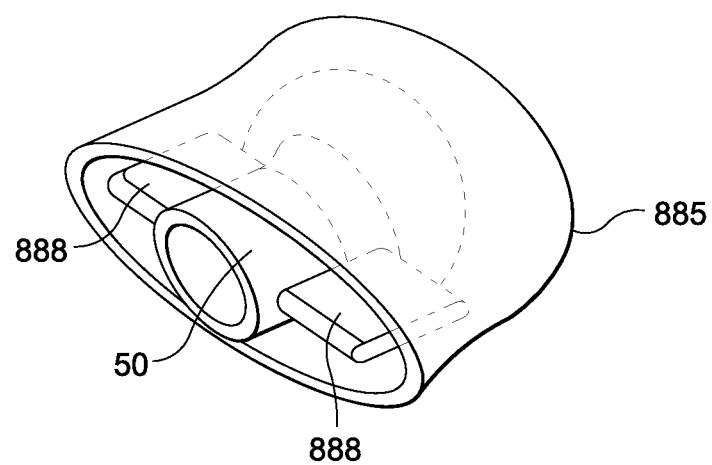

In FIGS. 83 and 84, the damping structure includes a single housing part 885 (e.g., constructed of a vibration damping material) that at least partially or fully encases the blower 50. In addition, damping support structures 888 (e.g., constructed of a vibration damping material such as TPE, TPU, silicone, etc.) are provided between the blower and the housing part to support the blower within the housing part and enhance the damping effect. In certain embodiments, the damping support structures may be overmoulded onto the blower.

Figure 85:
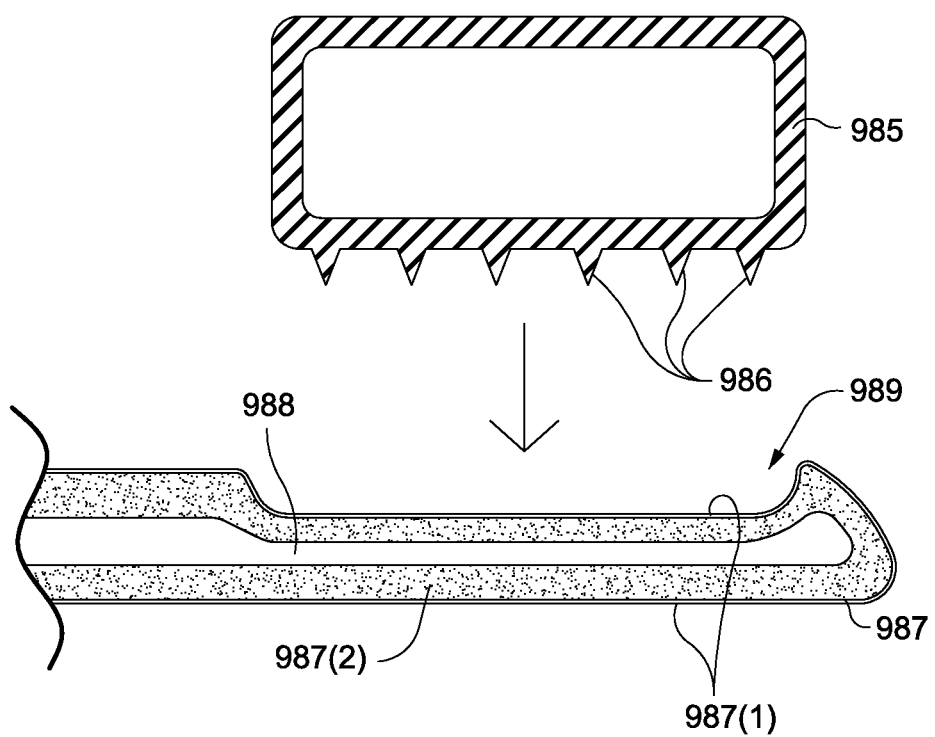
FIG. 85 shows a blower including a damping structure according to certain embodiments.

In FIG. 85, the blower is encased or enclosed within a casing 985 constructed of a vibration damping material (e.g., rubber or other suitable materials). The casing may be overmoulded onto the blower, or formed separately from the blower and then assembled onto the blower. As illustrated, the base of the casing includes a plurality of supports or feet 986 (e.g., conical supports) structured to support the casing on headgear (as described below) and create an air gap between the casing and the headgear to dampen vibrations.

In the illustrated embodiment, the headgear strap 987 adapted to support the casing 985 (and blower therewithin) includes a thermoformed, multi-layered, composite material including outer fabric layers 987(1) and an inner foam layer 987(2). As illustrated, a damping insert or bladder 988 (e.g., constructed of foam, gel, liquid, moulded silicone, TPE, TPU, spacer fabric, etc.) may be inserted into a pocket or recess formed in the foam layer. Also, the headgear strap may include a recessed portion 989 adapted to receive and position the casing 985 on the headgear strap.

1.1.1.7 Certain Embodiments of the Blower with Silicone Bladder

Figure 86:
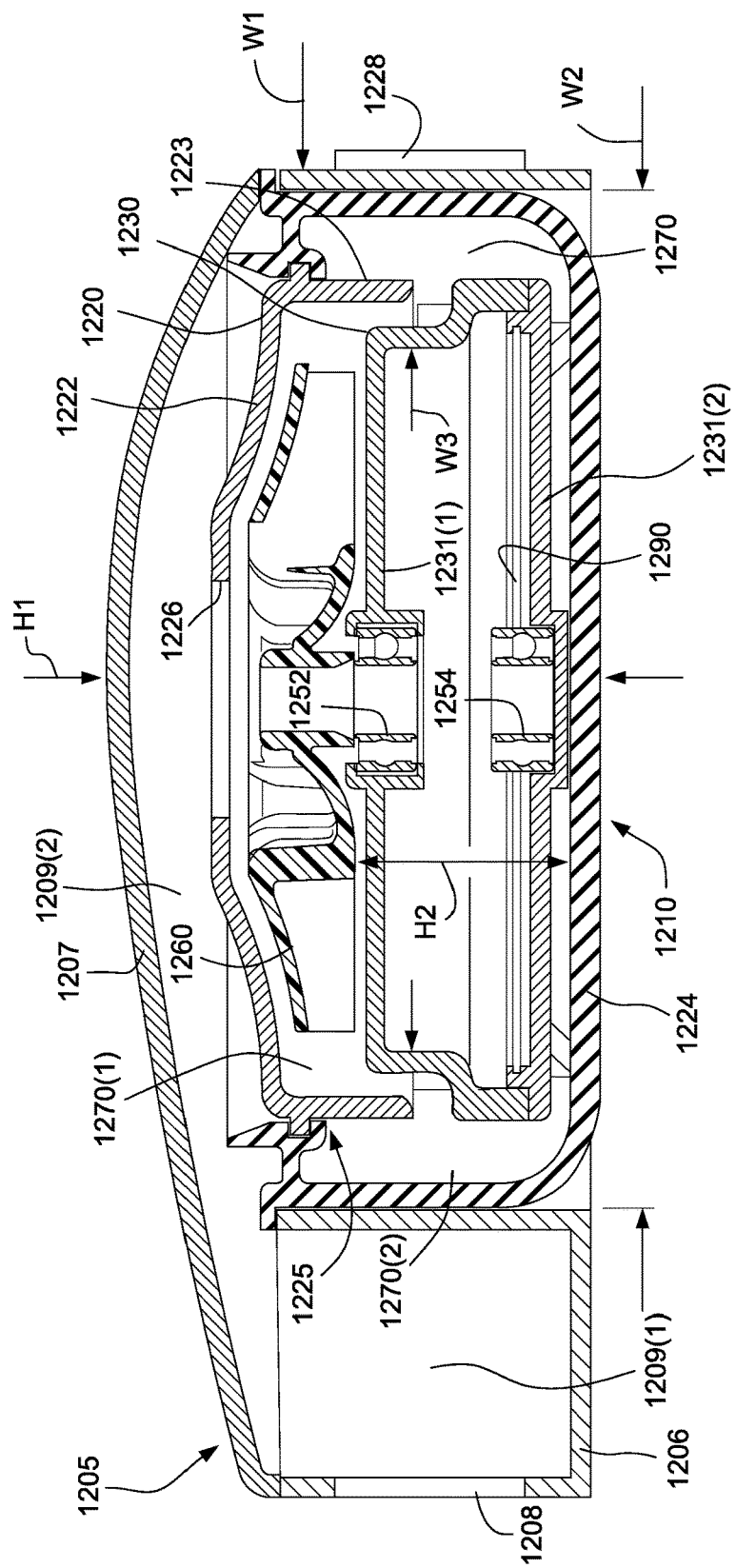
FIG. 86 is a cross-sectional view of a blower according to certain embodiments.
Figure 87:
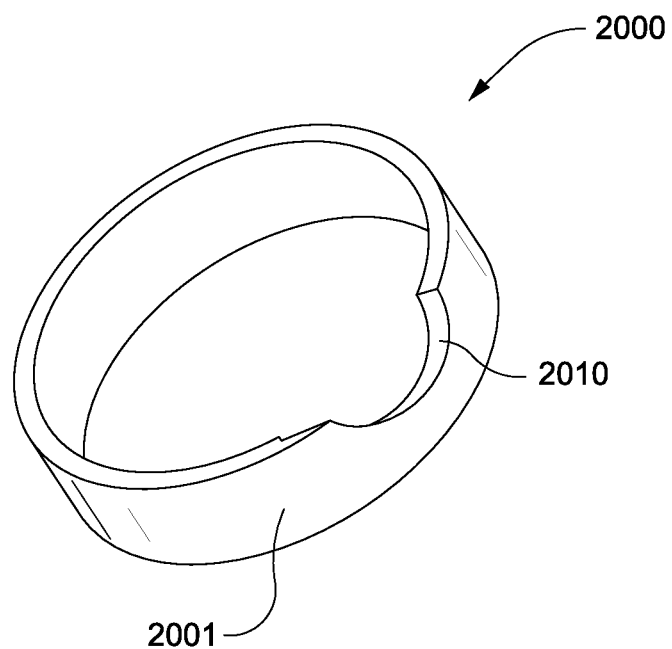
FIG. 87 is a perspective view of a lower portion of a blower housing according to certain embodiments.
Figure 88:
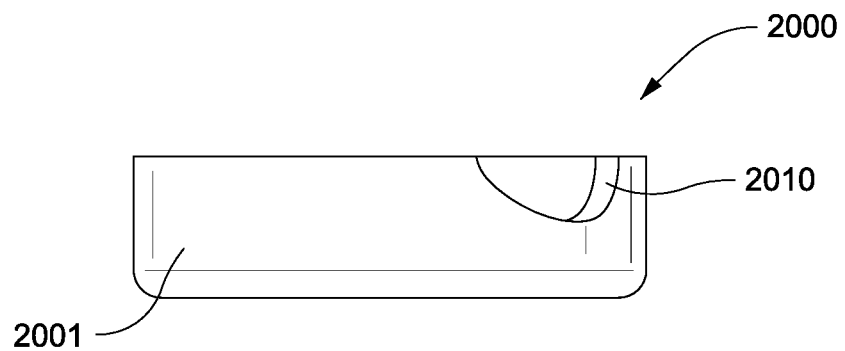
FIG. 88 is a side view of the lower portion shown in FIG. 87.
Figure 89:
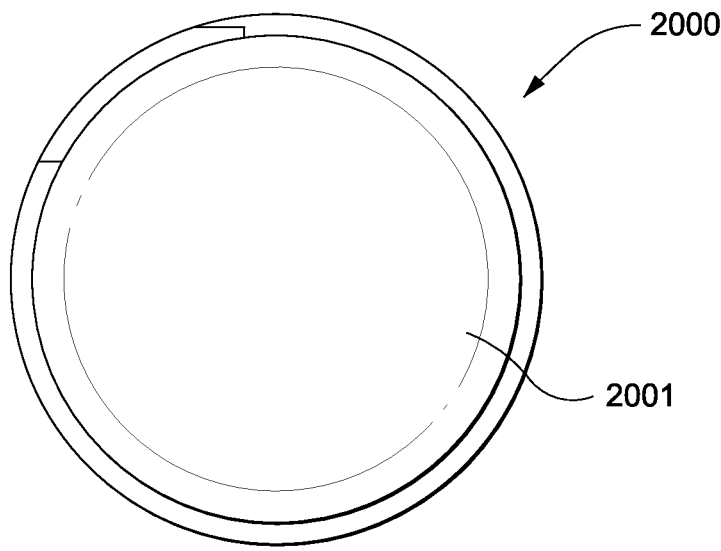
FIG. 89 is a bottom view of the lower portion shown in FIG. 87.
Figure 90:
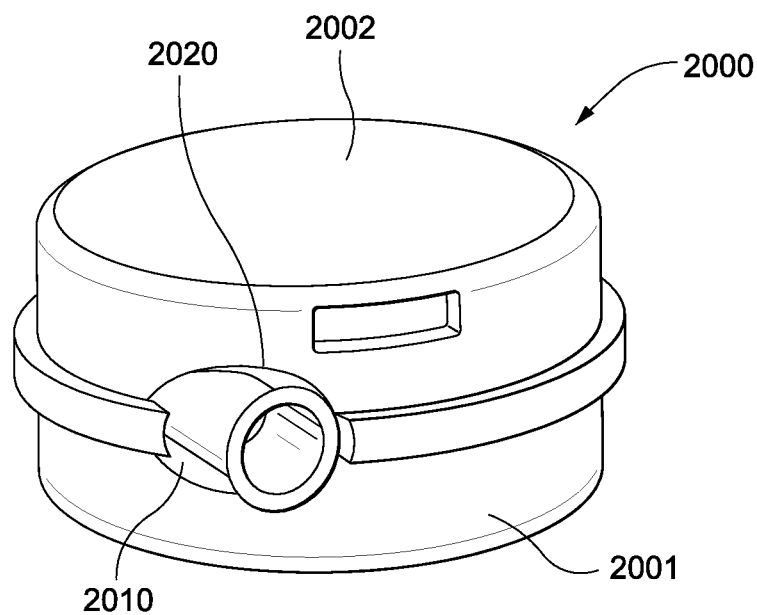
FIG. 90 is a perspective view of the blower housing including the lower portion of FIG. 87.
Figure 91:
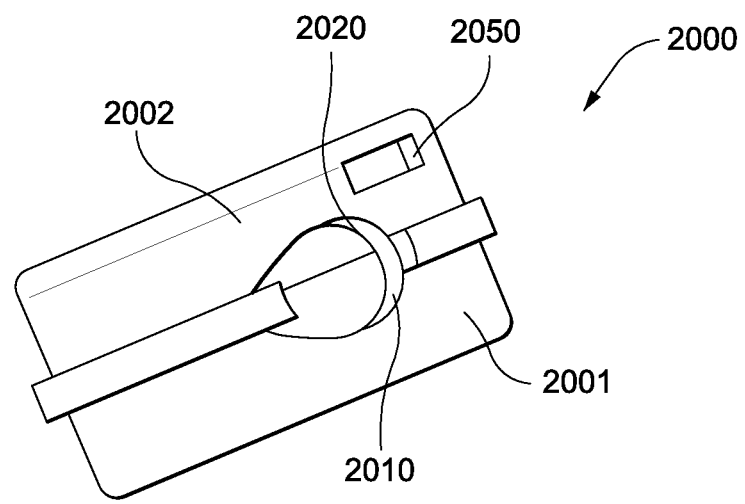
FIG. 91 is a side view of the blower housing shown in FIG. 90.
Figure 92:
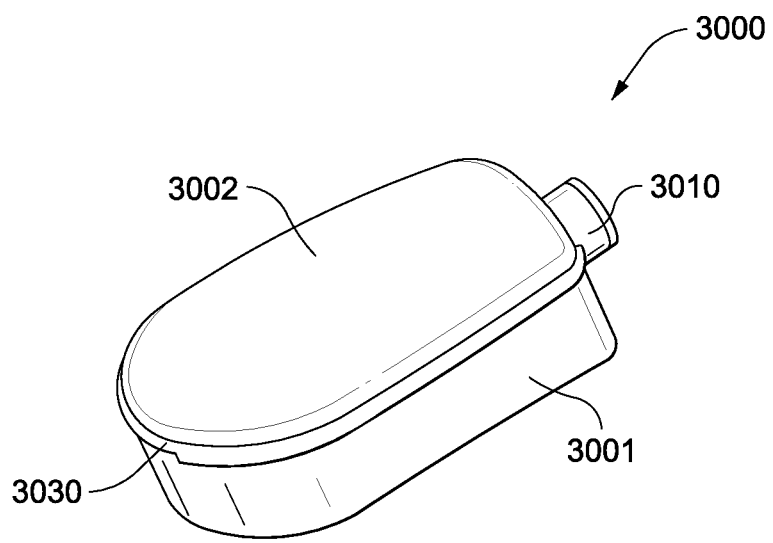
FIG. 92 is a perspective view of a blower housing according to certain embodiments.
Figure 93:
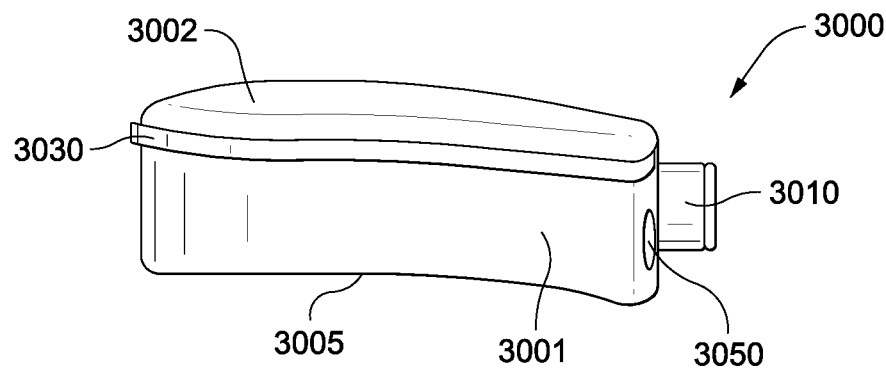
FIG. 93 is a side view of the blower housing shown in FIG. 92.
Figure 94:
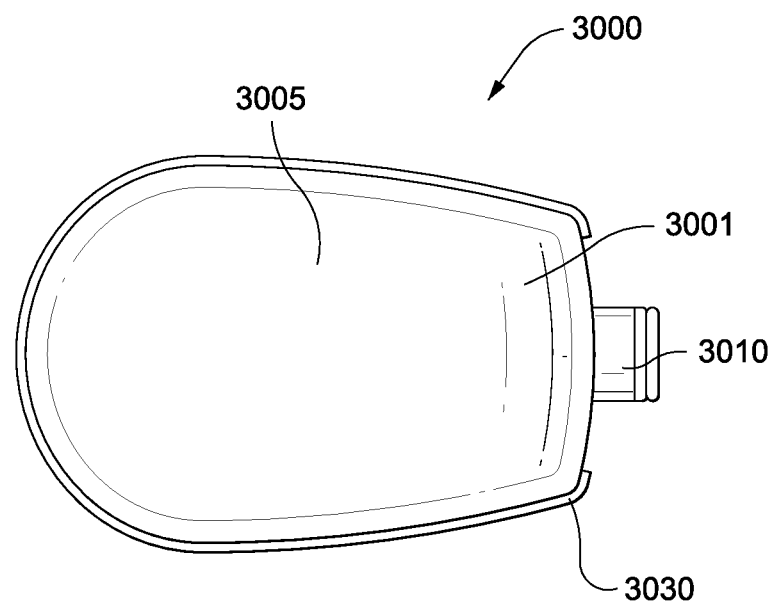
FIG. 94 is a bottom view of the blower housing shown in FIG. 92.
Figure 95:
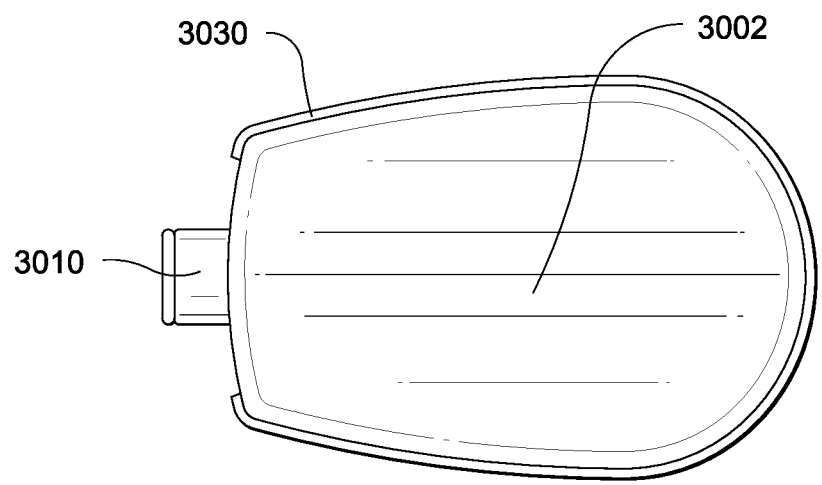
FIG. 95 is a top view of the blower housing shown in FIG. 92.
Figure 96:
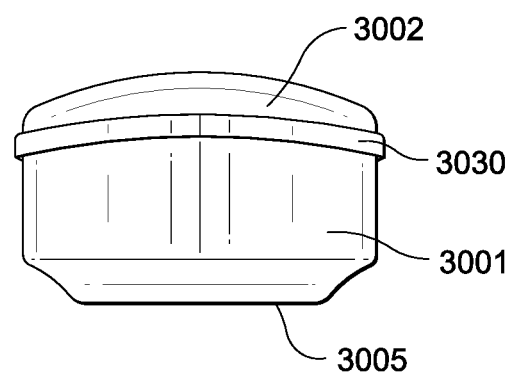
FIG. 96 is a rear view of the blower housing shown in FIG. 92.

FIG. 86 illustrates a blower 1210 according to another embodiment. In this embodiment, a portion of the housing is formed of silicone which acts as a vibration isolator and/or outlet muffler in use.

The blower 1210 includes a housing 1220 with first and second housing parts 1222, 1224, a stator component 1230, a motor positioned within the stator component 1230 and adapted to drive a rotatable shaft or rotor (not shown), a PCBA 1290 for motor control, and an impeller 1260 provided on one side of the stator component 1230 and adapted to be coupled to an end portion of the rotor. In addition, the blower may include an outer housing structure 1205 communicated with the inlet 1226 and structured to act as a muffler for incoming air.

In the illustrated embodiment, the first housing part 1222 provides the inlet 1226 and the second housing part 1224 provides the outlet 1228. The first housing part 1222, second housing part 1224, and stator component 1230 cooperate to define the volute 1270 that directs air towards the outlet. Also, the first housing part 1222 provides a separating wall 1223 that separates the volute 1270 into two regions, i.e., a high speed airpath region 1270(1) and a low speed airpath region 1270(2). The first and second housing parts 1222, 1224 may provide a joint 1225 (e.g., tongue and groove arrangement) to facilitate alignment and/or connection.

Moreover, the second housing part 1224 (which provides an exterior portion, outer wall portion, or pressure side of the volute) is formed of a silicone material. This arrangement allows the second housing part 1224 to act as an air cushion or bladder in use, e.g., second housing part may at least partially inflate when pressurized in use. In use, the silicone second housing part 1224 supports the first housing part 1222, stator component 1230, motor, and impeller 1260 in a flexible, vibration-isolated manner. Thus, vibrations and/or other movement generated by these components in use are substantially isolated, e.g., from the outer housing structure 1205. Moreover, the silicone second housing part 1224 acts a muffler for air exiting the outlet 1228 in use. The second housing may include barbs or stilts to act as shock absorbers. The barbs may be continuous with the bladder or separately attached.

Thus, the silicone second housing part prevents vibration conduction into the patient's skull, vibration conduction into the headgear, and noise conduction down the air delivery conduit. In certain embodiments, headgear may attach directly to the bladder or to the outer housing structure (if provided).

In the illustrated embodiment, the stator component 1230 includes first and second parts 1231(1), 1231(2) that are coupled to one another, e.g., by a joint. The first and second parts cooperate to define a hollow interior adapted to support and maintain the motor and rotor in an operative position. Also, the first and second parts of the stator component are structured to retain hearings 1252, 1254 that rotatably support the rotor. For example, the first part 1231(1) may include a recess for supporting one bearing 1252 and the second part 1231(2) may include a recess for supporting the other bearing 1254. The first and second parts may be structured to support bearings of the same or mixed bearing sizes. In addition, the first part provides an opening along its axis that allows the end portion of the rotor to pass there through for engagement with the impeller 1260.

The outer housing structure 1205 includes a base 1206 that extends around the exterior of the second housing part 1224, and a cover 1207 that encloses the top of the blower including the inlet 1226. The base 1206 provides an inlet 1208 with an inlet chamber 1209(1) to reduce at least a portion of the noise produced by incoming air. In addition, the cover 1207 provides a small chamber 1209(2) downstream from the inlet chamber to muffle noise entering the inlet 1226.

In certain embodiments, foam or gels may also be used in one or more portions of the blower to muffle noise and vibration. The foam may be positioned to fill any open volumes in the blower housing to stabilize the blower in position in the housing and to absorb vibration, noise and/or frequency of noise. The foam may be an open cell foam, a closed cell foam, or combinations thereof. The foam may be skinned or unskinned. The foam may also be utilized to space or position the inlet of the blower away from the wall of the housing to prevent the blower from choking and to prevent the blower from sucking itself on to the housing wall.

In certain embodiments, the blower may be structured to provide pressurized air in the range of 12-14 cmH$_2$O, about 25000 rpm, and flow rate of about 80-100 L/min.

In certain embodiments, as shown in FIG. 86, H1 may be about 30-35 mm (e.g., less than 35 mm, 31 mm), H2 may be about 10-20 mm (e.g., less than 20 mm, 14 mm, 18 mm), W1 may be about 80-90 mm (e.g., less than 90 mm, 83 mm), W2 may be about 65-7 5 mm (e.g., less than 75 mm, 69 mm), and W3 may be about 40-50 mm (e.g., less than 50 mm, 44 mm, 41 mm). However, other suitable dimensions are possible.

In alternative embodiments, the blower may be suspended from the top case of the blower housing by a skin or bladder. The bladder may be constructed of a polymer or other flexible material. For example, the bladder may be constructed of a silicone or thermoplastic elastomer (TPE). The silicone may be about 5-70 Shore A. The TPE may be about 5-70 Shore 00. The bladder may have varying wall thicknesses. For example, the region adjacent the top cover of the blower may be thinner than the region proximal to (but not attached to) the bottom case of the blower housing. This may be to support the weight of the blower at a region of the bladder and allow flexibility at a region of the bladder. Preferably, the thickness of the thicker region of the bladder may be approximately 2-5 mm. Preferably, the thickness of the thinner region of the bladder may be less than 2 mm. Suspending the blower from the top region of the blower may increase the distance of the blower to the patient, thereby reducing noise and vibration effects. The bladder may space the lower portion of the blower from the bottom region of the blower housing to enable air intake into the blower, In additional embodiments, the bladder suspending the blower from the top portion of the blower housing may have an outer side wall or walls. The outer side walls may be positioned on a side wall surface not adjacent the blower, that is, the outer side walls are external to the blower. These walls may include barbs or shock absorbers on the outer face of the side wall. The barbs may deform when in contact with another region of the blower housing. The barbs may prevent or reduce the transmission of forces from the blower and/or motor and/or prevent or reduce the transmission of vibration to the blower housing. The barbs may be a conical or cylindrical shape. Other shapes may also be used if suitable. The length of the barbs may vary, for example, the barbs may be approximately 2 mm long. The barbs may be constructed of an elastic material or other suitable materials so that they can substantially recover to their original shape after being loaded, so that they may absorb a second force or further forces. The barbs may be constructed of a viscoelastic material. The barb or shock absorber may be a single continuous skirt around the bladder. The barbs or shock absorbers may also comprise multiple, individually spaced or combinations thereof, discrete elements around the bladder.

1.1.2 Certain Embodiments of the Motor Isolation

Electromagnetic waves may be transmitted directly to the patient due to the direct coupling of the motor to the patient. A shunt gate may be added to the motor to shield the patient from the electromagnetic fluxes. The shunt gate may be a ferrous material positioned between the patient and the motor.

In addition, in certain embodiments, the motor may be positioned as far away from the patient as the configuration or set up of the system will allow. For example, the arrangement shown in FIG. 86 shows the blower positioned such that the motor will be close to the patient's head. However, it may be possible to turn the blower upside down or 180° rotated so that the motor is positioned further away from the patient's head to reduce the effects of electromagnetic radiation.

1.1.3 Certain Embodiments of the Blower Inlets

The blower may be provided with an inlet or inlets. In addition to inlet(s) on the blower, the blower housing may include an inlet or inlets.

In certain embodiments, the blower and blower housing inlets may be configured so as to minimize occlusion by bed clothing or other items as this may choke the blower. The inlets of the blower housing may be positioned on the same plane as the face of the patient when in use. Alternatively, the inlet or inlets of the blower housing may be positioned at the top or superior position such that its radial axis is substantially vertically upwards. Alternatively, the blower housing inlets may be towards the lateral or side portions of the blower housing. In this arrangement there may be multiple inlets so that if the patient rolls on to their side and occludes one or more inlets, other inlets positioned opposite or distal from the occluded inlets will still be open for receiving air. Other suitable arrangements may also be used.

The blower or blower housing inlet(s) may have a filter (for example, a fibrous filter or a foam) to filter incoming gases.

The blower and/or blower housing inlet may further have a snorkel or lead-in, to extend the length of the air path coming into the blower. The longer the air path to the blower, the more laminar the flow of the gases and therefore the quieter the system. The snorkel or lead-in may further alter the position of the air intake or inlet, to a position that is unlikely to be occluded. For example, the blower inlet may be positioned at the rear or back portion of the blower or blower housing. If the patient is lying on their back, it is likely that such an inlet may be occluded by bed clothes, or a pillow. A snorkel or inlet extension may therefore be provided to this inlet position to alter the direction of this air inlet. Alternatively, a snorkel or extended inlet tube may be provided to position the inlet away from the patient's ears. Alternatively, a snorkel or extended inlet tube may be provided to position the inlet away from the patient's hair.

The inlet and/or snorkel may have rounded edges to allow the smooth flow of gases into the inlet.

The air inlet may have a substantially oval or circulate cross section. This profile may have a lower noise output than a square inlet for example. However, other suitable cross sections are possible.

The inlet to the blower may be spaced away from the blower housing or muffler. In certain aspects, there may be, for example, at least a 10 mm gap between the inlet to the blower and the housing wall. In certain aspects, there may be, for example, at least a 5 mm gap between the inlet to the blower and the housing wall. In certain aspects, there may be, for example, at least a 2 mm gap between the inlet to the blower and the housing wall. This is to prevent or minimize choking the blower.

The cross section of the inlet or inlets of the blower housing may be sufficient to ensure the function of the blower, that is, to avoid choking the blower. The inlet(s) of the blower housing may have a cross section that may be equal to or greater than the cross section of the outlet of the blower. In an exemplary embodiment, the cross section of the inlet(s) may be 150-400 mm$^2$. Preferably, the cross section of the inlet(s) may be 100-200 mm$^2$.

1.1.4 Certain Embodiments of the Blower Outlet

The blower may have an outlet or air exhaust, for delivering the pressurized gas to the air delivery tube. The outlet of the blower may be coupled to the housing or muffler by a coupling tube. The coupling tube may be flexible. The couple tube may be made of a polymer, such as silicone. The wall of the coupling tube may be 1.5 mm thick. Preferably, the wall of the coupling tube may be less than 5 mm. Most preferably, the wall of the coupling tube may be less than 2 mm. The coupling tube may prevent or minimize the blower from movement or travel within the housing. The coupling tube may act: as a dipole cancellation or absorb vibration from the blower. The coupling tube may prevent hard coupling of the blower to the blower housing, thereby preventing or minimizing the transmission of vibration or noise to the blower housing.

The outlet of the blower housing may be coupled to an air delivery tube. The air delivery tube connects the blower housing to the patient interface. The outlet of the blower housing may include a connection ring or portion of a tube for connection or coupling with the air delivery tube. The connection ring may interface with the air delivery tube by mechanical means such as a taper lock, push fit, snap fit or other suitable means.

In a further alternative, the tube connecting the outlet of the blower may directly couple to the air delivery tube, such that there is no intermediate connection with the blower housing.

1.1.5 Certain Embodiments of the Blower Housing

The blower may be positioned in housing or positioned in a damping structure to reduce noise output from the device and to position the blower on the patient. In certain embodiments, the housing should be the largest volume possible to muffle noise output from the blower, however should also be the smallest volume possible to reduce the weight and size of the system to reduce visual bulk and avoid discomfort to the patient.

In certain embodiments, the blower may be small and compact so as to minimize the obtrusiveness and increase the comfort of the system. The blower may be constructed and arranged to have an axial inlet and a tangential outlet to minimize the size of the blower. Alternatively, the blower may be constructed and arranged to have an axial inlet and an axial outlet to minimize noise.

In certain embodiments, the height of the blower or blower housing may be as minimal as possible to reduce the visual bulk of the system and minimize the moment or torque produced by the component. In certain embodiments, the height of the blower or blower housing may be as minimal as possible to reduce the visual bulk of the system. In certain embodiments, the height of the blower or blower housing may be, for example, less than 100 mm, less than 80 mm, less than 60 mm, less than 40 mm, or less than 20 mm. In certain embodiments, the height of at least a portion of the blower or at least a portion of blower housing may be, for example, less than 100 mm, less than 80 mm, less than 60 mm, less than 40 mm, or less than 20 mm.

In certain embodiments, the volume of the housing may be, for example, less than 350 cm$^3$, less than 300 cm$^3$, less than 250 cm3 or less than 200 cm$^3$.

In certain embodiments, the blower housing including the blower and excluding the weight of the batteries may weigh, for example, less than 500 g, less than 300 g, less than 250 g, less than 200 g, or less than 150 g.

In certain embodiments, the noise output by the blower and housing may be, for example, less than 70 dBA, less than 60 dBA, less than 50 dBA, less than 46 dBA, or less than 40 dBA. In certain embodiments, the noise output by the blower and housing may be approximately between 44-46 dBA. In certain embodiments, the noise output by the blower and housing may be, for example, about 37-45 dBA. In certain embodiments, the noise output by the blower and housing may be less than 40 dBA. In certain embodiments, the noise output by the blower and housing may be, for example, between 30 dBA and 70 dBA, 35 dBA and 60 dBA, 40 dBA and 60 dBA, 40 dBA and 50 dBA, or 43 dBA and 46 dBA.

In certain embodiments, the wall thickness of the housing or muffler may be optimized for noise and/or vibration damping as well as weight and size. In certain embodiments, the wall thickness of the housing or muffler may be, for example, less than 8 mm, less than 7 mm, less than 5 mm, or less than 3 mm. In certain embodiments, the wall thickness of the housing may be, for example, 3 mm. In certain embodiments, the wall thickness of the housing or muffler may be, for example, between 8 mm and 3 mm, between 6 mm and 3 mm or 7 mm and 3 mm.

In certain embodiments, the noise output of the blower or blower housing (in dBA), the height of the blower or blower housing (in mm), the volume of the housing (in cm$^3$), the housing weight (in grams), the wall thickness of the housing or muffler (in mm) may be combined in various combinations to provide PAP systems with acceptable visual bulk, acceptable moment or torque, acceptable weight, acceptable noise output, acceptable noise and/or vibration damping or combinations thereof. The housing may be constructed or formed from a polymer such as polypropylene, polyethylene, thermoplastics such as ABS (acylonitrile butadiene styrene), nylon (including glass reinforced nylon). Alternatively the housing may be produced from a metal such as stainless steel. Alternatively, the housing may be constructed from a combination of metal and polymer, for example metal over moulded with polymer portions.

The top face or portion of the housing (i.e., the region positioned furthest from the patient when in use) may be weighted or include securement means to prevent vibration of the surface. Securement means may include ribs, thickened wall sections or additional weights added to the region. Alternatively, the top portion of the blower housing may be constructed of a material that has a high density. Combinations of these securement means and higher density materials may also be used.

The blower housing may be separate or provide an isolated region where the PCB (printed circuit board) may be positioned. This may be to prevent the PCB from being in the air path of the patient.

In certain embodiments, the blower housing may be shaped to conform to the patient's head or body. For example, the lower portion of the blower housing facing the patient's head may be curved or generally dome shaped to match the crown of a patient's head or to match the front portion of a patient's head between the crown and the forehead of the patient. In addition, the blower housing may be curved or dome shaped to prevent transmission of vibration or drumming. Additionally, the blower housing may have curved walls to protect the blower. The curvature of the housing may be shaped to guard the blower, such that if the system were to be dropped the curved surface would be hit first rather than a face of the housing adjacent the blower (e.g., see FIG. 86). The housing portion may also include various baffles or ridges to muffle transmitted or emitted noise.

The blower housing may include location features such as cut outs or ribs to position the blower and/or other elements within the blower housing.

The blower housing may be sealed. The blower housing may be hot plate welded, ultra sonically welded or otherwise sealed.

The blower housing may include a light to indicate the status of the blower. The light may indicate if the blower is on or off. The light may indicate if the battery is charging, charged or running out. The light may indicate if there is a fault in the system. There may be multiple lights on the blower housing.

The blower housing may also include an on and off switch. The blower housing may also include a pressure ramp for the patient and/or clinician to adjust the pressure delivered by the system.

1.1.5.1 Certain Embodiments of a First Blower Housing

FIGS. 87-91 show certain embodiments of a blower housing 2000. Blower housing 2000 may be substantially circular when viewed from the top (e.g., see FIG. 90). Blower housing 2000 may include a first outlet portion 2010 on its lower portion 2001 and a second outlet portion 2020 on its upper portion 2002 (e.g., see FIG. 91). The outlet portions 2010 and 2020, when positioned adjacent each other, may form an orifice for the outlet of the blower to be placed in (e.g., see FIG. 90).

Upper portion 2002 may also include an inlet 2050. Inlet 2050 may optionally be positioned on lower portion 2001, or there may be multiple inlets 2050 on either or both of upper portion 2002 and lower portion 2001 or any given surface.

The blower housing may be 20-50 mm high. The blower housing may be, for example, 20-40 mm high. The blower housing may be, for example, 30-40 mm high. Other heights may also be used.

The blower housing may have, for example, a diameter of less than 100 mm, a diameter of less than 90 mm, a diameter of less than 80 mm, or a diameter of less than 70 mm. Other diameters may also be used.

1.1.5.2 Certain Embodiments of a Second Blower Housing

FIGS. 92-99 show a certain embodiments of a blower housing 3000. Blower housing 3000 is substantially a semi-oval shape but may be other shapes so as to fit the blower within. Blower housing 3000 has a top portion 3002 and a bottom or lower portion 3001. Lower portion 3001 has a curved face or region 3005 (e.g., see FIG. 93) that may abut or rest on the patient's crown or apex of the head in use. Alternatively, the blower housing may be adapted to abut or rest on the front portion of a patient's head between the crown and forehead regions.

Caps or clips 3030 may be placed around the top portion for securing the top portion 3002 to the bottom portion 3001. Clips may latch or secure onto a face or surface on bottom portion 3001.

Bottom portion 3001 may also have an outlet 3010 for connection with an air delivery tube for supply a patient interface with breathable gas. Outlet 3010 may be substantially cylindrical, however other shapes are also possible. Outlet 3010 may extend to the inner portion of the blower housing 3000 to a connection portion 3015 (e.g., see FIGS. 98 and 99). Connection portion 3015 may interface with a second tube and/or blower outlet for conveying the pressurized gas from the blower to the air delivery tube.

Figure 97:
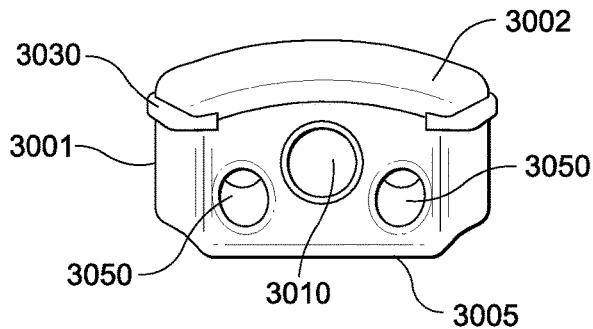
FIG. 97 is a front view of the blower housing shown in FIG. 92.
Figure 98:
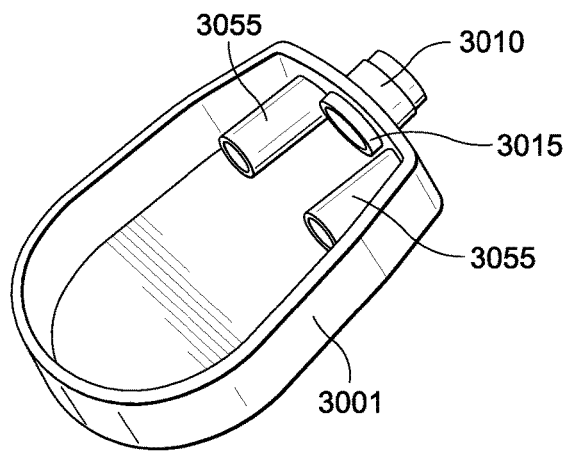
FIG. 98 is a top perspective view of the blower housing shown in FIG. 92, wherein an upper portion of the housing has been removed to show the lower portion and the interior.
Figure 99:
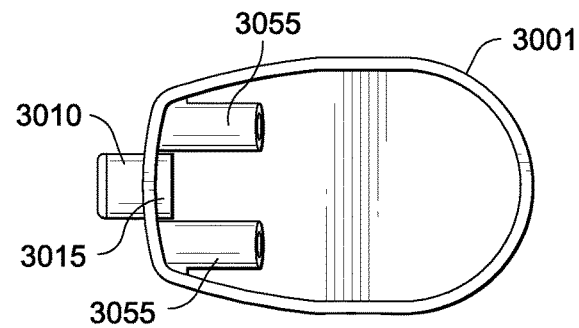
FIG. 99 is a top view of the lower portion shown in FIG. 98.
Figure 100:
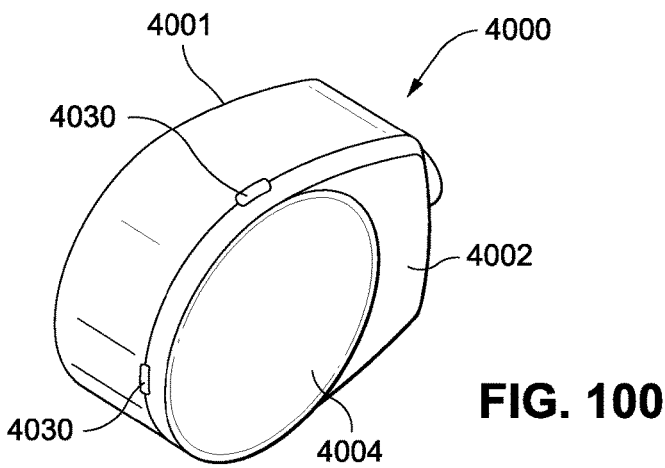
FIG. 100 is a perspective view of a blower housing according to certain embodiments.

Blower housing 3000 may also have inlets 3050, as shown in FIG. 97. Inlets 3050 may be substantially circular as shown, however, other shapes are also possible. Inlets 3050 may lead to lead-ins, snorkels, conduits or feeders 3055 (see FIG. 98) for delivering incoming air to the inlet of the blower. Conduits 3055 may be as long as possible, or suitable, so as to encourage laminar flow of the incoming gases, thereby reducing the noise and increasing the efficiency of the system. Circular or rounded inlets may encourage laminar air flow and thereby reduce noise and vibration. In this embodiment, the inlets are substantially cylinder-shaped, however, other shapes are possible.

The blower housing may be, for example, 20-50 mm high, 20-40 mm high, or 30-40 mm high. Other heights may also be used.

The blower housing may have, for example, a volume of approximately 200-300 cm3. Other volumes may also be used.

1.1.5.3 Certain Embodiments of Third Blower Housing

Figure 101:
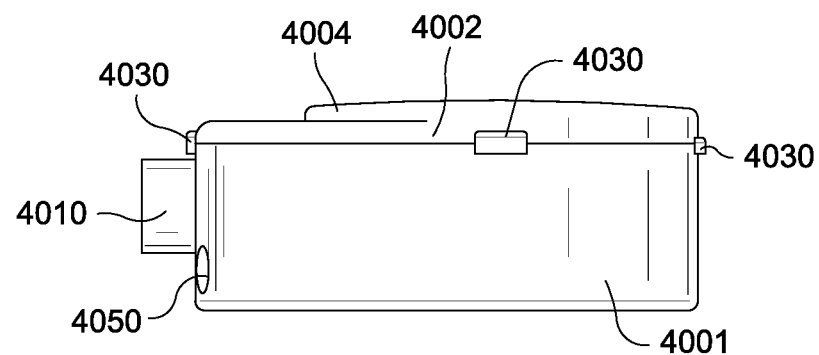
FIG. 101 is a side view of the blower housing of FIG. 100.
Figure 102:
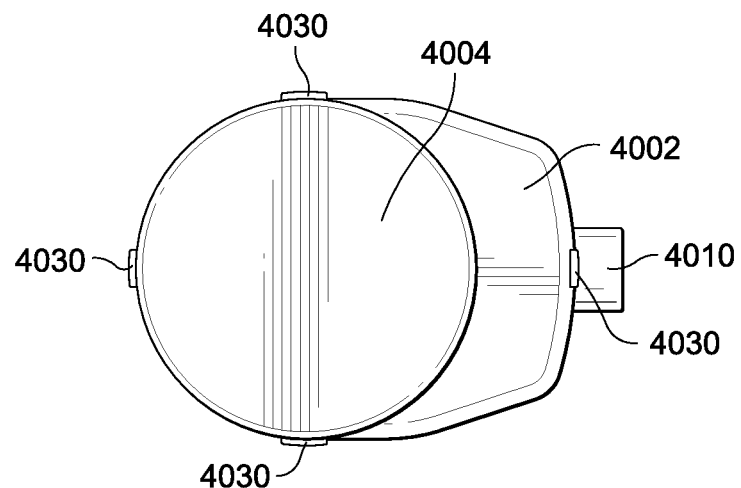
FIG. 102 is a top view of the blower housing of FIG. 100.
Figure 103:
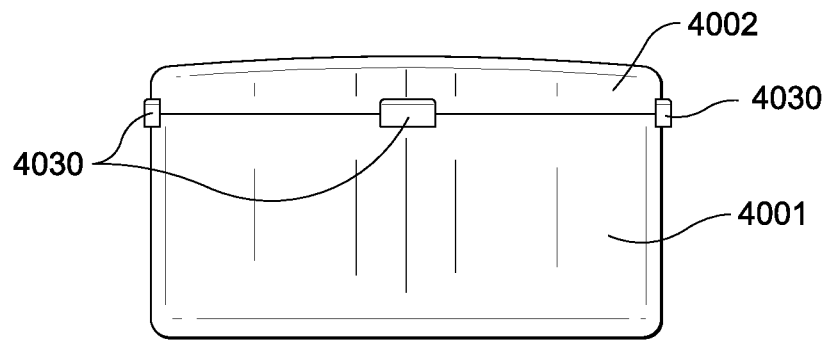
FIG. 103 is a rear view of the blower housing of FIG. 100.
Figure 104:
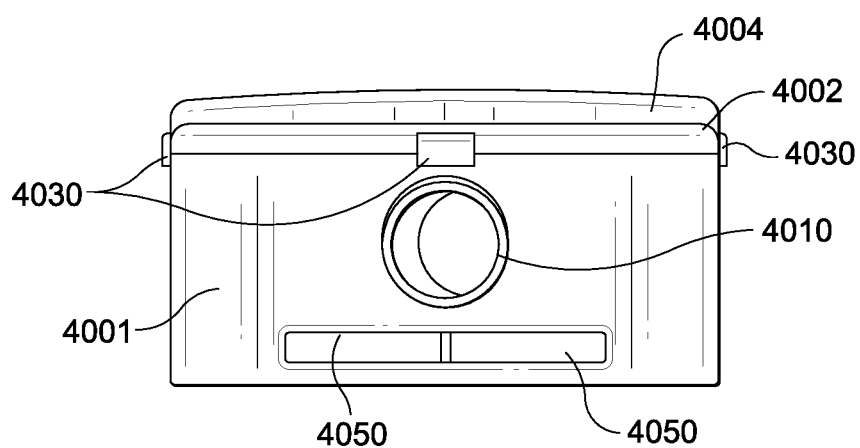
FIG. 104 is a front view of the blower housing of FIG. 100.

FIGS. 100-106 show another embodiment of the present technology. Blower housing 4000 includes a top portion 4002 and a bottom portion 4001. Top portion 4002 further comprises a raised or elevated portion 4004 to accommodate the blower. The blower may be positioned underneath or within elevated portion 4004. FIG. 101 shows elevated portion being higher than the rest of the top portion 4002.

Caps or clips 4030 are placed around the top portion for securing the top portion 4002 to the bottom portion 4001. Clips may latch or secure onto a face or surface on bottom portion 4001.

Bottom portion 4001 may also have an outlet 4010 for connection with an air delivery tube for supply a patient interface with breathable gas. Outlet 4010 may be substantially cylindrical, however other shapes are also possible. Outlet 4010 may extend to the inner portion of the blower housing 4000 to a connection portion 4015. Connection portion 4015 may interface with a second tube and/or blower outlet for conveying the pressurized gas from the blower to the air delivery tube. Ribbed or necked region 4016 (FIG. 106) may extend around a portion of the circumference of the connection portion 4015 to enable retention between the connection portion 4015 and a second tube or blower outlet.

Figure 105:
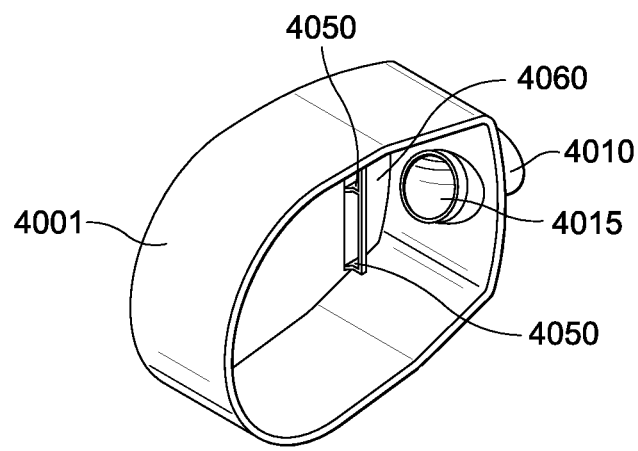
FIG. 105 is a perspective view of the blower housing shown in FIG. 100, wherein an upper portion of the housing has been removed to show the bottom portion and the interior.
Figure 106:
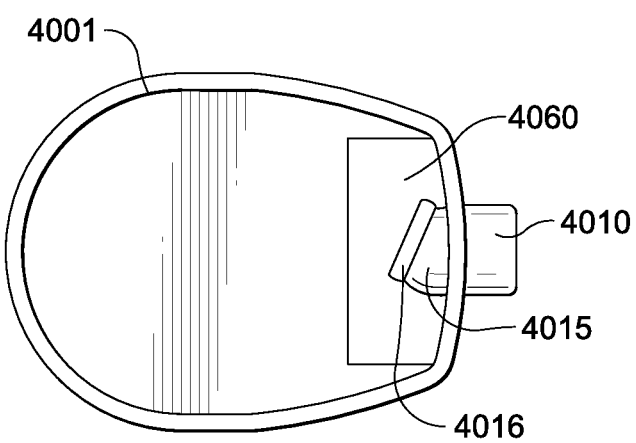
FIG. 106 is a top view of the lower portion shown in FIG. 105.
Figure 107:
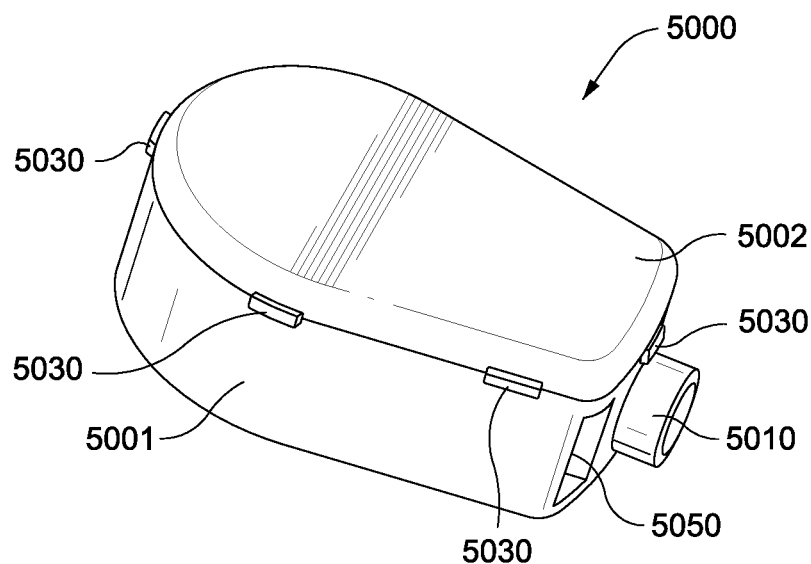
FIG. 107 is a perspective view of a blower housing according to certain embodiments.
Figure 108:
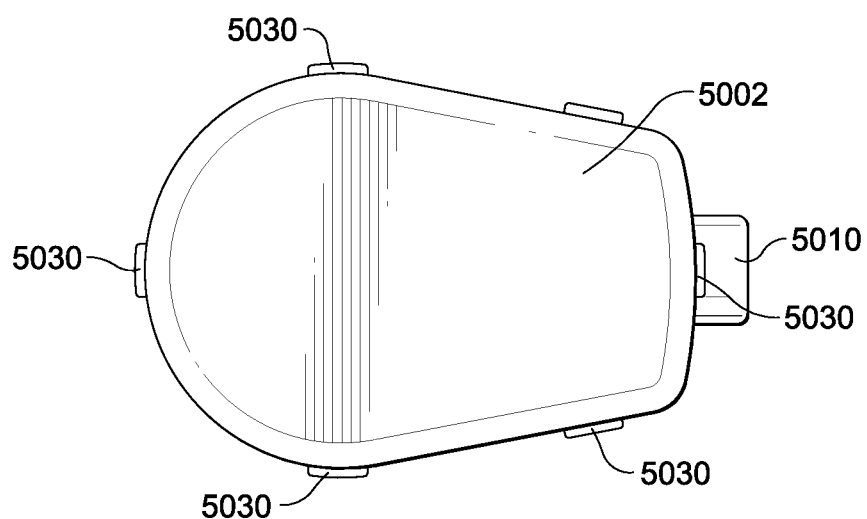
FIG. 108 is a top view of the blower housing of FIG. 107.
Figure 109:
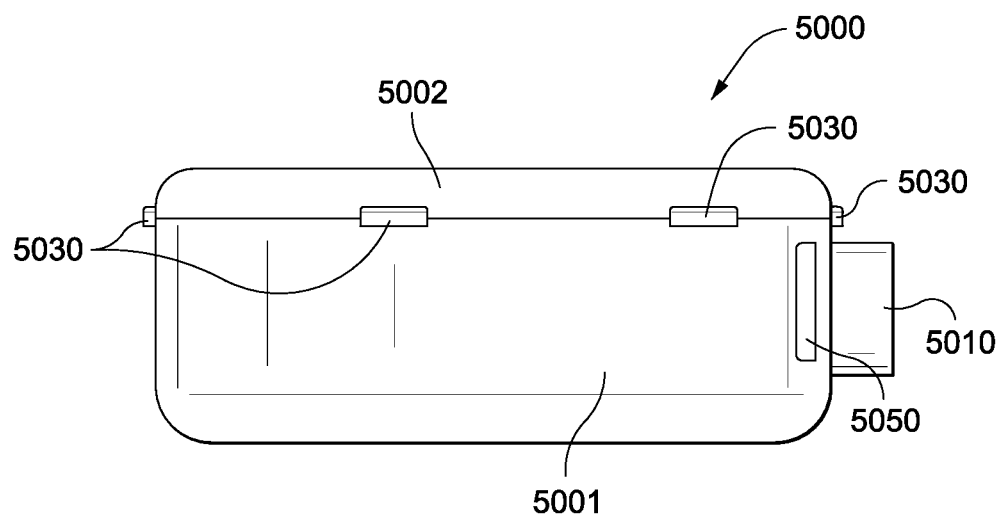
FIG. 109 is a side view of the blower housing of FIG. 107.
Figure 110:
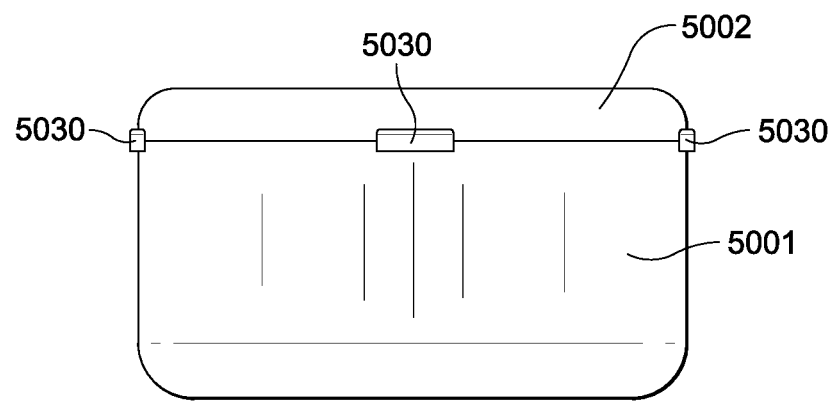
FIG. 110 is a rear view of the blower housing of FIG. 107.

Bottom portion may also comprise inlets 4050 (FIG. 105). Inlets 4050 may be substantially rectangular shaped and may be positioned underneath or below the outlet 4010, although it should be appreciated that other shapes and locations for the outlets may be used. Inlets 4050 may extend within the inner portion of the blower housing 4000. A shelf or platform 4060 may extend along a portion of the inner portion of the blower housing to encourage the incoming gases to develop laminar flow, thereby reducing the noise from the system.

1.1.5.4 Certain Embodiments of a Fourth Blower Housing

A blower housing according to certain embodiments is shown in FIGS. 107-112.

Blower housing 5000 may have top portion 5002 and bottom portion 5001. Top portion 5002 may include clips or attachment means 5030 similar to previous embodiments.

Bottom portion 5001 may also have an outlet 5010 for connection with an air delivery tube. Outlet 50 I 0 may extend within 1the inner portion of the blower housing 5000 as a connecting portion 5015. Connecting portion 5015 may connect to a second tube or outlet of the blower. Connection portion 5015 may also include a rib or neck 5016 (FIG. 112) for ease and retention of attachment to a second tube or blower outlet.

Figure 111:
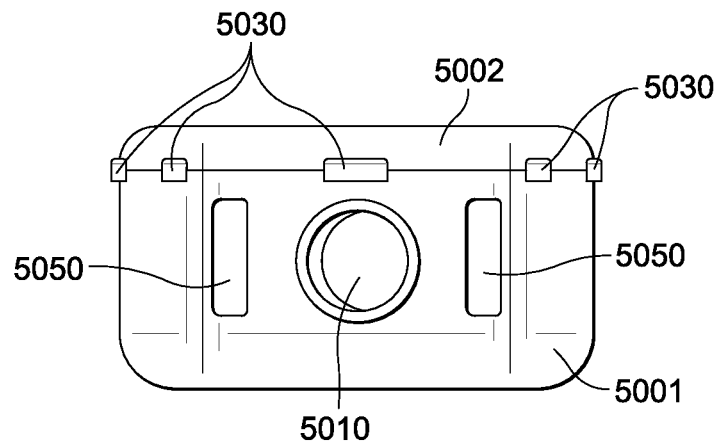
FIG. 111 is a front view of the blower housing of FIG. 107.
Figure 112:
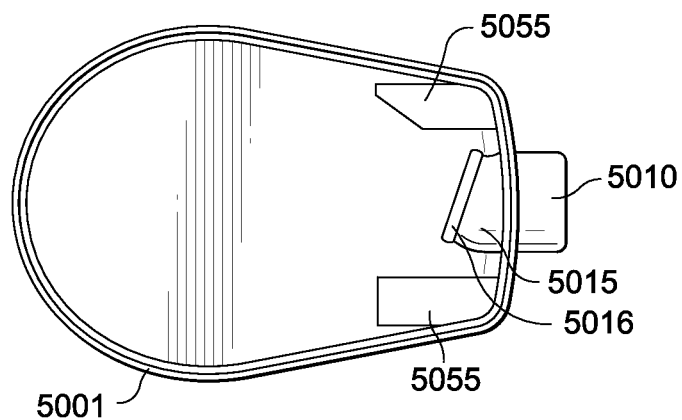
FIG. 112 is a top view of the blower housing shown in FIG. 107, wherein an upper portion of the housing has been removed to show the bottom portion and the interior.
Figure 113:
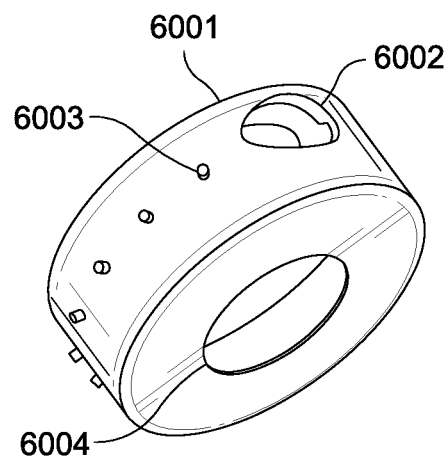
FIG. 113 is a perspective view of an enclosure for a blower or air generator according to certain embodiments.
Figure 114:
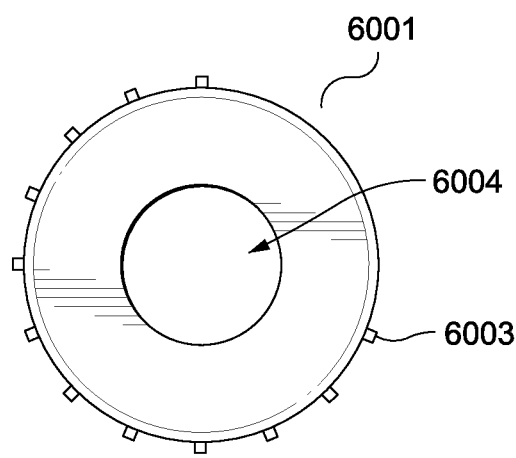
FIG. 114 is a bottom view of FIG. 113.
Figure 115:
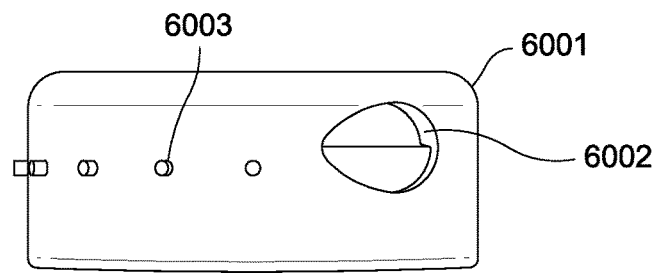
FIG. 115 is a side view of FIG. 113.
Figure 116:
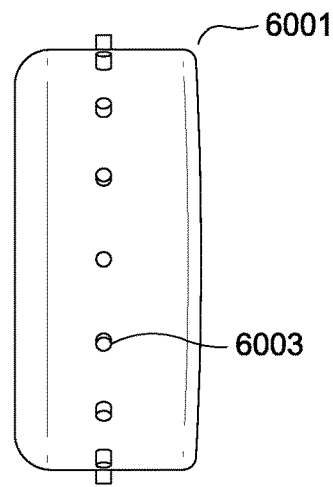
FIG. 116 is an alternate side view of FIG. 113.
Figure 117:
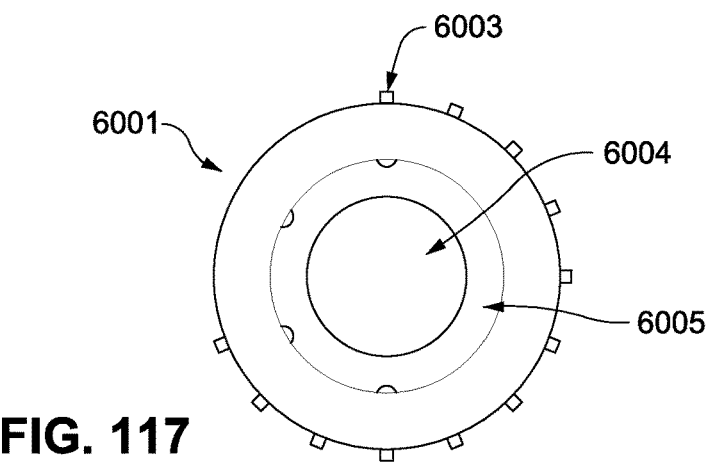
FIG. 117 is a top view of FIG. 113.

Bottom portion 500 I may include inlets 5050 (FIG. 111). Inlets 5050 may be substantially rectangular shaped and extend on either side of the outlet 50 I 0, although it should be appreciated that other shapes and locations for the outlets may also be used. Inlets 5050 may extend to the inner portion of the blower housing as ducts 5055, to allow incoming gases to develop into laminar flow.

The inlets of the embodiments may be oriented in a direction normal to the plane of the patient's face or extending upwards from the head of the patient. Inlets facing either the side of the patient's head or back of the patient's head may be avoided in situations where bed clothes or pillows are likely to or could possibly occlude or limit the air flow into the blower or pump. However, other configurations may also be used if desirable.

Also, the inlets may include redirection snorkels or lead-ins 5055 to redirect the air incoming air flow. Wherein the inlets are forward facing or extending in direction normal to the patient's face. The air flow may be redirected in a vertical orientation extending up and away from the patient's head. Wherein inlet facing upwards, the configuration may give rise to an additional advantage of a reduction in air flow noise perceived by the user or patient's ears.

In certain embodiments, the blower and the motor are decoupled, or substantially decoupled, from the headgear and patient's head. The better the decoupling, the better the reduction of transmitted vibrational noise carried by the patient's skull or the headgear. Various forms of suspending the blower or the motor may be effective in achieving at least a portion of decoupling.

1.1.6 Certain Embodiments of a Blower Encapsulation

The blower may be decoupled from the interior of the housing by foam or silicone suspension systems. Other suitable suspension systems may also be used. A silicone suspension system, according to certain embodiments, is depicted in FIGS. 113-117.

The blower may include a motor and a fan that are at least partially encapsulated in an elastic polymer jacket 6001. The jacket 6001 is adapted to absorb noise and vibration generated by the blower in use. The blower for use with this jacket may be a single stage centrifugal blower (not shown).

The jacket 6001 includes a first aperture 6002 positioned in the side of the jacket 6001 adapted to receive the tangential outlet of the blower.

The jacket may also include additional apertures on the top 6005 and bottom 6004 of the jacket 6001. Either of these apertures may receive the inlet of the blower.

The jacket 6001 is adapted to be: connected or joined to upper portion of the housing in a manner to suspend the blower away from the bottom portion of the housing and the side wall of housing. This may decouple, or substantially decouple, the blower from the housing and receive transmitted noise and vibration. The top aperture 6005 may be adapted to engage a respective upper mating portion of the housing and the bottom aperture 6004 may be adapted to receive the inlet for the blower.

There may be at least a 5 mm clearance gap between the inlet of blower and inside surface of the lower portion of the housing. This clearance gap may be constructed and maintained by the jacket 6001 suspending the blower.

Further, the side walls of the jacket 6001 include a series of vibration absorbing protrusions 6003. In this embodiment, there are twelve protrusions arranged around the circumference of the jacket 2001. However, other suitable numbers of protrusions may be provided. The protrusions limit sideways vibration of the blower and reduce transmitted vibration to the side walls of the housing.

The jacket may be made of relatively soft, elastic material such as moulded silicone, but other materials may also be used for this purpose.

1.1.7 Certain Embodiments of a Blower within the Housing

FIGS. 118-122 illustrate an exemplary embodiment of a blower 7050 within a blower housing 7000, which blower housing acts as muffler in use. The blower housing 7000 may include one or more aspects similar to that shown in FIGS. 92-99 described above.

As illustrated, the blower housing 7000 includes a bottom portion 7001 and a top portion 7002. The bottom portion 7001 includes a curved surface 7005 adapted to conform to the contours of the patient's head. A seal may be provided between the top and bottom portions. Also, the top and bottom may be secured to one another by a cap, clips, ultrasonic welding or combinations thereof.

The bottom portion 7001 includes an outlet 7010 adapted to connect to an air delivery tube. The outlet 7010 extends to an inner portion of the blower housing to a connection portion 7015. The connection portion 7015 interfaces with a tube member 7020 communicated to the outlet of the blower 7050.

Figure 120:
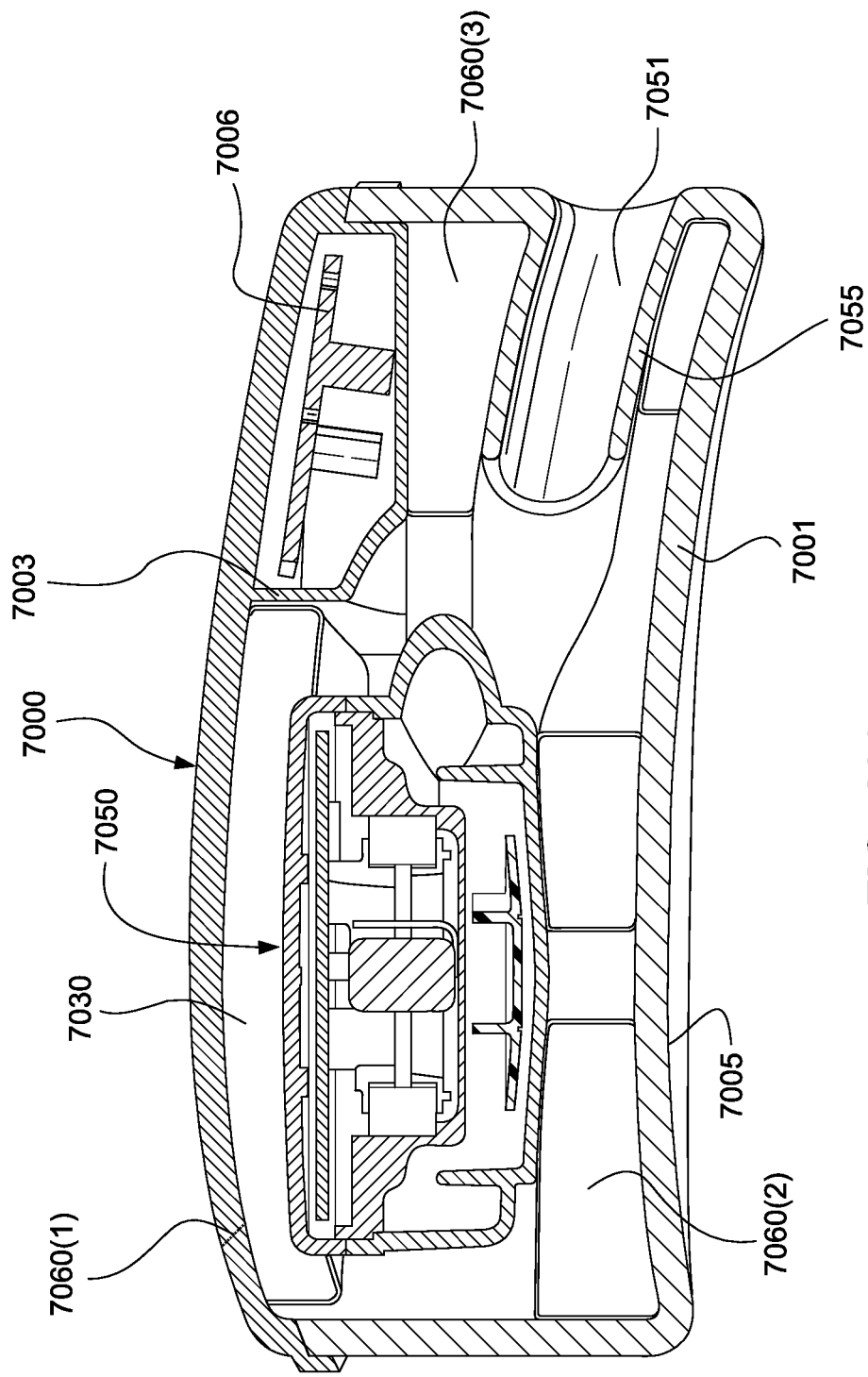
Figure 121:
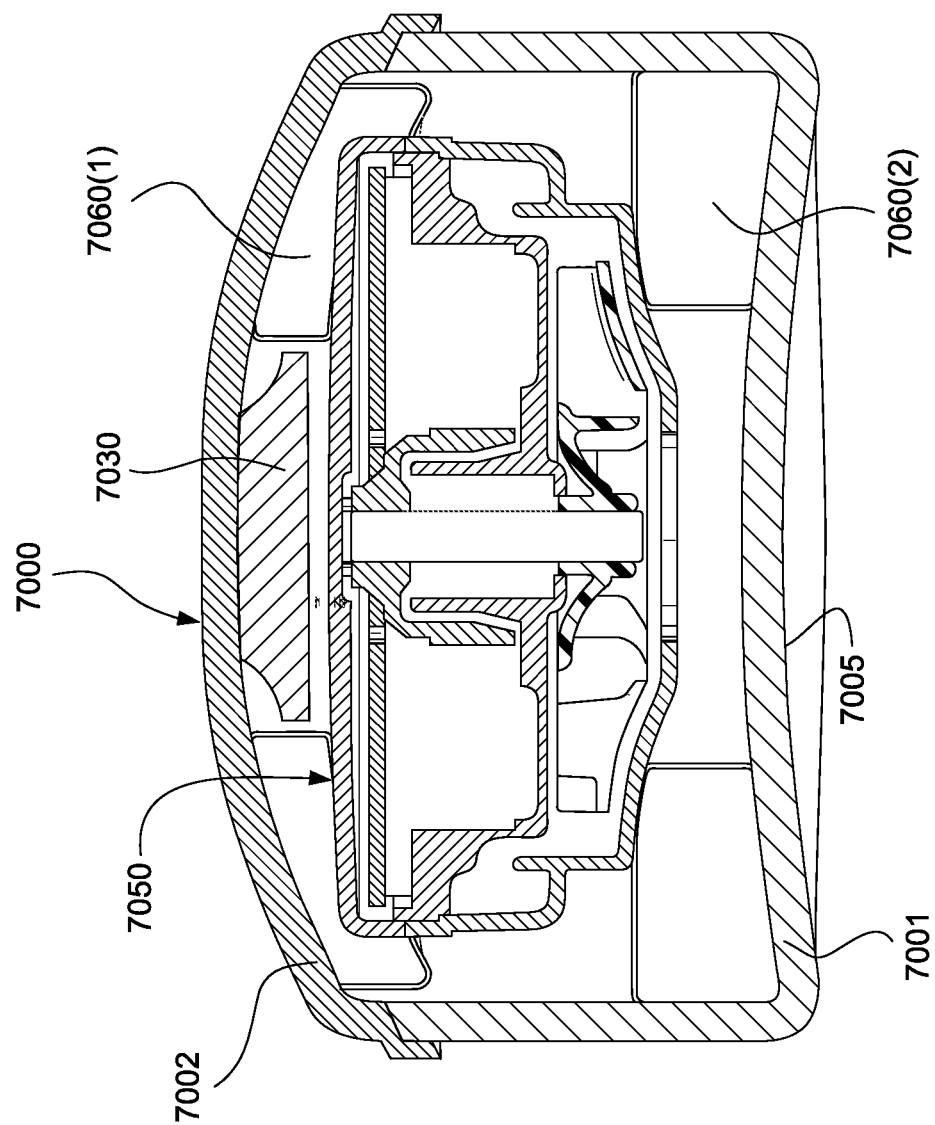
Figure 122:
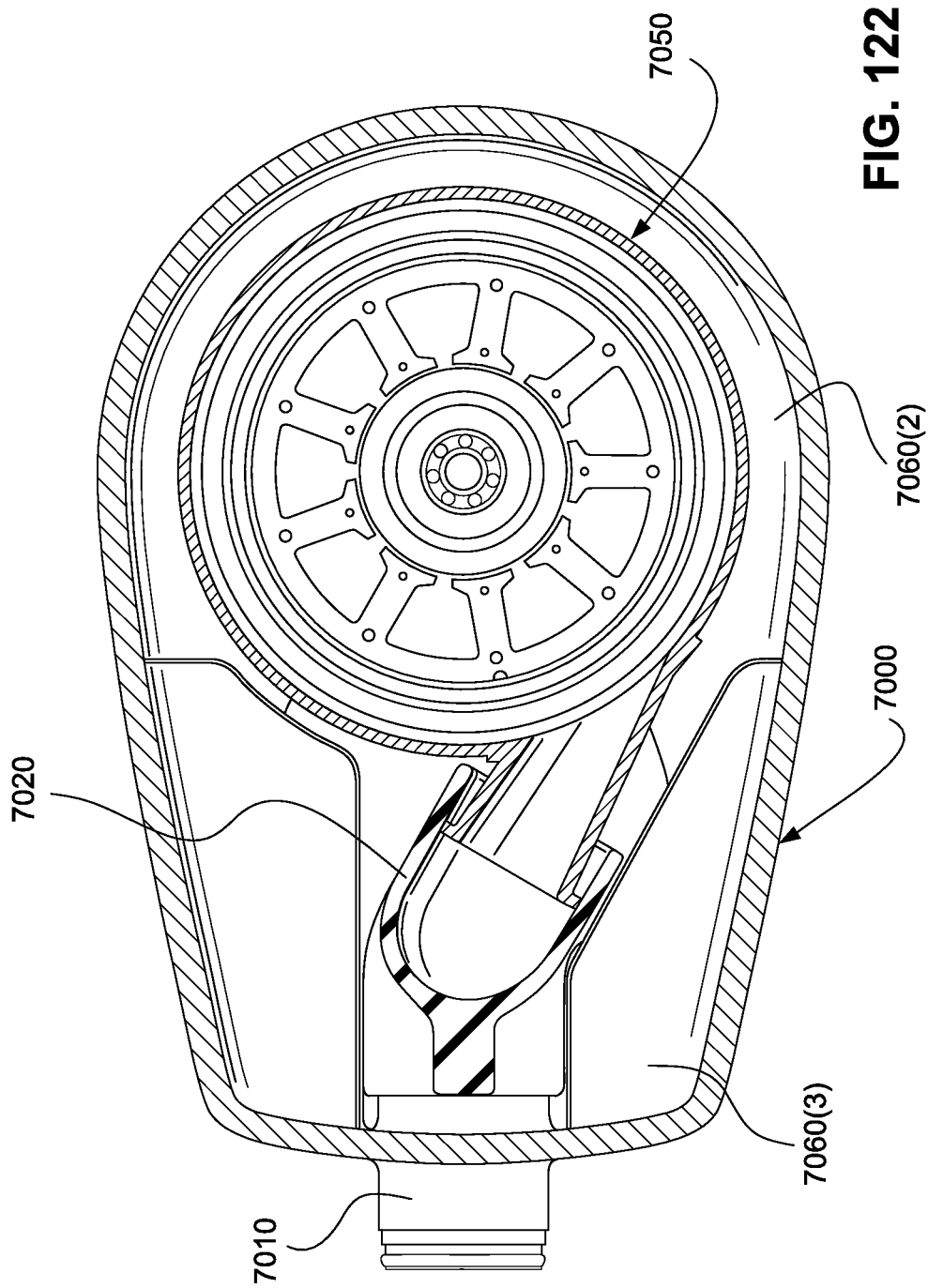

The bottom portion 7001 also includes two inlets 7051, one of which is shown in FIG. 120. As illustrated, each inlet 7051 leads to conduits or feeders 7055 for delivering incoming air to the inlet of the blower.

The top portion 7002 includes a separating wall 7003 that provides an isolated region where the PCB 7006 (printed circuit board) may be positioned, e.g., to prevent the PCB from being in the air path. Also, a mass 7030 may be provided to the top portion 7002, e.g., to reduce vibration and prevent "drumming".

The top or bottom portion also includes a wire/cable exit (e.g., opening) for electrical connections.

The blower 7050 is supported within the blower housing 7000 by one or more foam portions (e.g., such as Accusorb™). The foam portions provide vibration damping, noise absorption, blower location, volume filling or combinations. However, such foam may be replaced with the silicone suspension and/or encapsulation system discussed elsewhere.

As illustrated, a foam portion 7060(1) is provided to the top portion 7002, a foam portion or foam circlip 7060(2) is provided along the bottom portion 7001, and a foam portion 7060(3) is provided along the inlets 7051. However, other foam portions may be provided.

The blower housing provides vibration isolation in use. For example, the foam portions include compliant foam adapted to compress and hold the blower in place from top to bottom. The foam portions 7060(1) and 7060(2) on the top and bottom portions limit the blower's vertical movement. Also, the circlip or c-shaped configuration of the foam portion 7060(2) on the bottom portion limits the blower's sideways movement. The tube member 7020 prevents back and forth movement of the blower. In addition, the mass 7030 on the top portion 7002 reduces the housing's vibration.

The blower housing provides radiated sound reduction in use. For example, the volume of the blower housing (e.g., about 200-300 cm3 (e.g., about 255 cm3) excluding the blower and PCB) functions as a muffler. The relatively long inlets 7051 reduce inlet noise. The foam portions act as sound absorbers and decouple the blower from the blower housing. The curved and domed exterior surfaces of the blower housing add to structural rigidity. Also, the wall thickness of the blower housing (e.g., 3 mm wall section (in one-shot polymer) helps reduce noise. The mass 7030 on the top portion 7002 prevents "drumming". In addition, the blower housing is fully sealed along the joint between the top and bottom portions 7002, 7001 and along the wire/cable exit.

Figure 118:
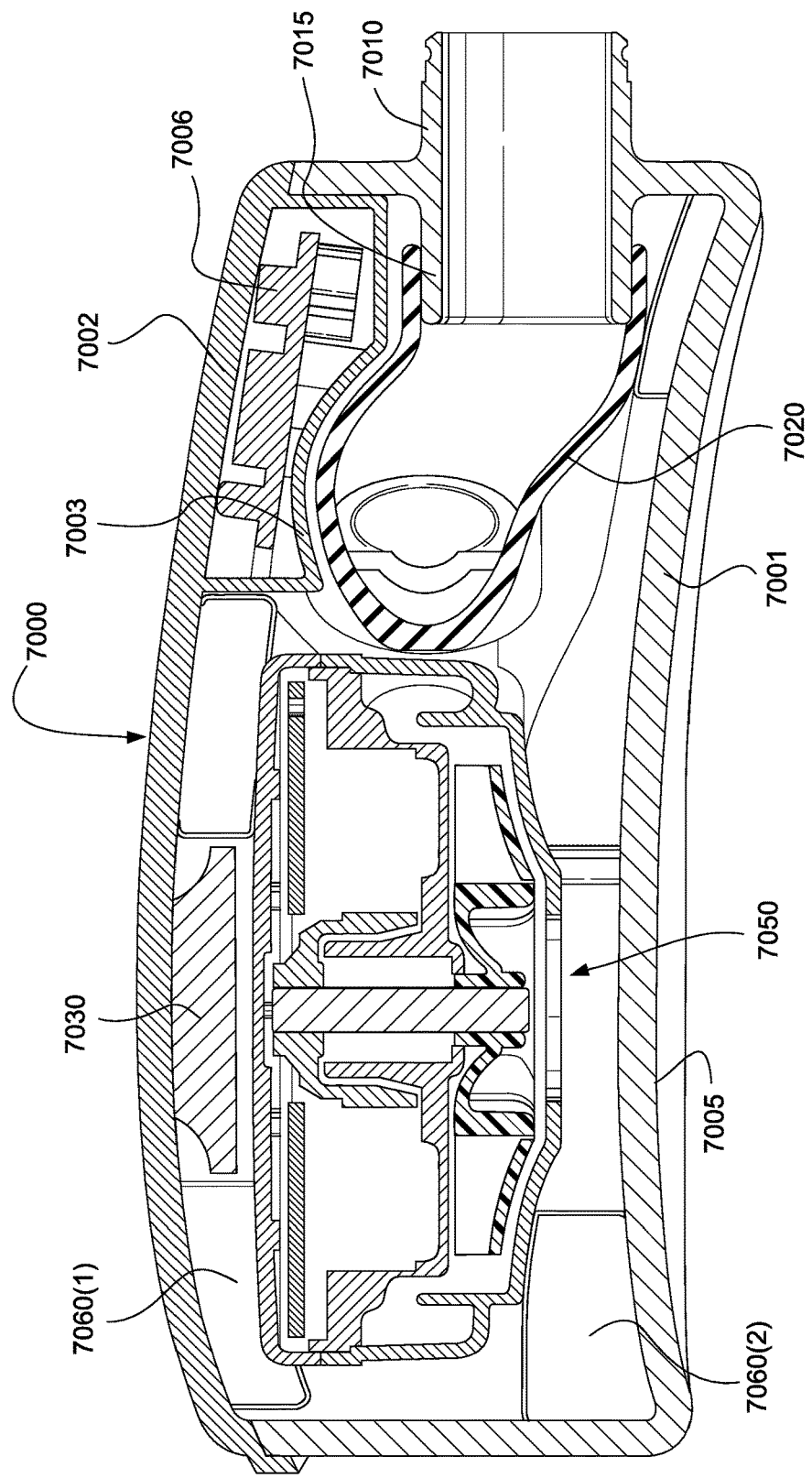
FIGS. 118-122 are alternative views of a blower within a blower housing according to certain embodiments.
Figure 119:
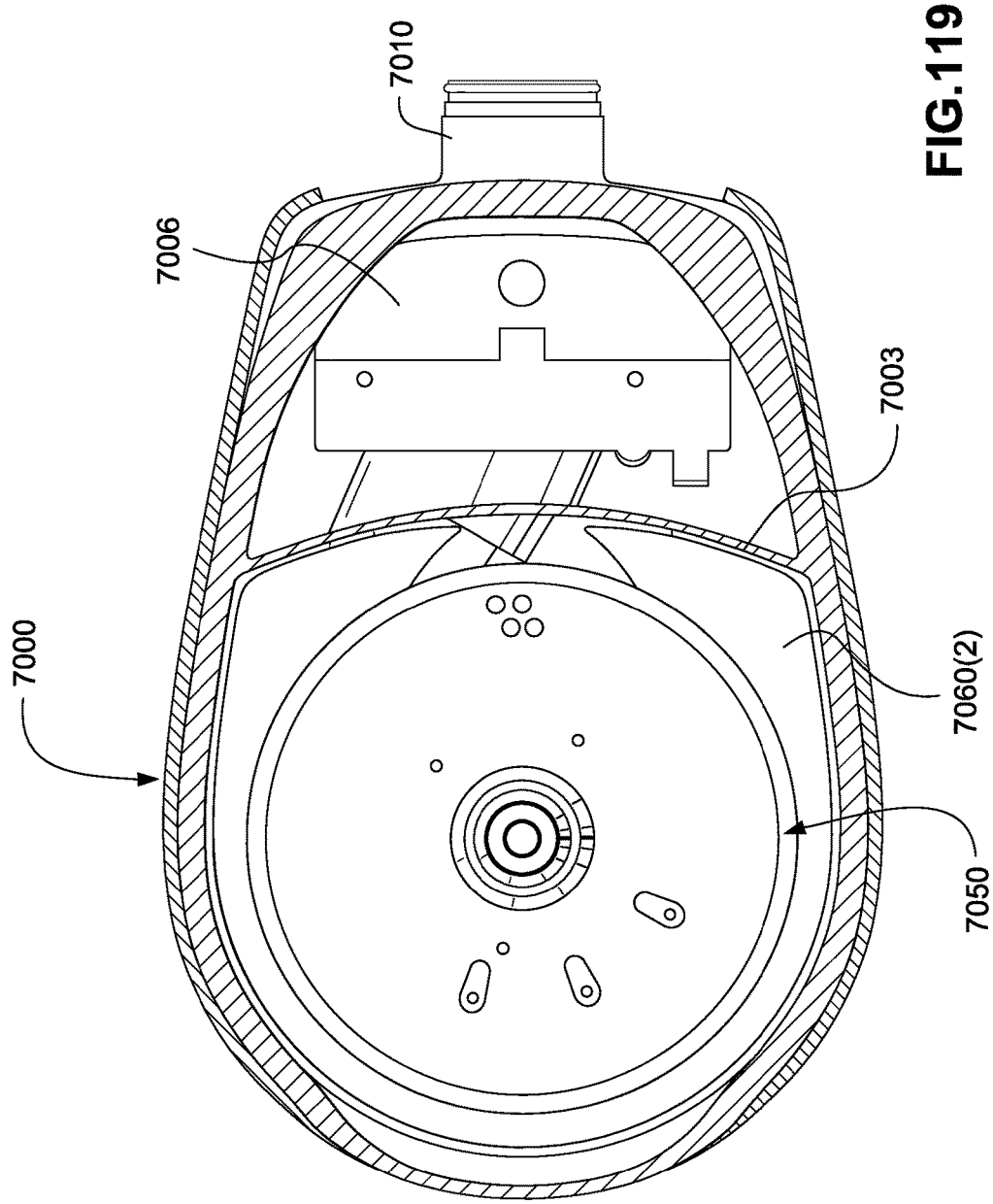

In the illustrated embodiment, the blower is inverted within the blower housing, i.e., the inlet to the blower is oriented downwardly as viewed in FIG. 118 for example. This arrangement reduces the overall height of the blower housing as it reduces or eliminates a clearance gap (e.g., of about 5 mm) on both sides of the blower. For example, a clearance gap is provided on the inlet side of the blower to be able to suck enough air, while a clearance gap is provided on the PCB side of the blower to reduce heat transfer to the patient's head. Inverting the blower means that a clearance gap may be eliminated on the PCB side of the blower as the gap is not needed to reduce heat transfer, and the blower can be positioned against the top portion of the blower housing or have a smaller clearance, e.g., less than 5 mm. Heat transfer from the top portion of the blower housing is not significant as this side does not come into direct contact with the patient's head.

The blower housing may be part of a wet air path, e.g., length of tubing connecting the patient's mask and the blower housing may be relatively short such that air expelled by the patient (likely having a high humidity level) may make the air path wet. It is noted that such back flow of air through the blower housing and blower is relatively minor as it may only occur for a relatively short time during peak exhalation. Accordingly, the components in the air path (e.g., foam portions 7060, tube member 7020, blower components (e.g., impeller, PCB, casing), top and bottom portions 7002, 7001, etc.) may be biocompatible or sealed from the airpath. For example, the foam portions within the blower housing may be adapted to be able to dry out, are biocompatible, and are not likely to break up or disintegrate during use. The system may include a first PCB mounted in the blower which provides computation and speed control and a second PCB governs power regulation, etc., and both PCBs are sealed against fluid ingress.

1.1.8 Certain Embodiments of a Flow Generator

Figure 137:
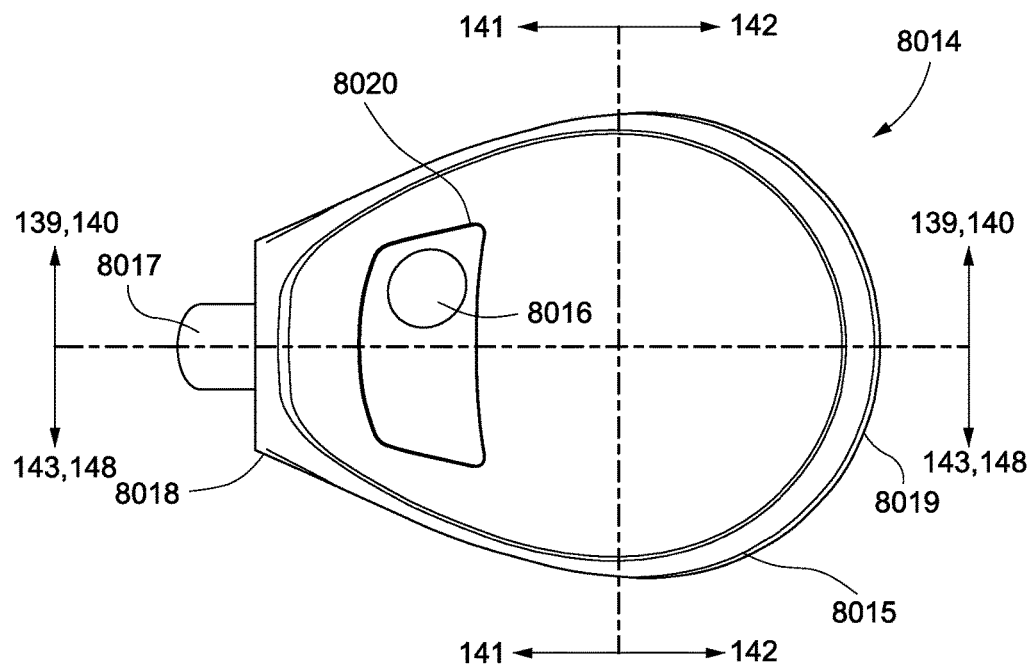
FIG. 137 shows a top view of a flow generator forming part of FIG. 130.

FIGS. 137-148 depict certain embodiments of flow generator 8014 for use with the PAP device or system. FIG. 137 depicts a top view of the flow generator 8014, wherein the housing 8015 is adapted to be joined to the extension portion 8003 of the headgear 8010. The housing 8015 includes a front facing portion 8018 and rear facing portion 8019. The front facing portion 8018 is adapted to be directed to the face of the patient, when in use.

Figure 145:
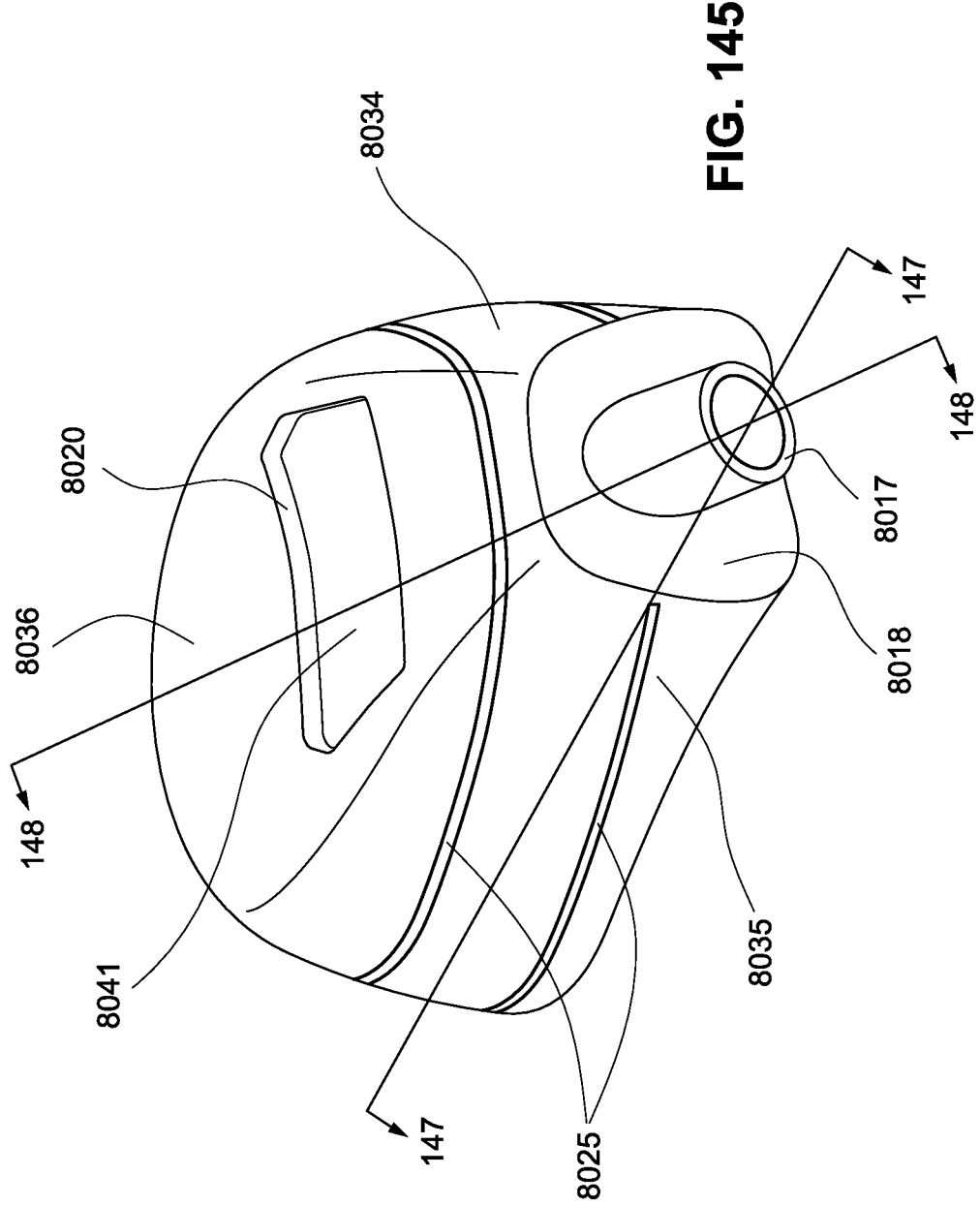
FIG. 145 shows a perspective view of certain embodiments of a flow generator.
Figure 146:
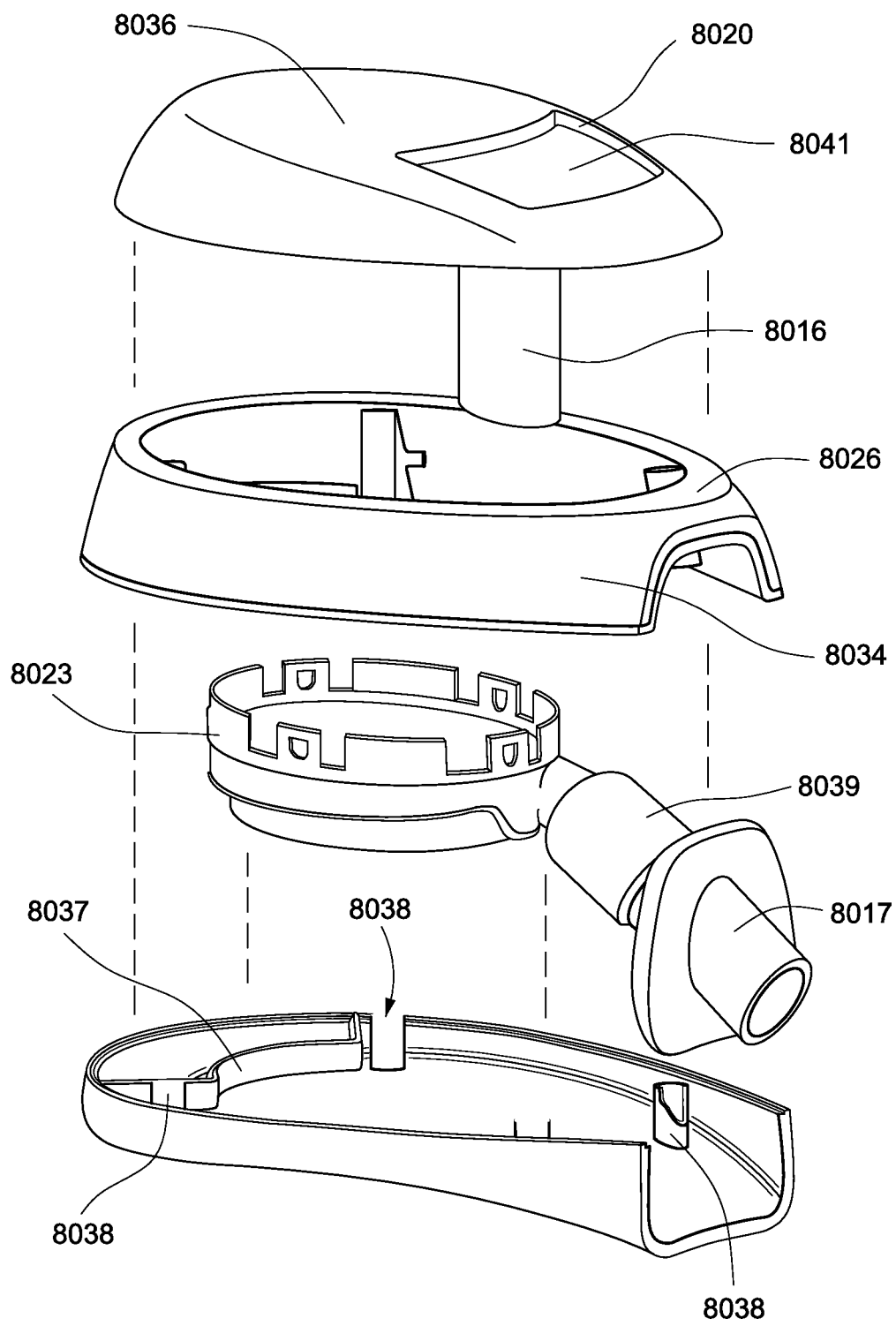
FIG. 146 shows an exploded view of FIG. 145.

The housing 8015 may include a three piece construction of an upper housing 8036, a middle housing 8034, and a lower housing 8035 as indicated in FIG. 145. The housing portions may be constructed of a relatively rigid material such as polymeric material, plastic and/or metal. The three housing portions may be sealed with press fit seals 8025. These seals are made of a TPE, TPU, rubber, silicone and/or similar soft elastic polymer.

The housing may be further improved for manufacturability purposes by reducing the number of housing portions. In further embodiments, it is possible to reduce the housing portion to one or two.

Figure 138:
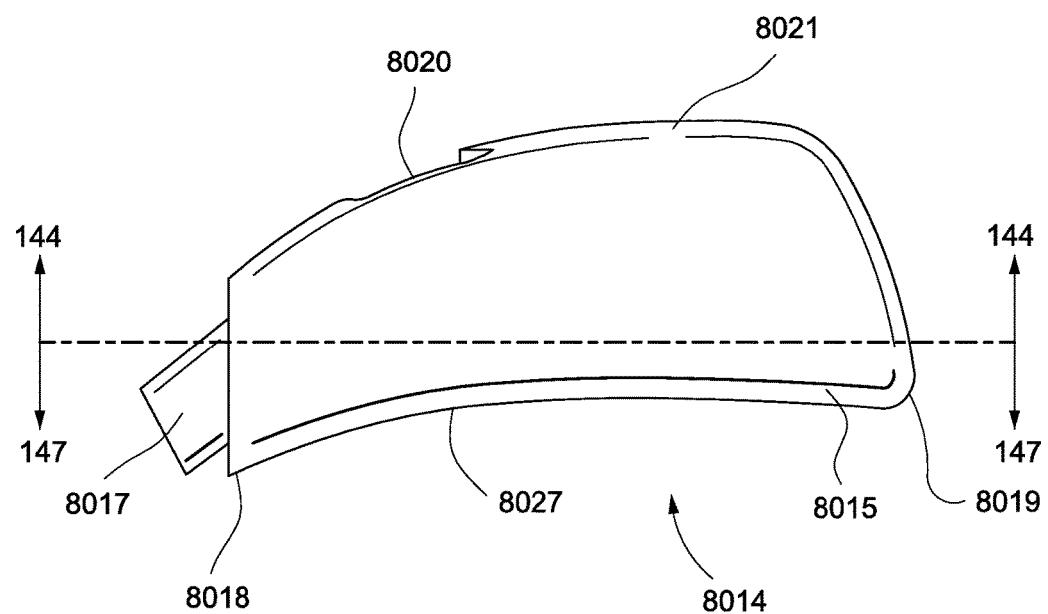
FIG. 138 shows a side view the flow generator depicted in FIG. 137.
Figure 139:
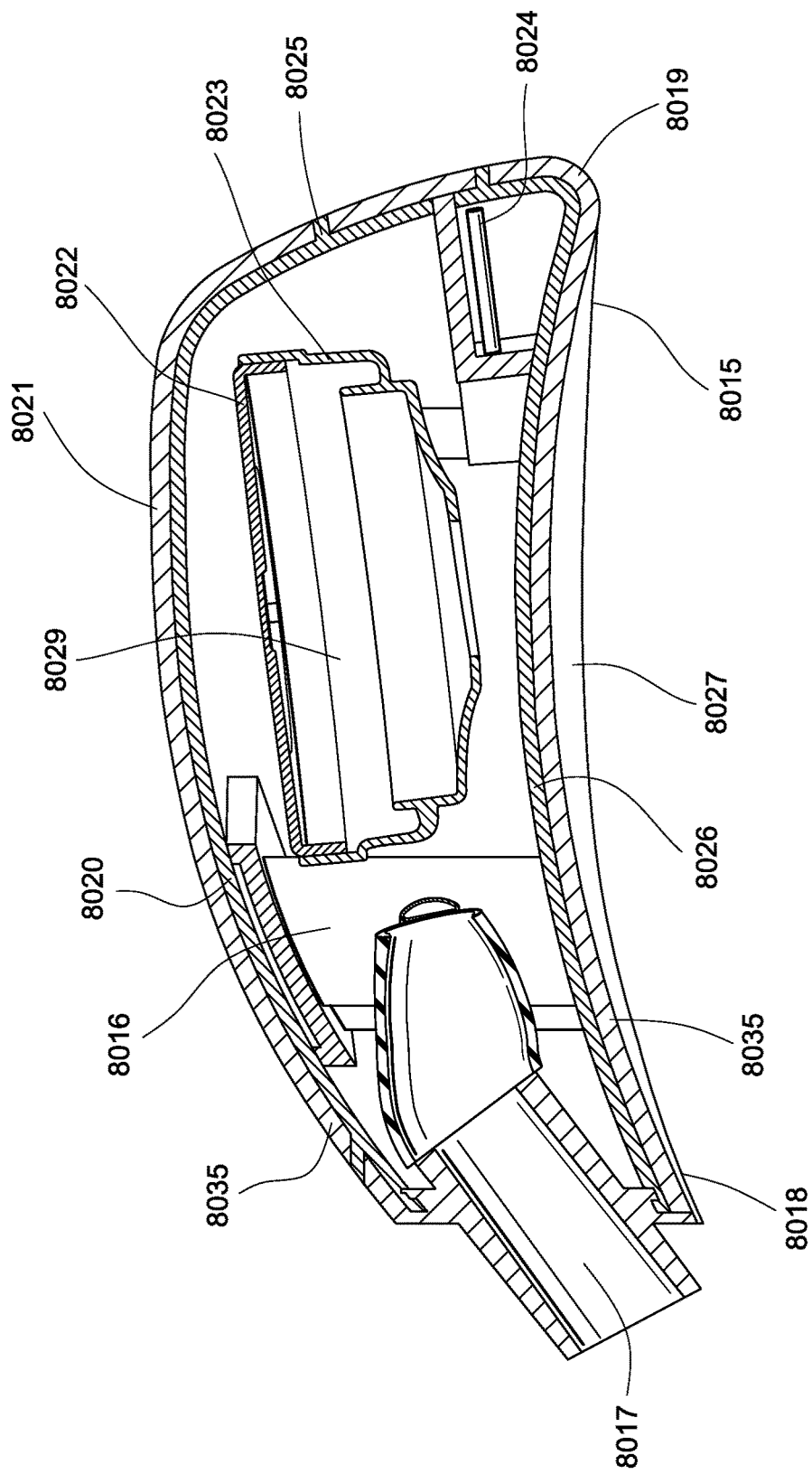
FIG. 139 shows a first cross-sectional view of the flow generator of FIG. 138.

In this embodiment, the side view profile of the housing 8015 is curved or arcuate along the length of the housing as seen in FIGS. 138-139. The radius of the lower surface 8027 of housing 8015 is between about 100-400 mm. The preferred radius is about 172 mm. The aforementioned range of radii is useful because this range suits the largest amount of patients and increases comfort.

Further the housing 8015 is also arcuate or curved along the width of the housing 8015 of the lower surface 8027. This can be seen in FIGS. 141 and 142, wherein the radius of lower surface 8027 of the housing 8015 along its width is between 100-1000 mm. The most preferred radius of the width of the lower surface 8027 is 210 mm. This provides the same or similar advantage to the radius along the length of the lower surface 8027.

The upper surface 8021 of the housing 801.5 is also curved or arcuate and this improves the look and profile of the flow generator 8014 when being worn. Additionally, it may prevent or limit the capacity of the inlet 8016 from accidental occlusion during use.

Figure 144:
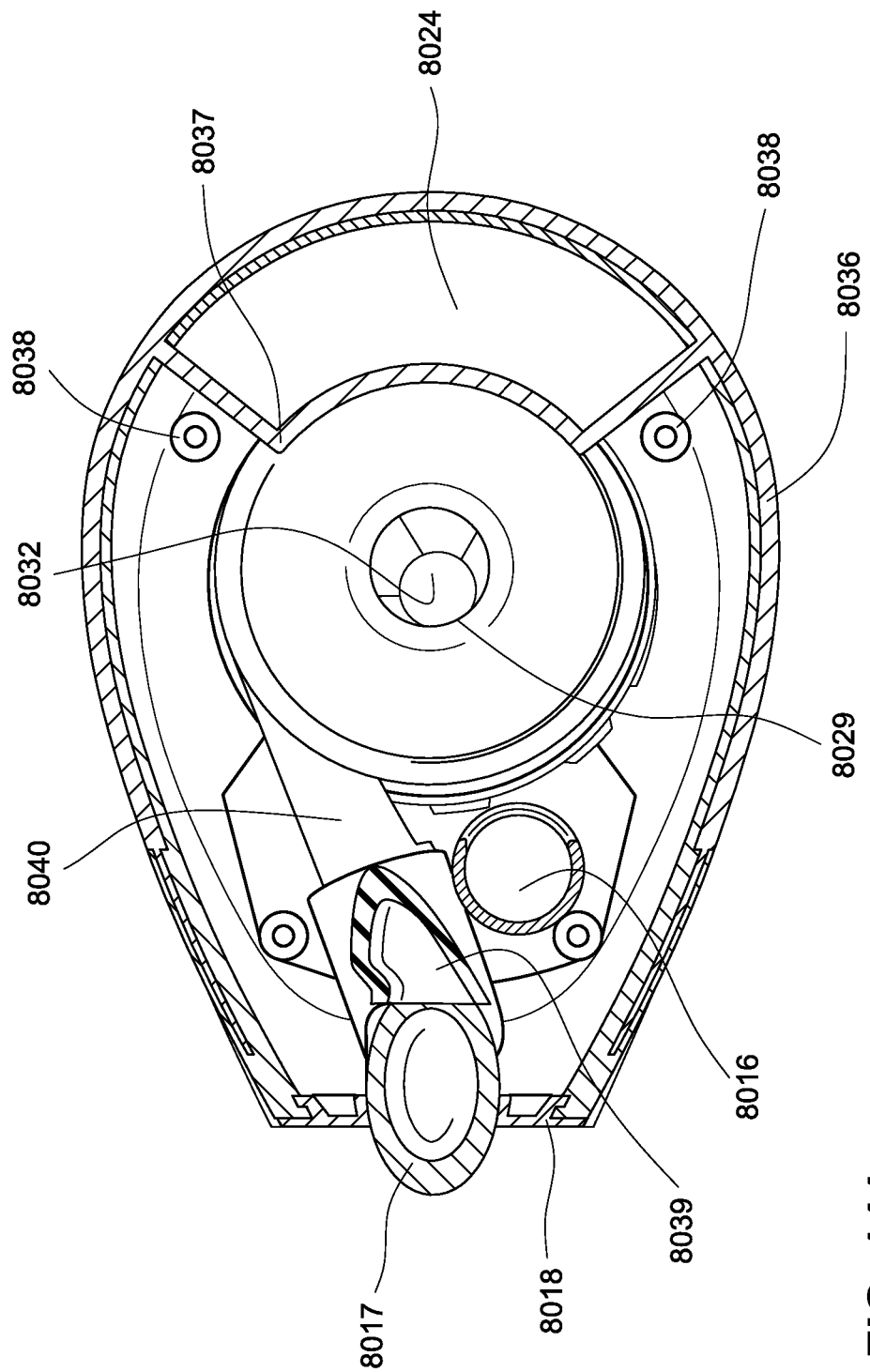
FIG. 144 shows a sixth cross-sectional view of the flow generator of FIG. 138.

The flow generator may include a small blower 8029. The blower includes an upper housing portion 8022 and a lower housing portion 8023 joined by snap locks or other fasteners. The blower may include a single stage centrifugal blower including a relatively flat profiled electric motor and an impeller for pumping gas when rotated. The motor may be mounted in the upper portion 8022 of the blower 8029 to separate the heat generated by the motor and its electronics away from the head of the patient. The lower portion includes a blower inlet 8032 and the impeller attached to the motor as shown in FIG. 144. The lower portion also includes a blower outlet 8040 joined to a volute formed in the lower portion 8023 of the blower 8029.

In certain embodiments, the blower 8029 has been surprisingly inverted in its orientation to minimize space taken up by the blower 8029 in the housing. This is because less empty space is needed between the upper portion 8022 of the blower 8029 and the upper housing 8036 of the flow generator housing 8015 (i.e. when the inlet 8032 of the blower 8028 is directed towards the patient), than in the reverse arrangement wherein the blower inlet 8032 is directed away from the patient. This may be due to the need for space to conduct heat away or dissipate heat generated by the motor or blower.

Additionally, this inversion of the blower in the housing increases the vibration isolation from the headgear and the patient's head leading to a more comfortable PAP system or device when in use.

Figure 140:
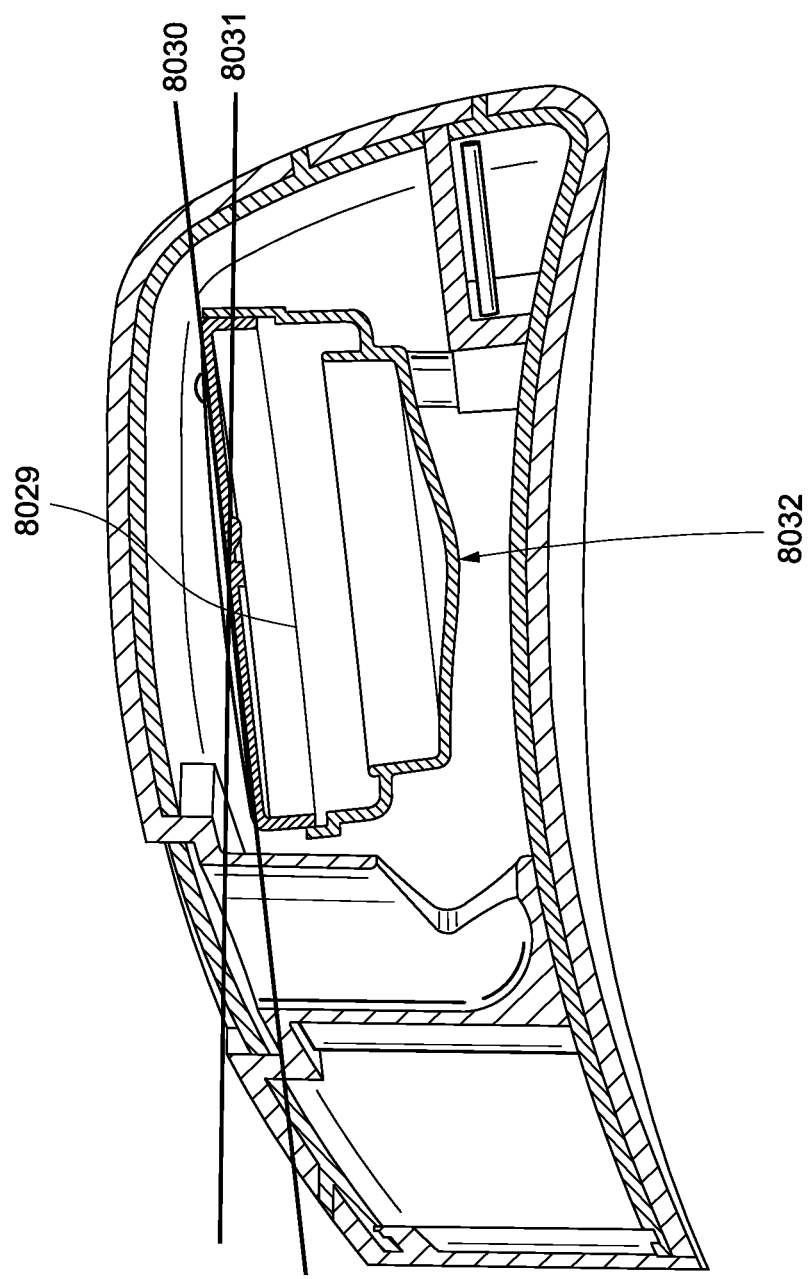
FIG. 140 shows a second cross-sectional view of the flow generator of FIG. 138.
Figure 141:
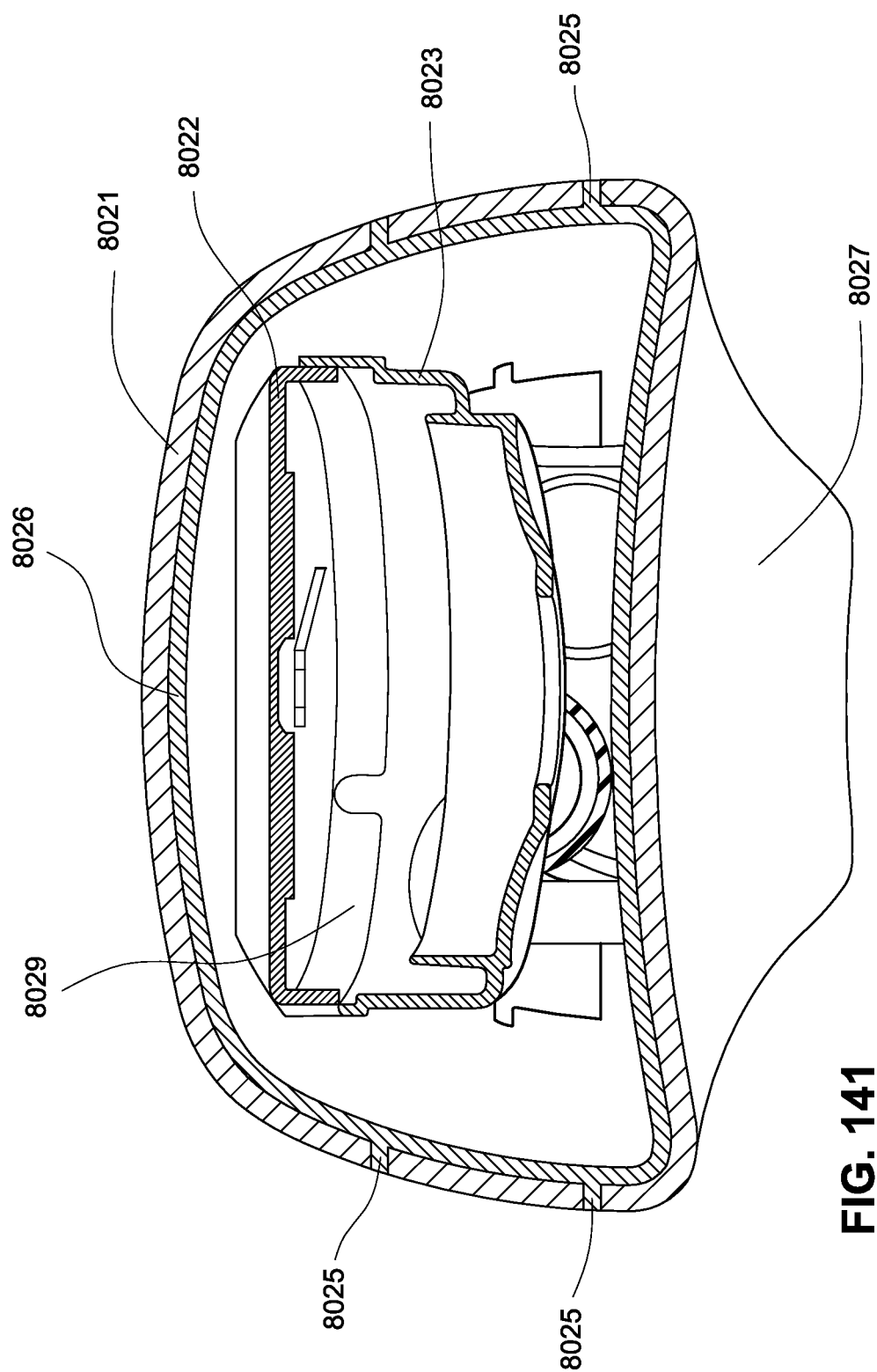
FIG. 141 shows a third cross-sectional view of the flow generator of FIG. 138.
Figure 142:
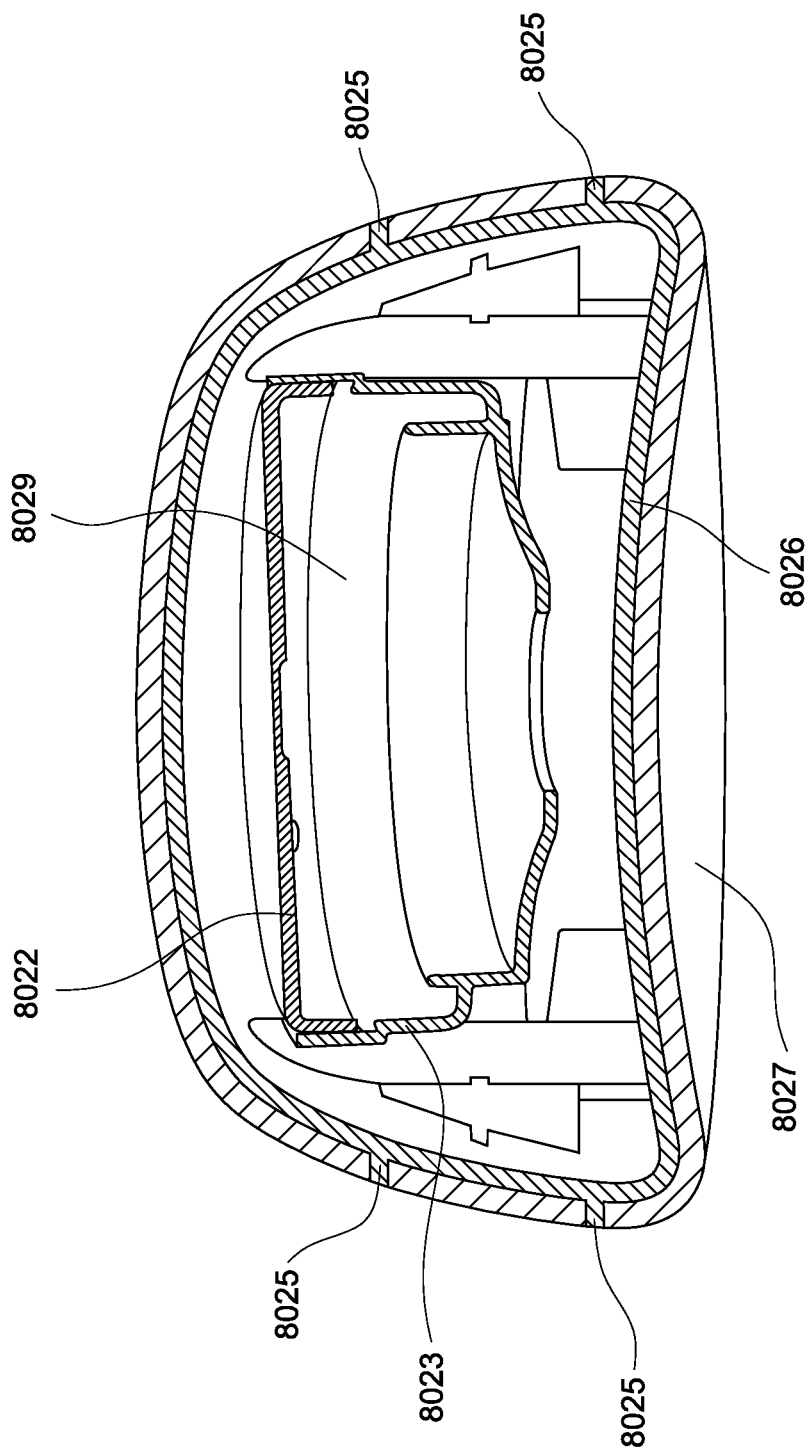
FIG. 142 shows a fourth cross-sectional view of the flow generator of FIG. 138.
Figure 143:
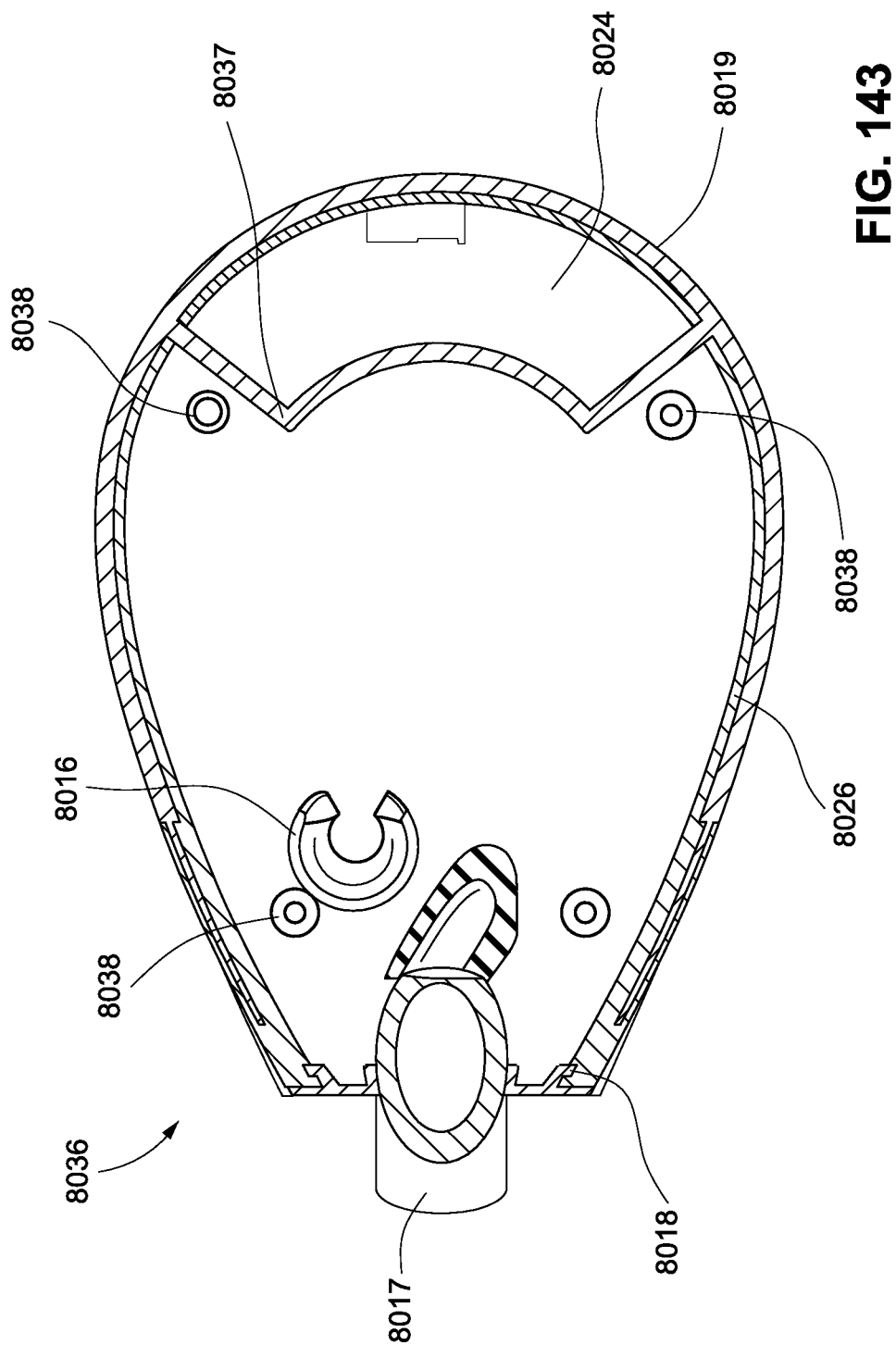
FIG. 143 shows a fifth cross-sectional view of the flow generator of FIG. 138.

The blower 8029 may be mounted in the housing 8015 at an offset angle relative to the plane 8031 defined the length of the housing 8015. One useful offset angle 8030 is depicted in FIG. 140. In this embodiment, the offset angle 8030 may be up to 30° clockwise or anti-clockwise. However, the preferred offset angle is approximately 7° anti-clockwise relative to the view of the right hand side shown in FIG. 140. This offsetting the blower 8029 in the housing 8015 may allow for further vibration and/or noise isolation relative to the headgear 8010 and/or patient's head. Additionally, this offsetting the: blower 8029 in the housing 8015 may also allow for aesthetic improvements to case design and/or also minimization of the overall volume of the housing of the flow generator.

In this embodiment, a housing inlet 8016 is formed in the upper housing portion 8036. A single inlet hole may extend from the: surface of the housing into it in a downward direction. The inlet then turns 90° and empties into a sealed cavity of the housing 8015. Breathable gas is delivered via inlet 8016 to the blower inlet 8032, wherein it is pressurized and delivered into the blower volute. From this location, the breathable gas exits the blower 8029 through blower outlet 8040, which in turn is connected to an outlet blower connector 8039. The pressurized breathable gas then exits via the housing outlet 8017 on the front facing portion 8018 of the housing 8015.

The housing inlet may include a filter receptacle 8020 for receiving a removable air filter 8041 as shown in FIG. 145. This prevents particulate matter from entering the blower 8029 or the patient's respiratory system. The filter is usually made of a gas permeable light weight mesh material specially cut to fit the receptacle 8020.

The inlet also includes a 90° bend. This further reduces noise exiting the inlet 8016. Additionally, it directs the inlet 8016 in a direction away from the patient's ears or face to reduce perceived noise, and also away from the hack of the head to reduce the risk of accidental blockage or occlusion when the patient is laying on pillow or similar item.

The sealed cavity within the housing 8015 forms a muffling body for the blower 8029 and further reduces noise and vibration transmission.

The housing outlet 8017 is fixed to the housing and is adapted for connection to tubing to deliver the pressurized breathable gas to the patient interface. The tubing and housing outlet 8017 may have a streamlined appearance and tubing continues along the patient's forehead at a similar or the same angle to the radii used to determine the curved lower housing surface 8027. The housing outlet 8017 connection to the tubing is generally a press-fit. The tubing may be constructed of silicone.

The blower outlet connector 8039 joins the housing outlet 8017 to the blower outlet 8040. Generally the connector 8039 is flexible and is adapted to seal around the outside of both the housing outlet 8017 and blower outlet 8040 at opposed ends of the connector.

Mounted in the housing 8015 is a printed circuit board control circuit 8024. This control circuit may be encapsulated in a separate sub-housing 8037. The sub-housing 8037 is adapted to prevent high humidity and fluid ingress into the control circuit 8024. The sub-housing may be sealed from the main cavity of housing 8015.

The three portions of the housing 8034, 8035, 8036 may be fastened together using screws. In this embodiment, the screw hole mounts, 8038 depicts the location of the fastener placement. The screws may alternatively be replaced with other type of secure fastening means including gluing or ultrasonic welding etc.

In this embodiment, the interior wall of the housing 8015 is a coating or lining 8026 with a noise deadening material deposited preferably by over-moulding processes. Other processes may be used. This lining 8026 may be constructed of TPE, TPU, rubber or a silicone polymer or similar soft elastic polymer. The lining 8026 may extend into the gaps between the housing portions 8034, 8035, and 8036 and forms part of the seal for the entire housing 8015. The lining 8026 may substantially increase the noise reduction of the housing 8015 body and further increase the vibration and/or noise isolation of the blower 8029.

Figure 147:
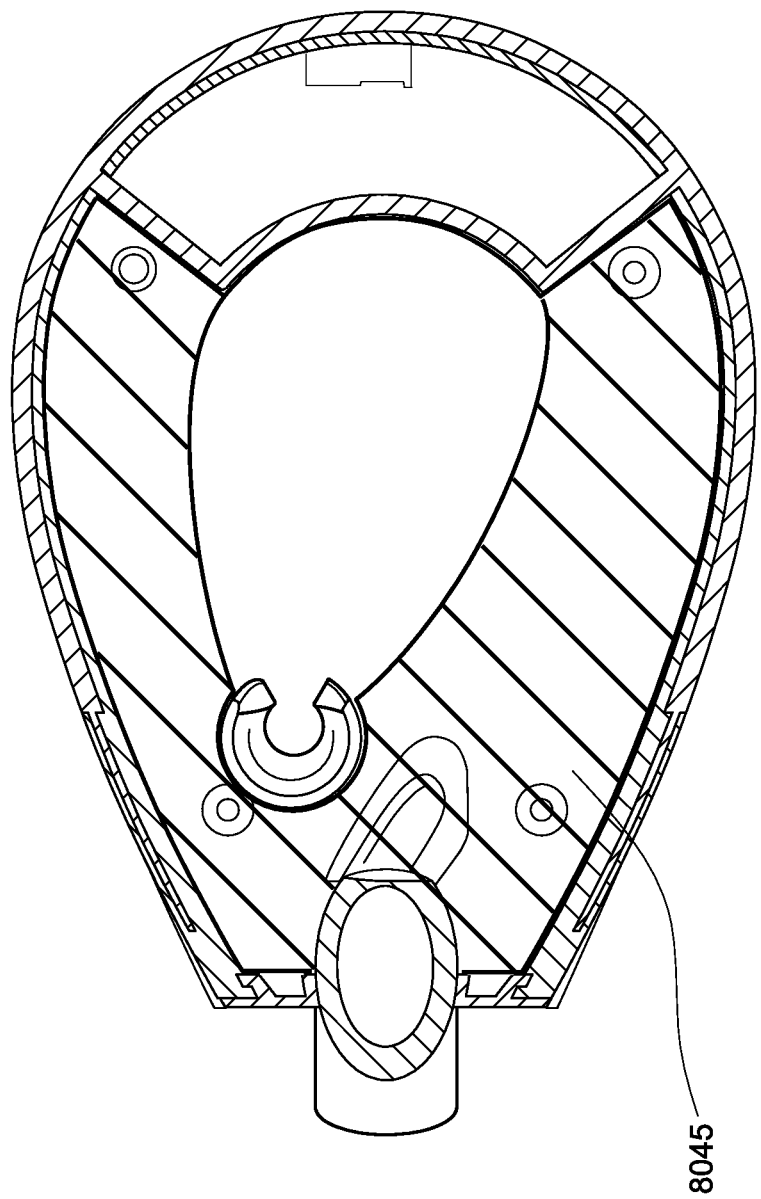
FIG. 147 shows a shows a first cross-sectional view of FIG. 145.
Figure 148:
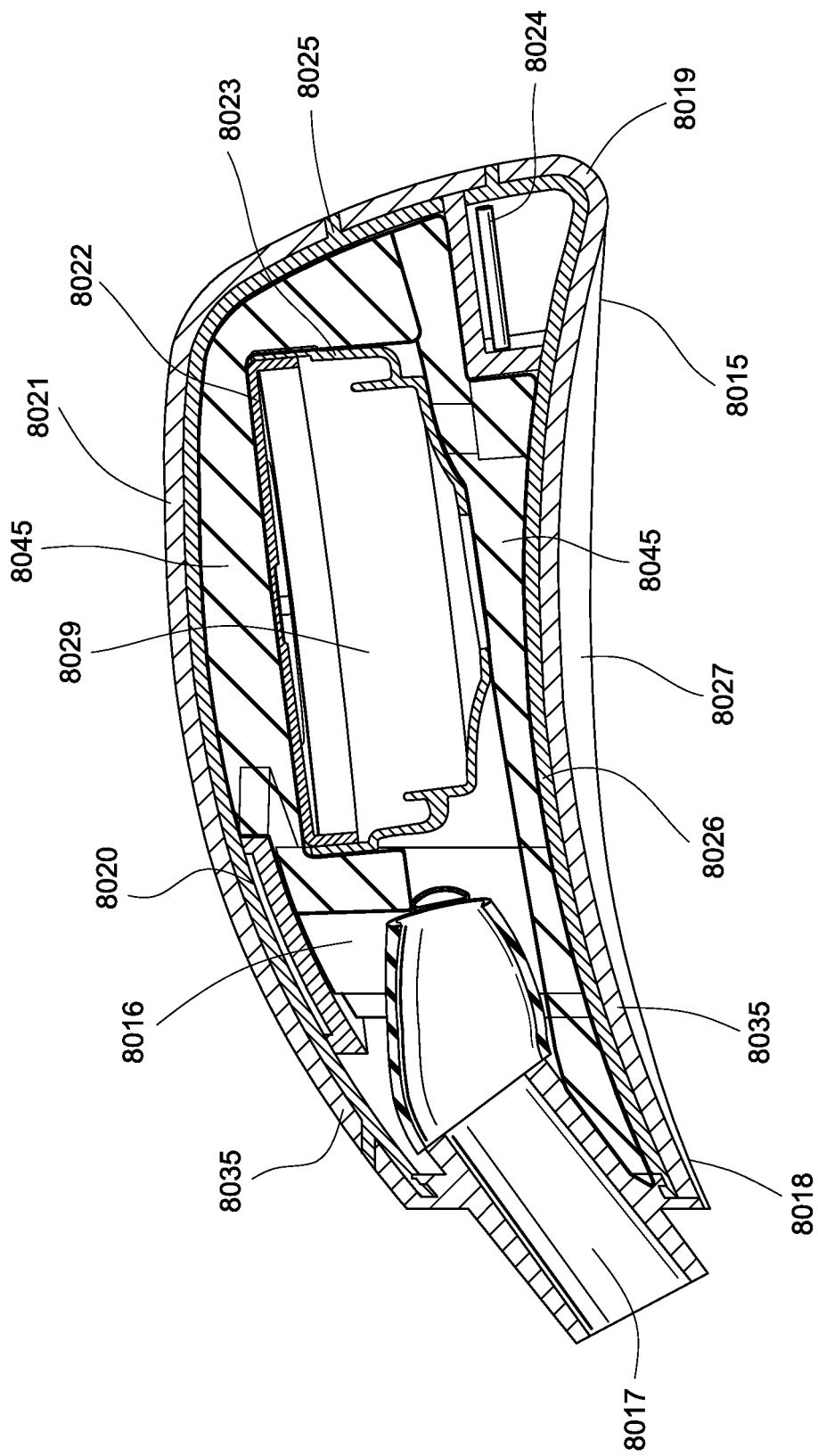
FIG. 148 shows a shows a second cross-sectional view of FIG. 145.
Figure 149:
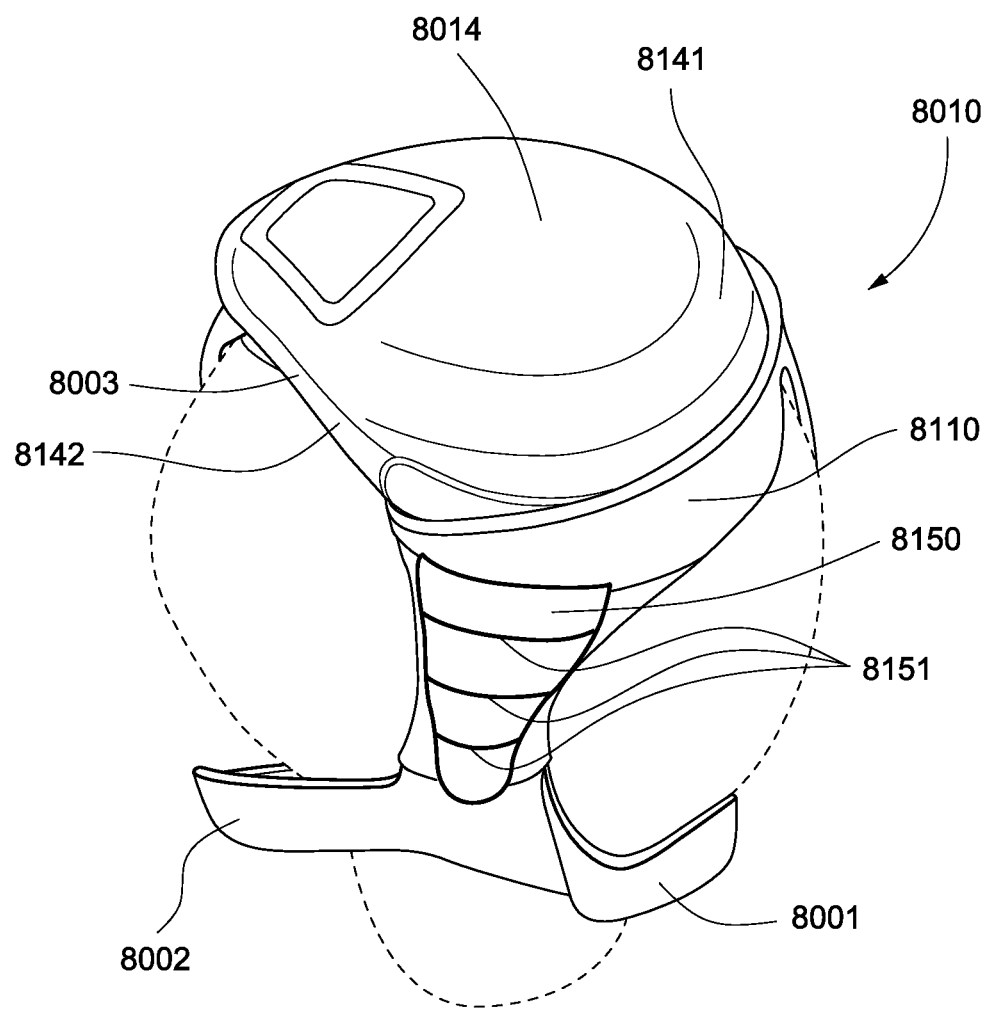
FIGS. 149 and 150 show perspective views of certain embodiments of a headgear and flow generator arrangement.
Figure 150:
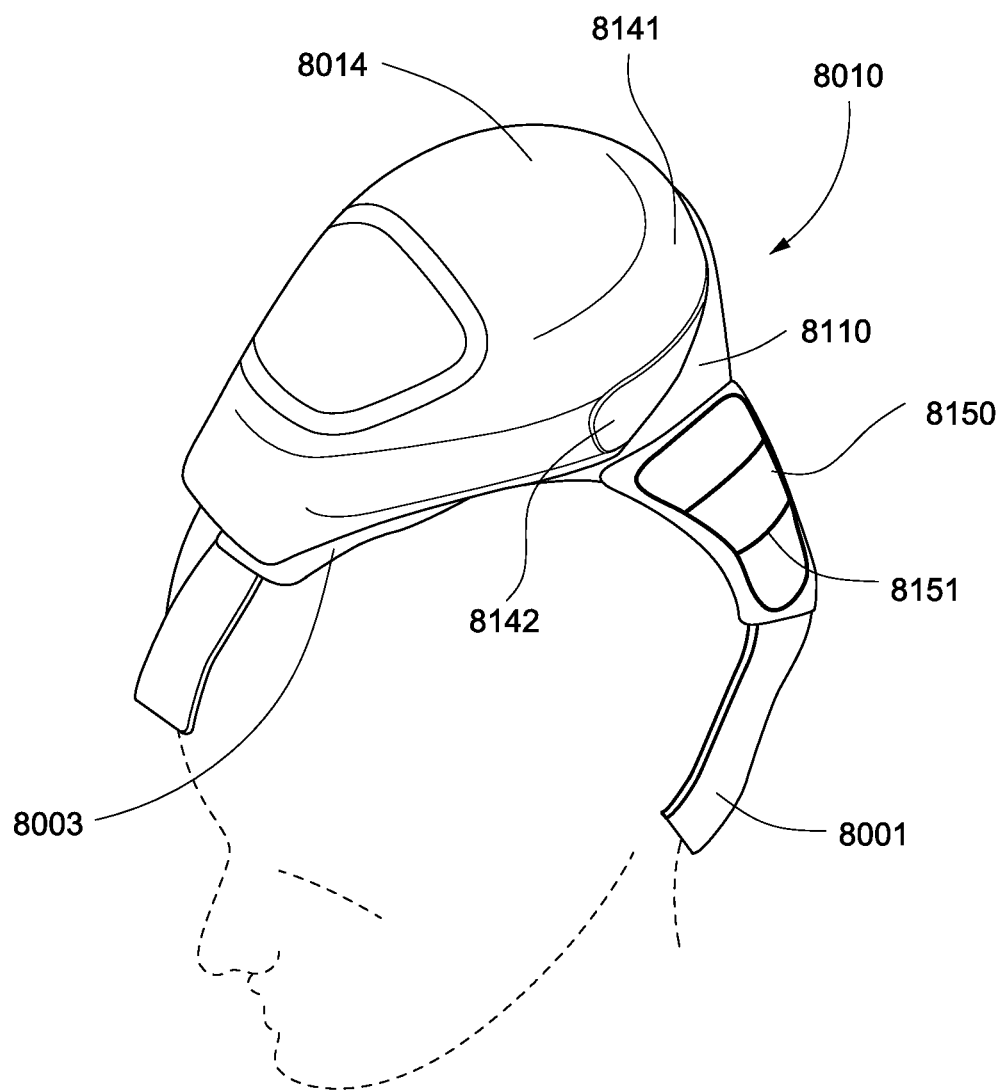
Figure 151:
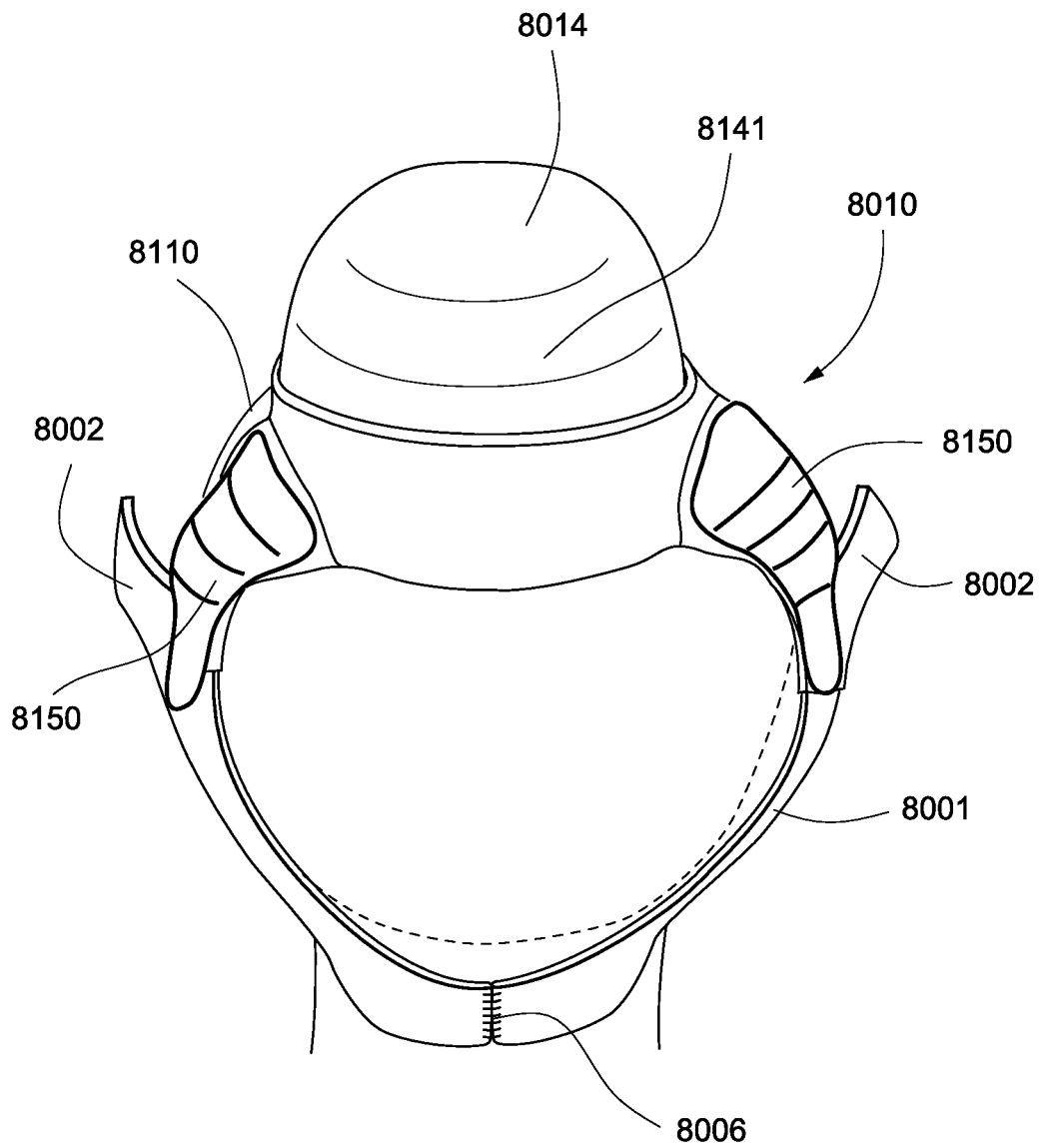
FIG. 151 shows a rear view of FIGS. 149 and 150.
Figure 152:
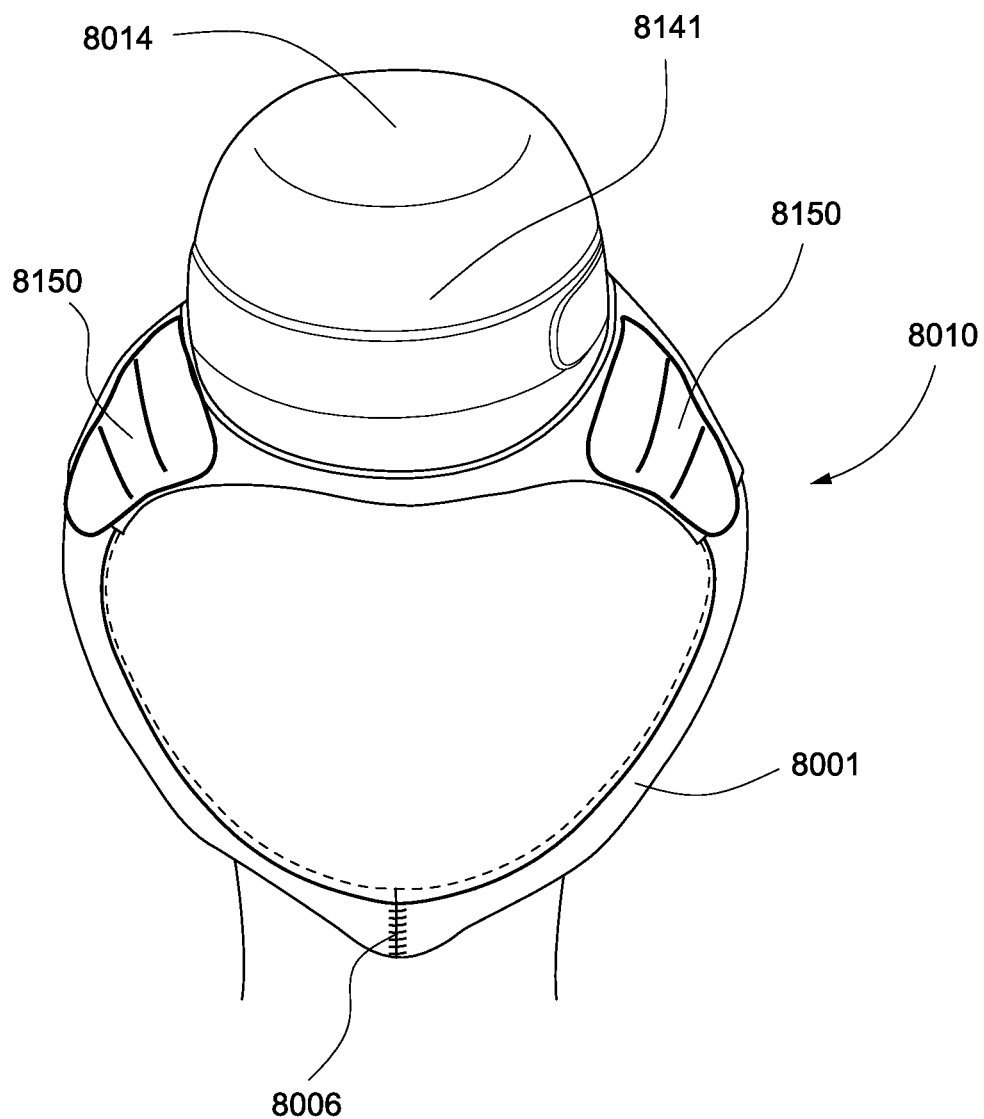
FIG. 152 shows a rear view of certain embodiments of a headgear and flow generator arrangement.

The blower 8029 may be held in position by foam suspension mechanism. The foam suspension mechanism is illustrated in FIGS. 147-148 as foam mounting 8045. The foam mounting 8045 may act to further reduce noise and vibration transmission and isolate the vibration of the blower 8029, when in use. The foam mounting 8045 may be constructed by moulding, die cutting or compression cutting techniques.

It is often desirable that the foam mounting 8045 be rigid enough to limit the movement of blower 8029.

Typically, the foam mounting avoids occluding or covering portions of the housing inlet 8016 and/or the blower inlet 8032.

The foam mounting may be constructed of polyurethane foam. An example of a foam for this purpose is Accusorb™ which has relatively good noise absorption characteristics. Accusorb™ is also known as Marathon MA32.-180 manufactured by Dunlop Foams which has a density of 31-32.5 kg/m$^3$, tear resistance of 350 N/m minimum, tensile strength 100 kPa minimum, elongation 175% minimum, resilience 45% minimum and a compression set 5% minimum. Accusorb™ foam has a spring constant of about 600 N/m in its linear zone of compression. Other possible mounting materials include silicon foam, which has a spring constant of about 1,700-1,800 N/m in its linear zone of compression; Poron™ foam, which has a spring constant of about 9800 N/m in its linear zone of compression; VS Integra™ foam which has a spring constant of about 400 N/m in its linear zone of compression; and glass packaging foam which has a spring constant of about 1,100-1,200 N/m in its linear zone of compression. According to certain embodiments the suspension mechanism, e.g. the foam mounting, may have a spring constant of about 400 N/m to about 1800 N/m, for example about 600 N/m to about 1,200 N/m. According to certain embodiments, the suspension mechanism, e.g. the foam mounting, may have a maximum spring constant. According to certain embodiments, the maximum spring constant may be about 1,800 N/m. According to certain embodiments, the maximum spring constant may be about 9,800 N/m.

The flow generator 8014 may be adapted so that is able to function at various angles and orientations, unlike standard PAP devices which are designed to sit typically on a flat horizontal surfaces like bed side tables. The embodied flow generator 8014 is adapted to work at angles and to generate minimal noise in these alternate orientations. The foam mounting 8045 provides support to the blower and supports and/or limits vibration in unusual orientations and may prevent the blower vibration and noise from being transmitted to the housing 8015 regardless of the angle of the blower or flow generator. The embodied flow generator 14 may also be adapted to work upside down when not attached to the headgear. This may allow the user or patient to simply place the flow generator 8014 on a bedside table and not even consider placing it in the normal orientation because of the curved and concave lower surface of the housing portion.

Additionally, the convex upper surface of the housing prevents or limits occlusion of the housing inlet 8016, even when the flow generator is inverted and the upper surface is directed down.

Preferably, the flow generator 8014 may also be adapted to be removed from the headgear 8010 and connected to an arm holster, chest holster or belt holster for improved comfort and useability.

Referring to FIGS. 204A to 204M, a PAP device 100 according to certain embodiments is illustrated. The PAP device 100 comprises an upper housing 101 and a lower housing 102 that form a housing for a blower, or flow generator, 105 that is configured to generate a flow of pressurized breathable gas. A filter cover 103 is provided on the upper housing 101 to cover a filter which may be replaceably provided in the upper housing 101. The filter cover 103 covers the filter inlet 131 on the housing for a blower, or flow generator, 105. The filter inlet 131 supports filter material such that the edges of the filter material remain in position. The filter cover 103 also includes retention features or ribs adapted to prevent collapse of the filter during air flow therethrough. Airflow F enters in the inlet 131 and down through an inlet tube 129 that directs air vertically downwards towards the lower housing 102. The inlet tube 129 may have a cross-sectional area of approximately 150 mm2 to approximately 300 mm2, or approximately 150 mm2 to approximately 250 mm2 or approximately 200 mm2. The inlet tube 129 has a vertical opening transversing from the filter inlet 131 towards the lower housing 102. The lower end of the inlet tube 129 terminates above the lower housing 102 with a gap such as a 10-18 mm gap, for example a 13-15 mm gap, to allow air flow out of the lower end of the inlet tube 129 and into the internal area of the housing 101, 102. The inlet tube 129 may comprise two vanes 133 at the lower end of the inlet tube 129 to prevent foreign objects from being trapped within the inlet tube 129 and blocking the inlet tube 129. It should be appreciated that one or more vanes or other structures may be used to prevent blockage of the inlet tube 129. Once the air exits the lower end of the inlet tube it is dispersed in all directions, or 360°, into the internal area of the housing and travels up to the inlet 127 of the blower 105. In a certain embodiment a noise absorbing material 134 such as foam, for example Accusorb™ foam, is attached to the lower housing 102 below the inlet tube 129 to assist in reducing or muffling the noise generated from the inlet 131. The foam 134 may have a thickness of about 3-8 mm, such as 4-6 mm, such as 4.5 mm. It should be appreciated that other thicknesses of foam may be used depending upon the size of the housing. In operation the inlet air flow is directed through the filter inlet 131, down the inlet tube 129 and into contact with the foam 134 below the inlet tube 129 and is dispersed throughout the internal cavity of the housing 101, 102. The direction and air flow path of the filter inlet 131 and inlet tube 129 reduce the noise level transmitted from the inlet 131.

Referring to FIG. 204B, the blower 105 is provided in the housing between foam supports 106. An air inlet guide, or chimney, 109 may be provided to the blower 105. For example, the chimney 109 may be over moulded onto the blower 105. An inlet cage 107 is provided between the foam support 106 and the chimney 109 to support the upper foam support 106 in a fixed position above the blower 105 and establish a fixed inlet path to the blower chimney 109.

As shown in FIGS. 204A and 204B, an outlet tube having a muffler chamber 104 is connected to the outlet of the blower 105 to reduce the, noise of the airflow generated by the blower 105.

The foam supports 106 may be provided above and below the blower 105. The majority of the vibration of the blower 105 is on one axis, from side to side. The blower 105 may be arranged such that it allows movement from side to side without touching, or substantially touching, structural features in the housing of the PAP device and so that the blower 105 is surrounded by air. The wires have been decoupled from the blower 105.

Vibration is absorbed for vibrations in the opposing axis, i.e. up and down. The foam supports 106 are placed on the top and bottom of the blower 105. The foam supports 106 may be a low compression foam, for example, 10-15%. The foam supports 106 may be formed of, for example, Accusorb™.

The upper housing 101 of the PAP device 100 is curved. To prevent the curvature of the upper housing 101 from causing the foam supports 106 to be more compressed at the sides, the foam supports 106 may include straight sidles 119, as shown in FIGS. 204H and 204I. The upper foam support 106 may also be shaped to have a corresponding curvature corresponding to the curvature of the upper housing 101 of the PAP device 100.

The chimney 109 encourages more laminar flow into the blower 105. The chimney 109 has a height of, for example, about 4 mm due to the limited space in the PAP device 100, although a taller chimney may improve acoustic performance. The diameter of the chimney is, for example, about 16 mm to match the inlet hole, but larger diameters may be used, for example, in a range of from 10-20 mm.

Referring to FIG. 204C, the blower includes a blower cover 111 having a blower inlet 127. An impeller is provided for radially accelerating the air flow. The impeller 112 may be as shown and described in, for example, U.S. Patent Application Publication 2008/0304986 A1, the entire contents of which are incorporated herein by reference.

The blower 105 also includes a bottom cover 118 which supports an electromagnetic shield 108, see FIG. 204B, adapted to protect the patient from electromagnetic fields emitted from the motor as described in more detail below. In the assembled motor, the motor magnet 11 7 and bearings 116 are inserted into the circular space within the stator 114 seen in FIG. 204C. The bearings 16 surround the motor shaft, and the motor shaft extends through the central opening to allow attachment of the impeller 112. The magnet may be as shown and described in, for example, WO 2007/048205 A1 and WO 2007/048206 A1, the entire contents of each being incorporated herein by reference. The bearings 116 may be as shown and described in, for example, U.S. Patent Application Publication 2008/0304986 A1.

The blower 105 further comprises a printed circuit board (PCB) 115 that includes circuitry configured to control the operation of the blower 105. A stator 114 is provided on the PCB 115. The stator 114 may be as shown and described in, for example, WO 2007/048205 A1 and WO 2007/048206 A1. An overmould 113 is provided between the stator 114 and the impeller 112. Referring to FIG. 204B, the electromagnetic shield 108 may be attached to the bottom cover 118 to assist with damping vibration. The EMF shield 108 may have a circular flat shape with a diameter of, for example, 55 mm, and a thickness of, for example, 0.6 mm. The EMF shield 108 may be made from magnetically conducted material, for example, stainless steel 430. The EMF shield 108 may be adhered to the bottom cover 118 of the blower 105 by adhesive, for example, double sided pressure sensitive adhesive.

As shown in FIGS. 204F, 204H and 204I, the inlet cage 107 may include a ring 124 that is configured to be inserted around the: chimney 109. The inlet cage 107 may also include ribs 125 that are configured to be received in recesses 126 (FIG. 204E) in the chimney 109 to align the inlet cage 107 to support the upper foam support 106 in a fixed position above the blower 105 and establish the fixed inlet path to the chimney 109. However, other means of retaining the inlet cage in position in relation to the chimney 109 may be utilized, such as ribs on the chimney 109 and slots or grooves on the inlet cage 107, an interference fit or snap fit between the ring 124 and the chimney 109, clips, fasteners, etc. Furthermore, it should be appreciated that the inlet cage 107 may be made in other forms or shapes and still provide a fixed inlet to the blower inlet via the chimney 109 and/or support the foam supports 106.

Referring to FIGS. 205A and 205B, the PAP device 100 may include a false chamber 110 added to the bottom of the lower housing 102. The false chamber 110 acts as a Helmholtz resonator and may have a volume of, for example, 40 ml. The ratio between the volume of the false chamber 110 and the volume of the housing 101, 102 of the PAP device 100 allows tuning of the noise generated by the PAP device 100. It should be appreciated that one of ordinary skill in the art that chambers having different volumes may be used. In addition, the false chamber 110 has a damping effect on the vibration by acting as a spring.

1.1.9 Certain Embodiments of Flow Generator Positioning

In certain embodiments depicted in FIGS. 130-148, a PAP device or system includes a flow generator 8015 that may be mounted or positioned on a patient's head using headgear 8010. The flow generator is positioned on the patient's head near the crown or apex of the patient's head or on a front portion of the patient's head between the crown and the forehead. The PAP device or system may be adapted to deliver pressurized breathable gas to a patient. The PAP device may be used to treat respiratory disease or insufficiency or alternately as a treatment for sleep apnea and or associated diseases. This PAP device or system is adapted to be light weight typically less than 500 grams and able to be carried or used when travelling (e.g. in planes, etc.) (most preferably, total weight of the system excluding power supply is 300-400 grams).

1.1.9.1 Certain Embodiments of the Headgear

Figure 130:
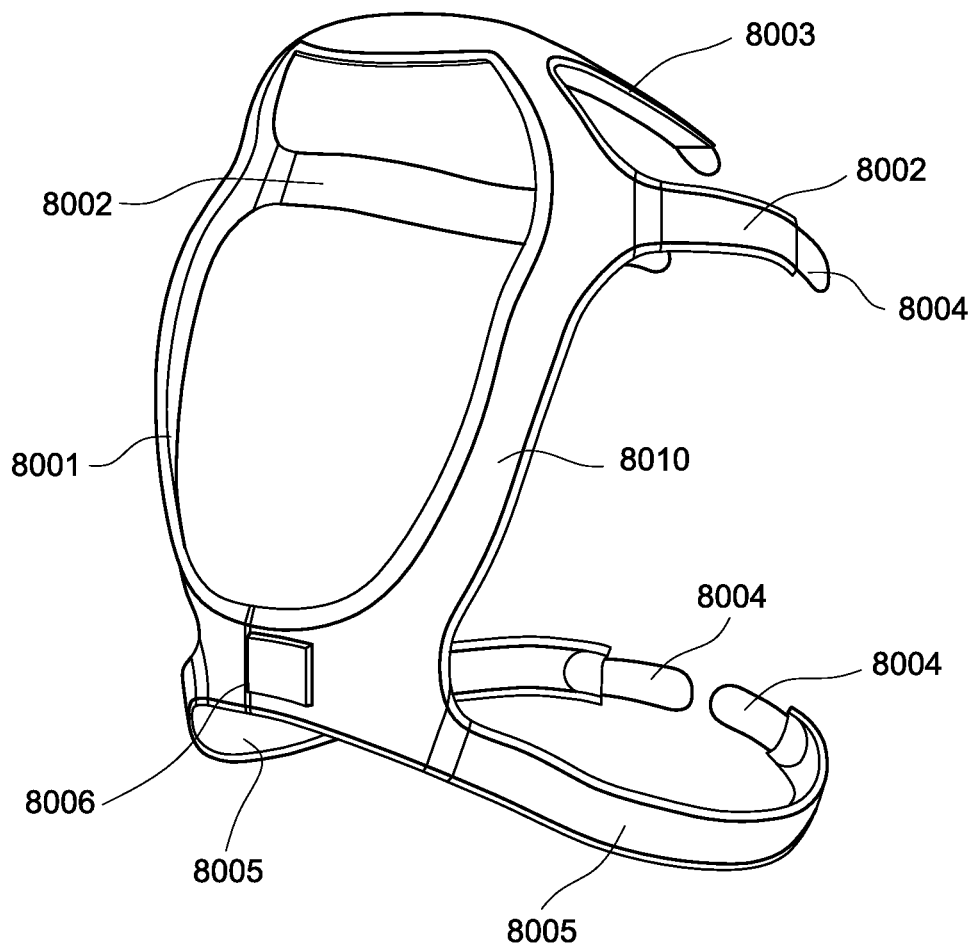
FIG. 130 shows a perspective view of a portion of a headgear according to certain embodiments.
Figure 131:
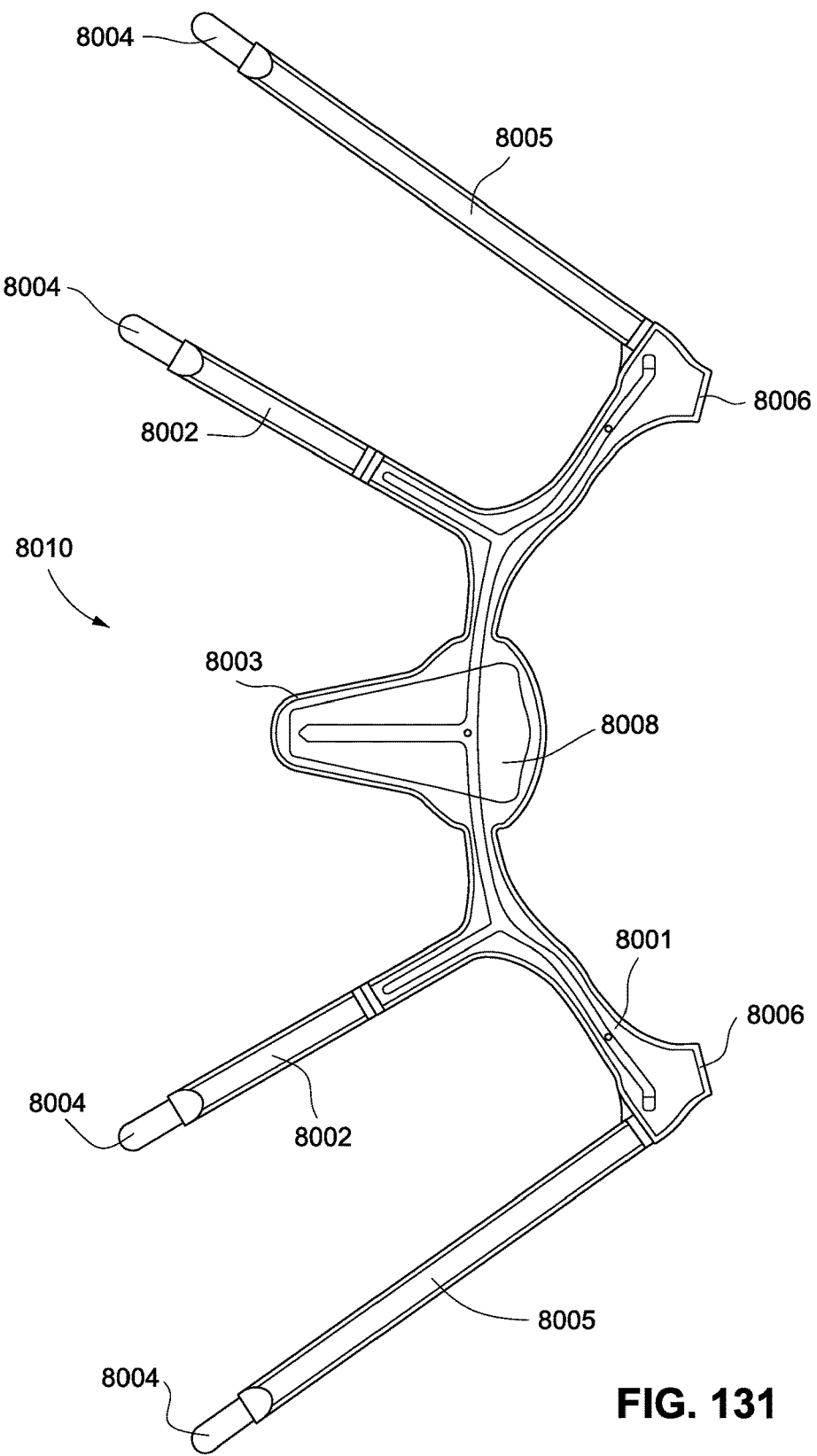
FIG. 131 shows a flattened top view of the headgear shown in FIG. 130.

FIGS. 130-136 depict certain embodiments of headgear that may be used with or as part of the aforementioned PAP device. FIG. 130 depicts the headgear in a shape or configuration as it may be preferably worn or donned by patient. The headgear 8010 includes an occipital ring 8001 joined by stitching, gluing or some other known method at joining location 8006. The occipital ring 8001 is adapted to at least partially encompass or enclose or engage the occipital portion of the patient's head. This may provide stable position for the headgear and allows for relatively even distribution of the forces applied to the patient's head to maximize comfort.

The joining location 8006 may be positioned proximal to the base of the patient's skull as that the stitching or gluing does not rub or become uncomfortable for patient during extended periods of use.

Preferably, the headgear 8010 includes two parallel (when positioned on a patient's head) upper straps 8002. These upper straps 8002 are oriented to be relatively horizontal, when worn, and extend from the occipital ring 8001 towards the front of the headgear where the patient's face is generally located.

The headgear 8010 may also include a further two relatively parallel (when positioned on a patient's head) lower straps 8005. These lower straps 8005 are positioned so that they also extend from the occipital ring 8001 towards the patient's face. The lower straps are generally oriented in parallel to the respective upper straps 8002, when worn, but the lower straps 8005 are adapted to extend from the lower portion of ring 8001 to the lower portion of the patient's face, while the upper straps 8002 generally may extend to an upper portion of the patient's face.

This configuration may generate a relatively stable headgear platform to mount portions of the PAP device which may include: flow generators, tubing, and/or patient interfaces (e.g. facial, nasal or mouth masks).

Positioned and joined on the extremities of the upper and lower straps 8002, 8005 are preferably fasteners 8004. In this embodiment, the fasteners are hook and loop fasteners (including Velcro™ tabs) adapted to engage slots (not shown) on a patient interface (not shown). The hook and loop fasteners tabs may be inserted through the said respective slots and used the engage and secure the patient interface against the patient's face.

The patient interface may be adapted to cover a portion of the patient's face and delivers pressurized breathable gas to the patient's respiratory system.

The headgear 8010 depicted in this embodiment may include an extension portion 8003 covering at least a section of the top of the patient's head. The extension 8003 may cover a portion of the patient's crown. In this embodiment, the extension is adapted to be a section of the headgear 8010 for mounting a flow generator 8014 (such the flow generator 8014 depicted in FIGS. 137-148).

The extension 8003 may be shaped to cover the entire lower surface of the flow generator 8014, when the flow generator 8014 is mounted. Additionally extension 8003 may include on its upper strap a type mounting fastener (not shown). It should be appreciated that the fasteners may include hook and loop fasteners, glues, and/or clips.

Figures 133, 134:
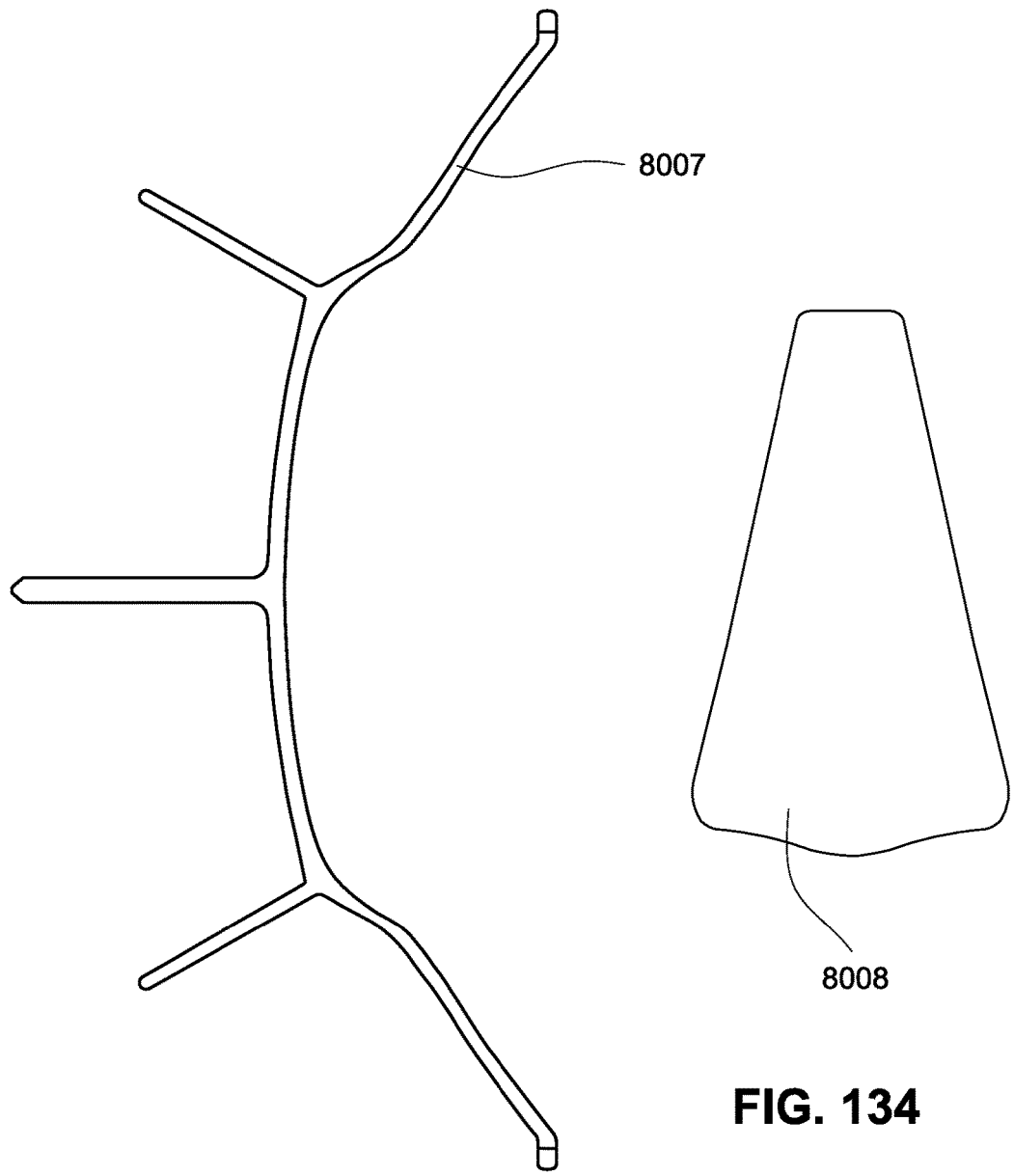
FIG. 133 shows a top view of a rigidiser forming a portion of FIG. 130.
FIG. 134 shows a top view of EMF shield forming a portion of FIG. 130.

The extension portion 8003 includes an electromagnetic force (EMF) shield 8008 as depicted in FIG. 134. In this embodiment, the EMF shield 8008 is a relatively small piece of sheet metal generally cut into a trapezium shape with a rounded bottom and rounded corners. However, the EMF shield may be made in other shapes. In certain aspects, the EMF shield may be in a shape that corresponds to the shape of the lower surface of the flow generator assembly. This EMF shield 8008 is adapted to be inserted or encapsulated within the headgear. The EMF shield 8008 may be positioned between the motor and electronics of the flow generator 8014 and the patient's head, this may prevent, limit or mitigate the potential for EMF or ionizing radiation adversely affecting the patient, when using the PAP device for extended periods of time, or during repeated uses.

Preferably the extension portion 8003 may only need to be connected to occipital ring 8001 in this embodiment and does not require more straps or head cover. This improves the useability and/or comfort of using the PAP device.

1.1.9.2 Certain Embodiments of the EMF Shield

The EMF shield 8008 may cover and block the path of EMF radiation emitting from the motor controls and flow generator electronics. The EMF shield may also function as a heat sink or a heat diverter. In this embodiment, the EMF shield 8008 may divert heat emitting from the flow generator 8014 away from the patient's head preventing burning or discomfort, when the flow generator is operating for extended time periods. In certain embodiments, the EMF shield covers 100% of the area between the flow generator 8014 and the patient's head, but this may be reduced to 50% to reduce the bulk, size and/or weight. In certain embodiments, the EMF shield may cover between 100 to 50%, 90 to 40%, or 95% to 50% of the area between the flow generator and the patient's head. The EMF shield 8008 may be flexible or rigid, however in this embodiment the EMF shielding is relatively rigid to prevent unnecessary movement of the flow generator 8014.

Generally, EMF or electromagnetic shielding is the process of limiting the penetration of electromagnetic fields into a space, by blocking them with a barrier made of conductive material. Typically it is applied to enclosures, separating electrical devices from the 'outside world', and to cables, separating wires from the environment the cable runs through. Electromagnetic shielding used to block radio frequency electromagnetic radiation is also known as RF shielding.

The shielding may reduce the coupling of radio waves, electromagnetic fields and electrostatic fields, though not static or low-frequency magnetic fields (a conductive enclosure used to block electrostatic fields is also known as a Faraday cage). The amount of reduction depends very much upon the material used, its thickness, the size of the shielded volume and the frequency of the fields of interest and the size, shape and orientation of apertures in a shield to an incident electromagnetic field.

Typical materials used for electromagnetic shielding include sheet metal, punched sheet metal and or metal foam. Any holes in the shield or mesh must be significantly smaller than the wavelength of the radiation that is being kept in or out, or the enclosure will not effectively approximate an unbroken conducting surface.

Another commonly used shielding method, especially with electronic goods housed in plastic enclosures, is to coat the inside of the enclosure with a metallic ink or similar material. The ink consists of a carrier material loaded with a suitable metal, typically copper or nickel, in the form of very small particulates. It is sprayed on to the enclosure and, once dry, produces a continuous conductive layer of metal, which can be electrically connected to the chassis ground of the equipment, thus providing effective shielding Electromagnetic radiation consists of coupled electric and magnetic fields. The electric field produces forces on the charge carriers (i.e., electrons) within the conductor. As soon as an electric field is applied to the surface of an ideal conductor, it induces a current that causes displacement of charge inside the conductor that cancels the applied field inside, at which point the current stops.

Similarly, varying magnetic fields generate eddy currents that act to cancel the applied magnetic field. The conductor does not respond to static magnetic fields unless the conductor is moving relative to the magnetic field. The result is that electromagnetic radiation is reflected from the surface of the conductor: internal fields stay inside, and external fields stay outside.

Several factors serve to limit the shielding capability of real RF shields. One is that, due to the electrical resistance of the conductor, the excited field does not completely cancel the incident field. Also, most conductors exhibit a ferromagnetic response to low-frequency magnetic fields, so that such fields are not fully attenuated by the conductor. Any holes in the shield force current to flow around them, so that fields passing through the holes do not excite opposing electromagnetic fields. These effects reduce the field-reflecting capability of the shield.

Equipment sometimes requires isolation from external magnetic fields. For static or slowly varying magnetic fields (below about 100 kHz) the Faraday shielding described above is ineffective. There exists a limited possibility of passively isolating a volume magnetically by using shields made of high magnetic permeability metal alloys such as Permalloy™. These materials may not typically block the magnetic field, as with electric shielding, but rather draw the field into themselves, providing a path for the magnetic field lines around the shielded volume. One shape for magnetic shields may be a closed container. The effectiveness of this type of shielding decreases with the material's permeability, which generally drops off at both very low magnetic field strengths, and also at high field strengths where the material becomes saturated. So to achieve low residual fields, magnetic shields often consist of several enclosures one inside the other, each of which successively may reduce the field inside it.

1.1.9.3 Certain Embodiments of the Rigidiser

In certain embodiments, the headgear 8010 may also include at least one rigidiser 8007 as shown in FIG. 133. The rigidiser 8004 may be a relatively flat piece of resilient and nonextensible material that may be constructed of plastic and/or metal. The rigidiser may be bent into the configurations shown in the Figs. The rigidiser also may be adapted to be more rigid than the flexible straps of the headgear 8010. In certain embodiments, the rigidiser 8007 may serve several functions. The first function may be to provide three dimensional structure or shape to the headgear 8010, when the occipital ring 8001 is joined. The rigidiser supports and maintains the shape of the occipital ring 8001 despite the fact that the headgear may be constructed of otherwise fairly flexible material including foams and fabrics. In this embodiment, the rigidiser 8007 extends along the upper straps 8002 to assist in retaining their shape.

The rigidiser 8007 also may serve a second function to redistribute the forces applied to the patient's head by loading of the flow generator 8014 and the patient interface (not shown).

Additionally, the rigidiser 8007 may assist in the positioning of the flow generator 8014 on the crown of the patient's head. In this embodiment, an arm of the rigidiser 8007 extends into the extension portion 8003. This secures the extension portion 8003 and prevents and/or limits unnecessary movement or motion of the flow generator 8014 relative to the patient's head. The rigidiser may also be affixed or joined to the EMF shielding 8008 to better secure the arrangement in place.

Figures 135, 136:
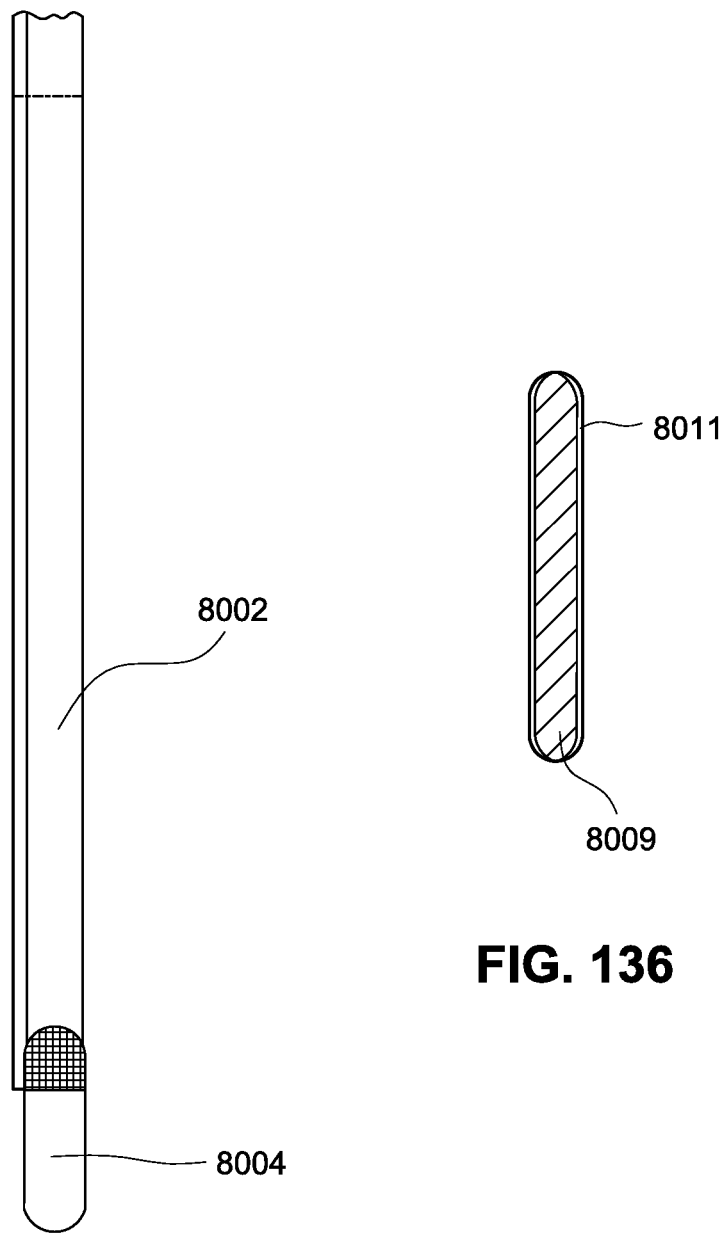
FIG. 135 shows a top view of a strap forming a portion of FIG. 130.
FIG. 136 shows a cross-sectional view of the strap of FIG. 135.

An appropriate cross-section of a portion of the straps in the headgear 8010 is depicted in FIG. 136. FIG. 136 shows two layers of fabric 8011 ultrasonically welded and cut encapsulating a layer of polyurethane foam 8009 between them. The edges of the strap have been ultrasonically welded and cut resulting in a rounded edge to prevent irritation to the patient's skin. The rigidiser 8007 may be inserted into strap prior to ultrasonic welding and be encapsulated within the strap or headgear 8010.

Figure 132:
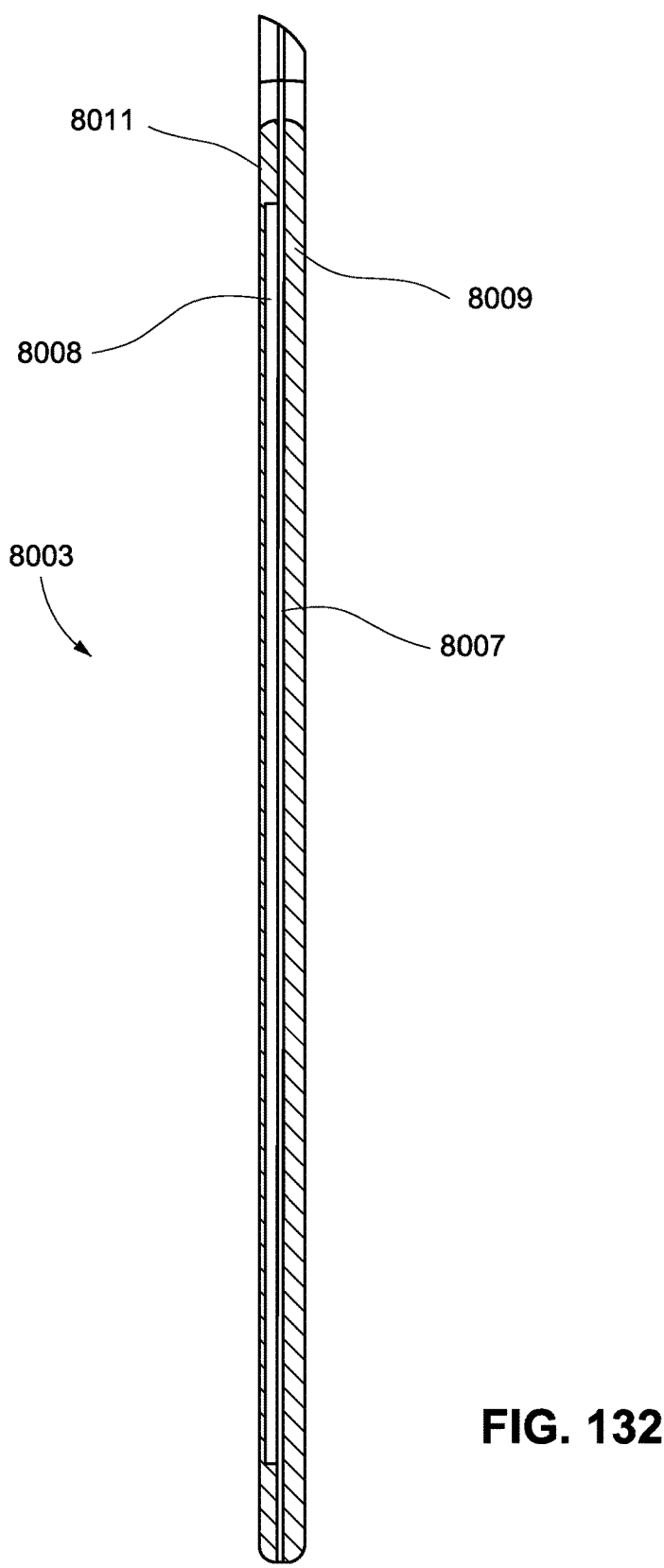
FIG. 132 shows a cross-sectional view of the extension portion forming a portion of FIG. 130.

FIG. 132 depicts a cross sectional view of the extension portion 8003 including two layers of fabric 8011 ultrasonically cut and welded around layers of foam 8009. Within the layers of fabric 8011 are encapsulated the EMF shield 8008 and a portion of the rigidiser 8007. Additionally, foam and/or fasteners may be attached to the upper surface of the extension portion 8003.

In this embodiment, as a result of the rigidiser 8007 and EMF shield 8008, the preferred flow generator may mounted on the crown of the patient's head or at the front of a patient's head without the need of a full helmet or covering that covers a majority of the patient's head. In this embodiment, the flow generator may be affixed to the headgear by a single attachment point to the extension portion 8003 and the extension portion 8003 is joined to the headgear 8010 by another single attachment point. This may improve the overall look of the PAP device, increase comfort and useability, or combinations thereof, of the PAP device/system.

1.1.9.4 Certain Embodiments of the Flow Generator Securement

The headgear and/or flow generator arrangement may include a mechanism to allow repositioning and realignment of the flow generator with respect to the headgear and/or the patient. In one form the mechanism absorbs vibration emitted from the flow generator. In one form the repositioning mechanism is structured to allow engagement and disengagement of the flow generator from the headgear. In another form, the repositioning mechanism is structured to secure and stabilize the flow generator once it is engaged with the headgear. In another form, the repositioning mechanism is structured to absorb vibration from the flow generator. In another form, the repositioning mechanism is structured to reduce the visual bulk of the system when in use by a patient or streamline the appearance of the system when in use by the patient. In certain embodiments, the headgear and/or flow generator arrangement may include a mechanism to allow repositioning and realignment of the flow generator with respect to the headgear and/or the patient that may absorb vibration emitted from the flow generator, is structured to allow engagement and disengagement of the flow generator from the headgear, is structured to secure and stabilize the flow generator once it is engaged with the headgear, is structured to absorb vibration from the flow generator, is structured to reduce the visual bulk of the system when in use by a patient, streamline the appearance of the system when in use by the patient or combinations thereof.

FIGS. 149-152 show alternative methods of ensuring the flow generator is secured in position on the headgear 8010. Cup or sling or cradle 8110 may capture or cover a portion of the flow generator 8014 to reduce the possibility of the flow generator 8014 displacing from the extension portion 8003 of headgear 8010. The cup 8110 may capture a rear portion 8141 and/or side portions 8142 of flow generator 8014. This may also assist the patient with aligning flow generator 8014 on extension portion 8003 of headgear 8010 if the flow generator is able to be removed from the headgear.

Cup 8110 may be integral to or formed with occipital ring 8001. Cup 8110 may be selectively attachable to the occipital ring 8001. Alternatively, cup 8110 may be attachable to a strap or other portion's of headgear 8010.

Cup 8110 may be flexible so that it may conform to the shape of the rear portion 8141 and side or back portions 8142 of the flow generator 8014 when in position. In addition, the cup 8110 may be flexible to absorb vibration and noise from the flow generator 8014. For example, cup 8110 may be made from fabric, polymer, foam or other flexible material or combinations thereof. Alternatively, cup 8110 may be rigid or semi-rigid so that the flow generator may abut or align to the cup.

Raised portions 8150 may be positioned adjacent extension portion 8003 so as to absorb noise and vibration from the flow generator 8014, to assist in alignment of the flow generator 8014 when placing it on extension portion 8003, and to secure the flow generator in position once it is positioned on extension portion 8003 so as to prevent it from moving from its intended position on headgear 8010. There may be one or more raised portions 8150. There may be two raised portions 8150 so as to secure the flow generator from at least two sides. There may be more than two raised portions 8150, such as three raised portions, to greater secure the flow generator. In certain embodiments, there may be 1, 2, 3, 4, 5, 6, 7, 8, or more raised portions.

Raised portions 8150 may be positioned on and/or in the occipital ring 8001. Raised portions 8150 may have a thickness that is greater than at least a portion of the occipital ring 8001. The raised portions 8150 may be thicker than the entire occipital ring.

Raised portions 8150 may be constructed from a flexible and/or resiliently deformable material such as foam, fabric, polymer, gel, etc. Raised portions may be formed or otherwise attached to the headgear 8010.

Raised portions 8150 may include ribs 815.1. In certain embodiments, the ribs may reduce visual bulk. Ribs may also assist in maintaining the desired shape of the headgear. Ribs may also strengthen the headgear in this region to enable better securement of the flow generator 8014.

The flow generator 8014 may have securement means attached on its underside, or at least a portion of the face that abuts the extension portion 8003. For example, the flow generator 8014 may include hook material on the face that touches extension portion 8003. Extension portion 8003 may be made from loop material so as to engage with the hook material of the securement means attached to the face of the flow generator 8014. Alternative securement means are possible such as push fit pins, slidably engageable hooks and loops, buttons, tacky materials etc.

Securement means may be a hook and loop material as this may further absorb vibration from the flow generator.

1.1.9.5 Certain Embodiments of Flow Generator Position Adjustment

Figure 153:
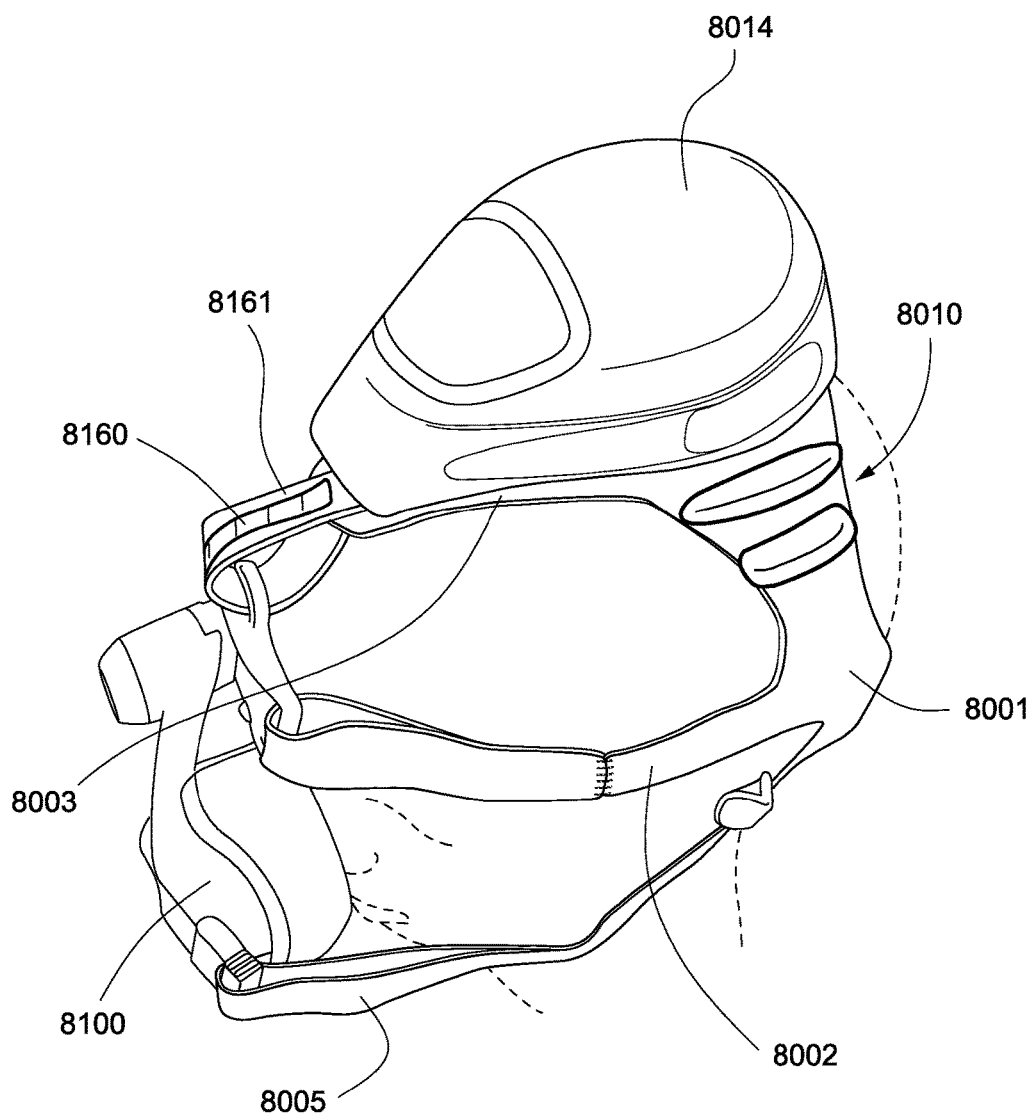
Figure 154:
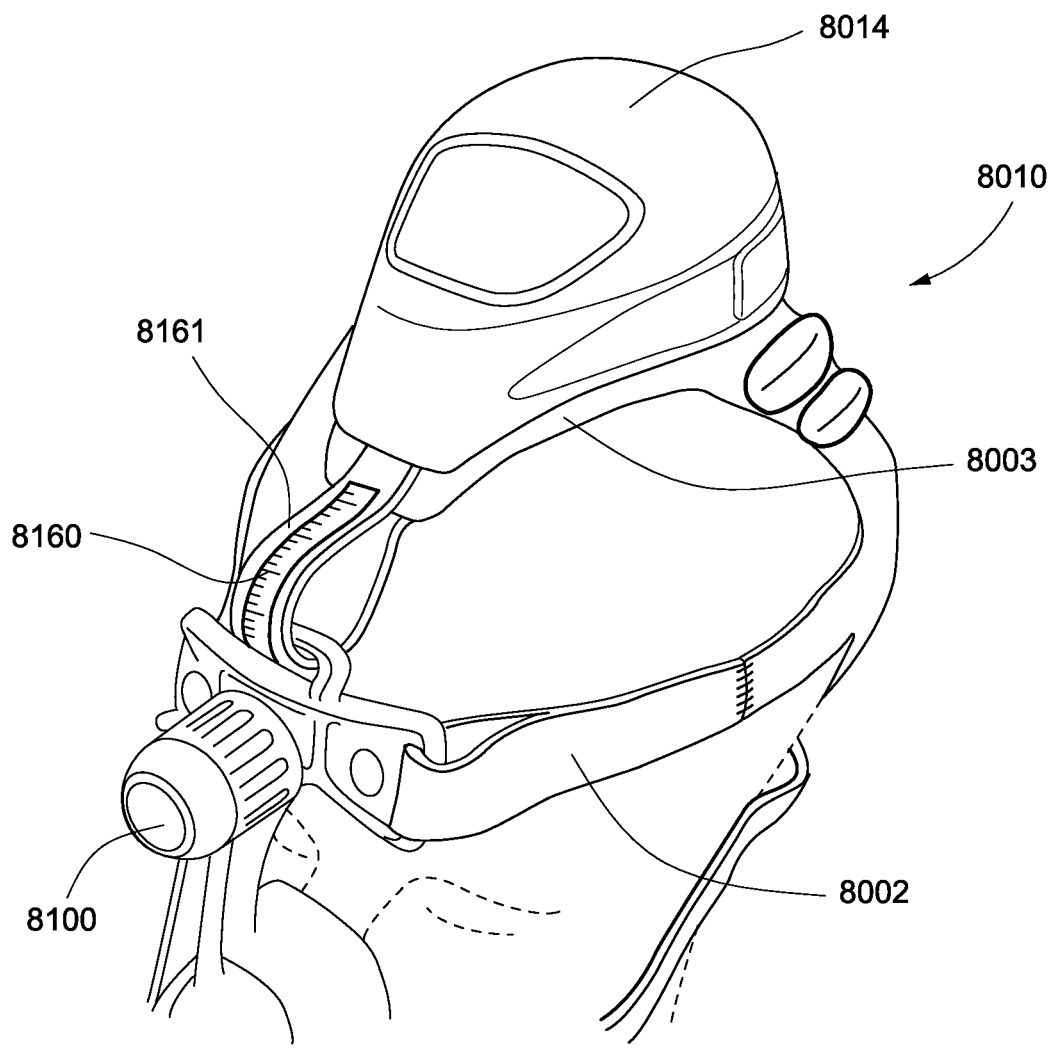
Figure 155:
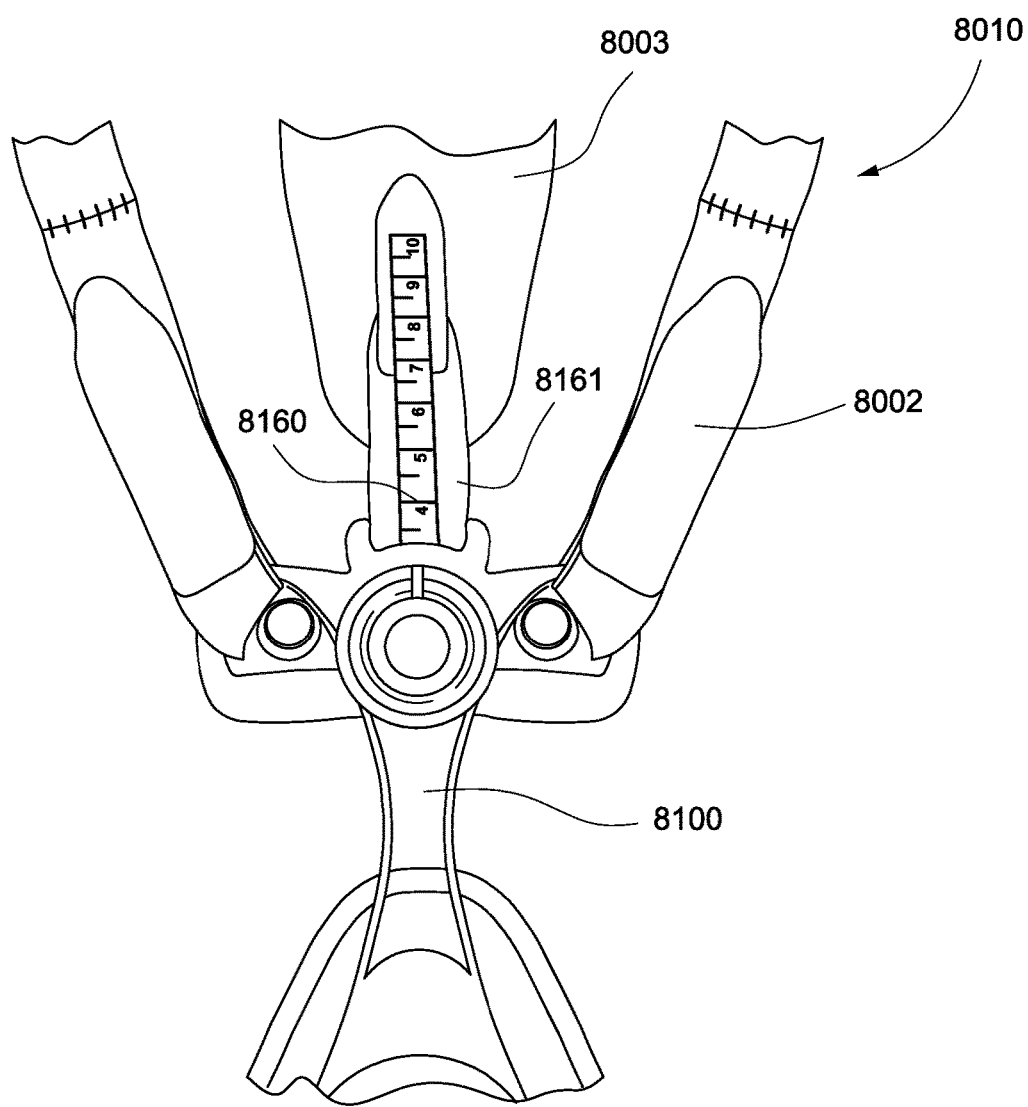

FIGS. 153-155 show an alignment feature for headgear 8010. Extension portion 8003 may include strap 8161 to connect extension portion 8003 to a portion of a patient interface 8100. This may enable better alignment and securement of the extension portion 8003 in relation to the patient interface 8100.

Strap 8161 may further include a ruler or measurement guide 8160 to indicate the tightness or length of strap 8161. The measurement guide 8160 may have any reasonable indication of adjustment such as numbers, letters and/or pictures.

This may assist the patient in adjusting the length or tightness of the strap 8161 to the same degree each time they set or adjust the headgear.

1.1.9.6 Flow Generator to Patient Interface Tubing

In a preferred embodiment of the present technology as depicted in FIGS. 156-160. A PAP system 8501 includes a flow generator 8500 preferably mounted or positioned on or near or in front of the crown or apex of a patient's head using headgear 8502. Preferably, the PAP system is adapted to deliver pressurized breathable gas to a patient. The PAP system may be used to treat respiratory disease or insufficiency or alternately as a treatment for sleep apnea and or associated diseases. This PAP system is adapted to be light weight, typically less than 500 grams, and able to be carried or used when travelling (e.g. when the patient is travelling such as on a plane, etc.).

The PAP system 8501 includes a mask 8503 for the delivering pressurized breathable gas to the airways of the patient 8505. In this embodiment, the mask 8503 is a nasal mask, but other ventilation or respiratory masks may be used.

The mask 8503 is connected to the flow generator 8500 by a first section of tubing 8504 which in turn connects to a second portion of tubing 8507. The second portion of tubing may be substituted with different lengths of tubing to accommodate different head sizes of various patients.

The mask may include a diffuse vent 8506 to allow the exhalation of gases from the mask and patient. In this embodiment, the vent may be mounted in the center of the surface of mask directed away from the patient.

In this embodiment, the mask 8503 includes a relatively soft cushion, which may be constructed of silicone and a more rigid and resilient frame body 8509. The frame body 8509 supports at least a portion of the tubing connecting the mask to the flow generator.

Figure 156:
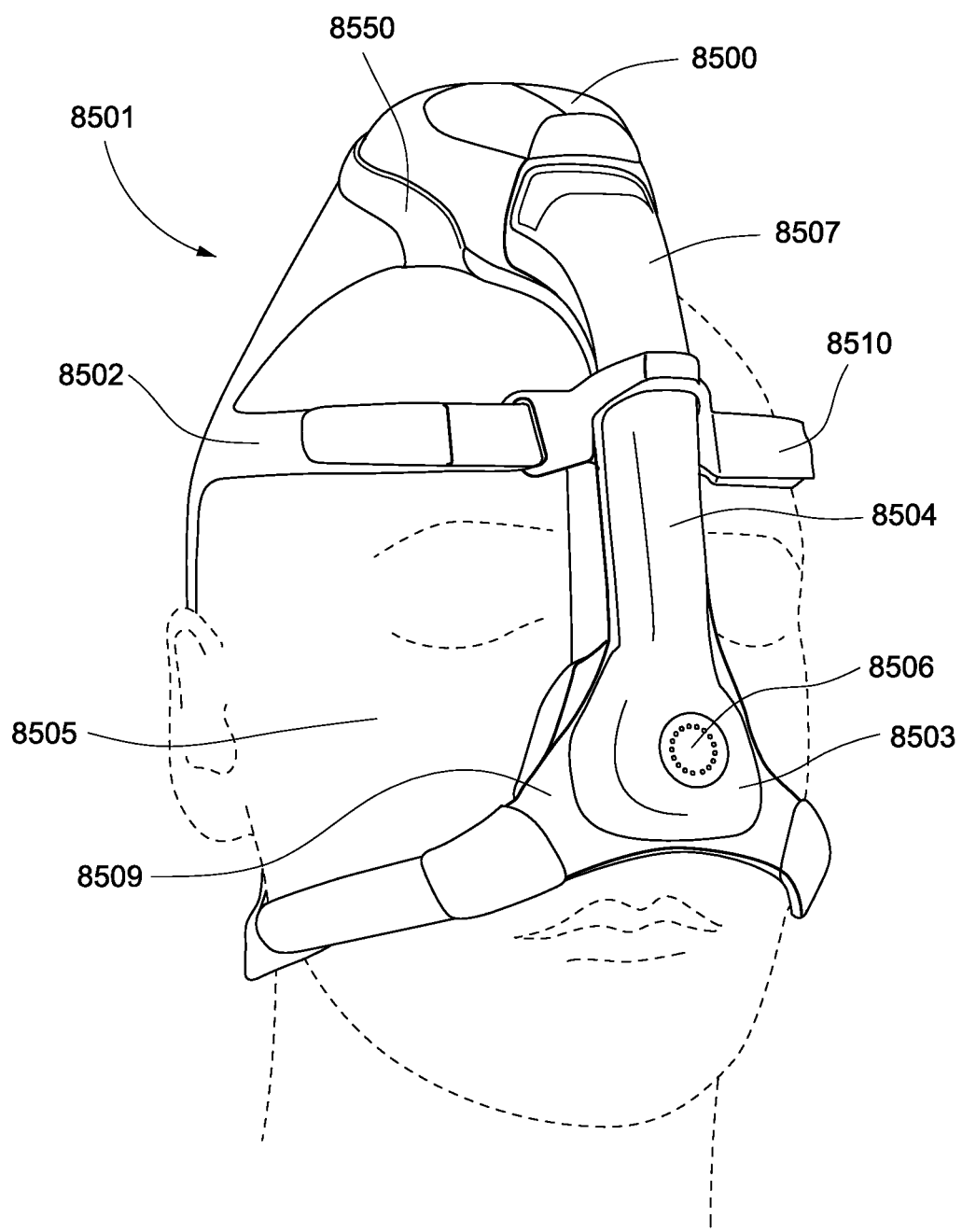
Figure 157:
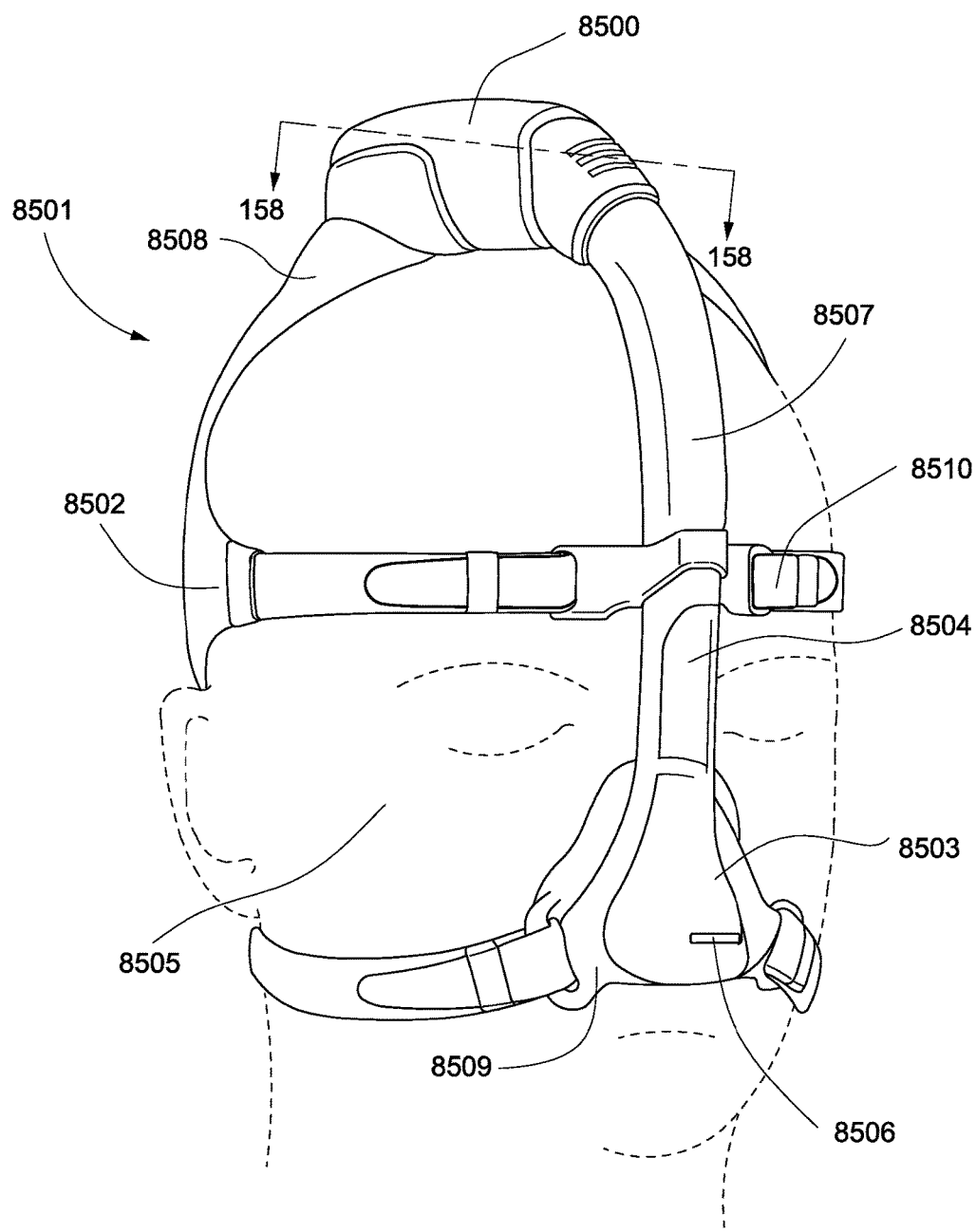

The headgear 8502 may secure the mask and flow generator with hook and loop (Velcro™) fasteners. Some of these fasteners are illustrated in FIG. 156 as 8510. The headgear 8502 includes a plurality of straps. The flow generator 8500 is positioned on or in front of the crown of the patient's head. On the straps extending away from the flow generator, padding 8508 has been added to reduce visual impact and size of the flow generator on a patient's head. Additionally, the padding may limit or reduce vibration, shock and/or noise transmission. The padding 8508 is typically constructed of foam inserted or encapsulated within the headgear 8502.

The flow generator 8500 may be selectively attached to the headgear 8502 using a cradle 8550. The cradle may comprise a base wall which engages the underside of the flow generator 8500 and a side wall.

In this embodiment, the base wall engages the entire underside of the flow generator but different sizing may be possible. The base wall may be larger than the surface area of the underside of the flow generator to allow the flow generator to be mounted at multiple sites. Specifically, the flow generator may be mounted further forward or back relative to the patient and this may allow the flow generator to be mounted on the crown of the patient's head regardless of the different anthrometric sizing of the patient.

Hook and loop fasteners (Velcro™) may be used to releasably connect to the flow generator 8500 onto the cradle 8550. An advantage with using hook and loop fasteners may be that the connection is softer and more flexible than other attachment means. The fasteners may allow for the connection between the cradle and flow generator to provide a damping means which may limit or reduce transmitted noise or vibration.

The side wall of the cradle 8550 may at least partially cover or extend along the side wall of the flow generator, when it is mounted in the cradle. The cradle may include two side walls to engage respective side walls of the flow generator. This allows for the flow generator to be positioned so that the outlet of the flow generator is facing forward (e.g. generally towards the face of the patient). Additionally, the side walls are adapted to engage the side walls of the flow generator in the various mounting sites or positions.

The side walls of the cradle may be joined with an elastic strap or extendible side wall adapted to extend along the back or rear of the flow generator, when mounted. The elastic strap may be adapted to expand and contract depending on the various positioning of the flow generator, when mounted in the cradle. The elastic strap is adapted to move forward and engage the back of the flow generator, even when the flow generator is mounted in a forward position (e.g. closer to the patient's face). In situation where the flow generator is directed or positioned more to the rear, the elastic strap expands to accommodate the new position. This permits various positioning of the flow generator on the patient's head.

Additionally, the cradle is generally constructed of soft fabric. The soft fabric may also give rise to the cradle functioning as a vibration damping means to reduce or limit the transmitted noise and/or vibration of the flow generator.

Referring to FIGS. 53A to 55B, a headworn PAP system according to certain embodiments is illustrated. As shown in the figures, the flow generator 8500 may be located on the front of the head of the patient 8505 between the crown and the forehead. This position of the flow generator on the front of the head may be more comfortable as the neck muscles at the back of the neck are bigger and stronger and are able to support the weight and prevent the head dropping forward better than the smaller muscles at the front of the neck. In tests conducted on users having varying forehead heights and head circumferences, the most comfortable position for the flow generator 8500 on the head, as measured on the forehead from the flow generator outlet to the top of the mask frame was identified as between about 30 mm and 60 mm. This represents an adjustment range of about 30 mm. The PAP system may have an adjustment range of 30 mm by providing the second section of tubing 8507 with a length of about 30 mm.

Figure 158:
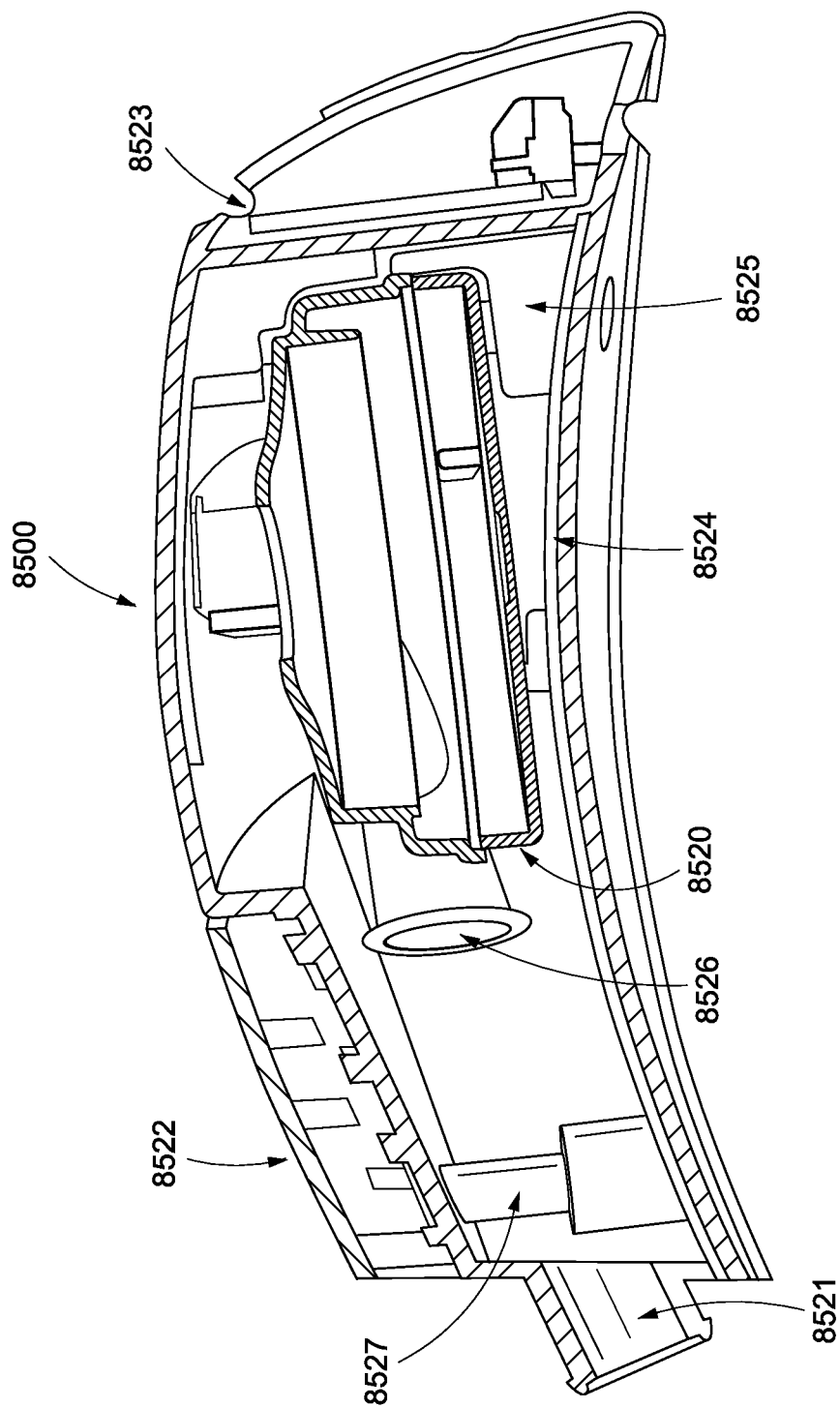
Figure 159:
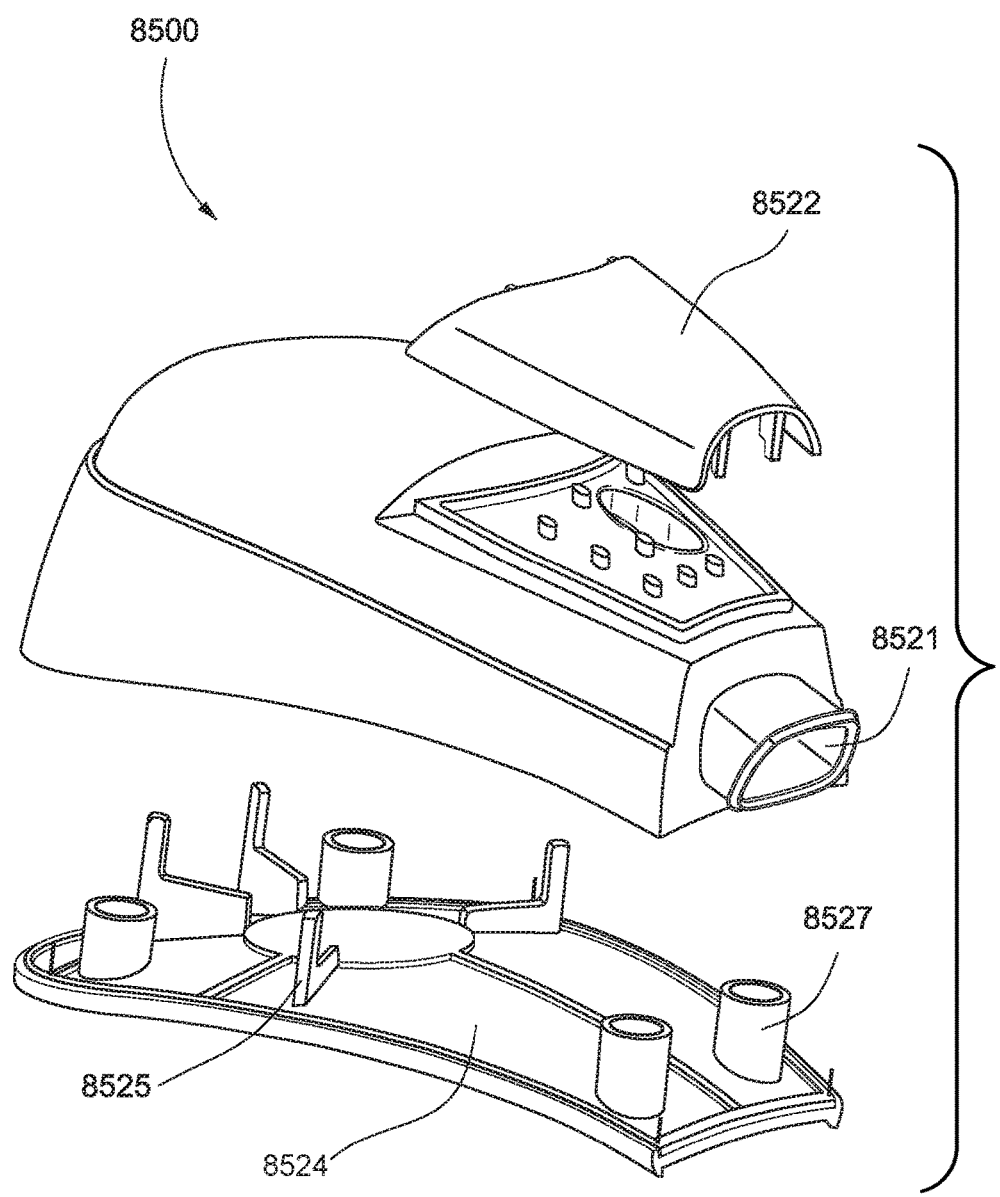

FIG. 158 illustrates a cross-sectional view of the flow generator 8500. The flow generator 8500 includes a blower 8520. The blower 8520 includes a blower outlet 8526 which is in turn connected to the housing outlet 8521. The blower motor is positioned with the inlet of the blower directed away from the patient towards the top of the flow generator. The housing portions may be secured and held together using screw mounts 8527.

The interior of housing of the flow generator 8500 is overmoulded with a relatively soft polymeric substance 8524 to absorb noise and/or vibration. The overmoulding extends into the housing cavity of the flow generator 8500 to form mounting brackets 8525 to hold and secure the blower motor 8520 in place. The mounting brackets 8525 may form protrusions extending upwardly from the base of the interior of the flow generator 8500. These protrusions are adapted to form a cradle for the blower motor at some position below the blower motor 8520. The housing cavity in the flow generator may be filled with a compressible foam material that dampens and/or reduces the vibration transmitted by the blower motor, when in use. When the foam is compressed or deteriorates the blower motor may eventually rest on the ends of the protrusions. The protrusions may also function to limit or reduce vibration by a damping mechanism. Four protrusions may extend into the cavity of the flow generator, but the number of protrusions may be increased to improve stability of the blower motor. The protrusions may be shaped and/or adapted to receive the blower motor and mate with the external shape of blower motor. The height of the protrusions may be less than the height of the blower motor suspension above the base of the interior of the flow generator.

The flow generator includes a housing inlet with an inlet cover 8522. Additionally the inlet cover 8522 may function as a muffler body.

The cavities of the flow generator may be filled with foam to suspend the blower and/or other components and to suppress noise and/or vibration.

Figure 160:
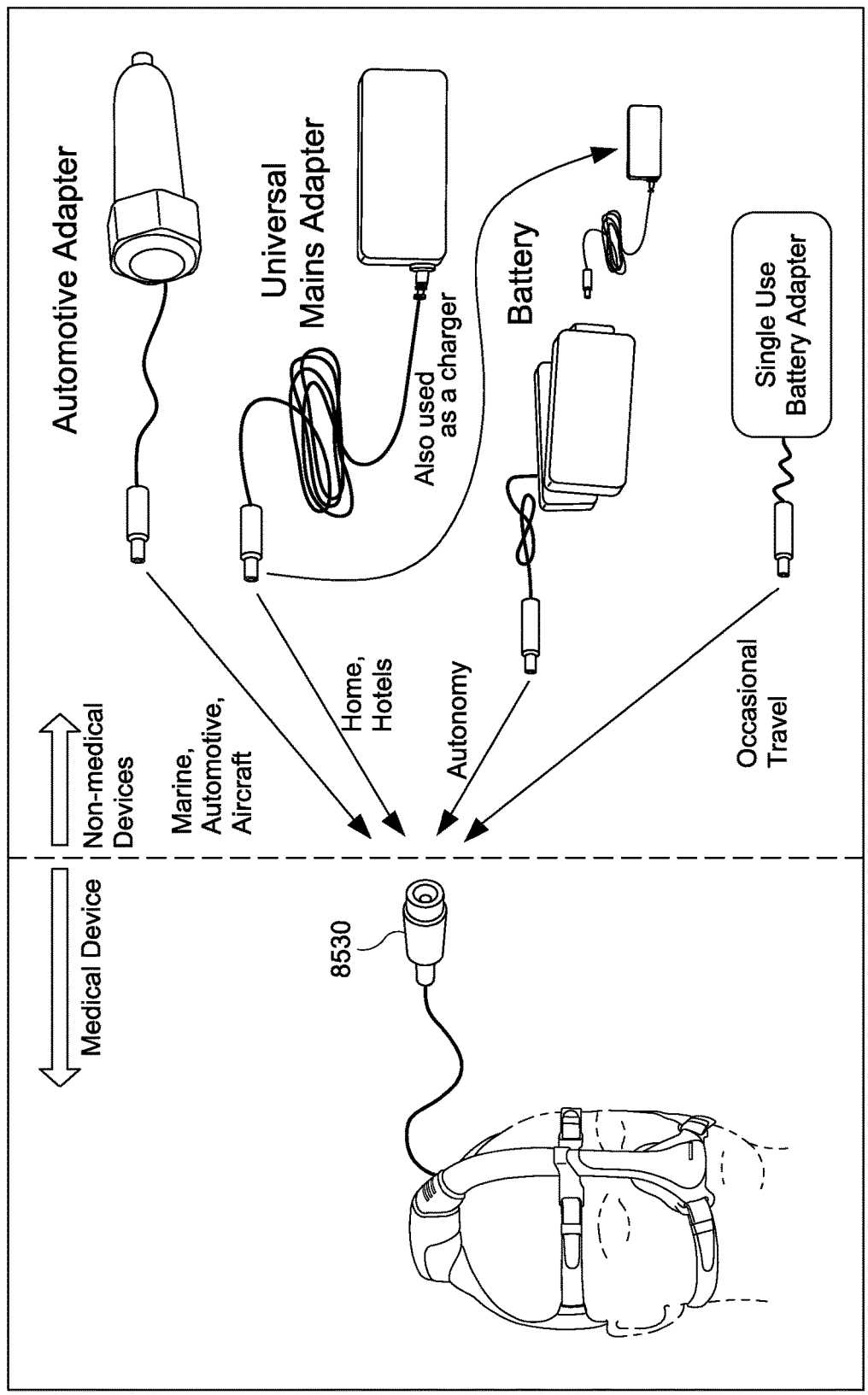

A hardware control circuit 8523 is vertically mounted at the back of the housing. The control circuit is driven by a 12v DC power supply (as shown in FIG. 160). The control circuit 8523 may be capable of being preset to a certain factory set motor speed to produce a predetermined level of pressure support. For example, the pressure support may be pre-set to 8, 10, or 12 cm H2O of pressure. Alternatively the device may include a plurality of preset pressure level settings. Each pressure setting adjusting the motor speed to provide the required pressure setting. Preferably the pressure level may be adjustable using a special tool, similar to a screwdriver, such that a health care provider or clinician is required to set the prescribed pressure level to prevent self-medication of the pressure level. The device may be turned on with power is supplied and turned off when the power is withdrawn such that no on and off switch is required. However, an on and off switch may be provided to control the operation of the device.

The control circuit may also include a flight mode switch. When flight mode is activated or engaged, the control circuit operates the blower at a predetermined pressure setting appropriate for therapy treatment which has been adjusted for an external ambient air pressure appropriate for about 6000 ft. This adjusts the control circuit to deliver the required therapeutic pressures while the patient is using the system in the normal cabin pressure of pressurized passenger aircraft. Specifically, the blower is operated by the control circuit at slightly increased speed to compensate for the lower air pressure in the cabin than when the patient is at ground level. In certain embodiments, 6000 ft is exemplary and other pressure settings may be selected or predetermined to adjust for an external ambient air pressure at elevated heights.

The flight mode switch may be activated either: manually by a patient activating a mechanical electrical switch mounted on the housing of the flow generator; or automatically by sensors mounted on the control circuit that detect the ambient air pressure external to the pressurized system.

In this embodiment, the power supply connection 8530 has been optimized and adapted for use with most DC power supplies or rectified currents. For example a wide DC operating range of 10 to 20 volts may be utilized. In certain applications between 10.2-18.7 volts may be used. FIG. 160 demonstrates some of the accessories that may be used to power the PAP system. For marine, automobile or aircraft travel, it may be suitable to use a cigarette lighter convertor to connect to a supply power. At home, a universal mains adaptor could be used to supply power. For occasional or short trip travel, single use or rechargeable batteries may be connected to the system. The socket 8517 for the power cord 8515 is designed to allow easy removal if the tension on the cord is too high to prevent any risk of strangulation.

Additionally, the present embodiment could be adapted for the treatment of asthma. The PAP system is light and portable and can be easily carried by patients due to its light weight and lack of bulk. The delivery of 8-12 cm H2O may be suitable to treat asthma and prevent or limit the severity of acute asthma attacks.

1.1.10 Certain Embodiments of the Nasal Mask System

Certain exemplary embodiments may be directed towards a nasal mask system that is easy and quick to fit (e.g., with little or no adjustment), enable reduced strap tension, is manufacturable in high volumes, provides high consumer appeal, provides comfort and seal, provides reliable quality, fits a suitable majority of the population or combinations thereof.

As described in greater detail herein, the nasal mask system includes a frame, a sealing arrangement (e.g., a cushion) provided to the frame and adapted to form a seal with the patient's nose, and an elbow, e.g., provided to the sealing arrangement, adapted to be connected to an air delivery tube that delivers breathable gas to the patient. A swivel ring may be optionally provided to couple the elbow to the sealing arrangement. Headgear may be removably attached to the frame to maintain the nasal mask system in a desired adjusted position on the patient's face. The nasal mask system is intended for use in positive pressure therapy for users with Obstructive Sleep Apnea (OSA) and/or other respiratory disorders.

While the illustrated examples below describe use of a nasal interface type, however, these non limiting examples may be adapted for use with other suitable interface types, e.g., full-face interface, nasal prongs, etc.

1.1.10.1 Certain Embodiments of the Patient Interface

Certain embodiments may be adapted to work, or to be used, with a light weight travel PAP device or system. The PAP system may be mounted on the body of the patient. The placement of the flow generator forming part of the PAP system is on or in front of the crown of the patient's head. However, other placements may also be used.

The first embodiment relates to patient interfaces including masks for the delivery of pressurized breathable gas to patient and for use with travel PAP devices and/or systems.

1.1.10.2 Certain Embodiments of the Patient Interface Sealing Arrangement

The sealing arrangement 9040 is structured to interface with the frame 9020 and form a seal with the patient's nose in use. The sealing arrangement 9040 may provide a nasal interface adapted to engage the patient's face generally along nasal bridge, cheek, and upper lip regions of the patient's face. However, other interfaces are possible, e.g., full-face. The sealing arrangement provides a compliant arrangement adapted to seal relatively quickly and maintain seal in use. The sealing arrangement may be structured to seal with or without air pressure.

1.1.10.3 Certain Embodiments of the Silicone Cushion

FIGS. 161-168 illustrate certain embodiments. In these figures, the sealing arrangement 9040 includes a cushion 9042 constructed of a substantially flexible material including but not limited to silicone, TPE, gel, other suitable materials or combinations thereof. The cushion 9042 defines a breathing chamber or cavity adapted to receive the patient's nose and provide air communication to the patient.

The face-contacting side of the cushion 9042 may include a dual-wall configuration wherein the cushion includes an undercushion and a membrane that at least partially covers the undercushion. The membrane may softer and less stiff than the undercushion and provides a seal against the patient's face in use. The undercushion may be structured to support the membrane and prevent collapse of the membrane when the nasal mask system is attached and tightened using the headgear. The undercushion may only be provided in selected regions of the mask system, e.g., along the cheek regions, or not at all. Also, the cushion may be frosted, e.g., for easy fit and comfort, and/or tinted.

The cushion includes a sickle-shape or question-mark configuration with a base portion and an upper portion that is radially offset towards the outside of the base portion, e.g., to reduce size and perceived bulk, minimize dead space within the breathing chamber, and/or add more flexibility to the undercushion and membrane in use. Such cross-section may be provided around the entire perimeter of the cushion or may only be provided in selected regions of the cushion. The "question-mark"-shaped cross-section in the upper lip region may include less curvature, e.g., to avoid overhang of the cushion into the patient's mouth and prevent nostril occlusion.

The gap or spacing between the membrane and undercushion may be adjusted, e.g., to reduce wrinkling and possibility of leaks, when in use. For example, the gap may be relatively small so that the membrane closely follows the geometry of the undercushion. The cushion may be moulded so that the gap is larger, but the membrane is preloaded to hinge closer to the undercushion after moulding. A bellows may be also provided or moulded with the membrane to bias the membrane closer to the undercushion.

The non-face-contacting or frame side of the cushion 9042 includes one or more interfacing structures adapted to interface or otherwise removably connect to the frame 9020. In the illustrated example, the cushion 9042 includes one or more elongated and spaced protrusions 9050, e.g., along the sides and bottom thereof adapted to engage or interlock with respective openings 9027 along the side wall 9026 of the frame 9020. As shown in FIGS. 176 to 178, such arrangement provides positive reinforcement that the connection has been established as the user can visually see the connection and optionally a proper connection may result in an audible clicking noise.

For example, a possible arrangement for connecting the cushion 9042 to the frame 9020 is disclosed in U.S. Pat. No. 7,000,614.

The non-face-contacting side of the cushion 9042 also includes an opening 9075 adapted to receive or otherwise communicate with the elbow 9070 as described herein.

As illustrated, the face-contacting side of the cushion (i.e. including the membrane and undercushion) may be co-moulded with or formed separately and attached to the non-face-contacting side of the cushion (i.e., defining the opening 9075 and breathing chamber). The face contacting side of the cushion and the non-face-contacting side of the cushion may be formed as a single component. This single component may be made from a flexible sealing material that is sufficiently biocompatible when in contact with patient's skin, including but not limited to silicone.

In this embodiment, the cushion defines an interior cavity. The cavity is connected to and in air communication with an inlet tube. The inlet tube may be adapted to be integrally moulded with the cushion in one piece. Additionally, the arcuate bridge may be attached or integrally moulded to the frame and forehead support regions.

1.1.10.4 Certain Embodiments of the Inlet Tube

The inlet tube 9070 includes a first end 9072 and a second end 9074, (e.g., see FIGS. 161-167). The first end 9072 provides an interfacing structure structured to interface or otherwise attach to the sealing arrangement 9040 or the cushion. The second end 9074 is adapted to be connected to an air delivery tube or intermediate tube. The first end is approximately angled about 90° with respect to the second portion and is to be positioned on the patient, when worn, in a substantially vertical orientation (i.e. upwardly along the patient's face to their forehead). However, the first and second end of the inlet tube may have other suitable angles with respect to one another, e.g., 0°, between about 70° and 90°, between about 90° and 120°, between about 75° and 85°, etc.

The inlet tube 9070 may be to be mounted between the two arms 9032 which, when in use, extend and support each side of the inlet tube 9070 of the patient interface.

The inlet tube 9070 may be adapted to be clipped and retained by a curved or accurate bridge 9038 of the forehead support 9030. The bridge is adapted to receive and mate with the inlet tube 9070 and apply compression force to the inlet tube. The compression force may be applied to either side of the inlet tube and adapted to provide a clamping force around the inlet tube. This force may be sufficient to retain and secure the inlet tube, however, not enough to collapse or occlude the inlet tube. The inner walls of the bridge 9038 grasp the outer wall of the inlet tube 9070 to hole and retain it in position without occluding the cavity for delivering pressurized breathable gas. Further the bridge may extend along the side walls of the inlet tube and join on the front (i.e. the side facing away from the patient) of the inlet tube.

The inlet tube 9070 may include D-shaped cross sectional profile when the cross section is taken across its width. The bridge 9038 may cover and engage the long side of the D-shape of the inlet tube 9070. The bridge 9038 wraps around and engages the corners of the D-shape of the inlet tube, The clip mechanism operating between the bridge and the inlet tube may be selectively releasably by the patient. This may aid in cleaning the patient interface.

The D-shape of the inlet tube may reduce its visual profile and/or impact when the patient interface is worn, as well as the shape may also reduce transmitted noise and/or vibration. The D-shape may also strengthen the inlet tube 9070 and limit the likelihood of accidental partial or full occlusion. The intermediate or connector tube may be substantially D-shape in various regions to allow similar advantages. It should be appreciated that other cross sectional shaped maybe used.

The bridge 9038 may be mounted near to or proximal to second end 9074 of the inlet tube 9070. This may allow the relatively softer portions of the patient interface to be reliably secured and prevent or limit unintended movement of the cushion and/or inlet tube by joining at the extremities of the patient interface.

The inlet tube 9070 may be made by co-moulding it with the rest of the cushion assembly. Additionally, the inlet tube 9070 may be constructed of silicone.

The length of the inlet tube may be, for example, between 40-65 mm. The length of the inlet tube may be, for example, approximately 55 mm.

1.1.10.5 Certain Embodiments of the Frame

As shown in FIGS. 169-179, the frame 9020 (also referred to an exoskeleton or skeleton) is structured to maintain or otherwise support the sealing arrangement 9040 (and also the elbow 9070) in an operative position with respect to the patient's face. In addition, the frame 9020 is structured to attach headgear to the nasal mask system.

As illustrated, the main body 9022 (e.g., see FIG. 169-179) of the frame 9020 includes an open construction with a central opening 9024 to allow the sealing arrangement 9040 to communicate with or receive a side wall 9026 structured to retain or otherwise engage the sealing arrangement 9040. In use, the frame 9020 of this example is not in the air path, i.e., sealing arrangement 9040 defines breathing cavity and is directly coupled to the inlet tube 9070 as described below. The frame 9020 may be semi-rigid or at least allow for some flexibility. The frame 9020 may be made from a single material, a combination of materials, or a combination of the same material in varying hardnesses. The frame 9020 may be made from polycarbonate, polypropylene, nylon, thermoplastic elastomer (TPE), silicone, or any other suitable material.

A forehead support 9030 extends from the top end of the main body 9022. The forehead support 9030 may be fixed (i.e., un-adjustable), adjustable (e.g., the height or length of elongated arm may be extendable, or the angle of the forehead support may be changeable), or interchangeable (e.g., various sizes of forehead supports for different sized patients or the elongated arm may be replaced with different various lengths of arm). The forehead support 9030 includes an elongated arm 9032 and an upper headgear connector 9034 providing slots or receiving holes 9035 at the free end of the arm adapted to receive respective headgear straps in use, thus using the padding of the headgear straps rather than requiring a separate pad. In an example, the headgear connector may be adjustable, e.g., with respect to the arm 9032 (e.g., tilt or angle towards the patient's forehead).

Lower headgear connectors 9036 are provided to respective sides of the main body 9022, each lower headgear connector 9036 including elongated arms 9038 and a slot or receiving hole 9039 at the free end of the arm adapted to receive a respective headgear strap in use. The elongated arm 9038 may be bendable or selectively deformable so as to allow the arm to bend towards or away from the patient's face in use, thereby pulling the headgear onto the patient's face, e.g., enabling side sleeping. The forehead support and headgear connectors may provide a relatively unobtrusive arrangement which minimizes the impact on the patient's line of sight. Preferably, each elongated arm 9038 may include a deformable hook positioned on the end of the arm opposed to the connection of the mask frame. The deformable and resilient hook may be constructed of silicone and may be selectively deformable to allow a strap of the headgear to pass over the hook but wherein the hook resists or limits the strap from being pulled from the mask accidentally.

In an example, the arms 9032 may be suitably formed, shaped, or contoured to follow the contours of the patient's face while avoiding the patient's line of sight or impeding their vision. Also, the arms 9032 may include some inherent flexibility to allow a range of adjustment. The elongated arms 9032 may be made from a substantially inextensible material such as aluminum, stainless steel, polycarbonate, polypropylene, TPE, or any other suitable material. Alternatively, the elongated arms 9032 may be continuous with the frame 9020 and therefore made from the same material, or the elongated arms 9032 may be made from the same material as the frame 9020 but not a single piece construction (i.e., the elongated arms 9032 may be attached to the frame 9020). However, wherein the elongated arm 9032 is made of different material from the frame 9020, the elongated arm 9032 may be secured onto frame 20 using an alternative fixing or securing method, e.g., such as gluing. The upper headgear connector 9034 may be made from the same material as the elongated arm 9032. Alternatively, the upper headgear connector 9034 may be made from a more flexible material than the elongated arm 9032 such as Hytrel™, silicone, nylon, or other suitable materials or combinations thereof. The lower headgear connectors 9036 may be continuous with the frame 9020 and therefore made from the same material, or the lower headgear connectors 9036 may be made from the same material as the frame 9020 but not a single piece construction. Alternatively, the lower headgear connectors 36 may be made from a more flexible material than frame 9020 such as Hytrel™, silicone, nylon, or other suitable materials or combinations thereof.

The forehead support and headgear connectors may be integrally moulded or otherwise attached to the main body of the frame 9020. The frame 9020 is constructed from a more rigid material than the sealing arrangement 9040 (e.g., made of silicone, foam). For example, the frame may be constructed of plastic (e.g., polycarbonate), metal materials (e.g., relatively thin metal material) or combinations thereof.

In an example, the arms 9032 may be relatively thin or slender (e.g., 1-3 mm). In an example, the forehead support 9030 and headgear connectors 9036 may be formed of a material (e.g., metallic material) which is different than the material of the frame main body 9022. In such example, the forehead support 9030 and headgear connectors 9036 may be attachable to the frame main body 9022. The relatively thin or slender arms 9032 may reduce the overall visual impact of the mask or embodiment.

In an example, upper headgear connector 9034 provides a flattened area for the attachment of straps from the headgear. In an example, the straps attach to the upper headgear connector 9034 through two apertures 9035 mounted on opposed sides of the upper headgear connector 9034 and the straps are adapted to extend through the apertures and elicit a force towards the patient's face and effectively pull the upper headgear connector 9034 towards the patient's forehead, in this embodiment.

1.1.10.6 Certain Embodiments of the Vent Arrangement

The cushion 9042 may include a vent arrangement for gas washout. The vent arrangement includes a plurality of holes (e.g., 1-100 holes, e.g., 20-50 holes, or about 45 holes). Each hole may include a contour or taper along its length. However, it should be appreciated that the vent arrangement may include other suitable arrangements, e.g., different number of holes, hole arrangement, vent insert with one or more vent holes, etc.

The vent may also, for example, be a diffuse vent as disclosed in U.S. Patent Application Publication 2009/0050156 A1, which is incorporated herein by reference in its entirety.

Various types of vents may be plugged into the vent arrangement 9075, and/or the vents are removable for cleaning.

1.1.10.7 Certain Embodiments of the Headgear

Headgear may be removably attached to the headgear connectors 9034, 9036 of the frame 9020 to maintain the nasal mask system in a desired position on the patient's face. In the illustrated example, the frame provides a four-point connection for a pair of upper headgear straps and a pair of lower headgear straps. However, the frame may provide other arrangements, e.g., two-point connection or three-point connection. Rigidisers or reinforcing materials may be provided to one or more of the straps.

Headgear may be constructed of an elastic or flexible material such as woven and non-woven fabric, TPE, polypropylene, nylon, or other suitable materials or combinations thereof. The headgear may also be reinforced with stiffening members that may add stability.

The nasal mask system may be used with headgear such as that described in Australian Provisional Application No. 2010900237, filed Jan. 22, 2010, which is incorporated herein by reference in its entirety.

Attachment/adjustment of such headgear may be provided by buckles or hook and loop material. For example, the headgear straps may be constructed of a nylon elastic material with strap adjustment provided by buckles without any hook and loop material. However, the nasal mask system may be used with alternative headgear arrangements.

1.1.10.8 Certain Embodiments of the Forehead Support

The forehead support 9030 is supported by the arm 9032. As shown in FIGS. 169-179, the forehead support 9030 may have flexible region 9031 built into the forehead support to allow it to spring from its natural v-shaped position or shape to a more linear position or shape. The flexible region may be a thinned portion of material (i.e., same material as rest of forehead support, but thinner to allow flex).

The flexible region may be a co-moulded portion of flexible material, such as thermoplastic elastomer (may also be colored). The remainder of the forehead support may be made from a less flexible material such as polycarbonate or polypropylene. Co-moulding may be via a chemical or mechanical bond between the two materials. The separately formed/assembled TPE part reduces breakage risks and enables assembly offsite with the headgear. The forehead support may include a frosted finish.

The flexible region provides an auto-adjust flex feature that is adjusted with headgear tension enabling greater biasing of the cushion to assist fit.

Alternatively, the forehead support may be made from a thickened, compliant material, such as foam, that can be compressed thereby achieving a similar result.

The position of the forehead support without any loading (i.e., natural state), may be demonstrated as angle $\alpha$, e.g., angle $\alpha$ may be about 5-90°, e.g., about 15°.

In use, the forehead support may allow about 15 mm of adjustment in the anterior-posterior direction. This may allow for a greater fit range of patients as it may accommodate a greater variety of anthropometrics, particularly at the nasal bridge region. In certain embodiments, the forehead support may allow for at least 10 mm, 12 mm, 15 mm, 16 mm, 18 mm or 20 mm of adjustment in the anterior-posterior direction.

Headgear may attach to the forehead support through loop holes 9035 or may attach through a loop through arrangement.

1.1.10.9 Certain Embodiments of the Tubing

Certain embodiments of the disclosure may be adapted to be connected to head connected pressurized breathable gas flow generator for the treatment of sleep apnea or respiratory conditions. The flow generator may be adapted to be relatively light and not relatively bulky when compared to traditional medical pressurized air flow generators. The headgear may be adapted to prevent or limit the transmission of noise and vibration along its component strap(s). The patient interface may be secured to the patient's face by the attachment of headgear straps and the flow generator may be also supported and secured by the headgear. The flow generator may deliver pressurized breath gas by a relatively short length of tubing 9100 (as shown in FIGS. 175-182), also referred to as an intermediate tube or connector tube.

This tubing 9100 includes a first 9104 and a second end 9103 connected by circular or cylindrical cavity extending throughout the middle of the tubing 9100.

In certain embodiments, the tubing 9100 at the second end 9103 is adapted to slidably connect within the inlet tube 9074. The second end 9103 include a small notch or shoulder 9105 to engage the top of the inlet tube 9074 and limit the extent to which tubing 9100 may be inserted into the inlet tube 9074.

The connector tube 9100 includes a D-shape, or substantially D shaped, cross section when the cross section is taken relative to the width of the tubing. This D-shape or rounded trapezoidal cross section, may reduce the visual impact of the connector tube 9100. Additionally, it may strengthen the connector tube 9100 and increase its resistance to accidental occlusion during use. It should be appreciated that other cross sectional shapes may be used.

The side profile and lengthwise cross section (as shown in FIG. 182 include a rounded or arcuate profile. This arcuate profile may be adapted to conform with the arc formed between forehead of the patient (which correlates with the top of the patient interface) and the crown or in front of the crown of the patient's head where the flow generator may be secured.

The length of the connector tube 9100 between the patient interface and the flow generator may be shorter than most similar lengths of tubing used for similar applications. Typically, the length of the connector tube is less than, for example, 30 cm but is sufficient to join the patient interface with the flow generator mounted on or in front of the crown of the patient's head. The short length of connector tube 9100 also has the advantage of reducing the amount of dead space between the patient interface and flow generator. This may lead to increases in the reliability of data acquired from sensors (e.g. pressure sensors in the flow generator).

The supplied PAP system may include several (e.g. 2-10) different lengths of connector tube 9100, so as to allow adaptability of the system to different patient head types and lengths. The length of the tubing may range from 1-30 cm.

Additionally, the connector tube 9100 may include positioning holes adapted to receive a mating spigot from the flow generator. This may ensure the correct orientation of the connector tube 9100 and may minimize vibration transmission from the flow generator.

The connector tube 9100 may be shaped or adapted to minimize noise or vibration transmission from the flow generator. The connector tube 9100 may include various baffles in the air path (not shown) or noise/vibration absorbing walls (not shown). Additionally, the lower side 9106 is adapted to contact the upper forehead of the patient. The lower side 9106 is flat, or substantially flat, and relatively wide when compared to the circumference of the cavity 9102. This may increase the contact area of the lower side 9106 with the patient and further reduce vibration of the flow generator, tubing and patient interface. The non circular shape of connector tube 9100 may reduce echoing of air passing through the tube and setup an interference pattern further reducing and damping noise and/or vibration.

The connector tube 9100 may be constructed of flexible polymer material, wherein the material may be resilient enough to retain its shape during use and/or resist accidental occlusion. For example, the tubing 9100 may be constructed of silicone. The connector tube 9100 may be softer and more flexible than the portions that it connects to. For example, the intermediate tubing 9100 is softer and more flexible than the housing or the outlet of the flow generator; and also the connection point to the patient interface. T, this may be achieved by including a lower durometer material for constructing the connector tube 9100. Additionally, the softer and flexible connector tube 9100 may also additionally dampen noise and/or vibration transmission from the flow generator to the patient interface.

The connector tube 9100 shown in FIG. 182 includes end portions which are relatively straight, however, other suitable configurations may be used. The first end 9104 may include a straight end of 10 mm and the second end 9103 may include a straight end of 15 mm. The two ends may be joined by a natural arc between them.

The length of the connector tube 9100 as measured along the midline chord between the first and second ends may be for example, about 116 mm. Other chord lengths may be used, for example, 80 mm and 150 mm to correspond to small and large sizes of tubing.

The sealing arrangement 9040 may be constructed of a soft and flexible material and co-moulded with the inlet tube 9070. Here, the cushion 9040 forms a mask that is retained and secured in position by the resilient and deformable frame 9020. T, the frame may clip onto the sealing arrangement by attaching the outer surface of the cushion 9040 and the bridge 9038 joining to the inlet tube 9070.

Figure 183:
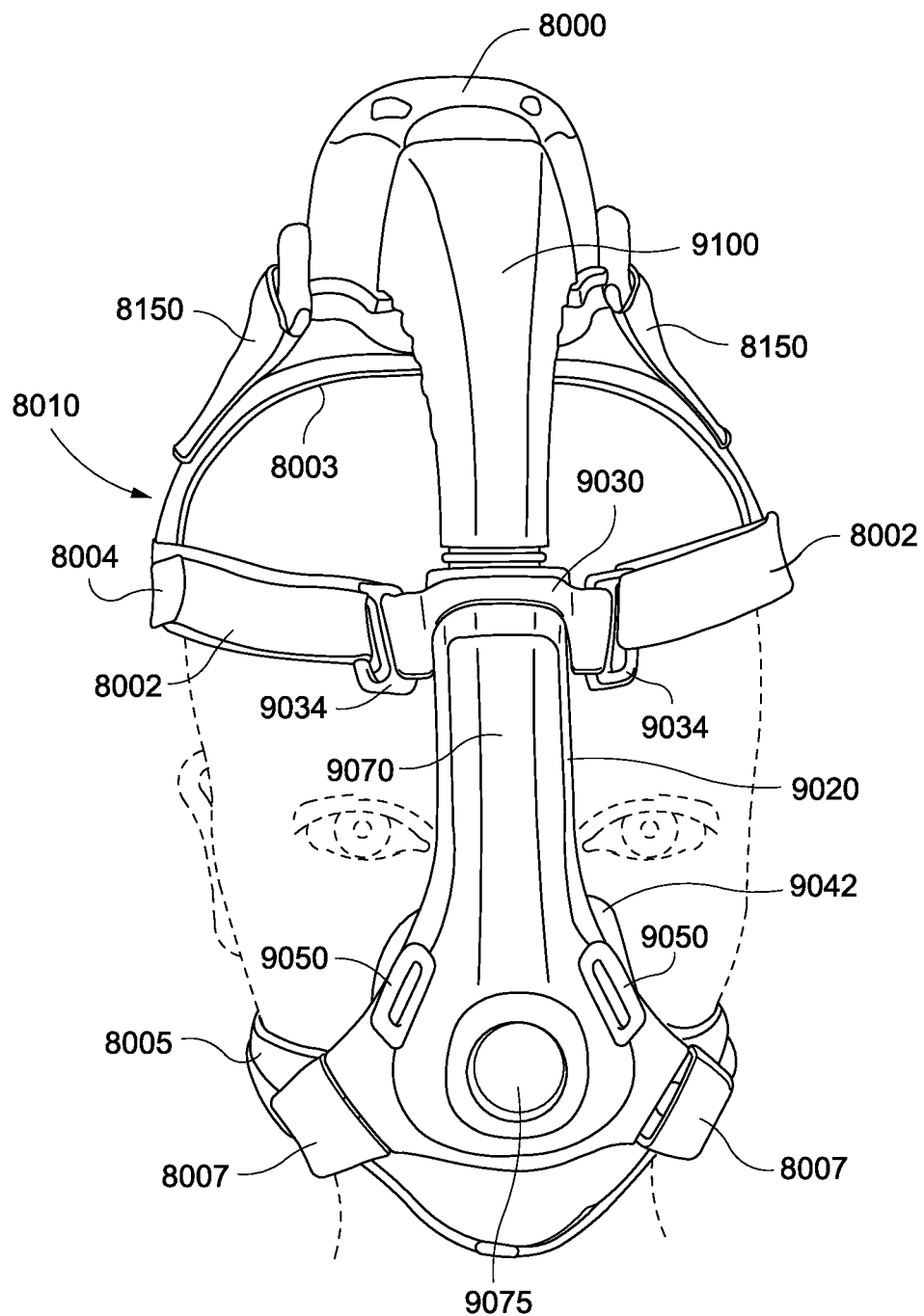
Figure 184:
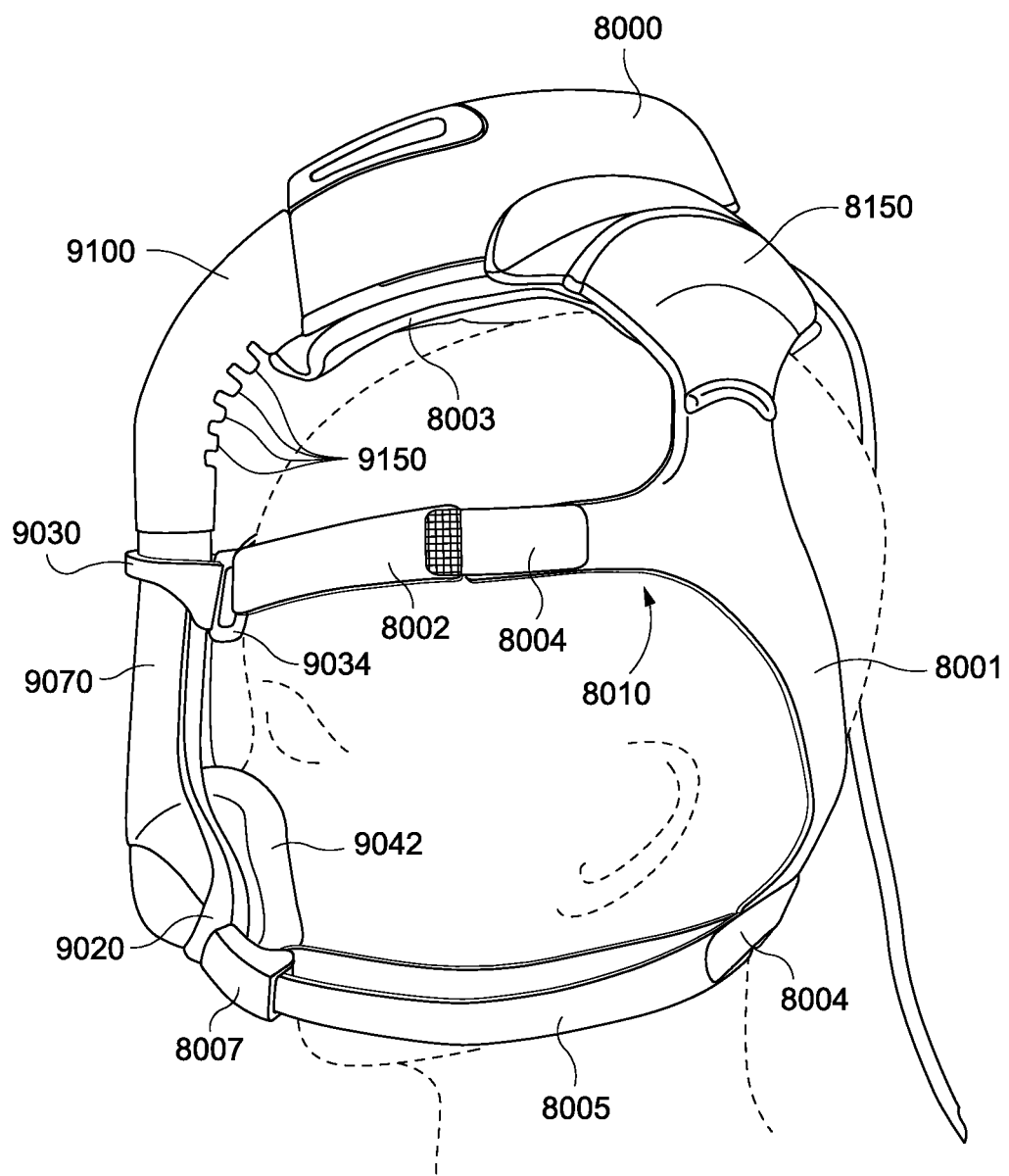

Referring to FIGS. 183-192, a headworn PAP system according certain embodiments comprises a PAP device 8000 that includes a blower or flow generator. Referring to FIG. 184, the PAP device 8000 is supported on an extension 8003 of a headgear 8010 and is secured between two raised portions 8150 that extend from the extension 8003 of the headgear. Upper headgear straps 8002 are connected to upper headgear connectors 9034 of a frame 9020 of a patient interface system that supports a patient interface device, or cushion, 9042 in sealing engagement with the face of the patient. The upper headgear straps 8002 are connected to the headgear by fasteners 8004.

Lower headgear straps 8005 are connected to the frame 9020 by headgear connector clips 8007 that attach to the frame 9020 in a manner described in more detail below. As shown in FIG. 184, the lower headgear straps 8005 are connected to the occipital ring 8001 of the headgear at the hack of the patient's head by fasteners 8004. The fasteners 8004 for the upper headgear straps 8002 and the lower headgear straps 8005 may be, for example, hook and loop fasteners, such as Velcro™.

Lower headgear straps 8005 are connected to the frame 9020 by headgear connector clips 8007 that attach to the frame 9020 in a manner described in more detail below. As shown in FIG. 184, the lower headgear straps 8005 are connected to the occipital ring 8001 of the headgear at the back of the patient's head by fasteners 8004. The fasteners 8004 for the upper headgear straps 8002 and the lower headgear straps 8005 may be, for example, hook and loop fasteners, such as Velcro™.

The patient interface system, which may be, for example, a nasal mask system or a full face mask system comprises the frame 9020 which supports the sealing arrangement 9040. The sealing arrangement 9040 comprises the cushion 9042 which is configured to sealingly engage the face of the patient. As shown in FIG. 183, the cushion 9042 includes elongated, spaced apart protrusions 9050 that engage the frame 9020 to secure the sealing arrangement, including the cushion 9042, to the frame 9020. As further shown in FIG. 183, the frame 9020 comprises a forehead support 9030 which supports the upper headgear connectors 9034. As shown in FIG. 184, the forehead support 9030 of the frame 9020 engages and holds the inlet tube 9070 of the sealing arrangement 9040. A short outlet tube 9100 is connected to the PAP device 8000 and delivers the flow of pressurized breathable gas from the PAP device 8000 to the inlet tube 9070 of the sealing arrangement 9040. The short outlet tube 9100 may comprise ribs 9150 which provide flexibility to the short outlet tube 9100 to accommodate patients with different facial shapes and sizes.

Figure 185:
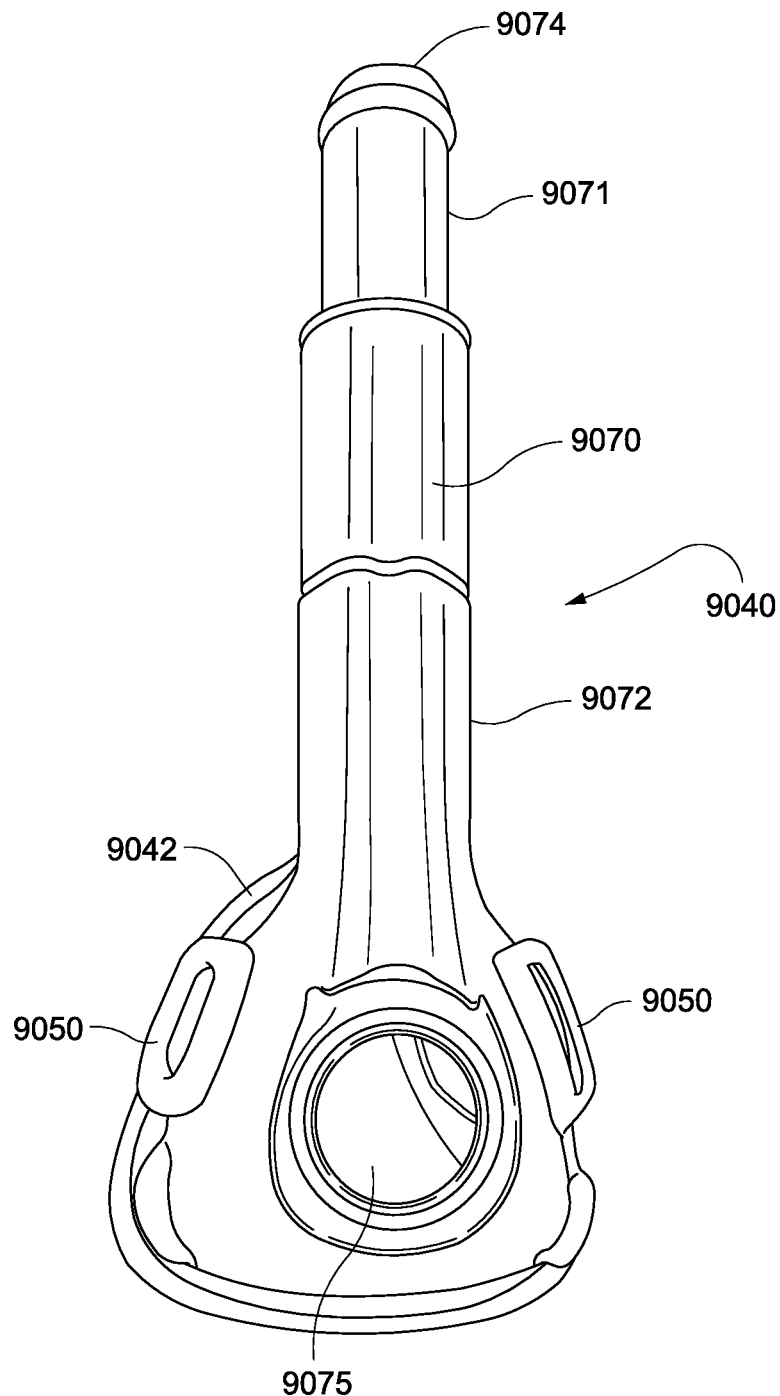

Referring to FIG. 185, the sealing arrangement 9040 comprises the cushion 9042 including the spaced apart, elongated protrusions 9050 that connect the sealing arrangement 9040 to the frame 9020 by engaging sidewalls 9026 (FIG. 190) of the frame 9020. The cushion 9042 may include an opening 9075 which receives a vent structure for venting exhaled gases.

The inlet tube 9070 of the sealing arrangement 9040 includes a first end 9072 adjacent the cushion 9042 and a second end 9074 that receives the flow of pressurized breathable gas from the PAP device 8000. The inlet tube 9070 includes a reduced diameter portion 9071 that is inserted into the short outlet tube 9100 that is connected to the PAP device 8000.

Figure 186:
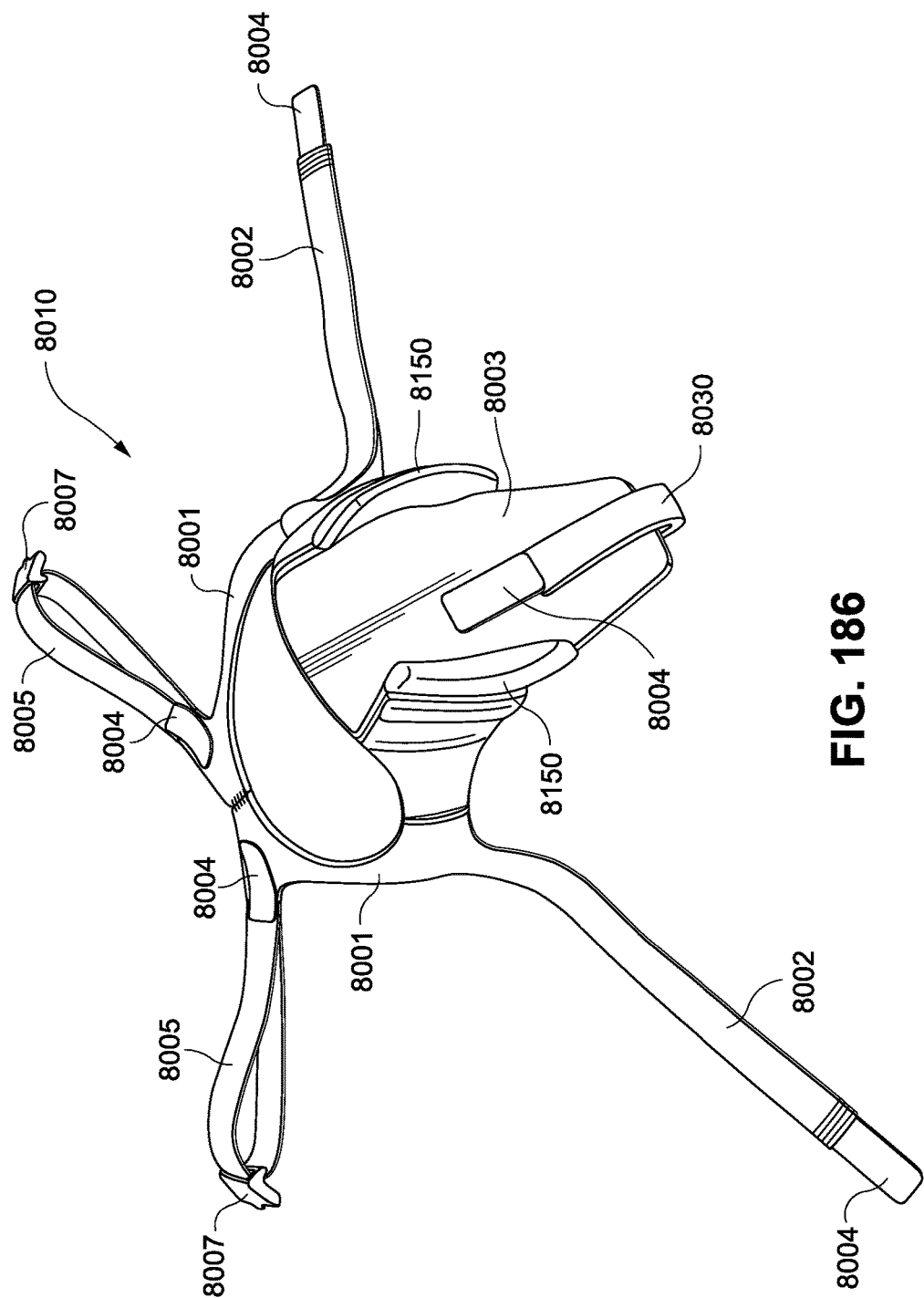

As shown in FIG. 186, the headgear 8010 includes the extension 8003 to support the PAP device 8000 between the raised portions 8150. A securing strap 8030 is provided on the extension 8003 of the headgear 8010 to secure the PAP device 8000 to the extension 8003 of the headgear 8010.

Figure 187:
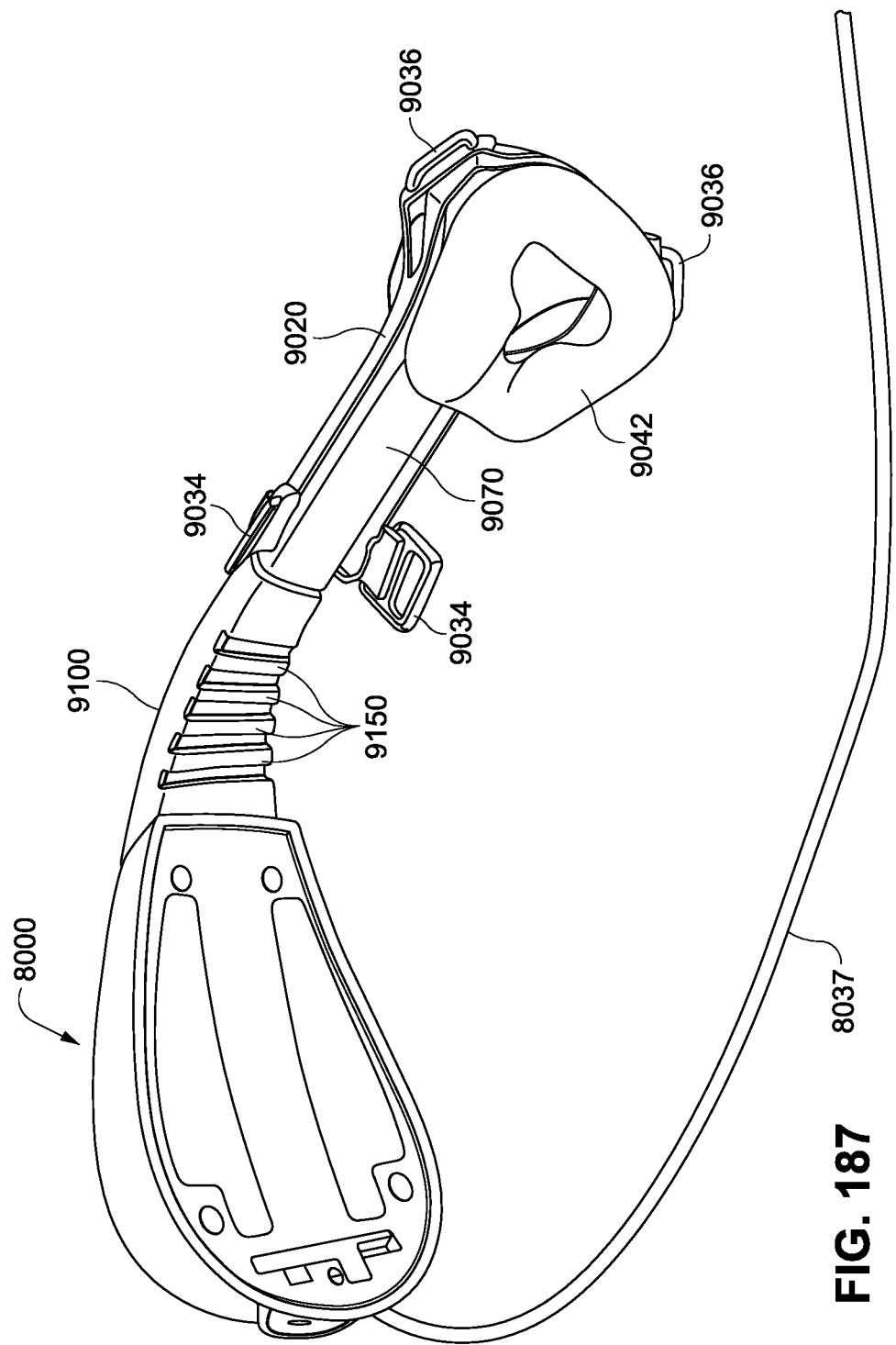
Figure 188:
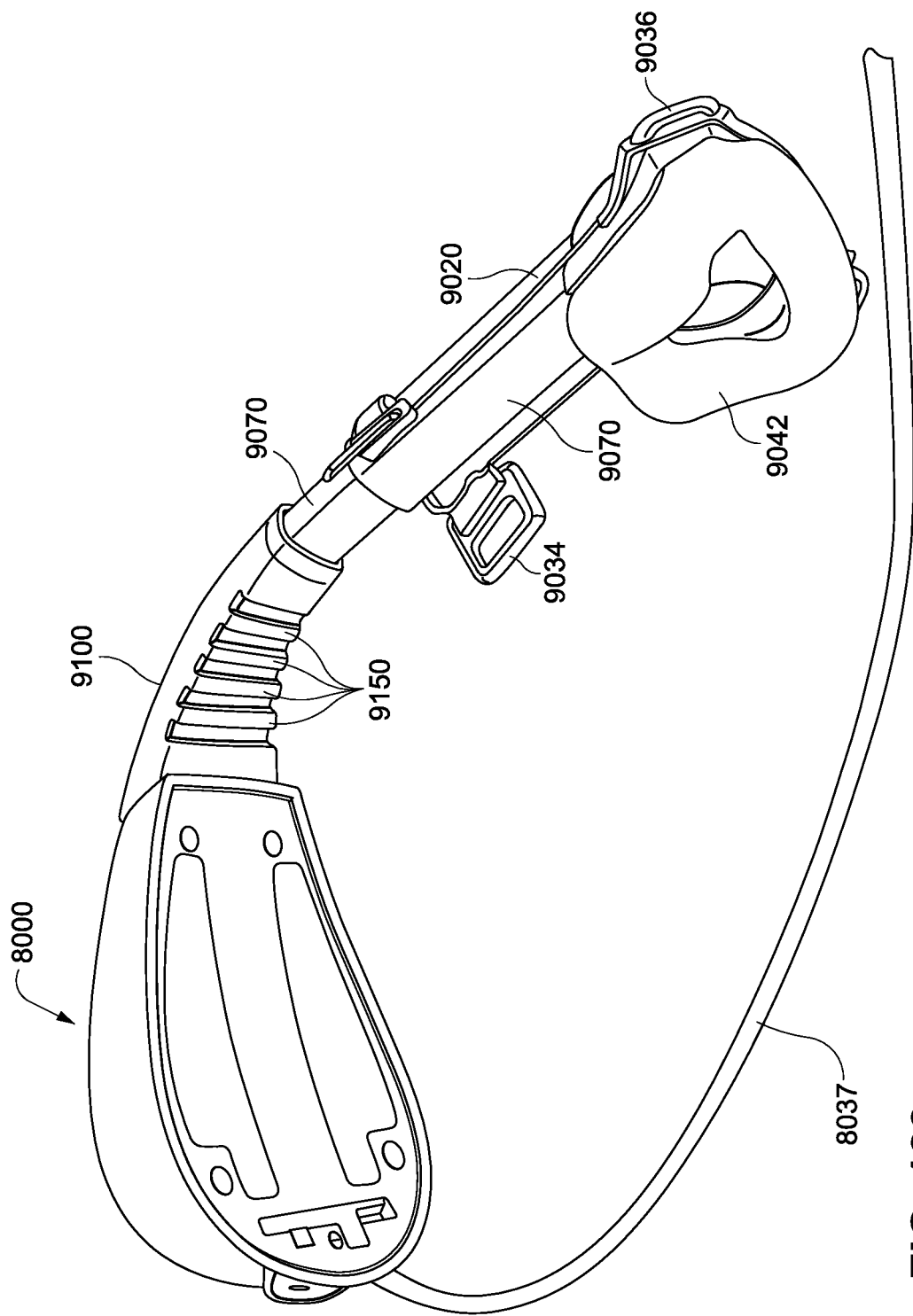
Figure 189A:
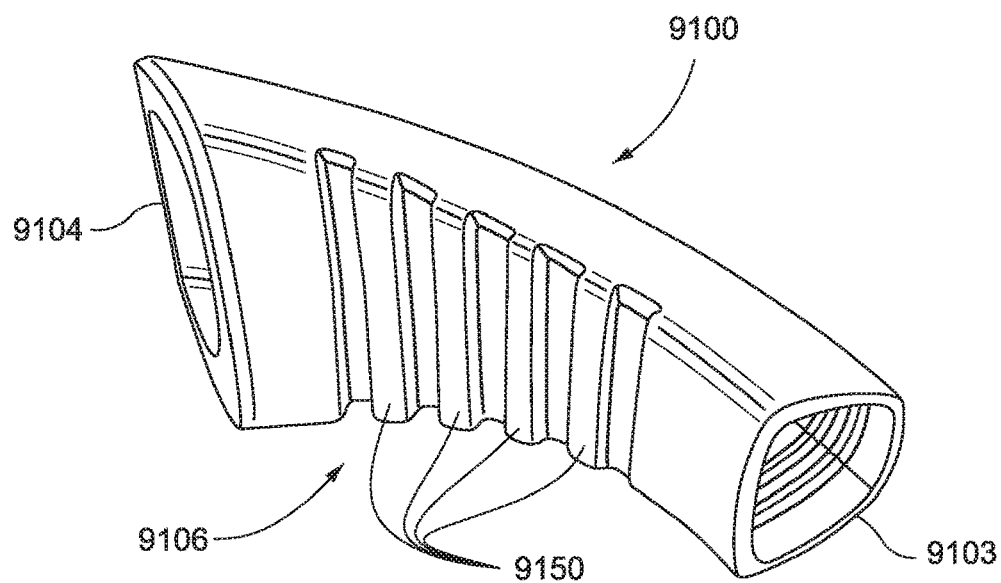
Figure 189B:
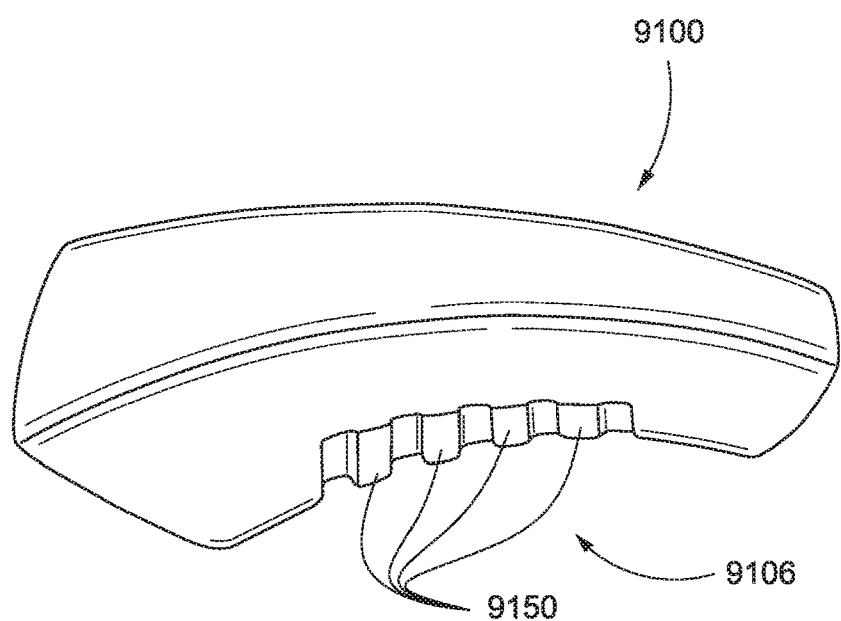
Figure 189C:
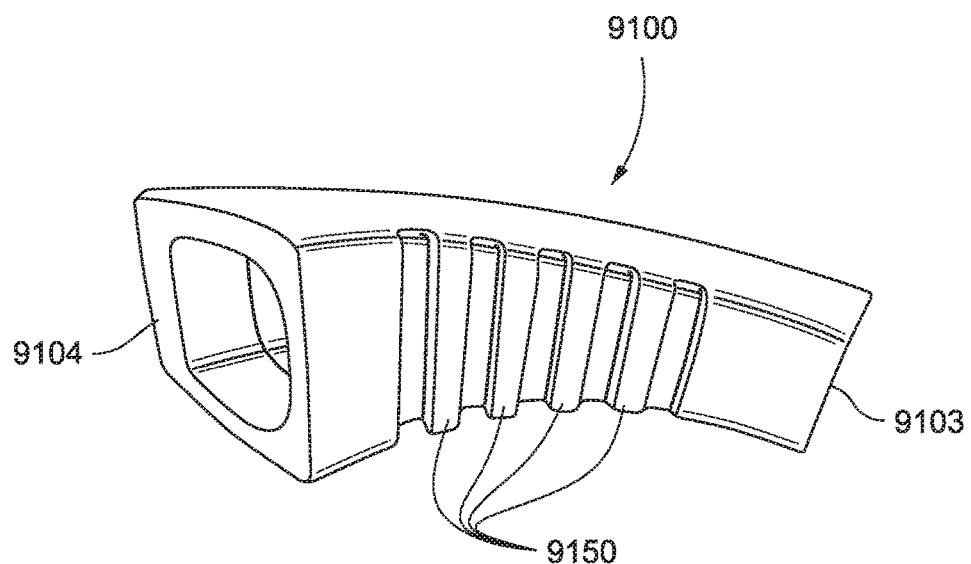
Figure 189D:
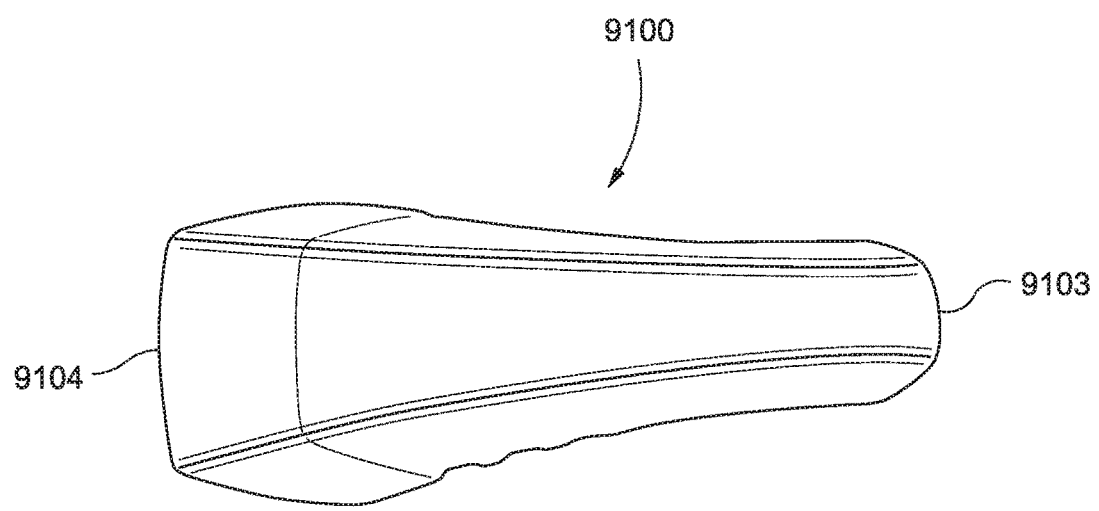
Figure 189E:
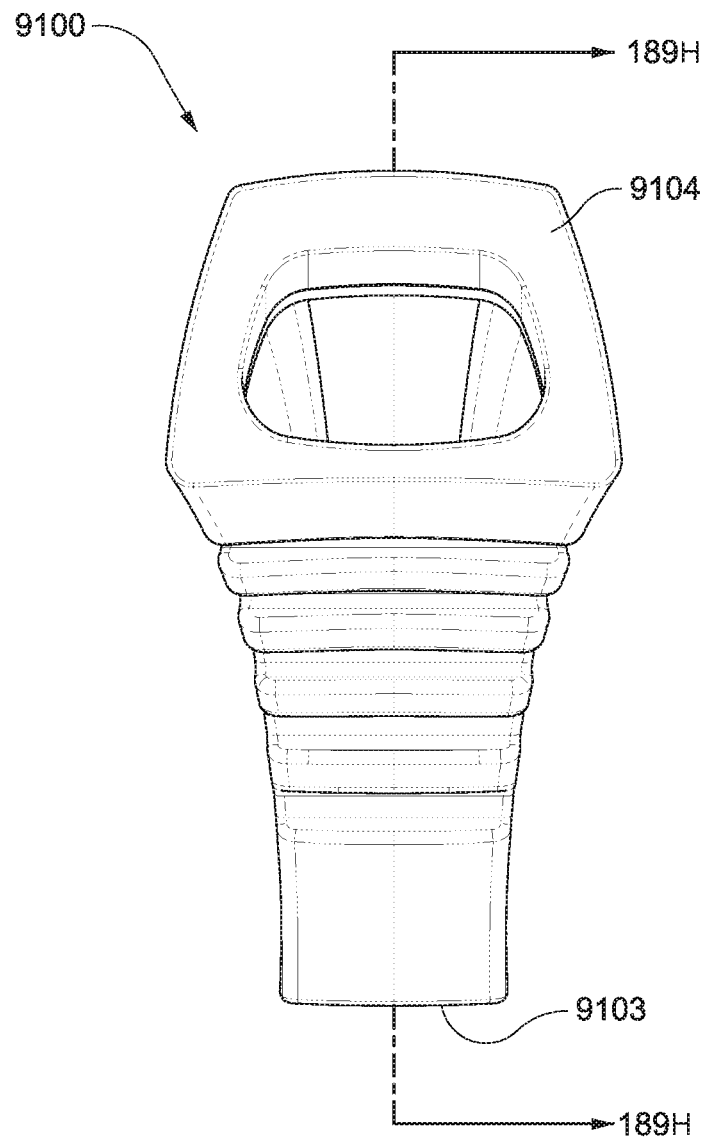
Figure 189F:
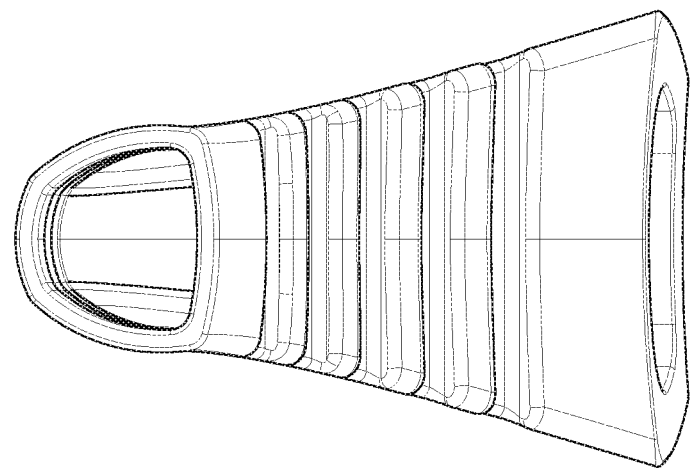
Figure 189G:
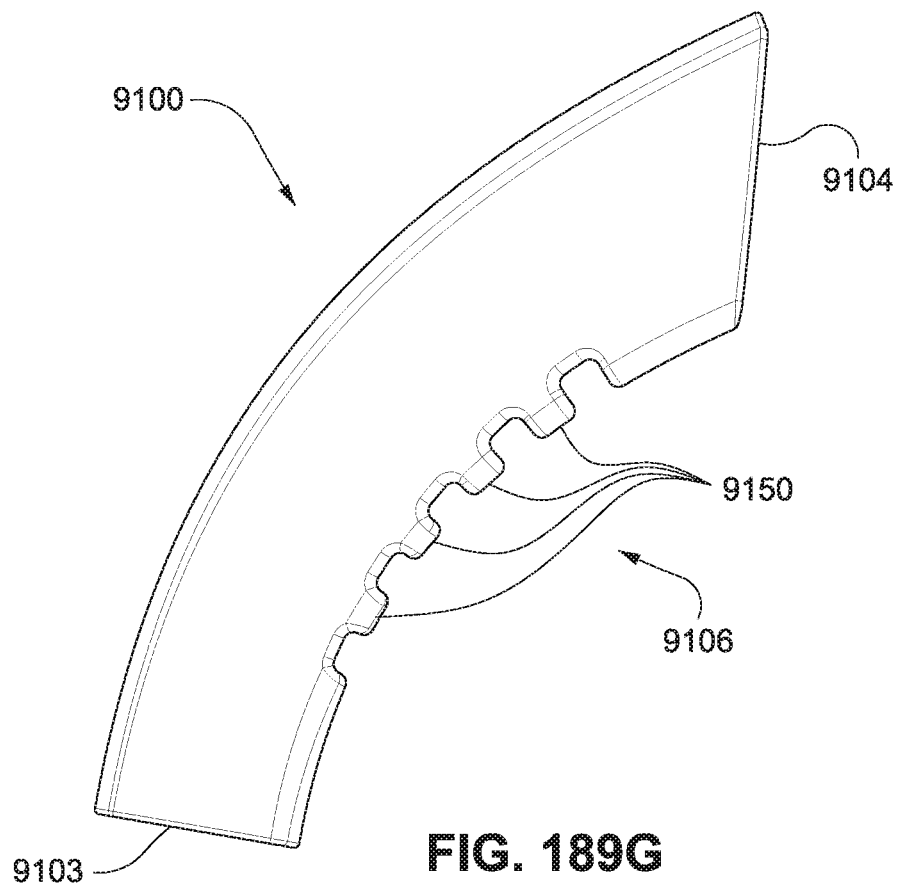
Figure 189H:
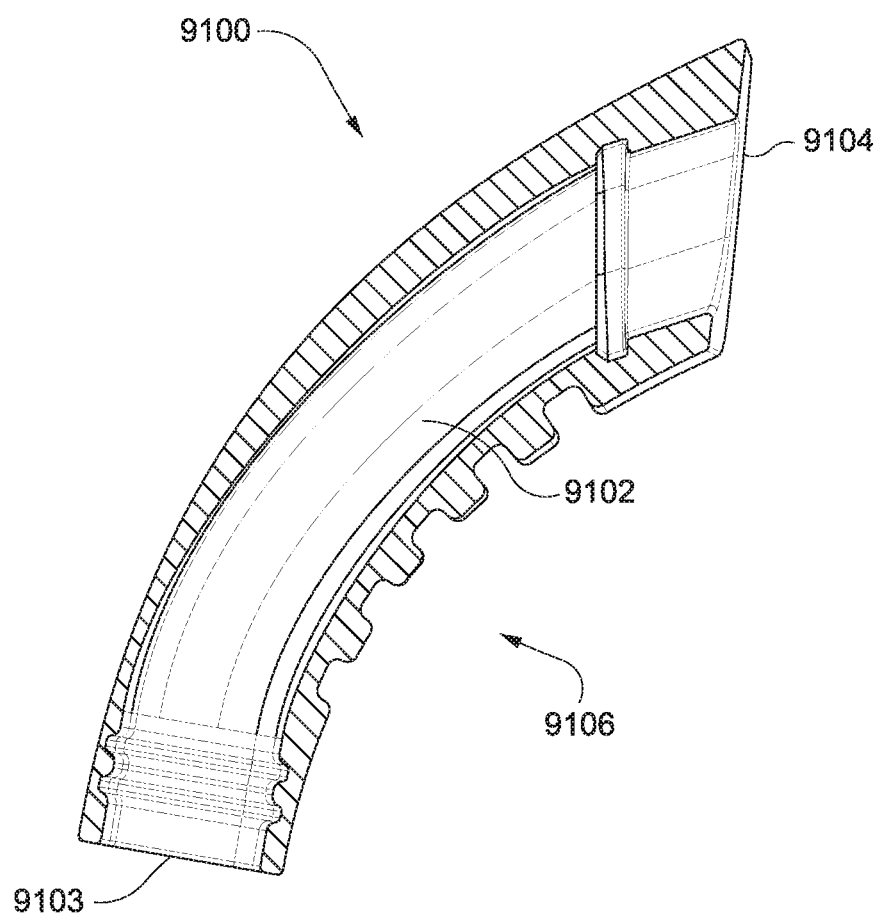

Referring to FIGS. 187 and 188, the frame 9020 of the patient interface system includes lower headgear connectors 9036 that receive the lower headgear clips 8007 of the headgear 8010 to secure the lower headgear straps 8005 to the frame 9020.

As also shown in FIGS. 187 and 188, the inlet tube 9070 of the sealing arrangement 9040 may be fully inserted into the short outlet tube 9100, as shown in FIG. 187, and the inlet tube 9070 may be extended from the short outlet tube 9109 as shown in FIG. 188 to accommodate patients with a larger head size.

Referring to FIGS. 189A to 189H, the short outlet tube 9100 has a first end 9104 configured to be connected to the outlet of the PAP device 8000 and a second end 9103 configured to receive the inlet tube 9070 of the sealing arrangement 9040. The lower side 9106 (i.e. the side facing the forehead of the patient) of the short outlet tube 9100 may comprise a plurality of ribs 9150 that increase the flexibility of the short outlet tube 9100. As shown in FIGS. 189A to 189H, the short outlet tube 9100 may be D-shaped in cross section and the lower side 9106 may be substantially flat when compared to the circumference of the cavity 9102. However, it should be appreciated that other cross-sectional shapes for the short outlet tube 9100 may be utilized.

Referring to FIGS. 190-192, the frame 9020 of the patient interface system comprises a main body 9022 that includes a pair of arms 9032 that supports the forehead support 9030. The forehead support 9030 may comprise an arcuate bridge 9038 that is configured to resiliently engage the inlet tube 9070 of the sealing arrangement 9040 to secure the inlet tube 9070 to the frame 9020. A central opening 9024 provided in the frame 9020 is configured to receive the cushion 9042 of the sealing arrangement 9040. The main body 9022 further comprises side walls 9026 that are configured to engage the protrusions 9050 of the cushion 9042 to secure the cushion 9042 to the frame 9020. The frame 9020 further comprises lower headgear connectors 9036 that are configured to be engaged by the lower headgear clips 8007 of the headgear 8010 to secure the lower headgear straps 8002 to the frame 9020. As shown in FIG. 191, the lower headgear clip 8007 may comprise a hook 807 5 configured to engage the lower headgear connector 9036 of the frame 9020. A release tab. 8077 may be provided on the lower headgear clip 8007 to allow the patient's finger to engage the lower headgear clip 8007 and disengage the hook 8075 from the lower headgear connectors 9036.

Referring to FIGS. 193A to 195B, a patient interface system according to another embodiment is shown. A connector tube 9200 is provided to connect the sealing arrangement 9040 to the short outlet tube 9100 that is connected to the PAP device 8000. The connector tube 9200 includes a first end 9201 that is configured to be inserted into the inlet tube 9070 of the sealing arrangement 9040 and a second end 9203 that is configured to be inserted into the short outlet tube 9100. The first end 9201 includes a. rib 9205 that may engage a first groove 9073 or a second groove 9075 in the inlet tube 9070, as shown for example in FIG. 195B. Although the engagement of the connector tube 9200 to the inlet tube 9070 of the sealing arrangement 9040 is shown as a rib being received in a groove, it should be appreciated that other connection structures for attaching the connector tube 9200 to the sealing arrangement 9040 may be used, for example, a screw connection.

The connector tube 9200 includes a circumferential flange 9211 that defines a maximum insertion position of the connector tube 9200 into the inlet tube 9070 of the sealing arrangement 9040, as shown in FIG. 194B. The second end 9203 of the connector tube 9200 includes a first rib 9207 and a second rib 9209 that are configured to engage a groove or grooves formed on the inner circumference of the short outlet tube 9100. The connector tube 9200 is inserted, retained and sealed in the inlet tube 9070 of the sealing arrangement 9040 by the rib 9205 and fits via an interference fit in the inlet tube 9070. The connector tube 9200 is fully inserted into the inlet tube 9070 as shown in FIGS. 194A and 194B, and may be extended from the inlet tube 9070 as shown in FIGS. 195A to 195B to accommodate patients having different head sizes.

Referring to FIGS. 196A to 197C, a connector tube 9200 according to certain embodiments includes a first end 9201 configured to be inserted into the inlet tube 9070 of the sealing arrangement 9040 and a second end 9203 configured to be inserted into the short outlet tube 9100 connected to the PAP device 8000. A circumferential flange, including two tabs 9219 is provided between the first end 9201 and the second end 9203. A first rib 9221 and a second rib 9223 may be provided to retain the tube connector 9200 in the inlet tube 9070 of the sealing arrangement 9040, and a first rib 9225 and a second rib 9227 may be provided to retain the second end 9203 of the connector tube 9200 to the short outlet tube 9100.

As shown in FIGS. 197A and 197B, the tabs 9219 of the connector tube 9200 may be received in slots 9021 formed in a forehead support 9030 of the frame 9020. The locking of the tabs 9219 into the slots 9021 maintains the axial alignment of the connector tube 9200 with the inlet tube 9070 of the sealing arrangement 9040 and the short outlet tube 9100. The tabs 9219 snap into the slots 9021 of the frame 9020 from behind and the frame momentarily flexes outwardly while the tabs 9219 push in, and the frame then pops back into position when the tabs are received in the slots 9021.

The connector tube 9200 may be manufactured in a range of different sizes to suit different size faces. The user may select the appropriately sized connector tube and connect the connector tube to the short outlet tube 9100 and the inlet tube 9070 of the sealing arrangement 9040.

Referring to FIGS. 198A to 202D, a patient interface system according to another sample embodiment is shown. The patient interface system includes a connector tube 9200 having a first end 9201 configured to be attached to a short outlet tube 9100 that is configured to be connected to the PAP device. As shown in FIG. 200D, the first end 9201 of the connector tube 9200 is configured to be inserted into a second end 9103 of the short outlet tube 9100.

Figure 4:
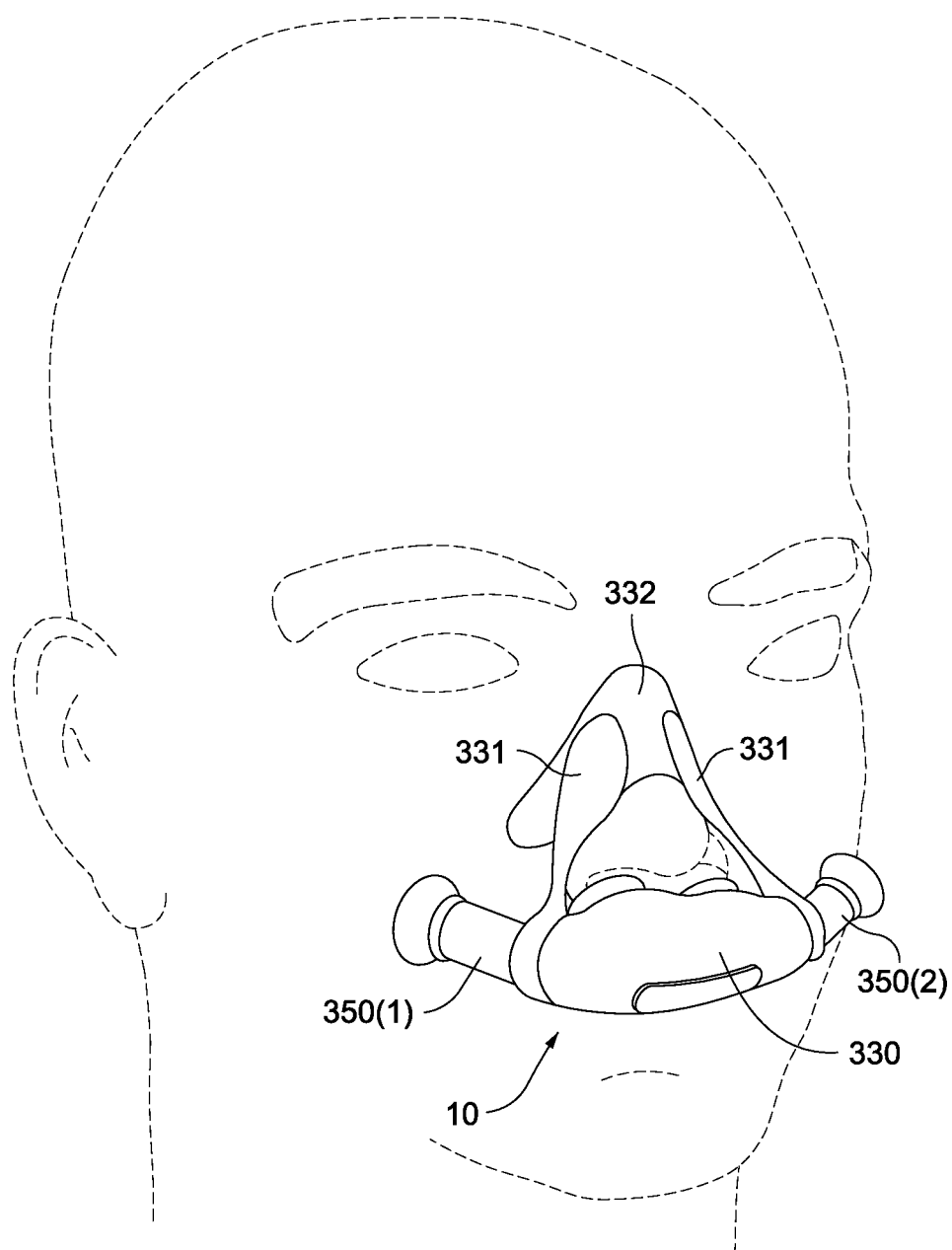
FIG. 4 shows a patient interface with a built-in blower mounted according to certain embodiments.

The connector tube 9200 includes a second end 9203 that is configured to be attached to the inlet tube 9070 of the sealing arrangement 9040. As shown in FIG. 198D, the connector tube 9200 includes a first rib 9207 and a second rib 9209 that are configured to engage the interior of the inlet tube 9070 of the sealing arrangement 9040, for example via an interference fit, to secure the connector tube 9200 to the inlet tube 9070 of the sealing arrangement 9040. The connector tube 9200 also includes a flange 9217 extending around the circumference of the connector tube 9200 to contact the second end 9103 of the short outlet tube 9100 when the connector tube 9200 is fully inserted into the short outlet tube 9100, as shown in FIG. 202-4.

Figure 201A:
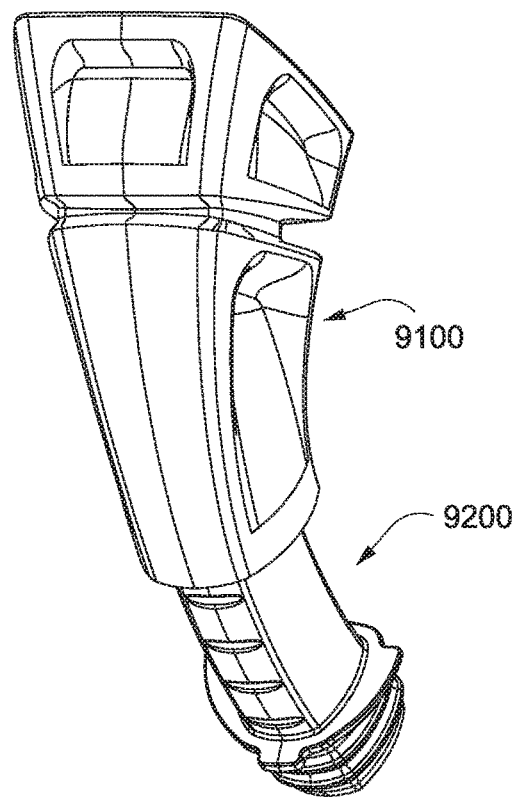
Figure 201B:
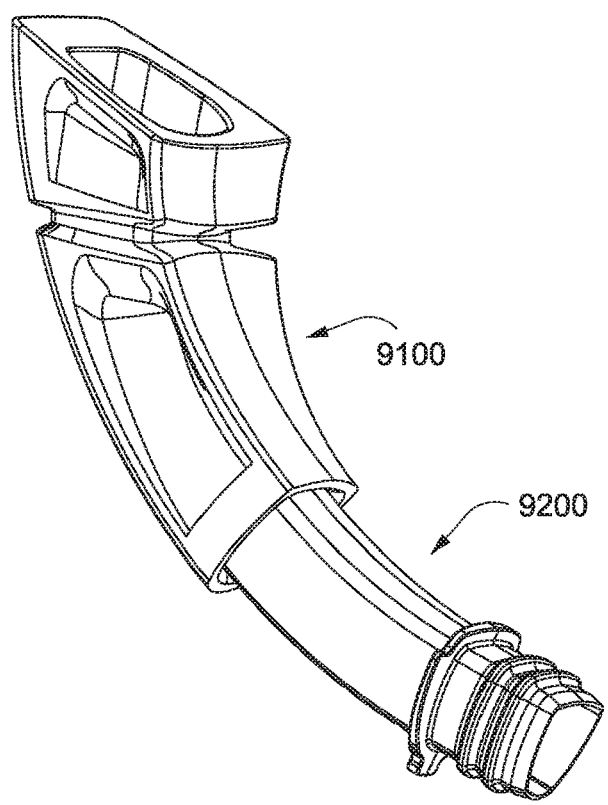
Figure 201C:
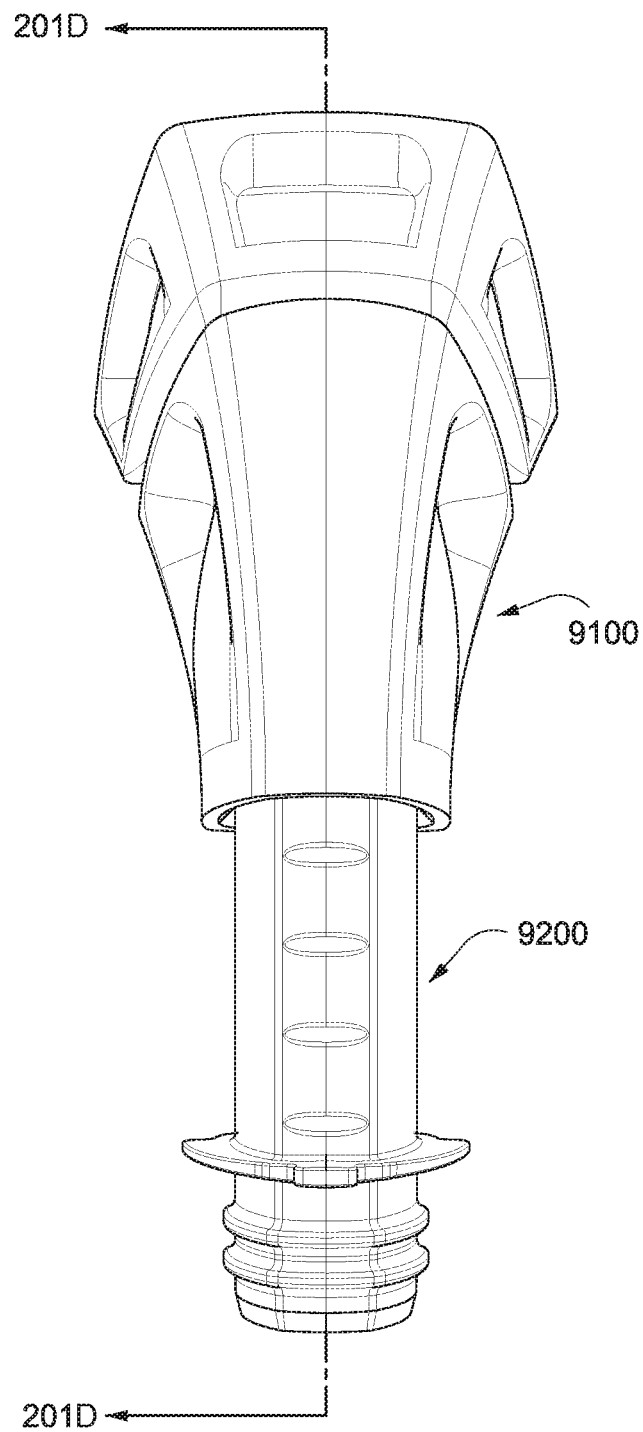
Figure 201D:
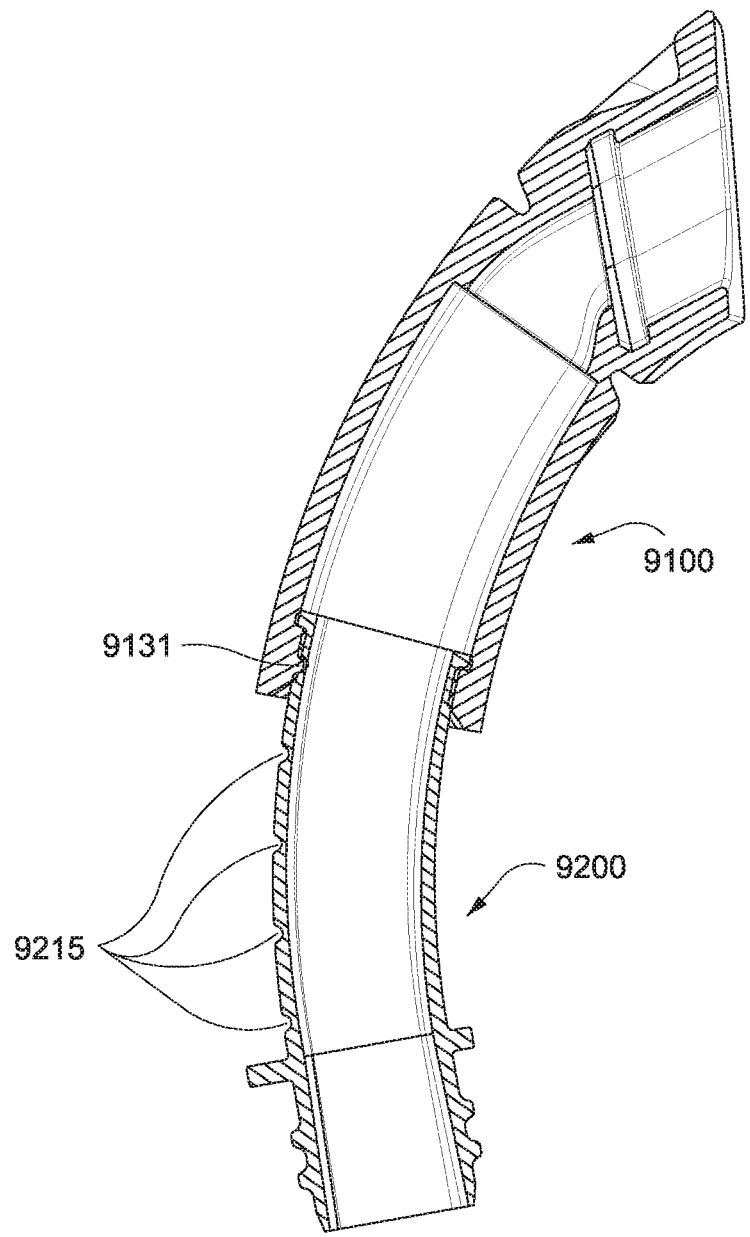
Figure 202A:
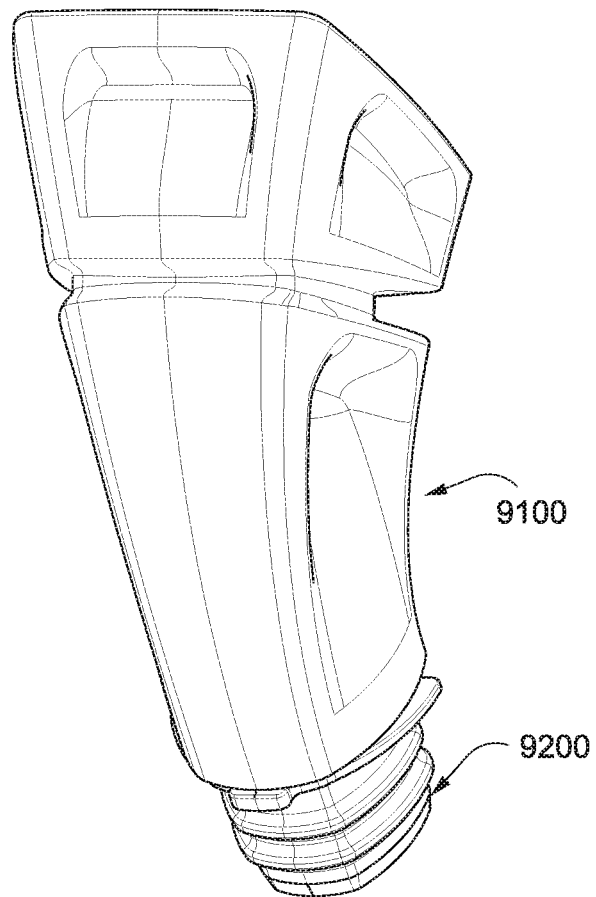
Figure 202B:
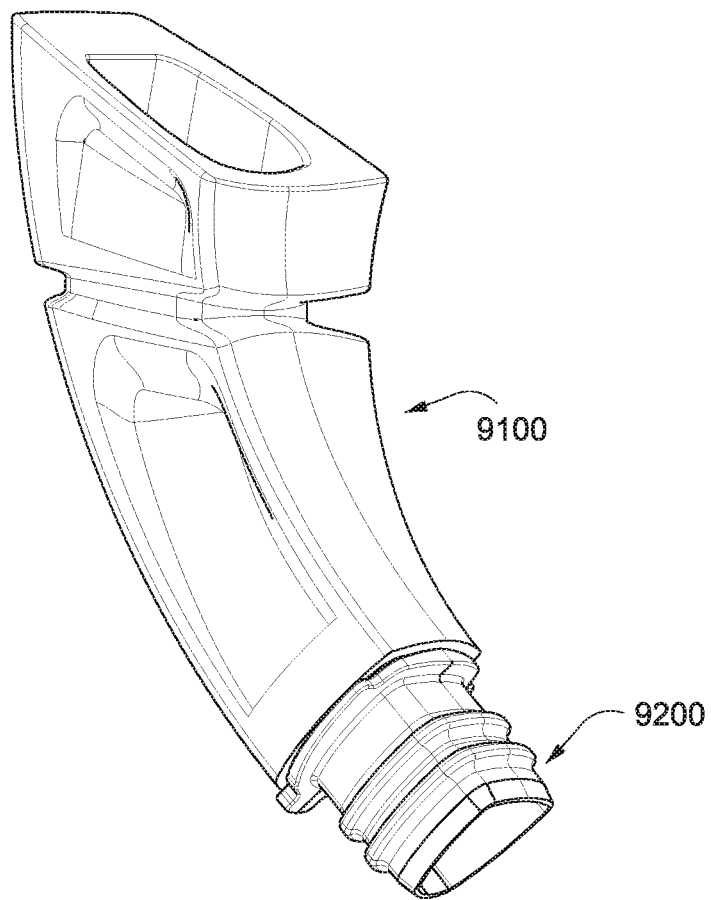
Figure 202C:
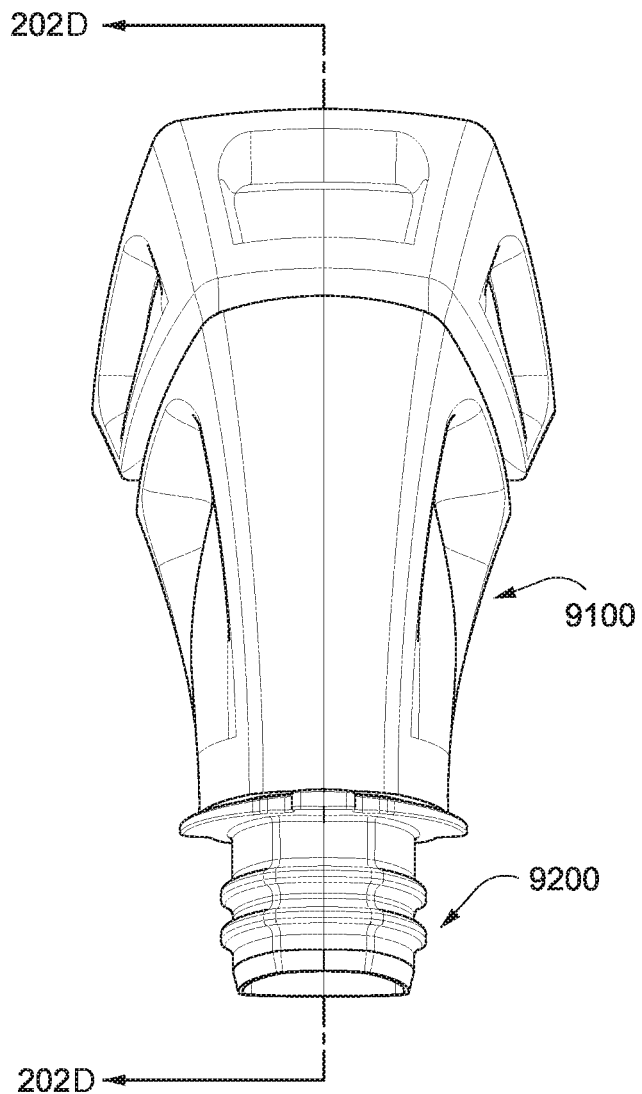
Figure 202D:
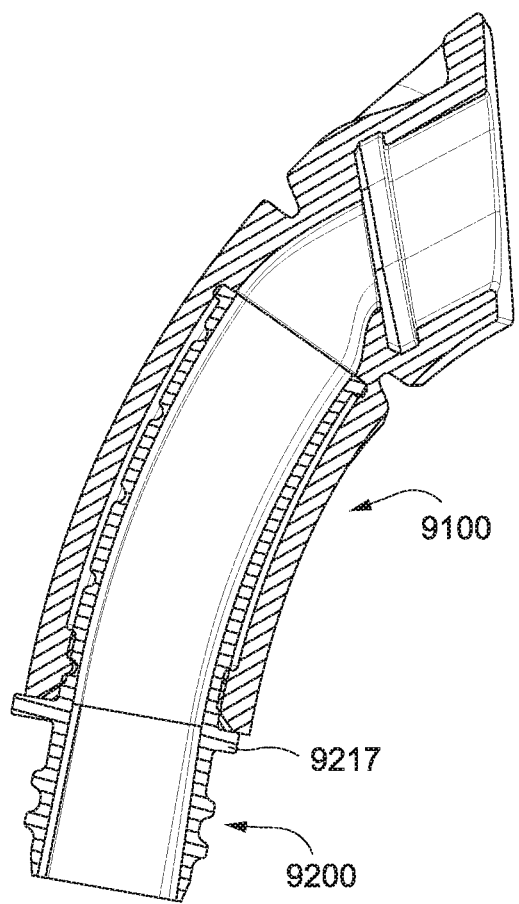
Figure 203A:
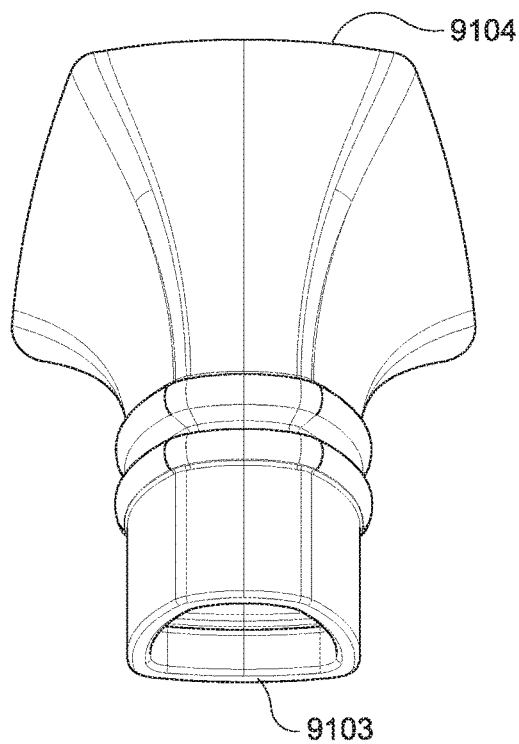
Figure 203B:
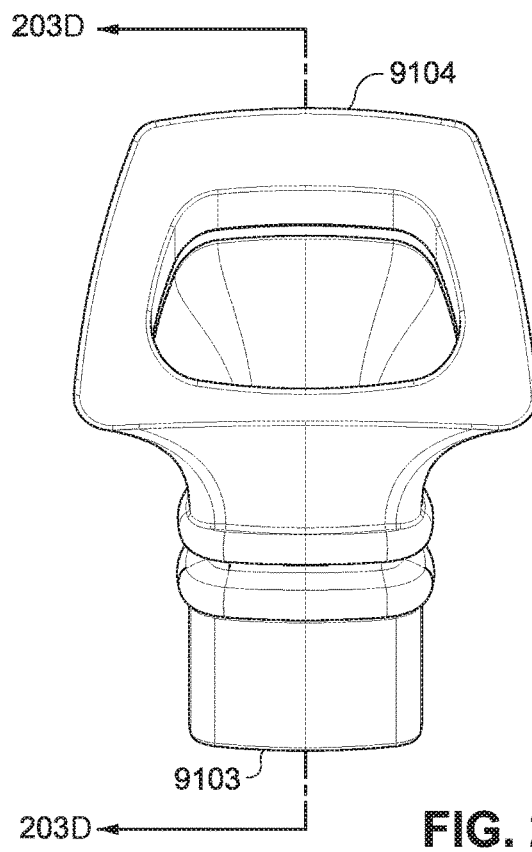
Figure 203C:
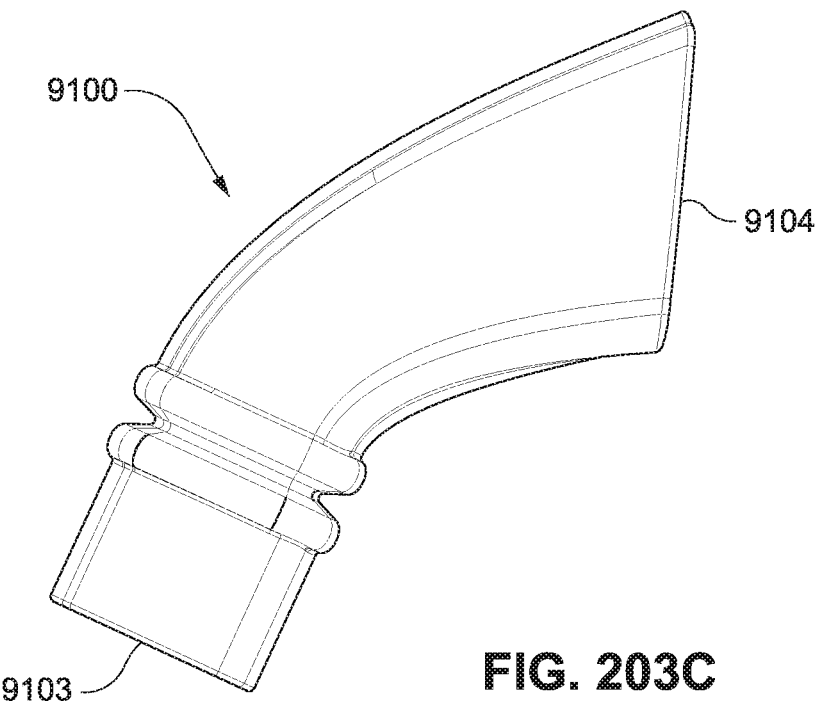
Figure 203D:
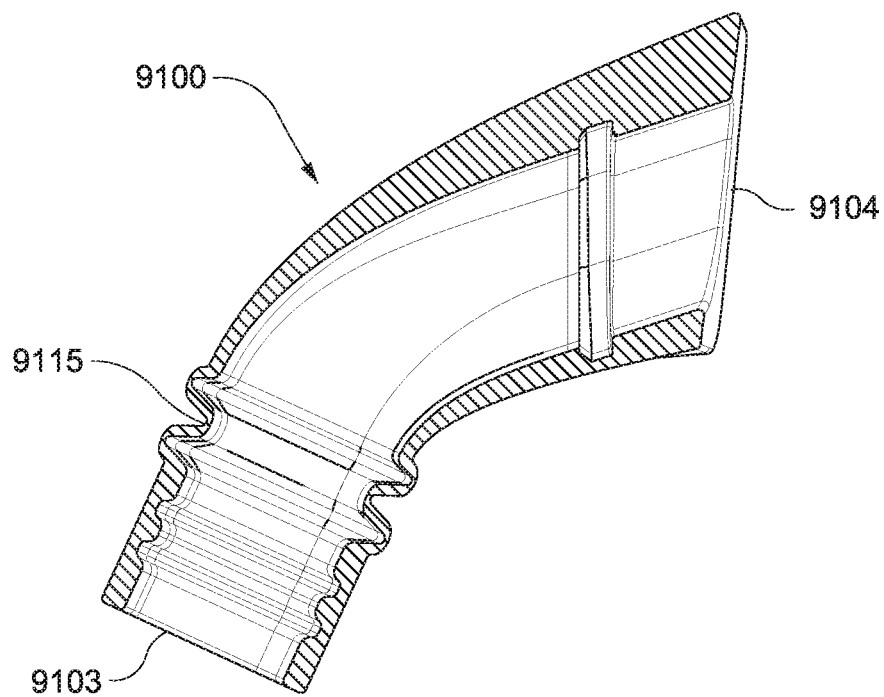
Figure 203E:
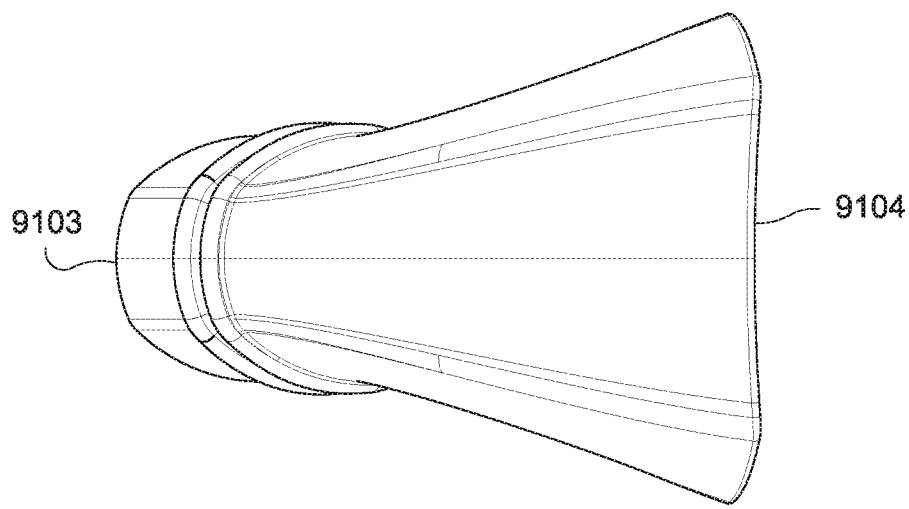

As shown in FIGS. 198A and 198D, the connector tube 9200 may include position indicators 9215, which may take the form of grooves or bumps, provided on an outer surface of the connector tube 9200 to indicate the extent to which the connector tube 9200 is inserted into the short outlet tube 9100, for example, as shown in FIGS. 201A and 201C.

The flange 9217 of the connector tube 9200 may engage slots in the frame, for example, the slots 9021 shown in FIG. 197A. In addition, the connector tube 9200 may also include a tab 9219 that is configured to be inserted into a slot 9023 formed in the forehead support 9030 of the frame 9020, as also shown in FIG. 197A.

As shown in FIGS. 198A to 202D, the connector tube 9200 telescopes within the short outlet tube 9100 to allow adjustment of the length of the air delivery tube to the patient interface to adjust for different size foreheads. In a sample embodiment, the position indicators 9215 of the connector tube 9200 may provide a tactile feedback of the position of the connector tube 9200. It should also be appreciated that the position indicators 9215 may not be used and friction may be used as an indicator of the position of the connector tube 9200. It should further be appreciated that a locking mechanism may be provided to lock in the adjusted height of the connector tube 9200 with respect to the short outlet tube 9100.

The connector tube 9200 is inserted, retained and sealed in the inlet tube 9070 of the sealing arrangement 9040 by the ribs 9207, 9209. The first end 9201 of the connector tube 9200 has a rib 9231 (FIG. 198C) that provides an interference fit with the interior of the short outlet tube 9100 as shown, for example, in FIG. 201D. The cavity 9102 of the short outlet tube 9100 includes an interior rib 9131 that is configured to engage the position indicators 9215 of the connector tube 9200 to retain the connector tube 9200 in a selected position relative to the short outlet tube 9100, as shown, for example, in FIG. 201D.

Although the connector tube 9200 has been described as including two ribs 9207, 9209, it should be appreciated that more than two ribs and more than two grooves in the inlet tube 9070 of the sealing arrangement 9040 may be used. It should also be appreciated that one rib and one groove may be used. The connector tube may be made from a resilient material, for example, silicone. It should be appreciated that other means of attaching the connector tube 9200 to the inlet tube 9070 of the sealing arrangement 9040 may be used, for example, a screw-in connection.

According to certain embodiments, the headworn PAP system may be configured to fit a percentage of the patient population, for example about 70-90%, such as 80%. The headworn PAP system may fit a head circumference of, for example, about 540-620 mm, and a forehead height of about 70-110 mm. In certain embodiments, the connector tube 9200 may allow a fit range of about 30-60 mm for the forehead tube, which provides an adjustment range of about 30 mm.

Referring to FIGS. 203A to 203E, a short outlet tube 9100 in accordance with another sample embodiment is illustrated. To provide further flexibility and adjustment around the patient's face, a bellows section 9115 is provided in the short outlet tube 9100, for example at the area where the short outlet tube 9100 bends (i.e. at the knuckle). The bellows section 9115 allows the tube to flex more easily.

1.2 Certain Embodiments of the Blower Built into the Mask

Certain embodiments relate to PAP systems in which the blower may be built into or incorporated into the patient interface and/or mask. In certain embodiments, the blower may be divided into two or more smaller blowers. Miniature blowers, such as the small 8 W blowers manufactured by Maxar having a diameter of 8 mm and a length of approximately 30 mm, may be utilized, or other commercially available blowers.

FIGS. 4 to 9C and 24-35 show masks with a built in blower according to certain embodiments.

In FIG. 4, the patient interface or mask system 10 includes a nasal prong or pillow arrangement 330 adapted to form a seal with the patient's nares. First and second blowers 350(1), 350(2) are provided to respective ends of the nasal prong arrangement to provide pressurized air to the nasal prong arrangement. The mask may be attached to the patient's face by a combination of hook and loop (e.g., Velcro) tabs and adhesive.

In certain embodiments, one blower may be used. In certain embodiments, at least one, two, three or four blowers may be used.

Blowers 350(1) and 350(2) may be encapsulated by a damping means. For example, damping means may include a muffler, such as a silicone casing, a foam and/or fabric layer, other suitable materials or combinations thereof.

Tab portions 353 may be connected to the nasal prong arrangement 330 for removably attaching it to an adhesive facial pad 332. Tab portions may include integrally moulded hooks to engage with loops provided on the adhesive facial pad. In an embodiment, attachment means may be provided as disclosed in pending U.S. Patent Application Publication 2010/0000534 A1.

Muffling and/or filtering materials may be provided to the air inlet portions of the blowers 350(1) and 350(2). For example, foam pads may be attached or otherwise formed with blowers at their inlet portion.

Figure 5A:
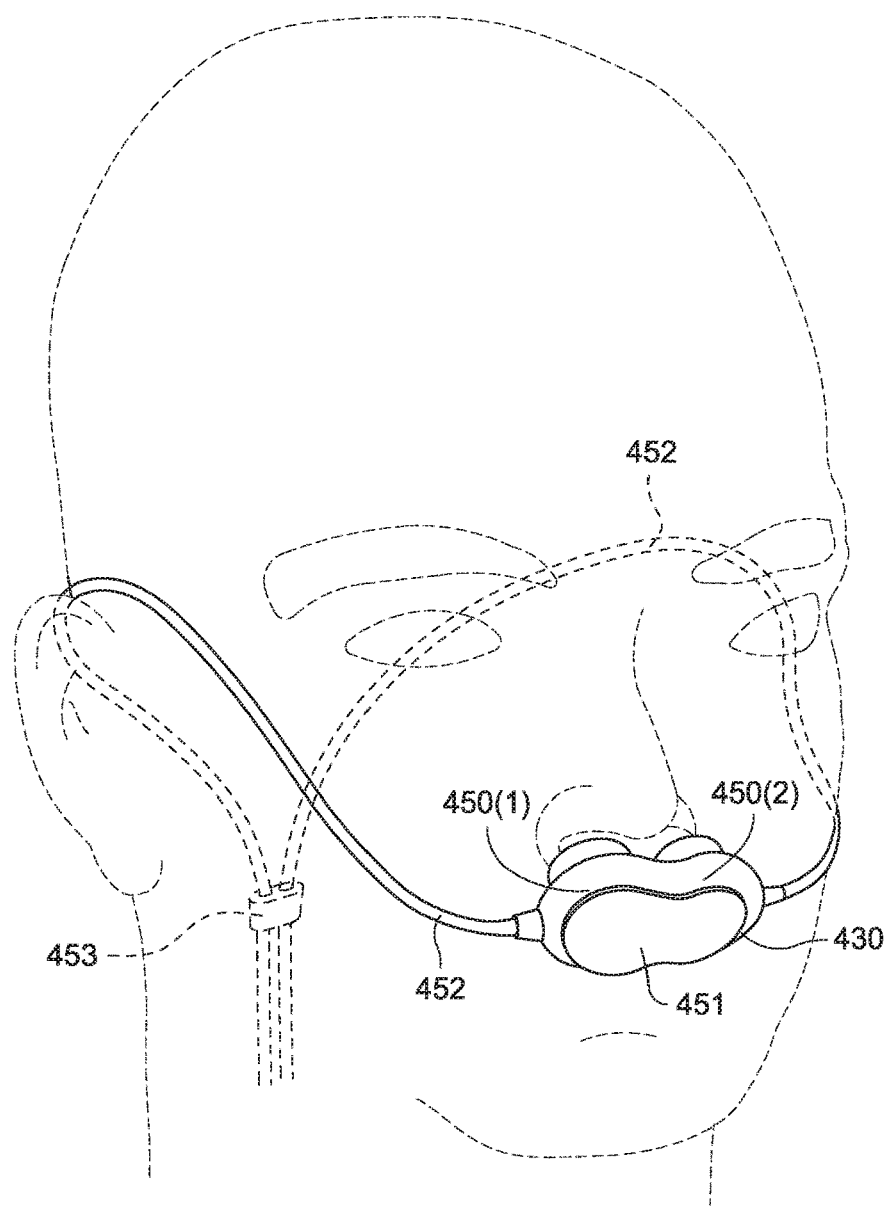
FIGS. 5A and 5B show a patient interface with a built-in blower according to certain embodiments.
Figure 5B:
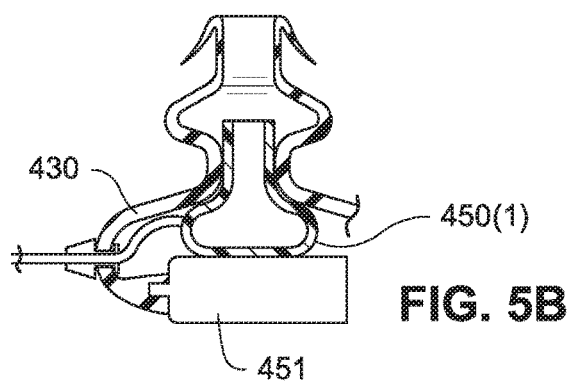

In FIGS. 5A and 5B, the patient interface or mask may include a nasal prong or pillow arrangement 430 adapted to form a seal with the patient's nares. First and second blowers 450(1), 450(2) are provided in-line with respective nasal prongs to provide pressurized air.

Nasal prongs may be provided with barbs or interference means to engage with an inner portion of a patient's nares.

The blower may be positioned such that the outlet directs airflow directly into a nasal prong, and the inlet receives air through an aperture in the cushion. The inlet may be adjacent or near a filter and/or muffler 451 so as to reduce noise and provide the patient with clean air. The filter and/or muffler may comprise a filter material, foam, fabric, mesh, other suitable materials or combinations thereof.

Headgear straps 452 may be connected to a cushion for securing the patient interface to the patient. The headgear straps may be connected at the rear of the patient's head by a slidably engaging portion 453. The headgear straps may connect to the blowers and comprise wiring to supply power to the blowers. Power is provided to the blower via a wire to a control unit that includes a power supply unit. The control unit may also comprise a user interface to allow the setting of parameters to control the blowers.

Figures 6A, 6B:
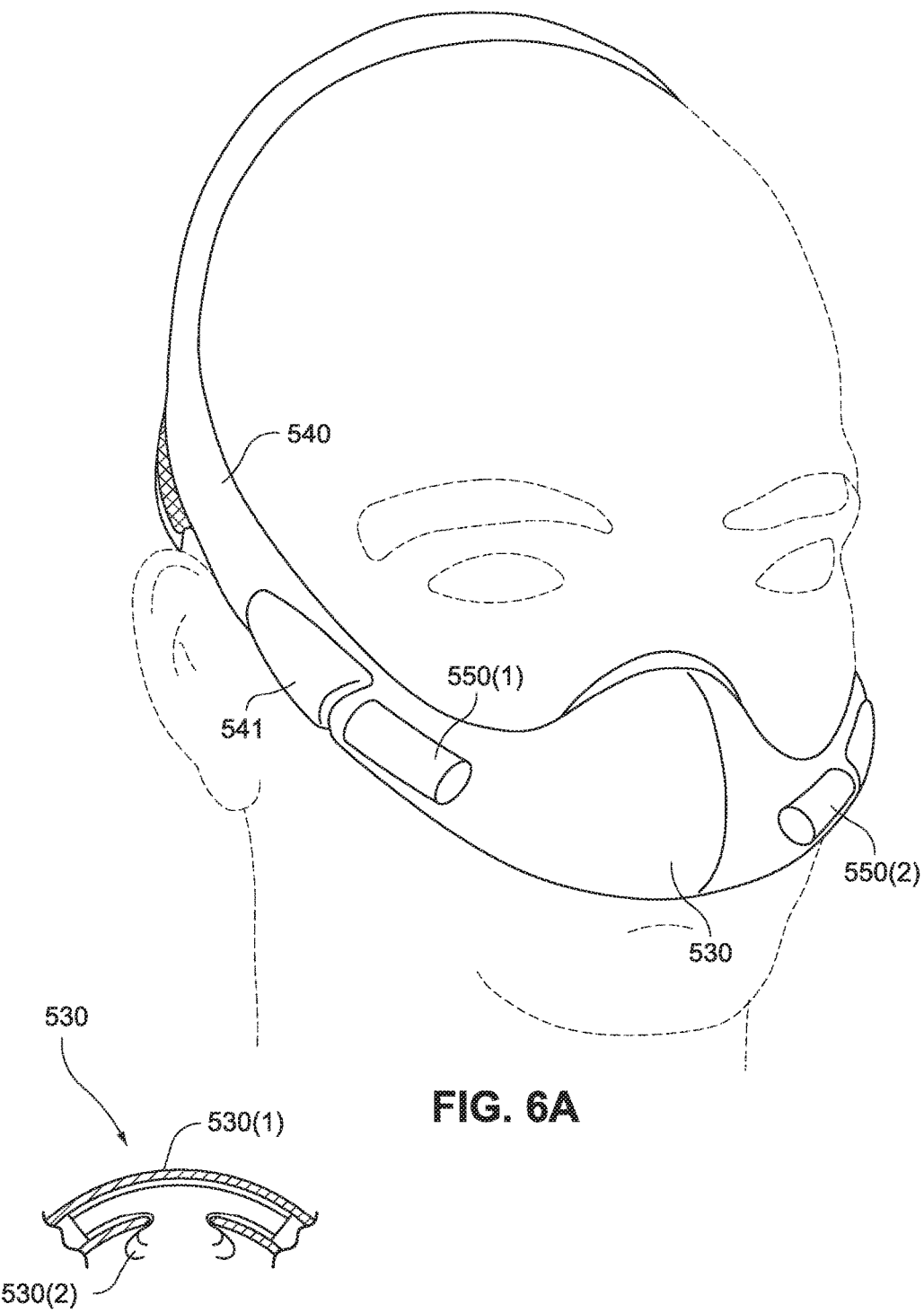
FIGS. 6A and 6B show a patient interface with a built-in blower according to certain embodiments.

In FIGS. 6A and 6B, the patient interface includes a nasal cushion 530 and first and second blowers 550(1), 550(2) provided to respective ends of the nasal cushion to provide pressurized air to the nasal cushion. The silicone cushion provides ducting to communicate pressurized air from the blowers to the nasal cushion.

In certain embodiments the first and second blowers 550(1), 550(2) may be directed to different nostrils and operate independently of one another. Each blower providing pressure support and flow to a different nostril. It is believed that at least some patients may breathe through one nostril at a time and rest the other nostril, with the breathing and nonbreathing nostrils changing periodically. The blowers may be adapted to detect from which nostril the patient is breathing and co-ordinate the supply of pressure from the first or second blower according to which nostril they are associated with. Alternatively the blowers may be configured to turn on and off the supply of pressure and flow to the different nostrils periodically according to a predetermined time pattern. The two blowers may each be on a timer and a communication system may control the operation of the two blowers. It is noted that such a two blower system may also be used with nasal pillows or prong interface system.

The cushion may be a thermoformed textile, e.g. see FIG. 6B including fabric portion 530(1) and silicone sealing portion and ducts 530(2). The textile could be woven or nonwoven. The cushion may include a foam and/or fabric layer. The thermoformed textile may include a sealing surface, such that is non-air permeable or at least minimally permeable. This may be achieved by silicone spraying, moulding or otherwise attaching a non-permeable or minimally permeable material to one or more portions of the fabric. Alternatively, the cushioning portion may be removably attached to the sealing surface. The sealing surface may include a patient contacting portion, a frame or support portion for maintaining the cushion away from the user's nose, and a ducted portion for attaching to air delivery tubes.

Headgear straps 540 may be formed by ultrasonic welding and/or thermoforming. Headgear straps may be made from a fabric and foam composite. Headgear straps may alternatively be a fabric. Headgear straps may include reinforcing portions. Headgear straps may further include additional baffling or muffling portions 541 to reduce noise from the blower and/or cushion. For example, muffling portions are shown in FIG. 6A positioned near or proximal to the patient's ears, to prevent excessive noise travelling to the patient's ears.

In FIGS. 7A and 7B, the patient interface includes a frame 620, a nasal cushion 630 provided to the frame, and a blower 650 provided to the front of the frame and communicated with the breathing chamber defined by the cushion. In certain embodiments, the headgear and/or patient interface may include one or more aspects as described in WO 2009/052560 A1 and U.S. Patent Application Publication 2009/0044808 A1, U.S. Pat. No. 7,318,437, or International Application PCT/AU2009/000241, filed Feb. 27, 2009, each of which is incorporated herein by reference in its entirety.

Headgear 640 shown in FIGS. 7A and 7B may include a cable or wiring system that is moulded into the headgear strap. For example, the wiring 640(1) may be encapsulated within a foam and/or fabric strap 640(2) as shown in FIG. 7B, wherein the foam and/or fabric may be formed by thermoforming and/or ultrasonic welding. The foam may be used to support the wires in position, insulate the cables and maintain the wires in an unobtrusive manner. The wiring is shown in the form of a ribbon cable, although other forms of wiring may be utilized.

Figures 8A, 8B:
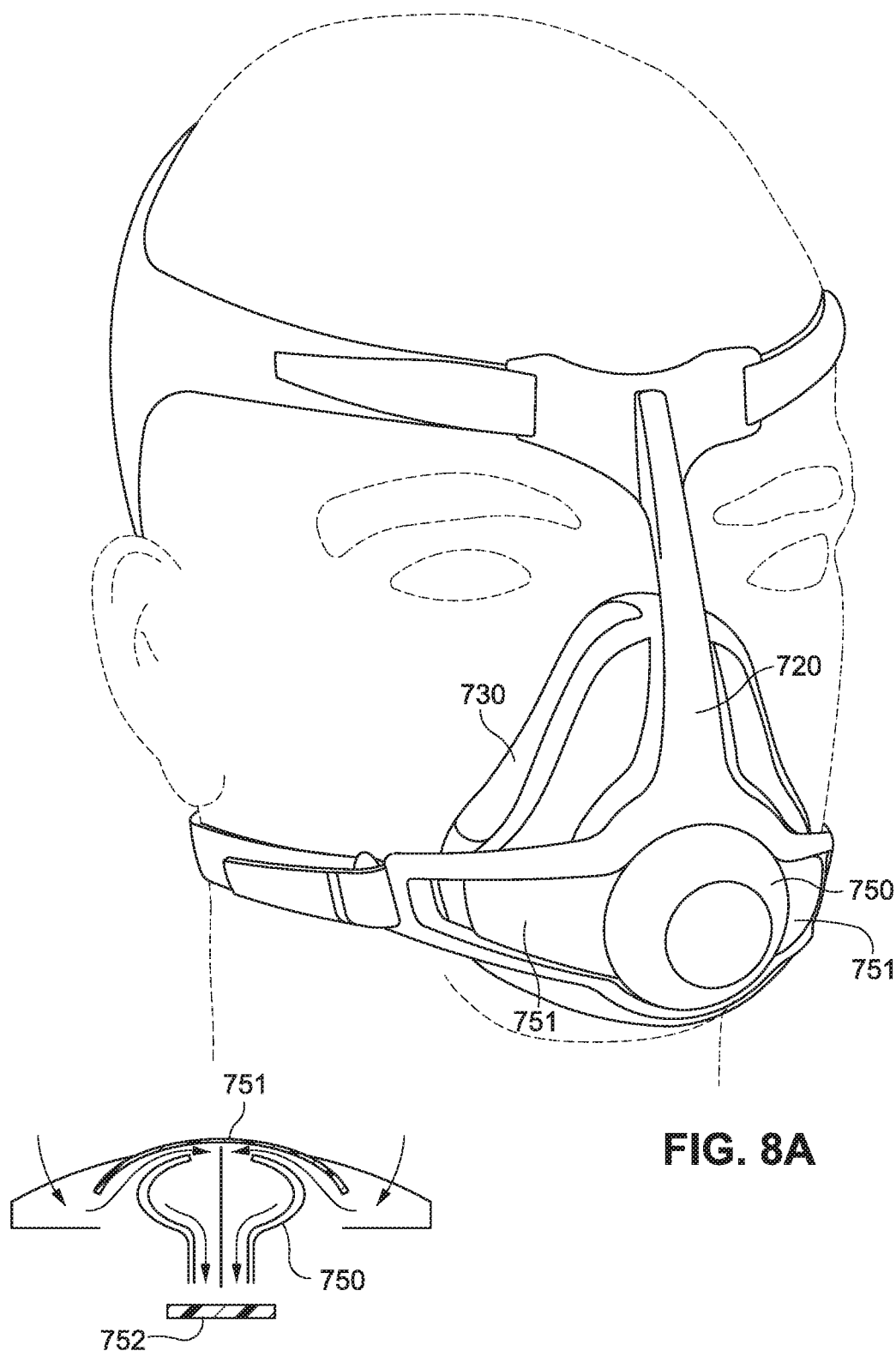
FIGS. 8A and 8B show a patient interface with a built-in blower according to certain embodiments.

In FIGS. 8A and 8B, the patient interface includes a frame 720 (including a forehead support), a full-face cushion 730 provided to the frame, and a blower 750 provided to the front of the frame and communicated with the breathing chamber defined by the cushion. A mesh vent 751 is mounted on either side of the blower. The mesh vent would allow air to flow into the blower as indicated by the arrows in FIG. 8B. The mesh vent acts as a first filter for the incoming air.

The frame 720 includes an aperture or ring for engaging with a blower 750. The blower may clip or otherwise engage with the frame.

A second filter 752, such as a HEPA filter, may be fitted to an inner portion of the mask near or proximal to the outlet of the blower to filter the air being delivered to or expired from the patient. It may also assist in damping the noise.

Figure 9A:
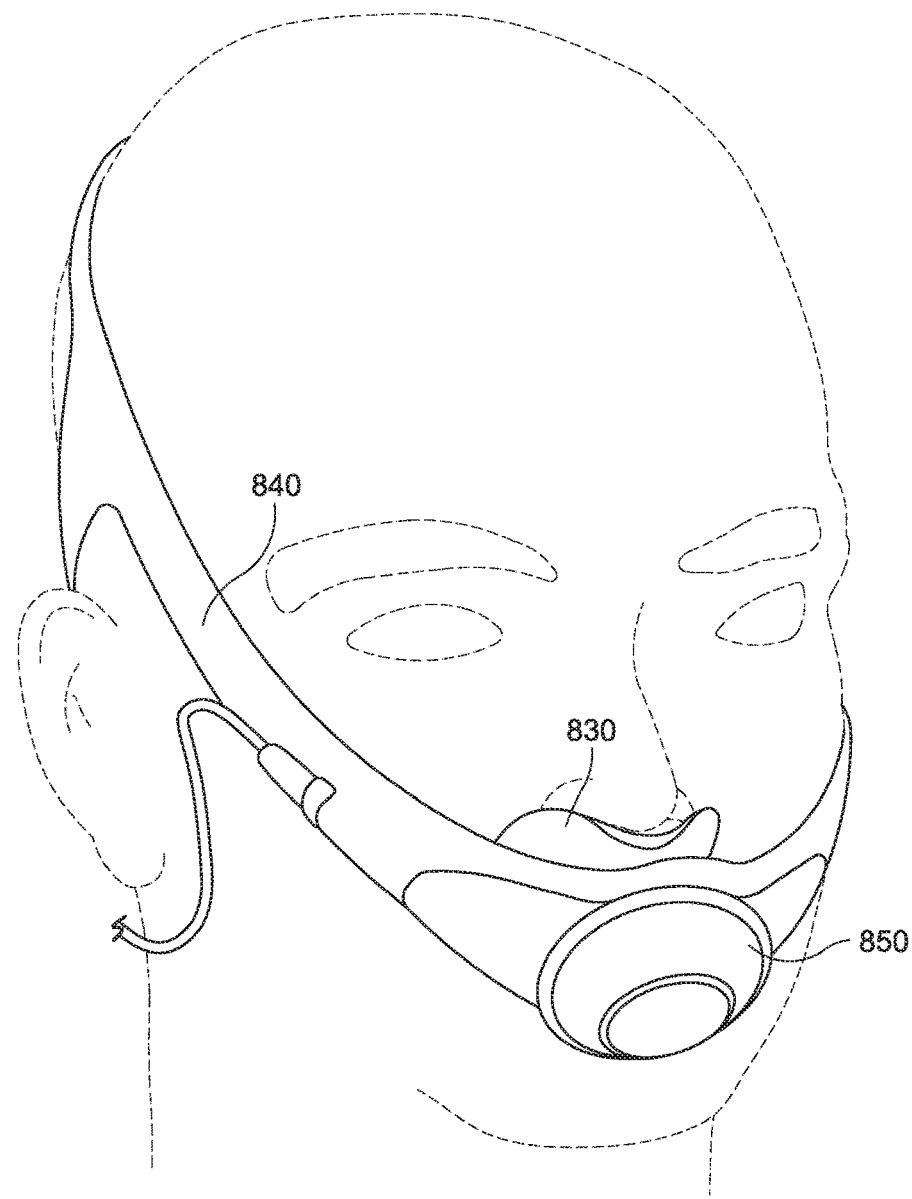
FIGS. 9A to 9C show a patient interface with a built-in blower according to certain embodiments.
Figure 9B:
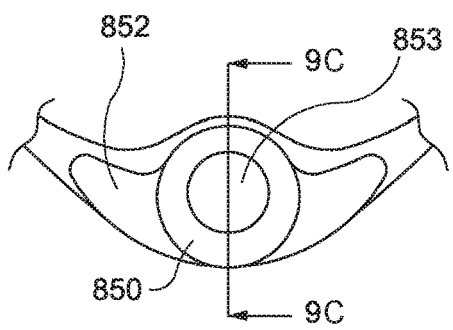
Figure 9C:
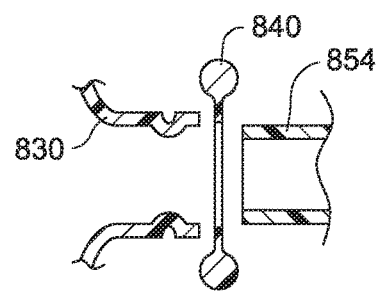

In FIGS. 9A to 9C, the patient interface includes a nasal cushion 830, headgear 840 to support the cushion in position on the patient's head, and a blower 850 supported by the headgear. The nasal cushion 830 may be constructed of a compliant material such as silicone, gel, or foam. The blower may be overmoulded or otherwise encapsulated in a housing, where the housing may be made from a plastic, metal, or other material that is able to maintain its shape. The housing may also function as a muffler to reduce noise. In certain embodiments, the cushion may include one or more aspects as described in Australian Application 2009902524, filed Jun. 2, 2009, which is incorporated herein by reference in its entirety.

Headgear 840 for supporting the mask 830 may include a channel or other attachment means for a power supply cable to connect the motor to a power supply. The channel may be contained within the headgear. The channel may protect the wiring, prevent entanglement or strangulation of the patient and give the system a streamlined appearance. The headgear 840 may be thermoformed or otherwise shaped.

A muffler or filter may also be fitted over an inlet 852 of the blower adjacent the mask 830. The muffler or filter may be a foam or fabric moulded or attached to the headgear, as shown in FIG. 9B. Alternatively, the muffler or filter may be a non-woven material. The muffler or filter may filter exhaled gases and/or reduce the noise from the mask and blower. In a further alternative, the muffler or filter may be integrally formed or apart of the headgear. As shown in FIGS. 9B and 9C, the outlet 853 of the blower may be connected to the cushion 830 through the headgear 840 by a motor cuff 854 of the blower.

Figure 27A:
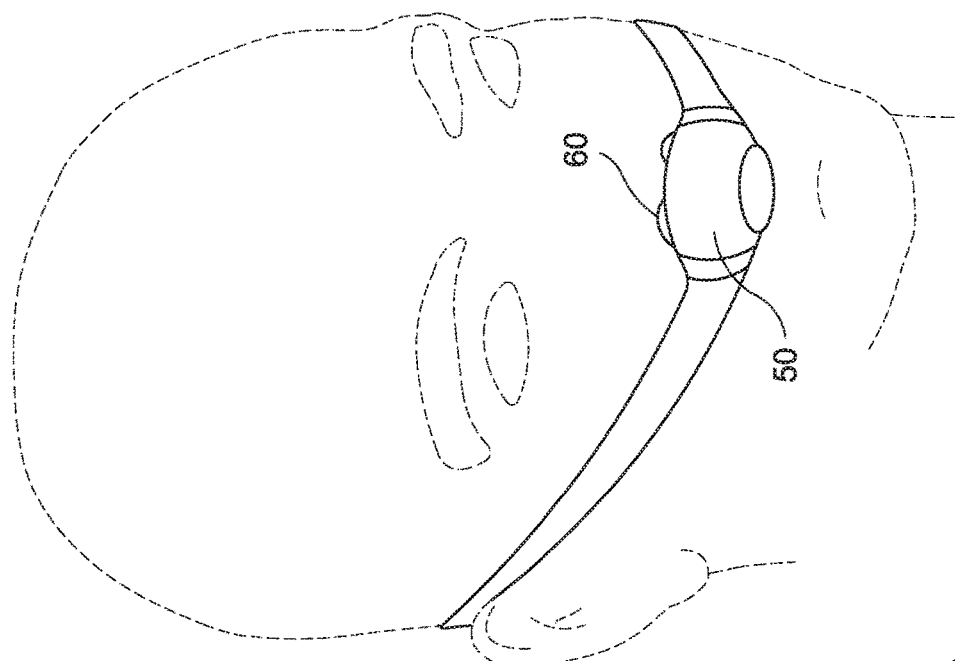
FIGS. 27A and 27B show a patient interface with a built-in blower according to certain embodiments.
Figure 27B:
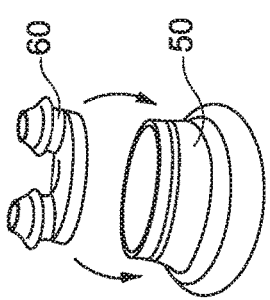
Figure 26:
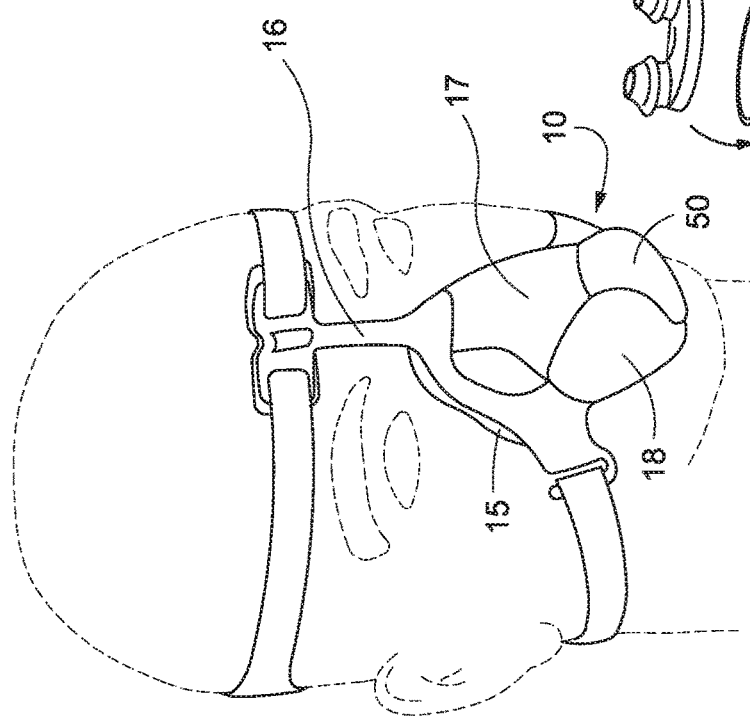
FIG. 26 shows a patient interface with a built-in blower according to certain embodiments.
Figure 28:
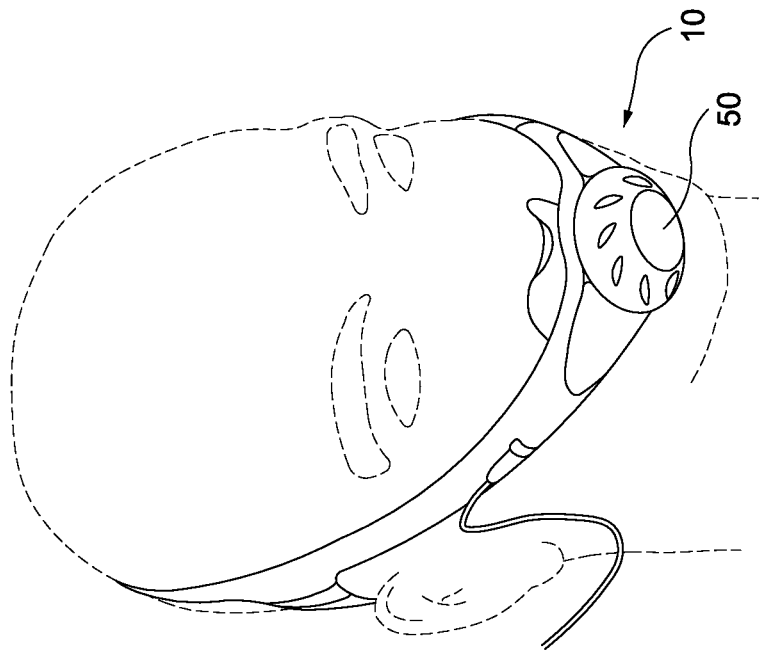
FIG. 28 shows a patient interface with a built-in blower according to certain embodiments.
Figure 29:
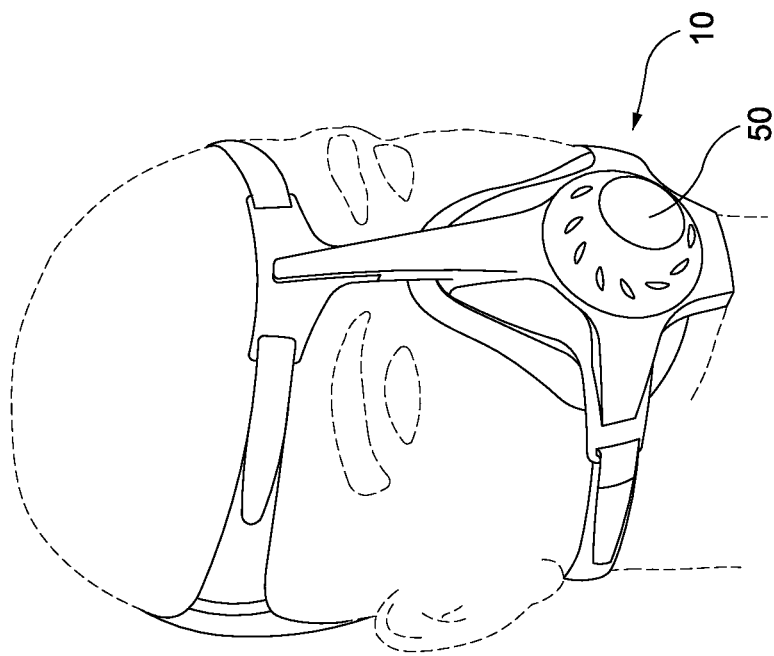
FIG. 29 shows a patient interface with a built-in blower according to certain embodiments.
Figure 31:
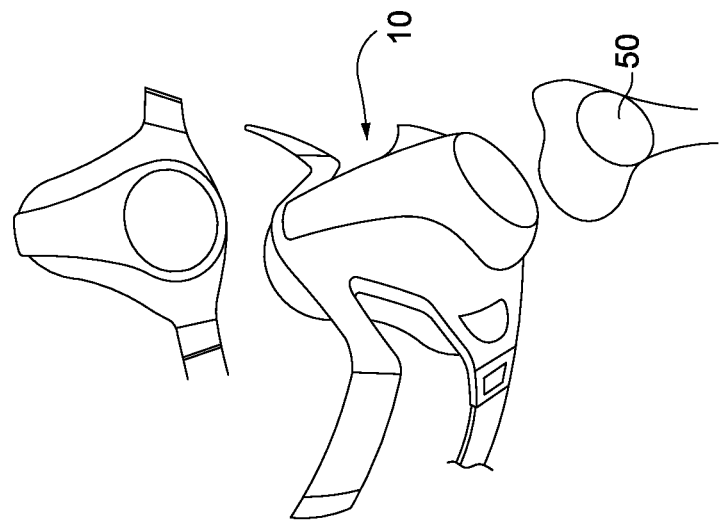
FIG. 31 shows a patient interface with a built-in blower according to certain embodiments.
Figure 30:
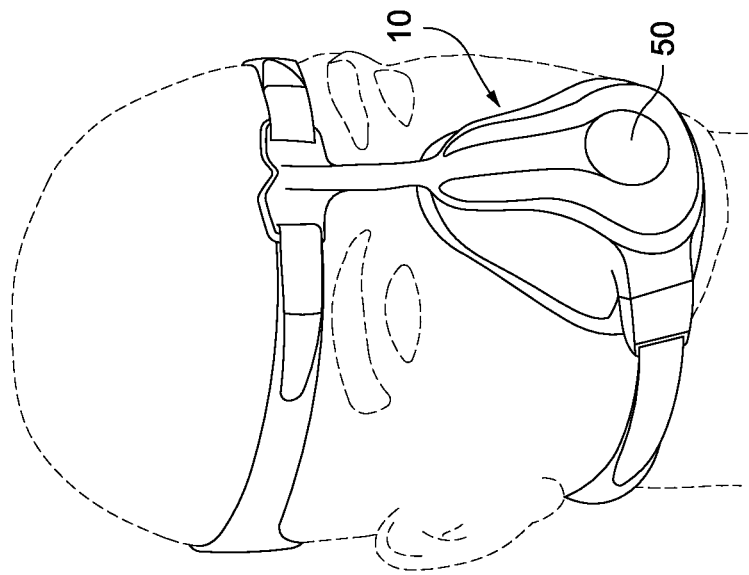
FIG. 30 shows a patient interface with a built-in blower according to certain embodiments.
Figure 33:
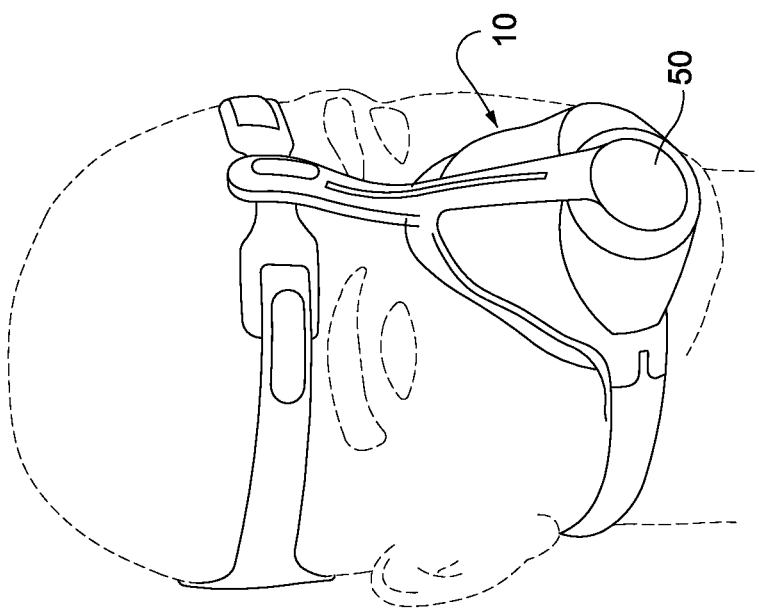
FIG. 33 shows a patient interface with a built-in blower according to certain embodiments.
Figure 32:
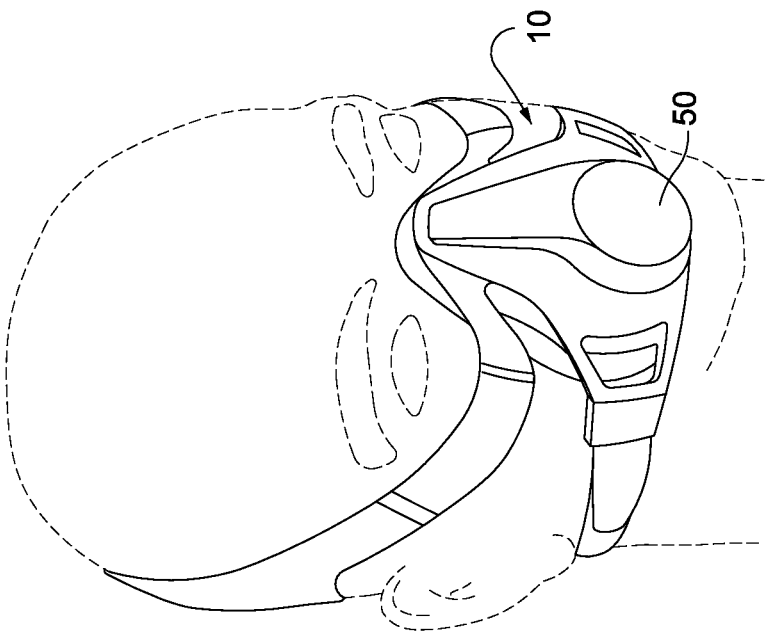
FIG. 32 shows a patient interface with a built-in blower according to certain embodiments.
Figure 35:
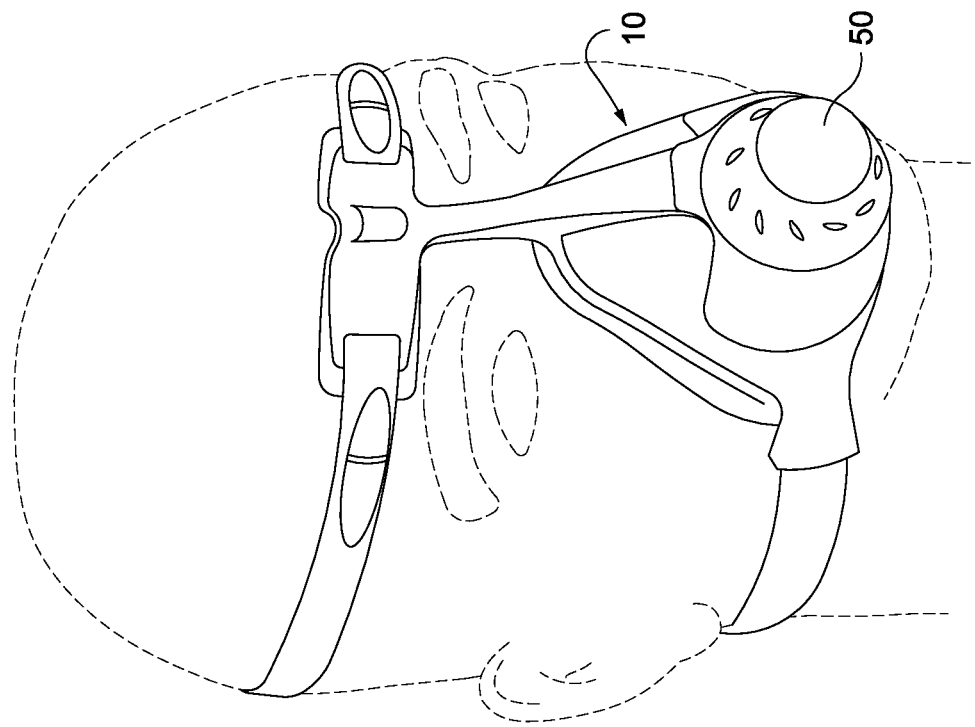
FIG. 35 shows a patient interface with a built-in blower according to certain embodiments.
Figure 34:
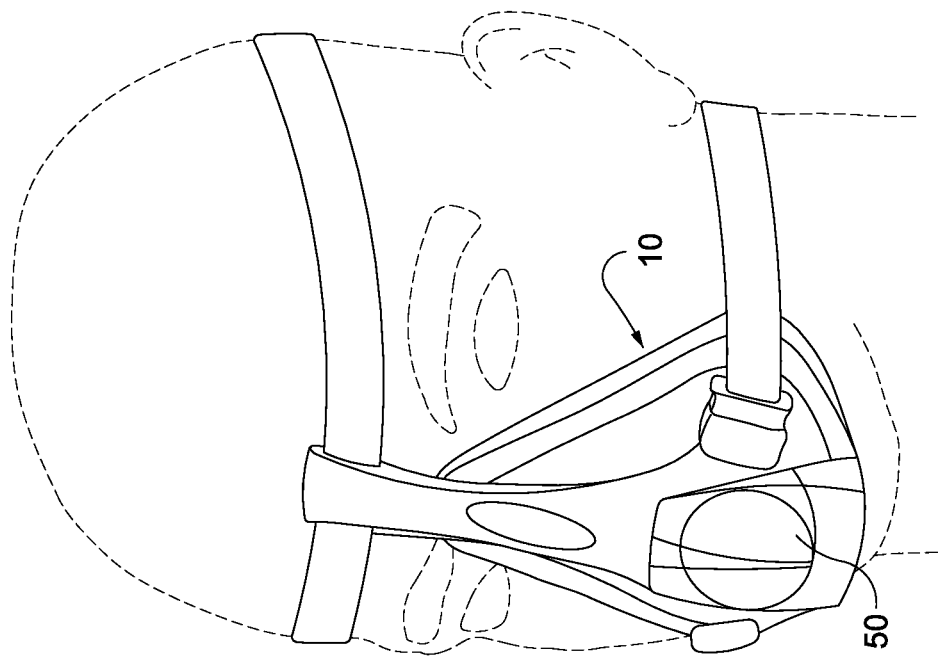
FIG. 34 shows a patient interface with a built-in blower according to certain embodiments.

FIGS. 24-35 show alternative frame configurations for attaching headgear, alternative headgear arrangements, alternative cushion or sealing arrangements, and/or alternative blower configurations. For example, in FIGS. 24 and 25, the patient interface 10 includes a blower 50 supported by the mask frame. As shown in FIG. 25, the blower may include a symmetrical housing that provides an aesthetically pleasing device. The housing includes an inlet 52 for the blower provided in a first half, and a muffler or filter 66 provided in a second half. In FIG. 26, a mask 10 wherein the blower is built into the mask is shown. The mask includes a frame 16 that supports a cushion 17 formed of, for example, silicone that includes a seal 15 to sealingly engage the patient's face. A blower 50 is mounted on the mask. An inlet filter and/or muffler 18 may be provided to filter the air and/or reduce the operating noise of the blower 50. In certain preferred embodiments, the mask 10 may be provided for ventilation, i.e. no venting of the mask may be provided. In FIGS. 27A and 27B, snap on pillows or nasal prongs 60 may be provided to the blower 50. In FIGS. 28 and 29, the patient interface 10 may provide a foam intake. In FIGS. 30-35, the blower is provided to the front of the mask and the mask includes a streamlined design.

For example, FIG. 24 shows a pair of blowers or blower housings mounted on to the mask or patient interface. The inlets of the blowers are positioned horizontally outwards in the medial-lateral direction. A similar configuration is demonstrated in FIG. 25.

FIGS. 27A and 27B depicts a blower outlet being connected directly to a patient interface. The patient interface shown is a pillows or prong arrangement. Alternative patient interfaces may be used, for example nasal cradles, nasal, full face or oro-nasal masks.

1.3 Certain Embodiments Relating to Portable

Certain embodiments of the present disclosure relate to portable blowers.

FIGS. 10-11, 36-39, and 45-48 show portable blowers according certain embodiments of the present technology.

Figure 10:
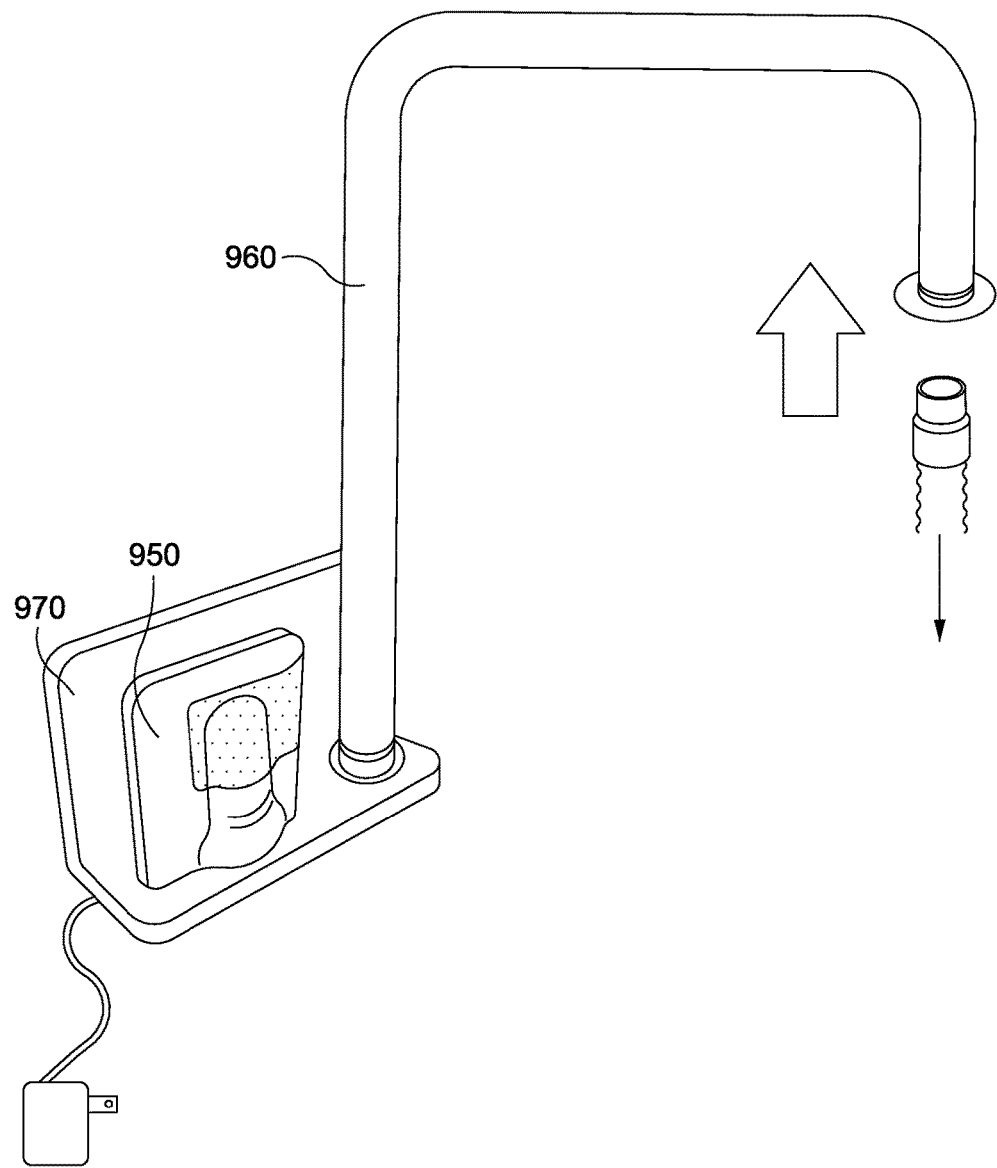
FIG. 10 shows a portable blower according to certain embodiments.

As shown in FIG. 10, the portable blower 950 may be adapted to be mounted by the patient's bedside or wall. The bedside embodiment may include a detachable blower mounted on a docking station 970 or nightstand. The detachable blower may include batteries, such as lithium ion batteries, for powering the device when not connected to the main/AC power. The night stand may be fitted with an overhead tube 960 (flexible tube, fixed shape tube, or combination thereof) adapted to connect to tubing associated with the mask. The overhead tube may be made from a metal such as stainless steel, or polymer such as thermoplastics or silicone, or combination thereof. The overhead tube may be able to rotate on the stand or bend in selected regions such as the top horizontal bar. The overhead tube includes a series of lights or LED's at the cuff or connection region with the mask tube which can be activated by touch or by a change in the system (such as detachment). Also the overhead tube can provide a soft light for the patient to see at night. The light may assist the patient when detaching or reattaching a flexible mask tube to the overhead tube. The color of the light may be associated with an activation reason. The cuff or connection region of the overhead tube may include a magnet that may attract a magnet or ferrous material at the end or connection region of the mask tube. This may aid attachment of the mask tube to the overhead tube.

Figure 11:
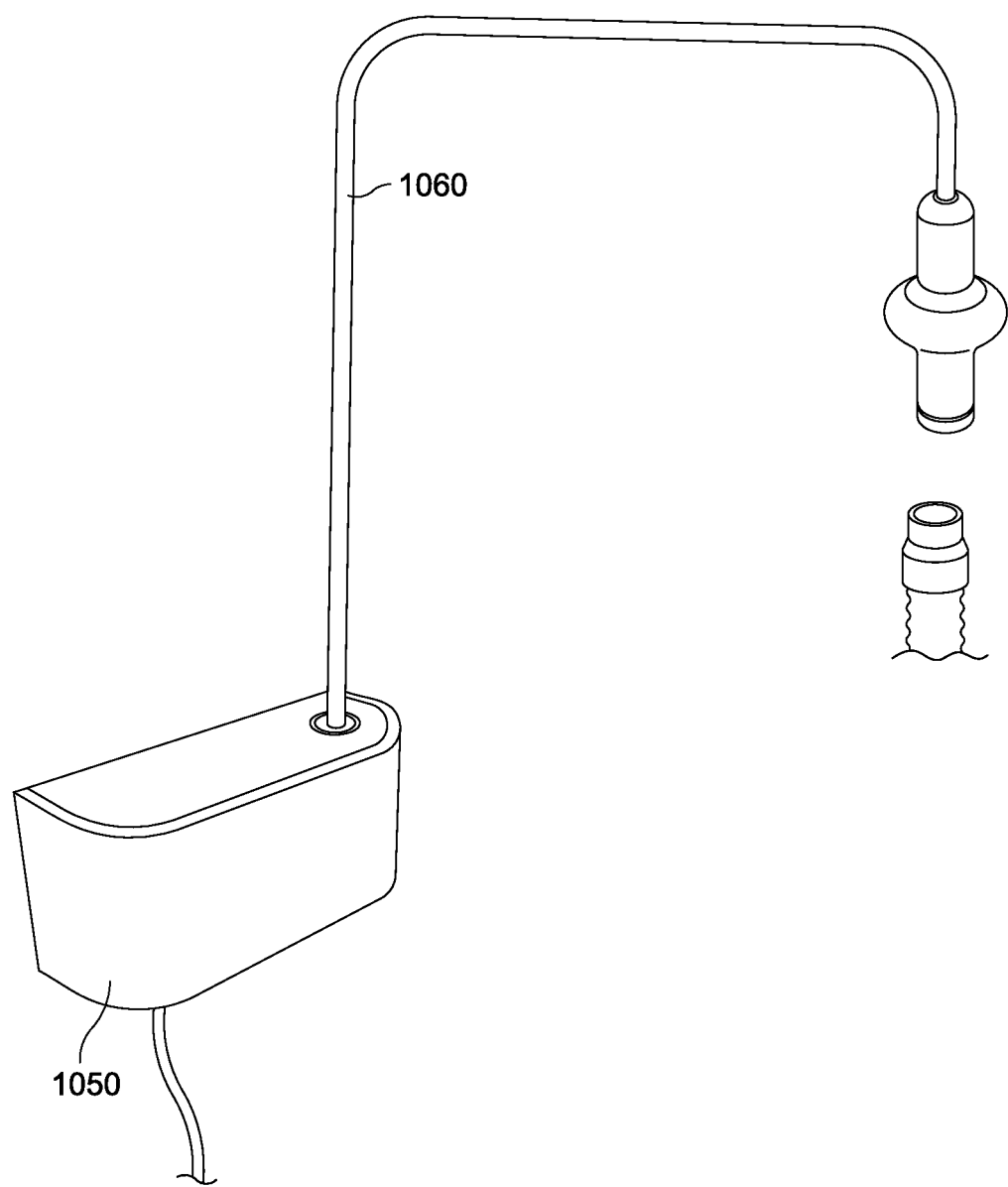
FIG. 11 shows a portable blower according to certain embodiments.

In FIG. 11, the blower is adapted to be mounted to the wall or bedhead. An overhead tube 1060 may extend from the blower and adapted to connect to tubing associated with the mask. A muffler and/or filter may be attached to the blower to filter gases being delivered to the patient and/or reduce the noise of the system. Similar to the embodiment in FIG. 10, the overhead tube may be attached to the bed, bed head, wall or any other region proximal to the patient. The overhead tube may connect to a case 1050, where the case 1050 receives a power supply for the blower system. The power supply may be a battery or mains power supply. The case 1050 may be constructed of a polymer such as thermoplastic elastomer, thermoplastic urethane, or may be constructed from a metal such as aluminum. The case 1050 may have a wire or other means of carrying the power supply to the blower attached to the end of the overhead tube. The case may also include a microprocessor and user interface to allow the control and setting of parameters for the blower.

Figure 36:
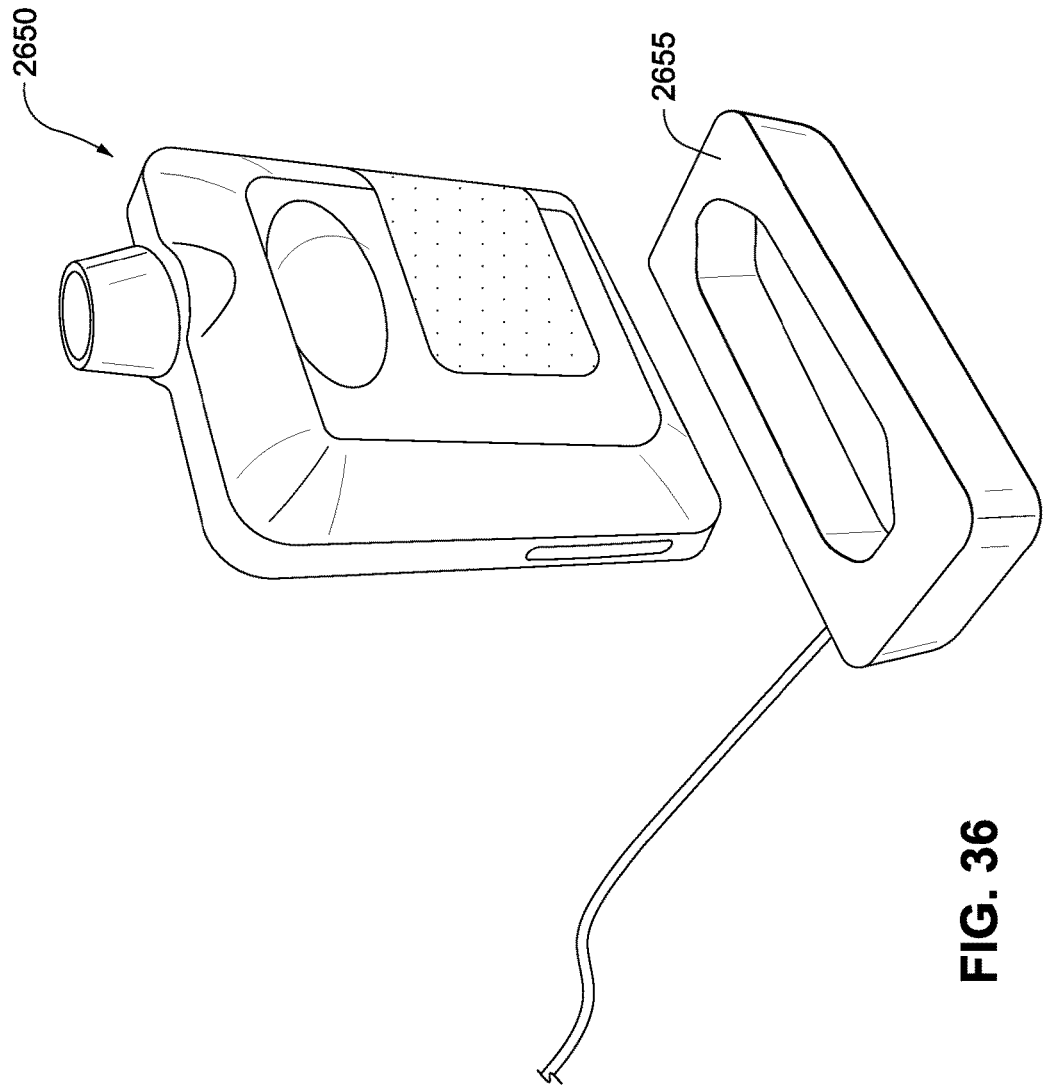
FIG. 36 shows a portable blower according to certain embodiments.
Figure 38A:
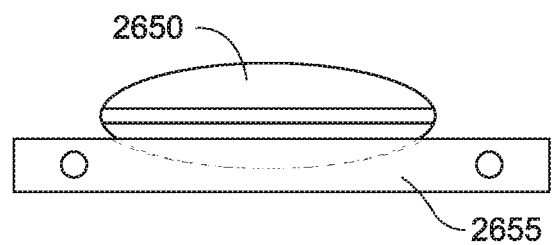
FIGS. 38A to 38D show a portable blower according to certain embodiments.
Figure 38B:
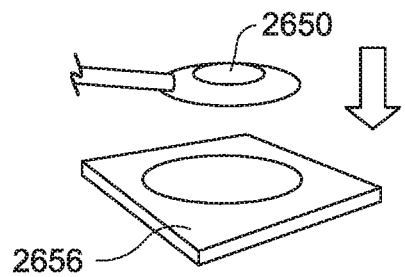
Figure 38C:
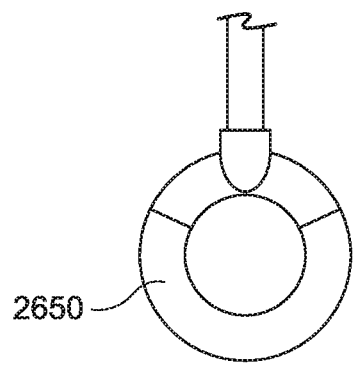
Figure 38D:
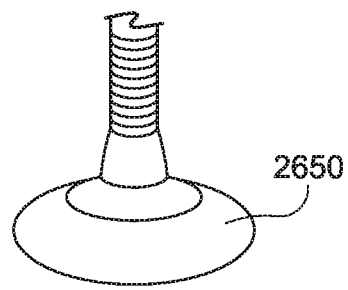
Figure 47:
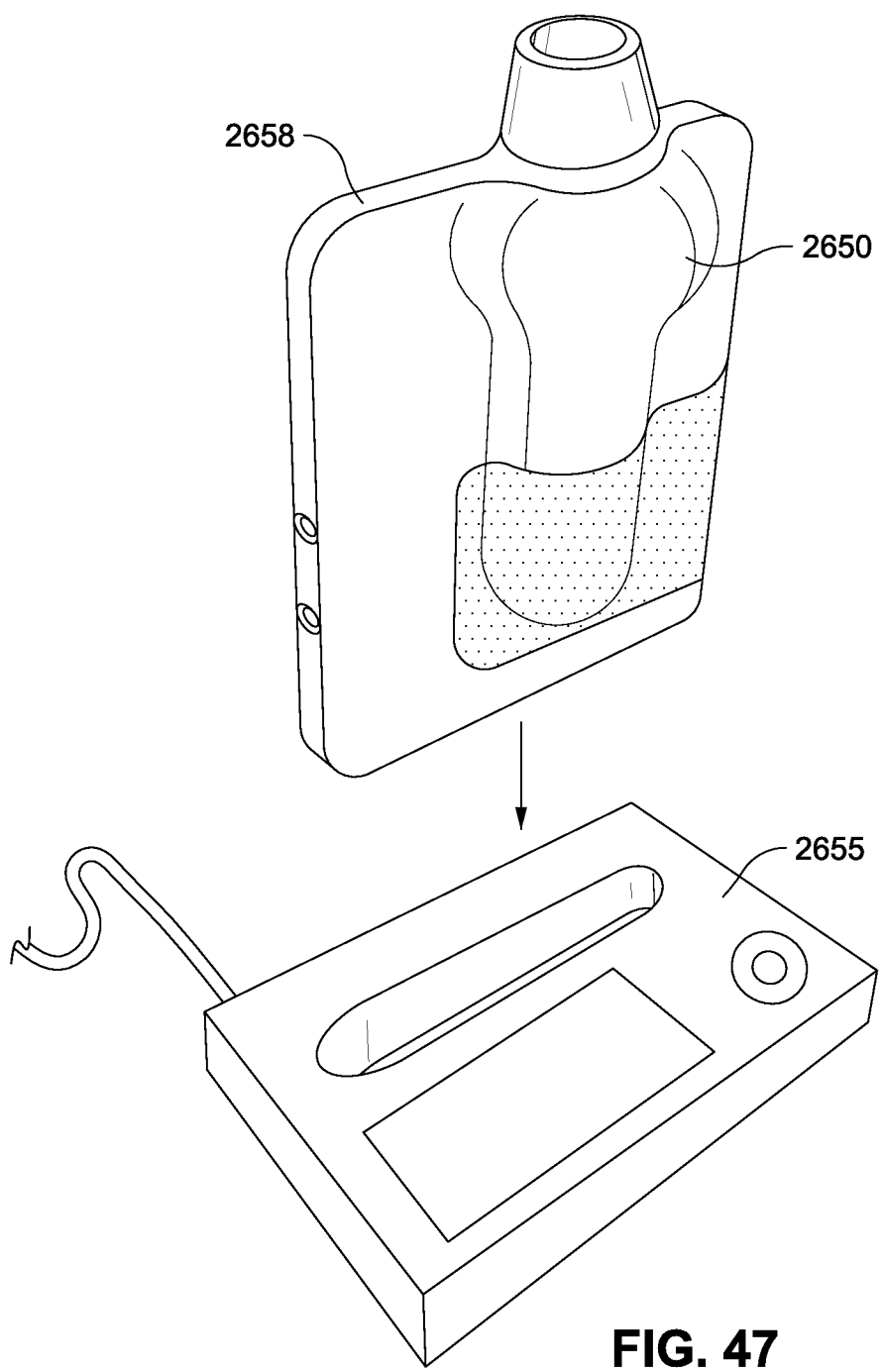
FIG. 47 shows a portable blower according to certain embodiments.

In FIGS. 36 and 47, the portable blower 2650 may be attachable to a blower dock 2655 which may be structured to retain, charge, and/or download diagnostics from the blower.

In FIGS. 37A and 37B, the blower 2655 is in the form of a blower pouch. The pouch may be deflatable when not in use for portability.

In FIGS. 38A to 38D, the portable blower 2650 may be provided to a base 2656 adapted to charge the blower by induction charging.

FIG. 39 shows embodiments of an overhead support 2657. A blower 2670 may be supported by the support 2657 and supply a flow of breathable gas to a patient 2679 by a tub 2678, which may include light-up tubing.

Figure 45:
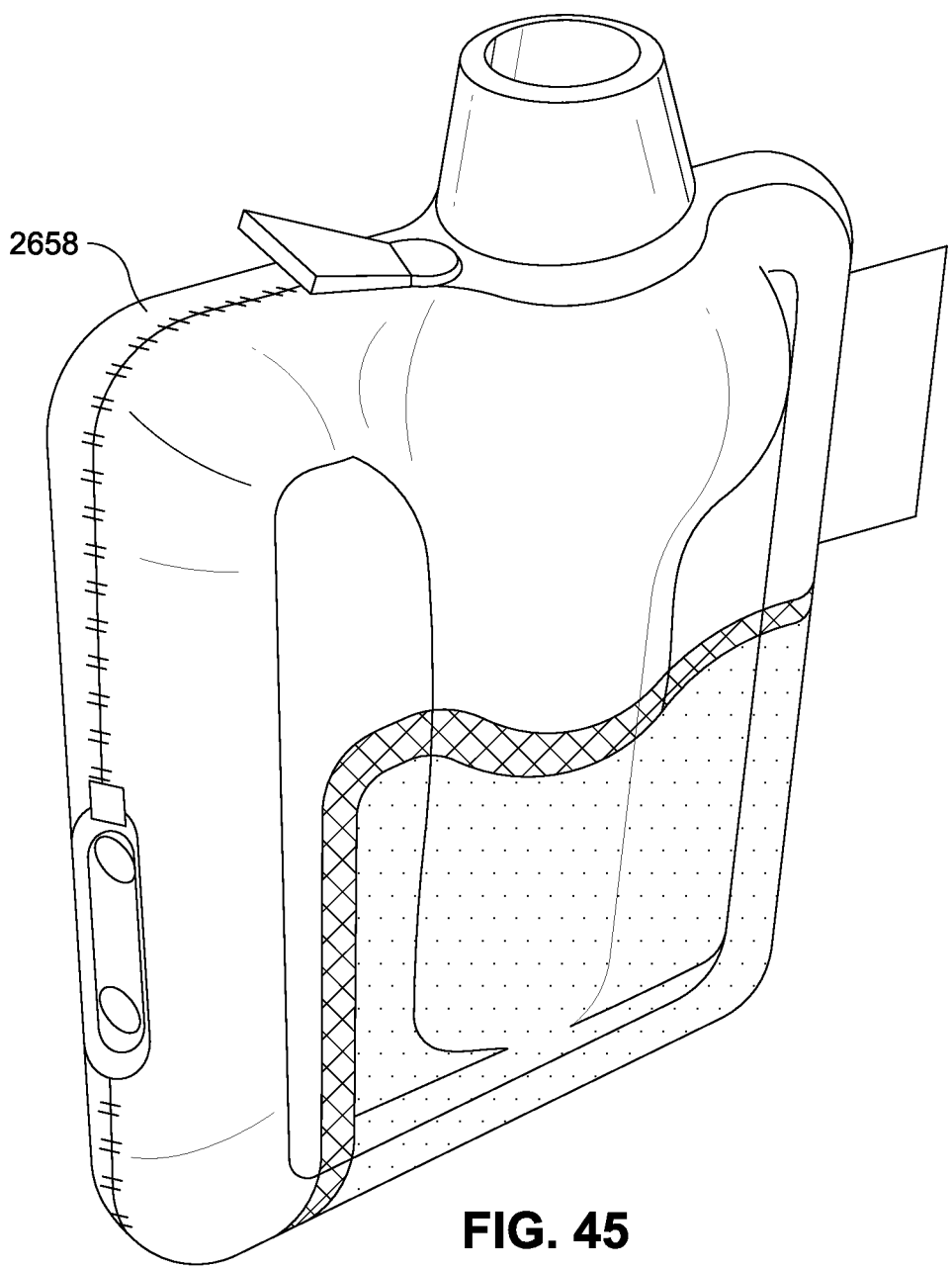
FIG. 45 shows a portable blower according to certain embodiments.
Figure 46:
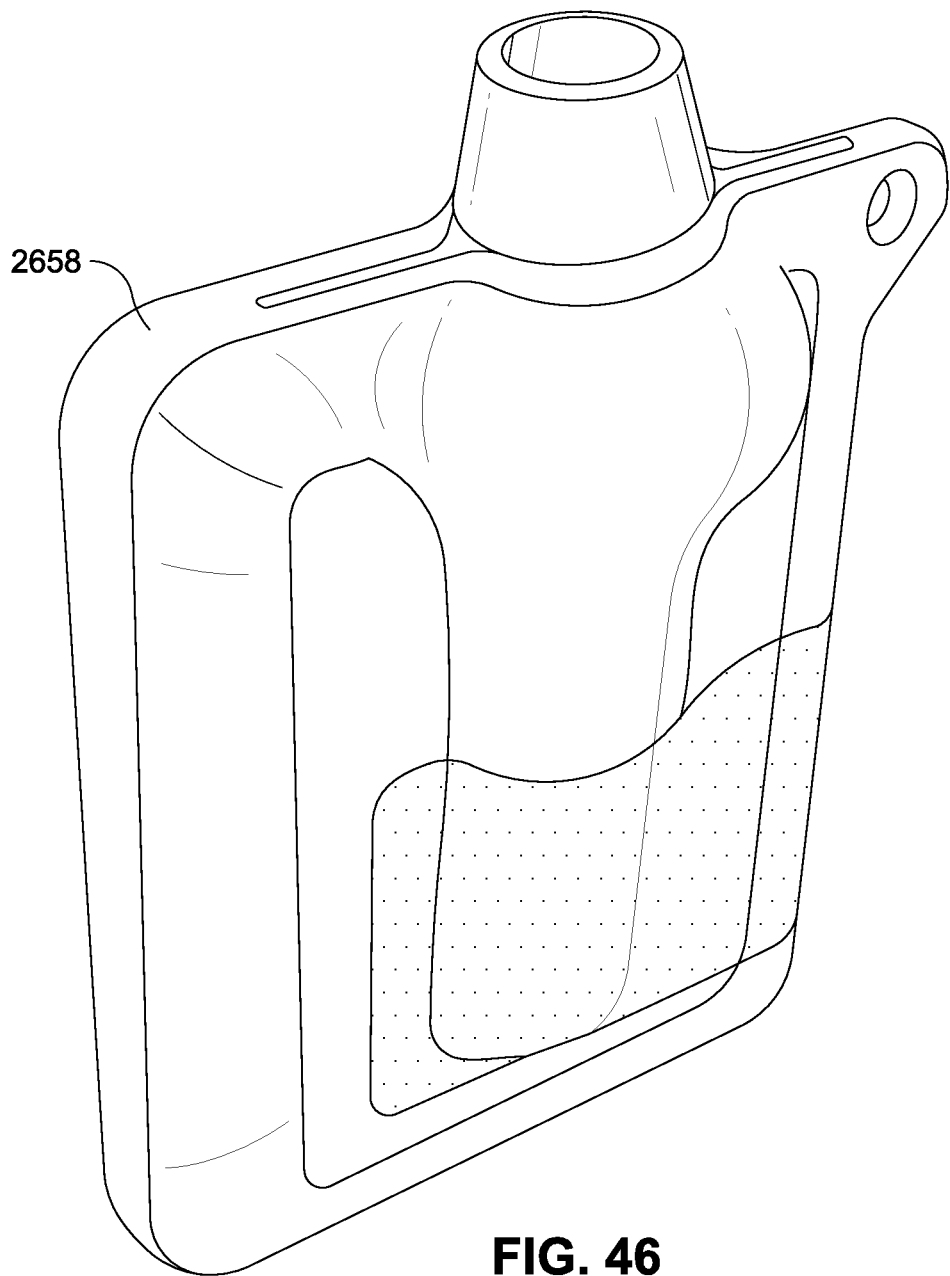
FIG. 46 shows a portable blower according to certain embodiments.
Figure 48:
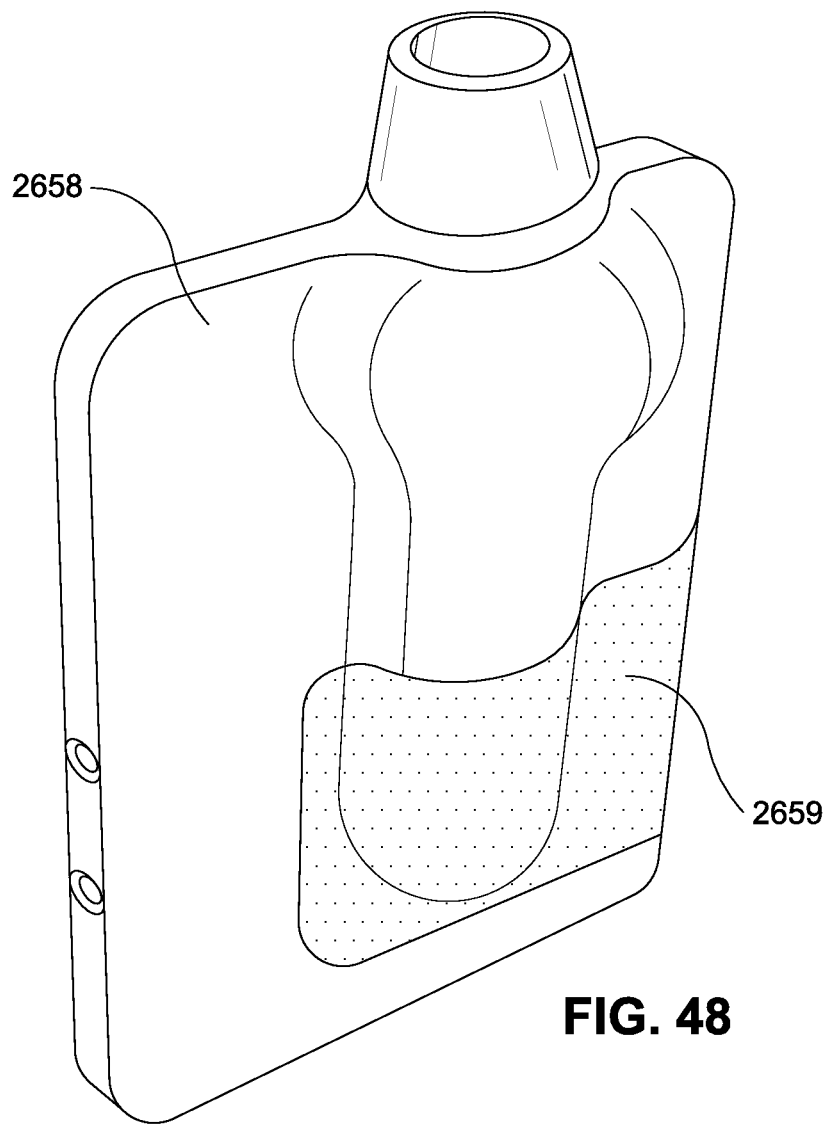
FIGS. 48 and 49 show a portable blower according to certain embodiments.
Figure 49:
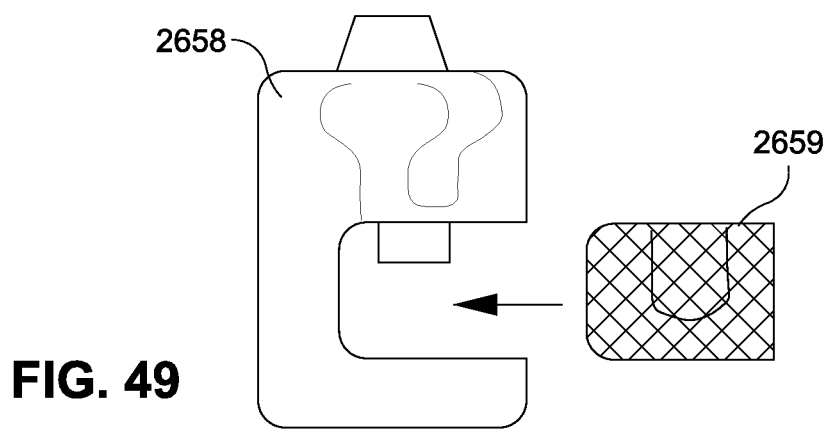

FIGS. 45, 46, 48 and 49 show alternative casings 2658 for enclosing or protecting a portable blower. For example, FIG. 45 shows a fabric or foam/fabric type case, FIG. 46 shows a silicone type case, and FIGS. 48 and 49 show an aluminum alloy type case. A foam or non-woven baffle or filter 2659 snaps in and out of the case 2658.

A battery pack may be provided with the mask and blower system. The battery pack may be worn on the body of the patient. Alternatively, the battery may be provided with a chord such that it may be positioned away from the patient, for example on a bed side table. The battery may be flexible such that if it is worn on the body of the patient it may bend and conform to the general shape of the patient. The battery may have a wire or cable connecting it to the motor. The cable may have a quick release or force release portion, such that if a force is applied to the cable, the cable will disconnect the battery from the motor. This may be beneficial to avoid strangulation of the patient, or quick removal of the power from the motor.

1.4 Certain Embodiments Relating to Wearable

Certain embodiments relate to blowers adapted to be wearable and/or carried by the patient and not mask or head mounted. In certain embodiments, the blower or blowers may be carried, wearable, positioned on the head, positioned on or adjacent the mask or combinations thereof.

FIGS. 40A to 44 and 50-52 show wearable blowers according to certain embodiments.

Figure 40A:
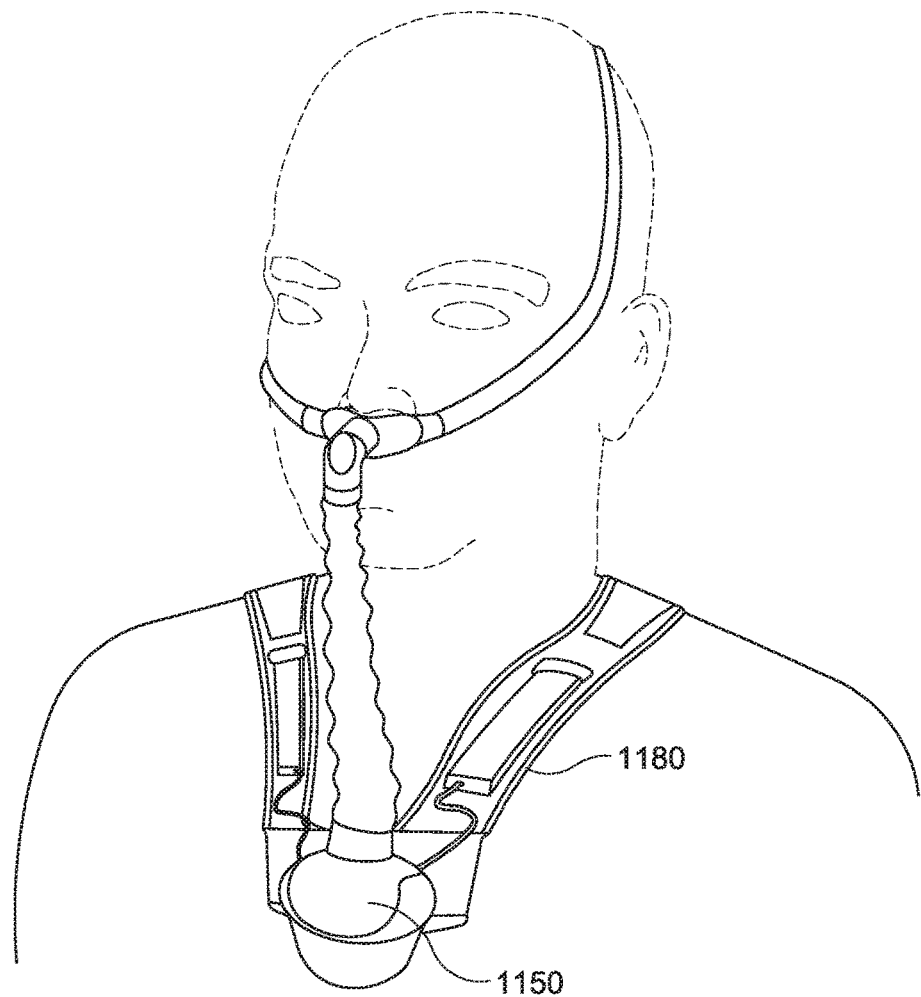
FIGS. 40A and 40B show a wearable blower according to certain embodiments.
Figure 40B:
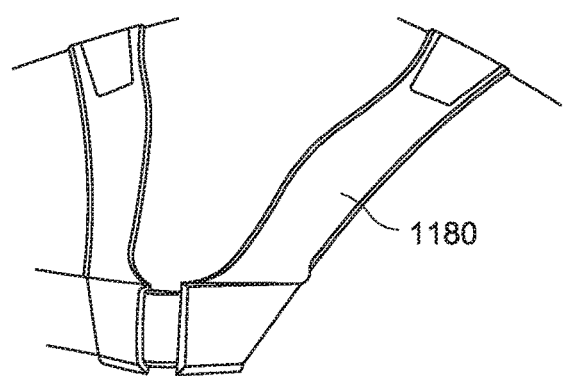

In FIGS. 40A and 40B, the blower 1150 is supported by a shoulder-type harness 1180 which supports the blower adjacent the patient's chest.

In FIG. 41A, the blower 50 is supported by a pendant-type arrangement 64. The pendant 64 may be part of a necklace, or pinned to the patient's clothing. The blower 64 includes an air tube connector 63 for connecting a tube to deliver the flow of breathable gas. FIG. 41B shows a blower 50 provided in a container configured to have a shape similar to a cologne bottle.

Figure 43:
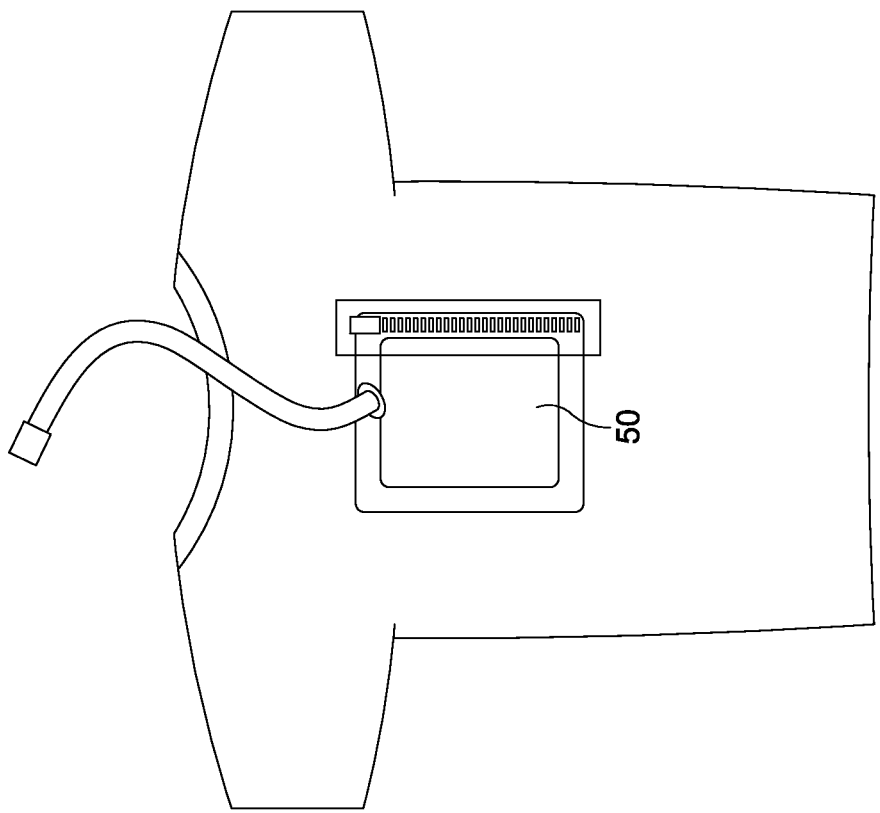
FIG. 43 shows a wearable blower according to certain embodiments.
Figure 52:
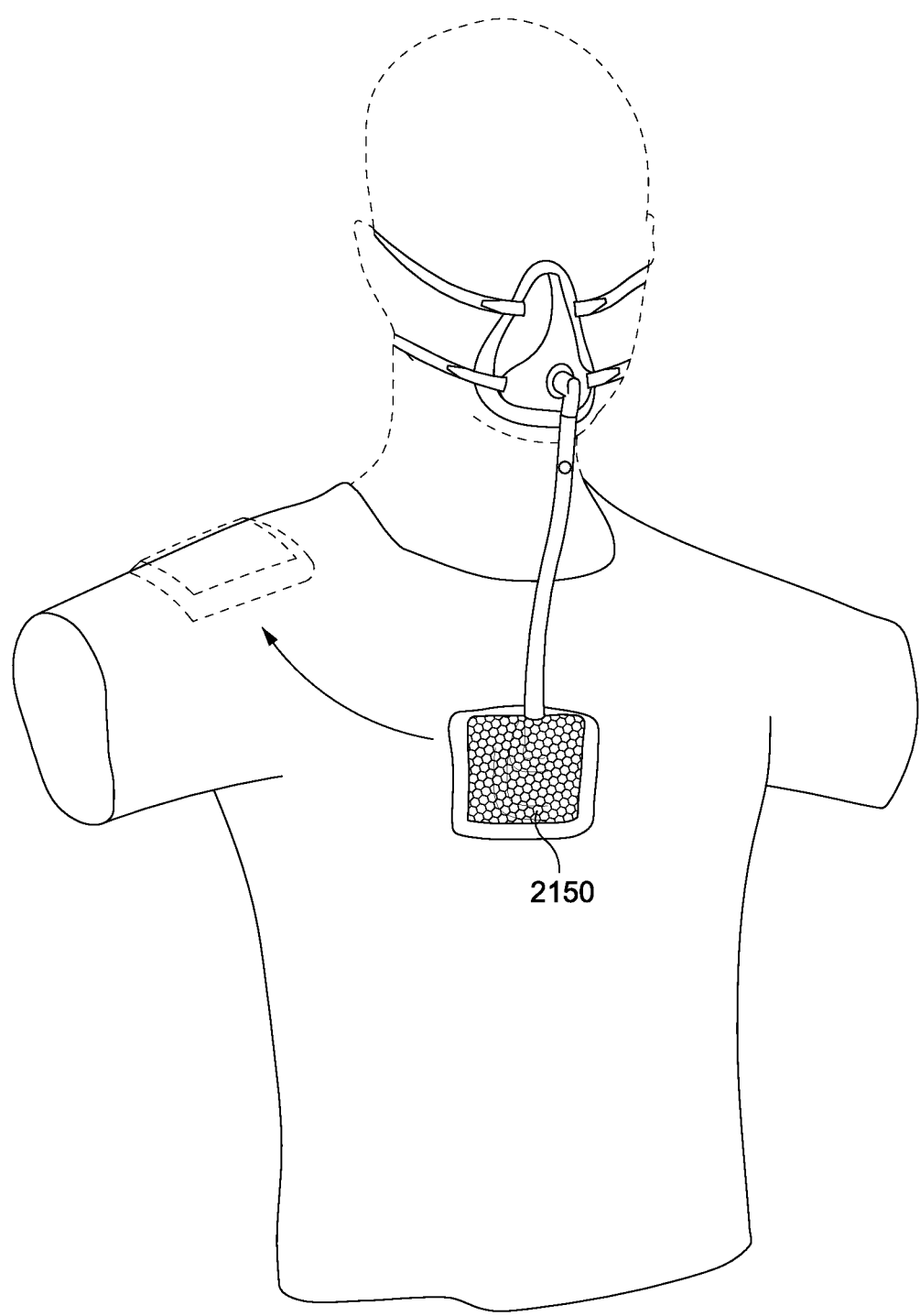
FIG. 52 shows a wearable blower according to certain embodiments.
Figure 53A:
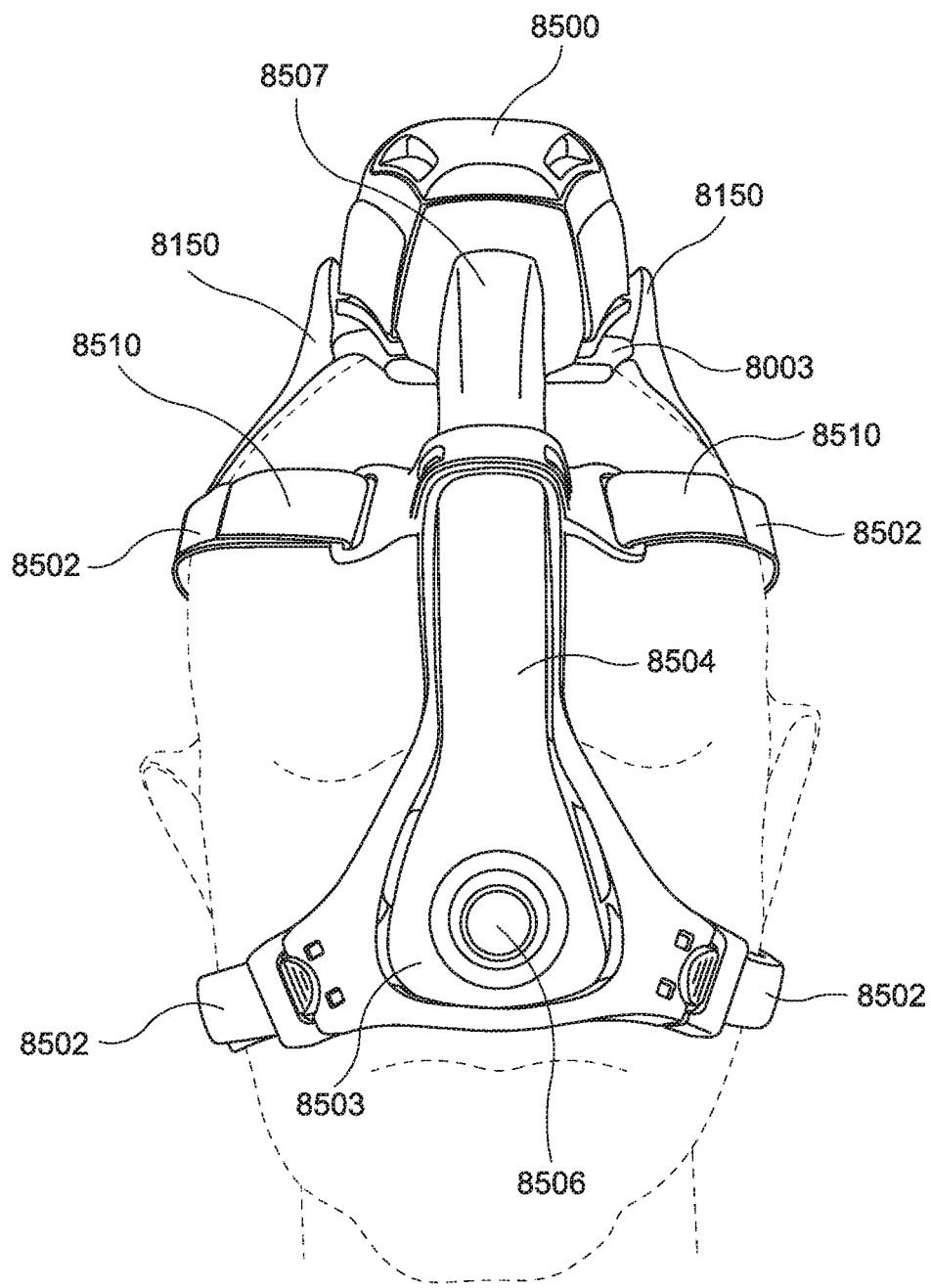
FIGS. 53A and 53B show a front and top view, respectively, of a headworn PAP system according to certain embodiments.
Figure 53B:
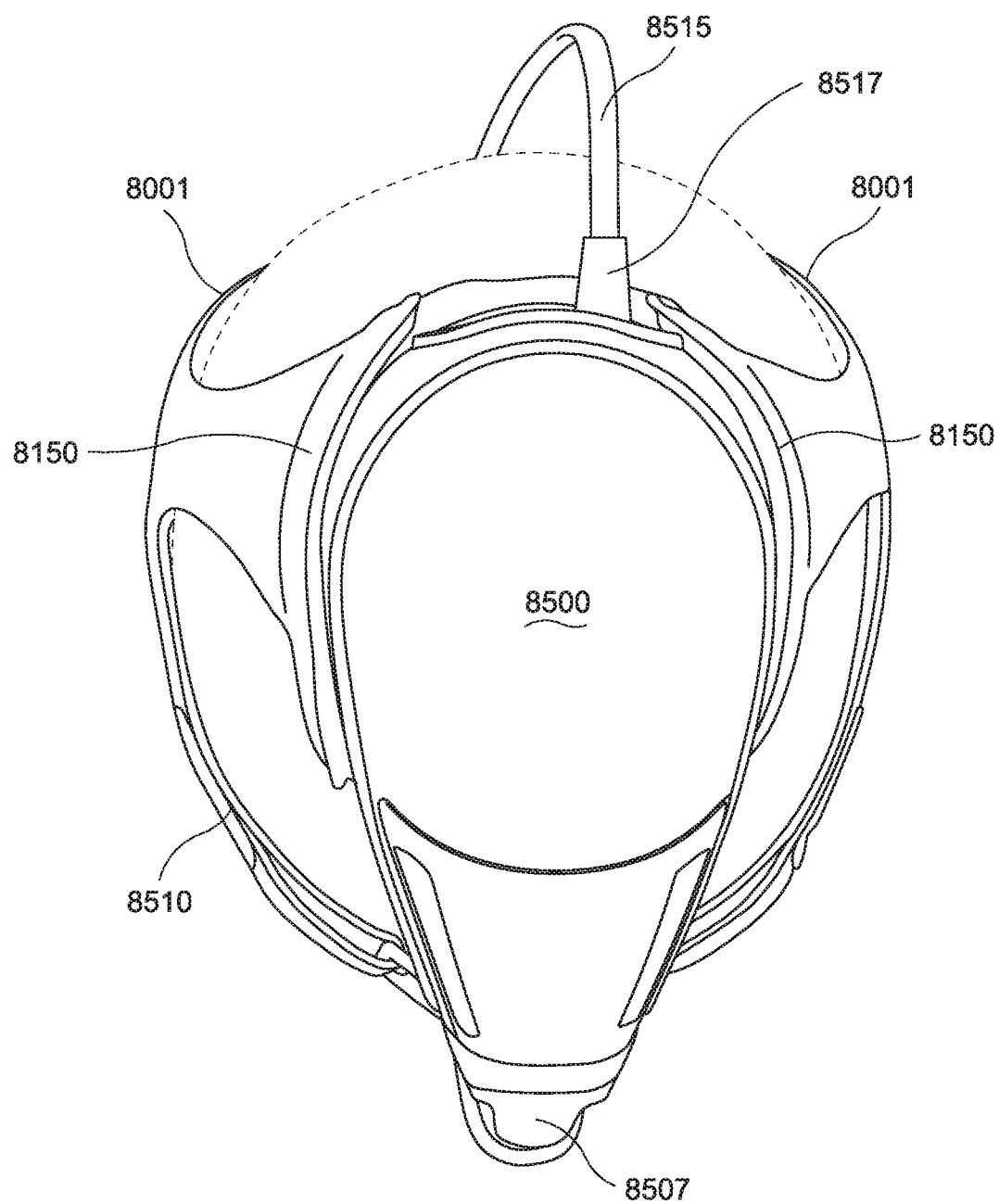
Figure 54A:
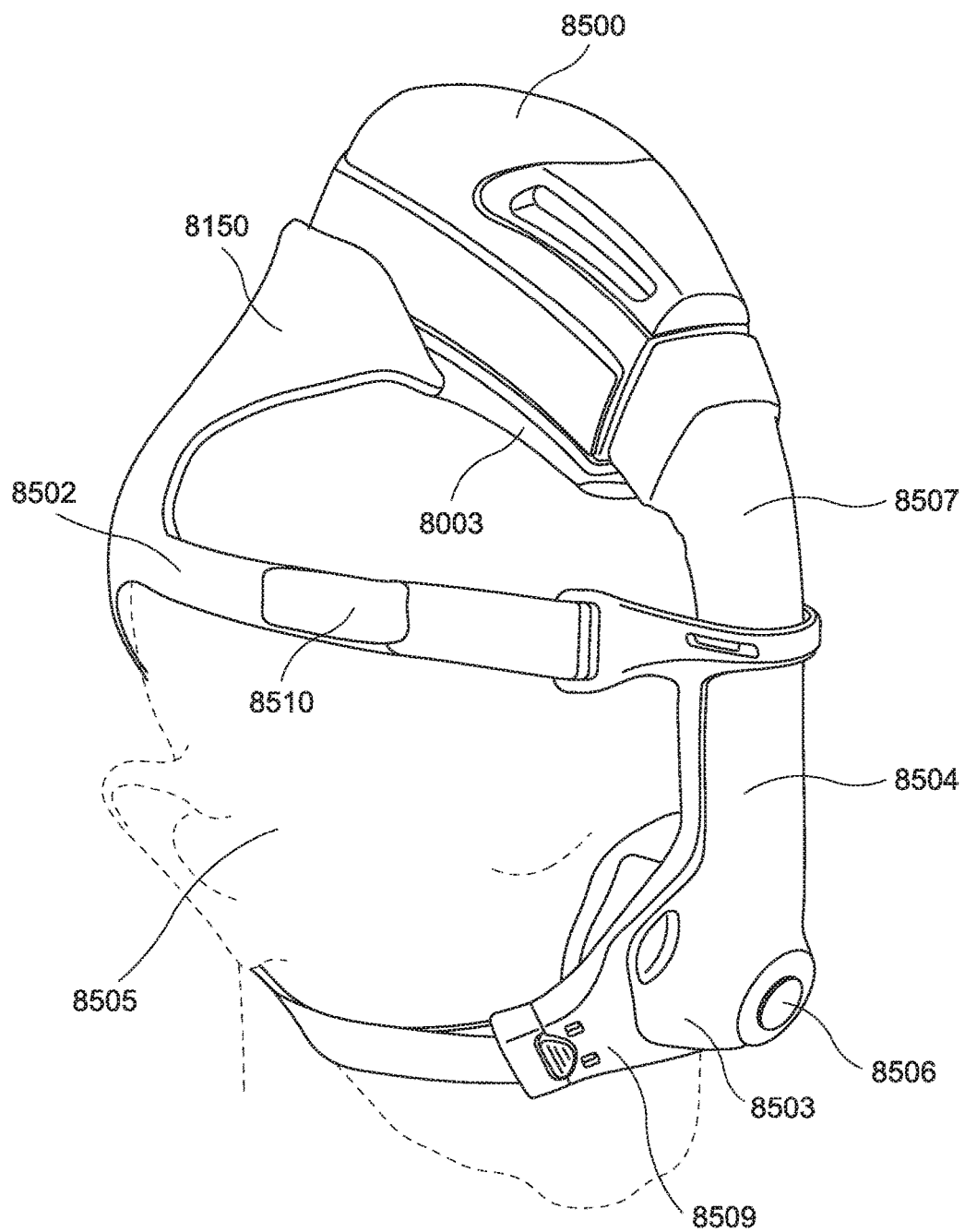
FIGS. 54A and 54B show right front perspective and right side views, respectively, of the PAP system of FIGS. 53A and 53B.
Figure 54B:
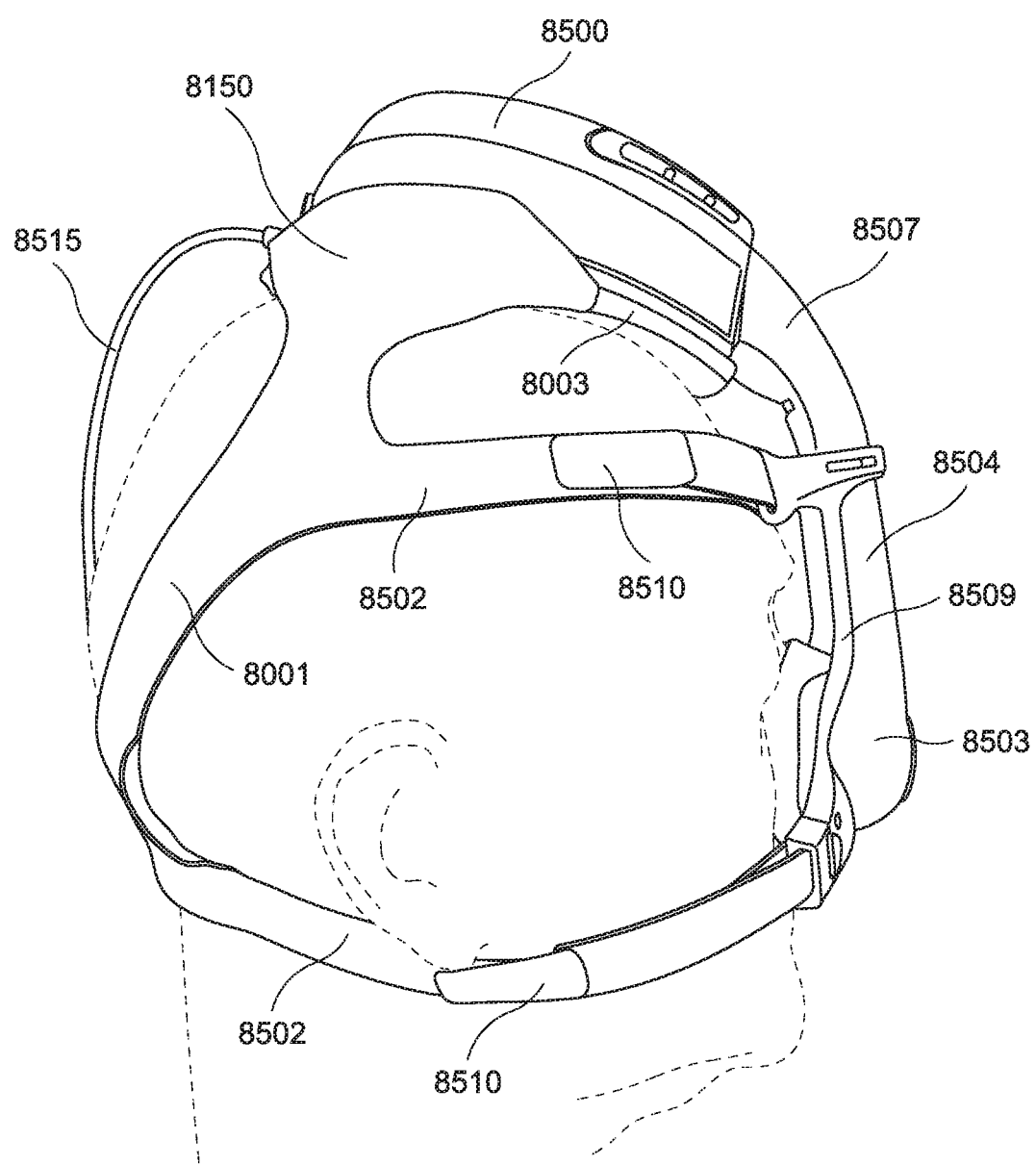
Figure 55A:
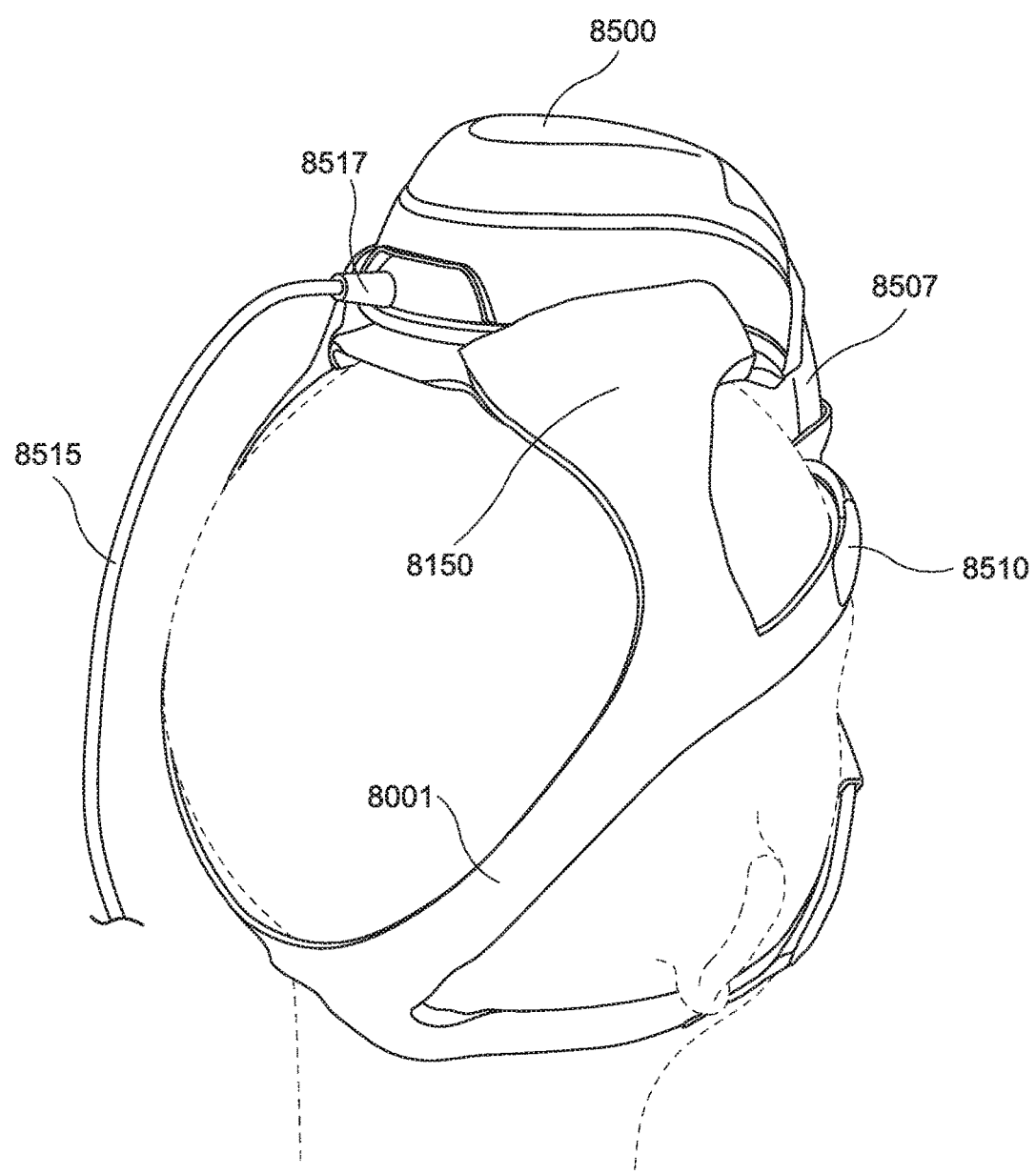
FIGS. 55A and 55B show right rear perspective and left rear perspective views, respectively, of the PAP system of FIGS. 53A to 54B.
Figure 55B:
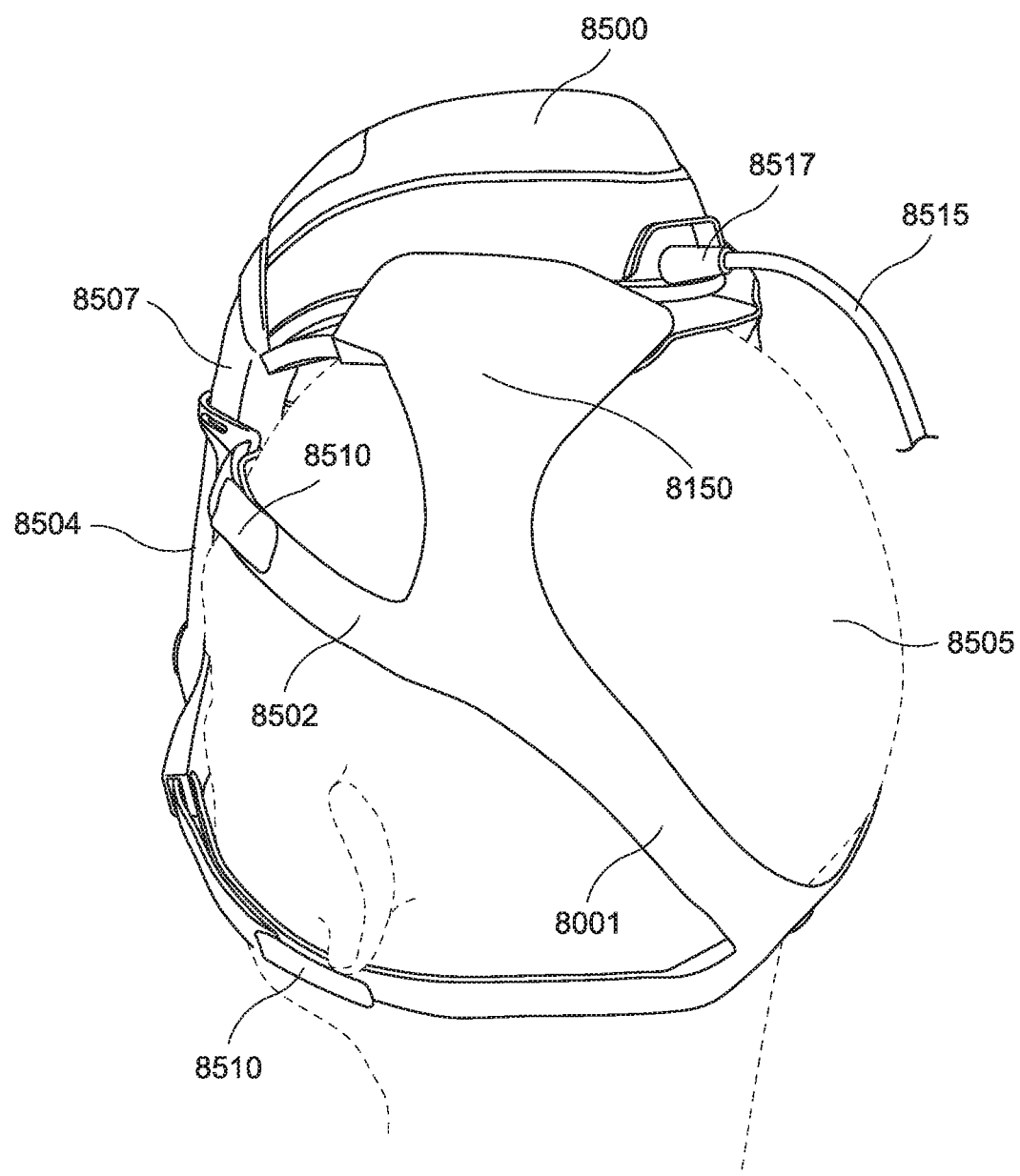
Figure 56:
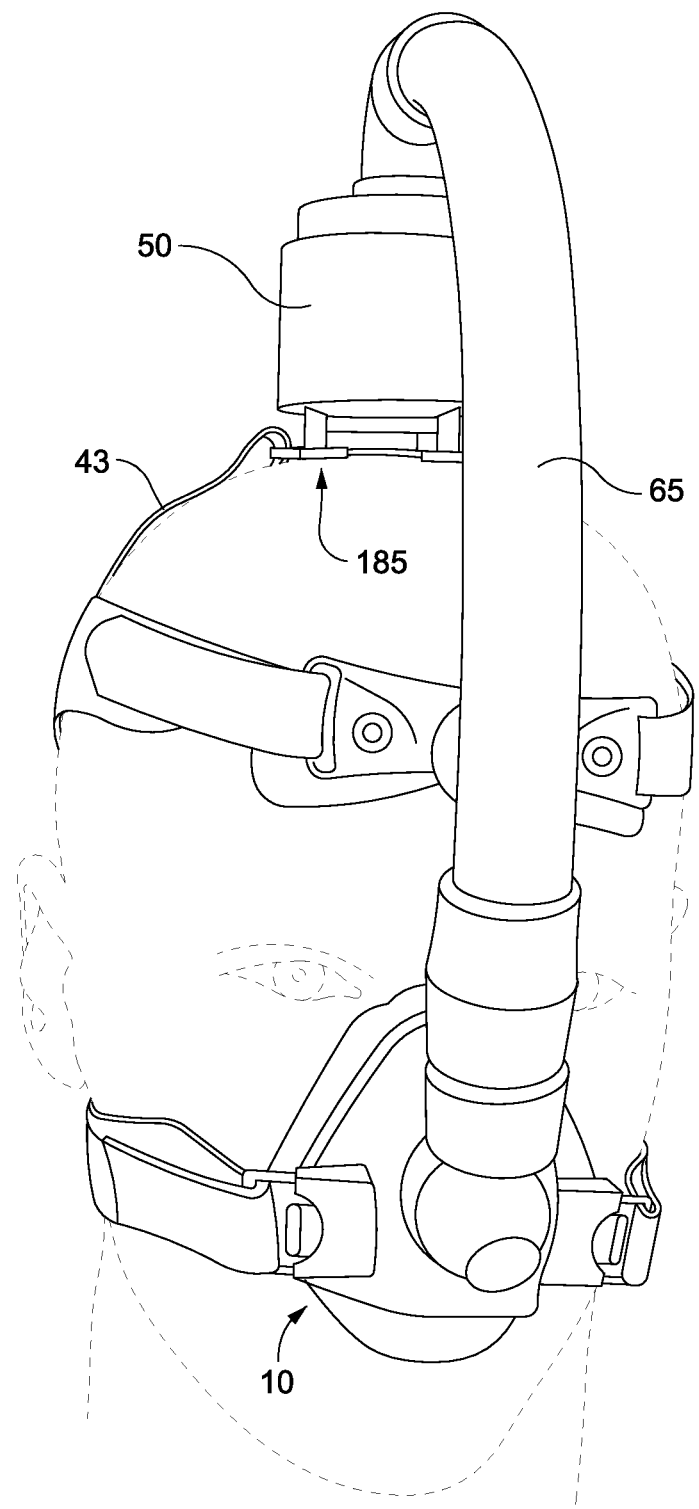
FIGS. 56 and 57 show alternative views of a headworn PAP system according to certain embodiments.
Figure 57:
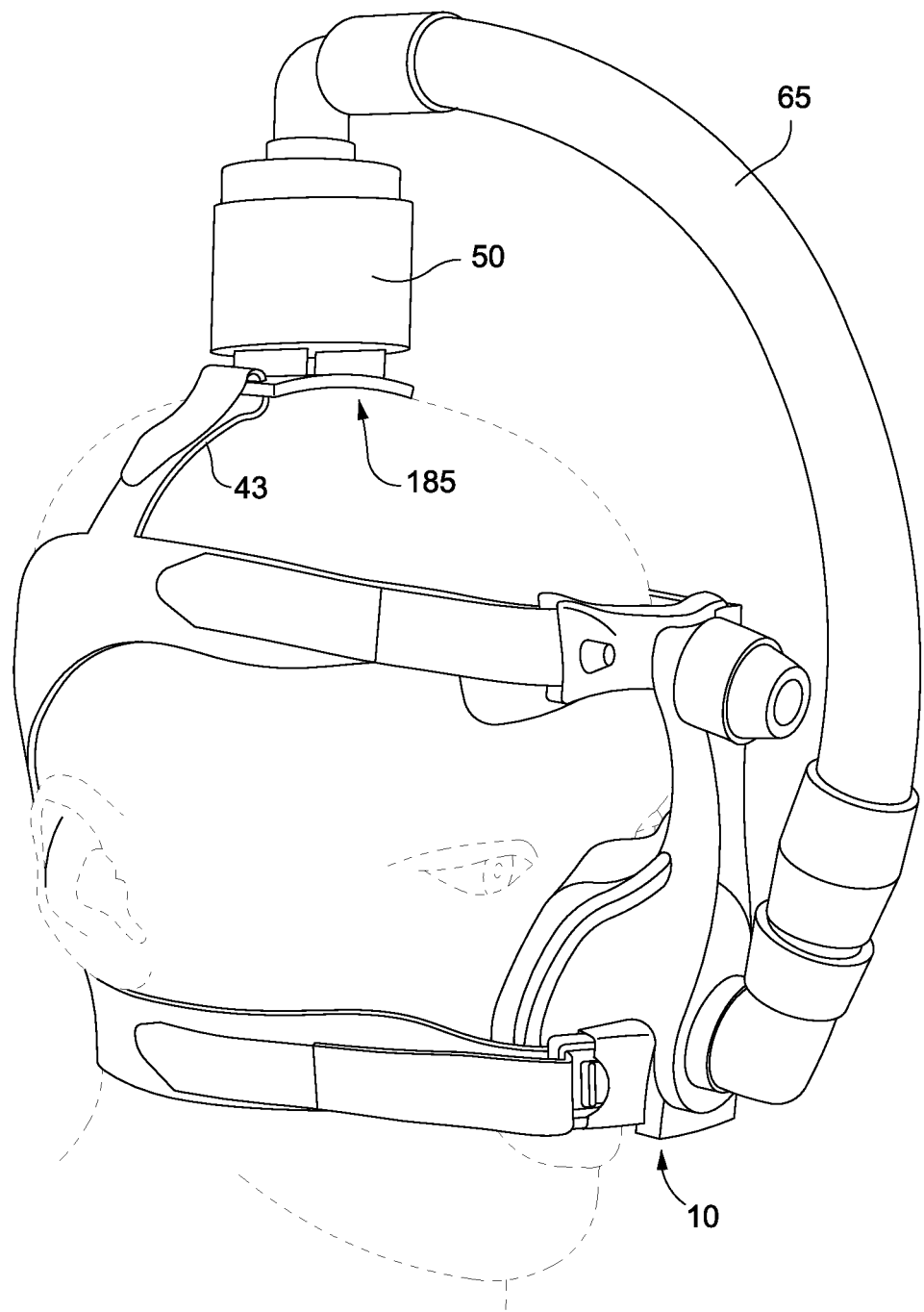
Figure 58:
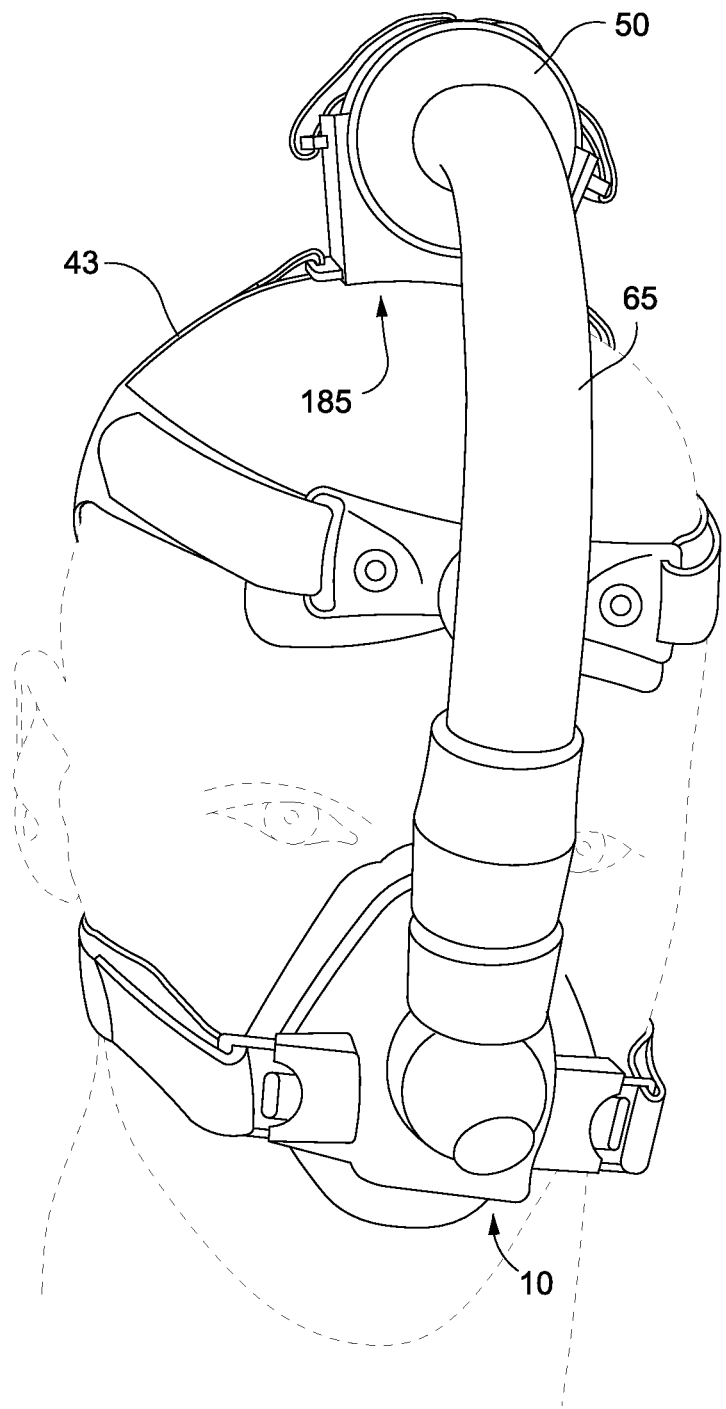
FIGS. 58 and 59 show alternative views of a headworn PAP system according to certain embodiments.
Figure 59:
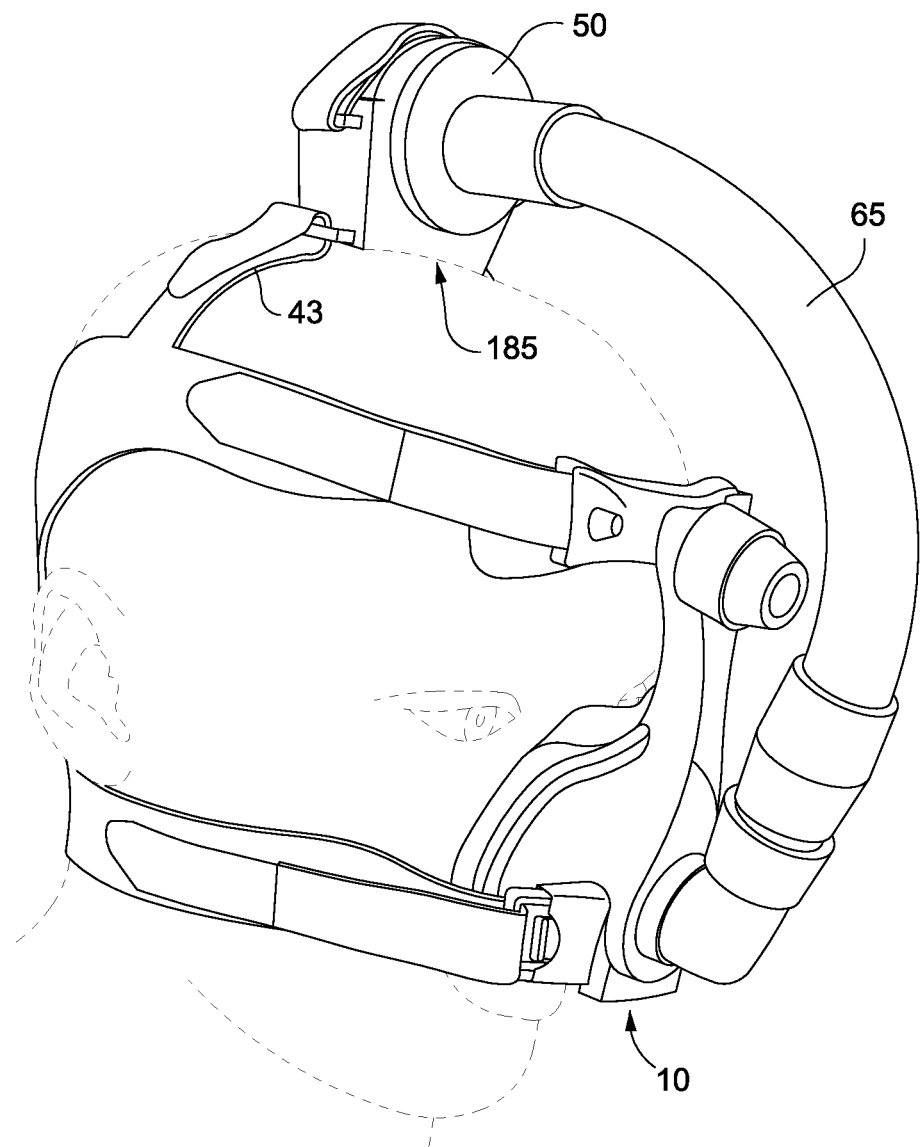
Figure 60:
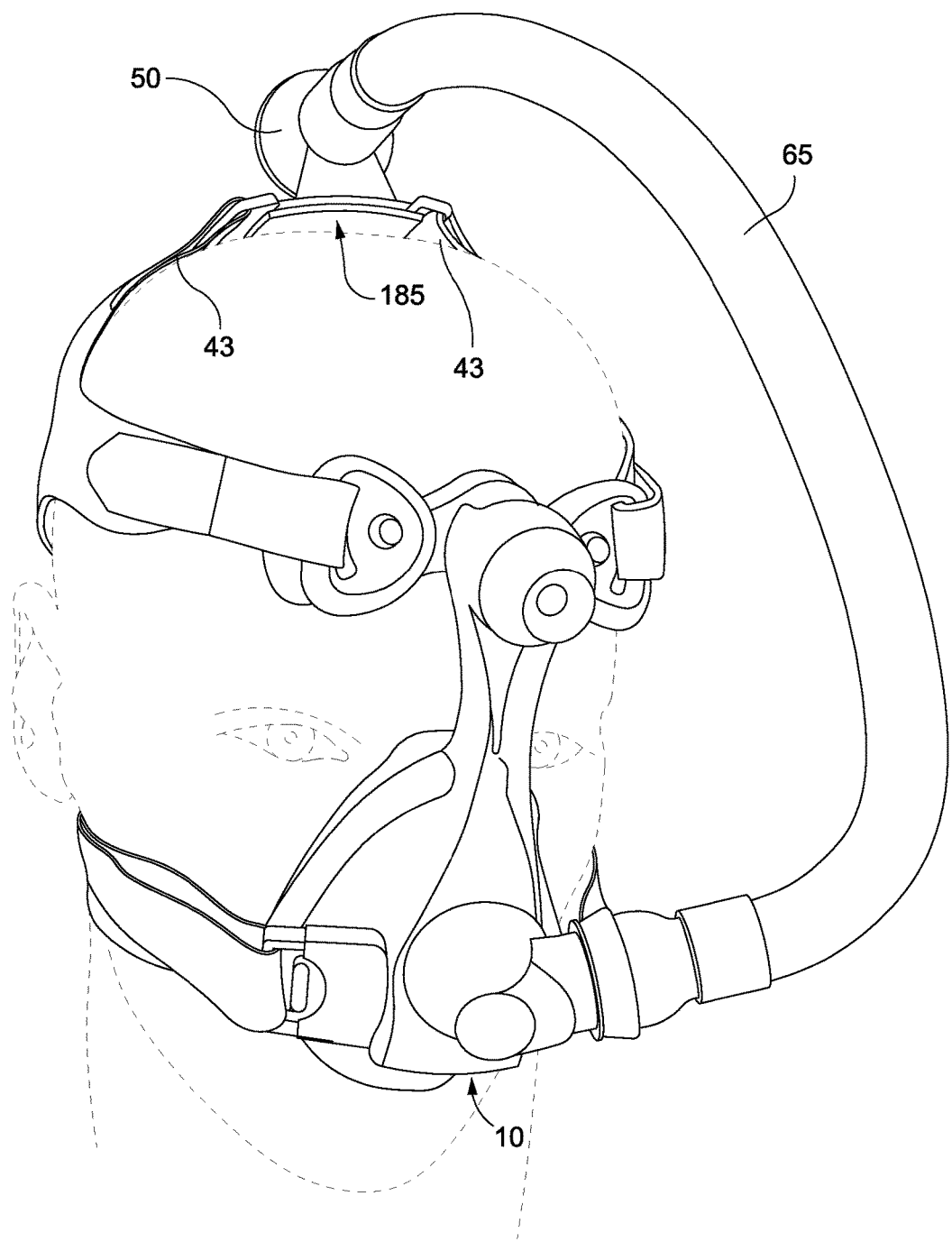
FIGS. 60 and 61 show alternative views of a headworn PAP system according to certain embodiments.
Figure 61:
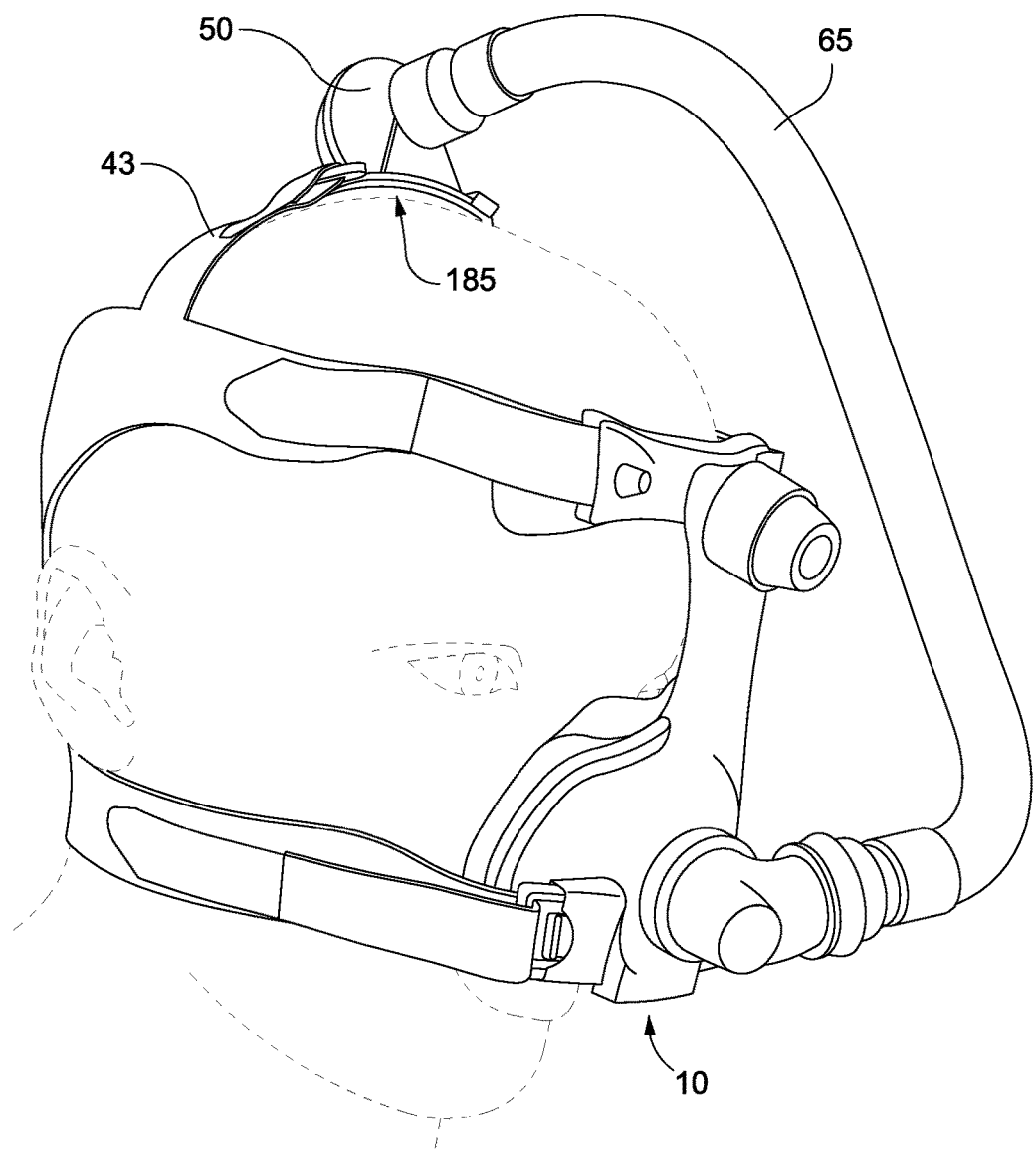
Figure 62:
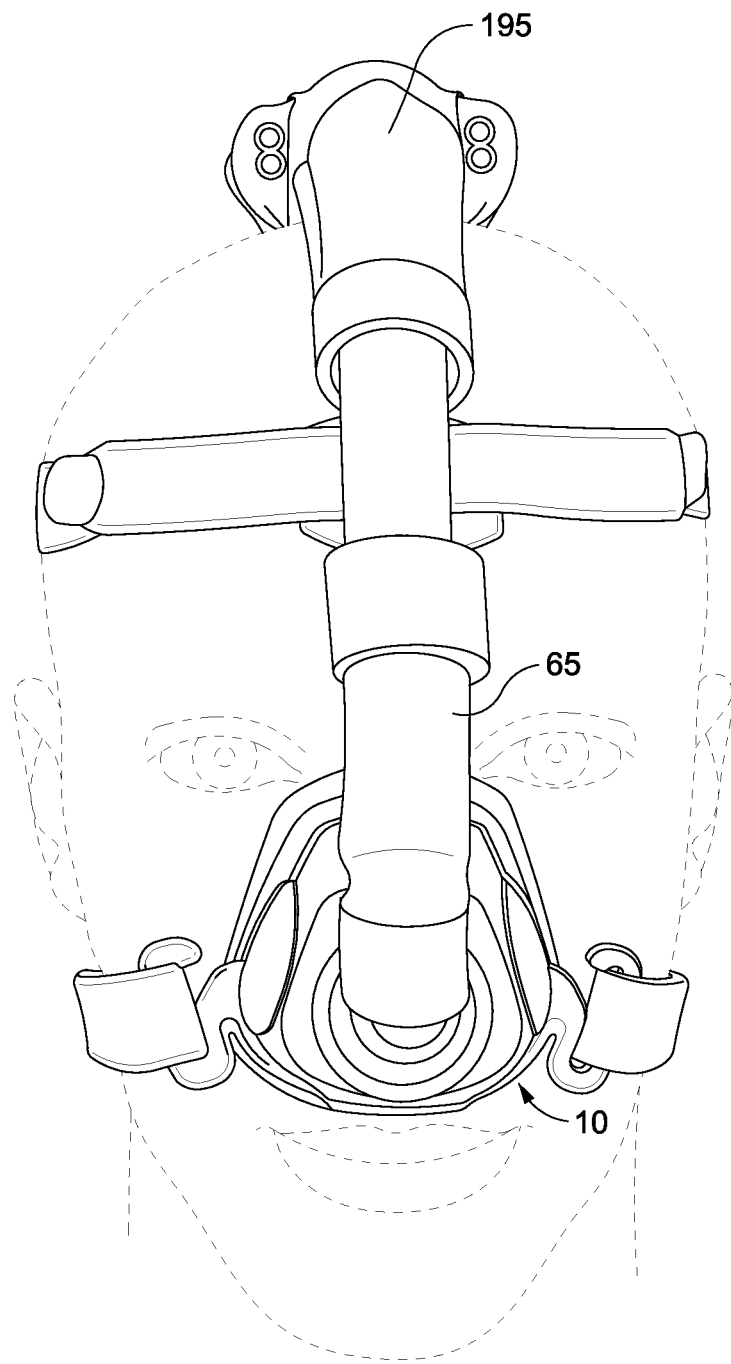
FIGS. 62 and 63 show alternative views of a headworn PAP system according to certain embodiments.
Figure 63:
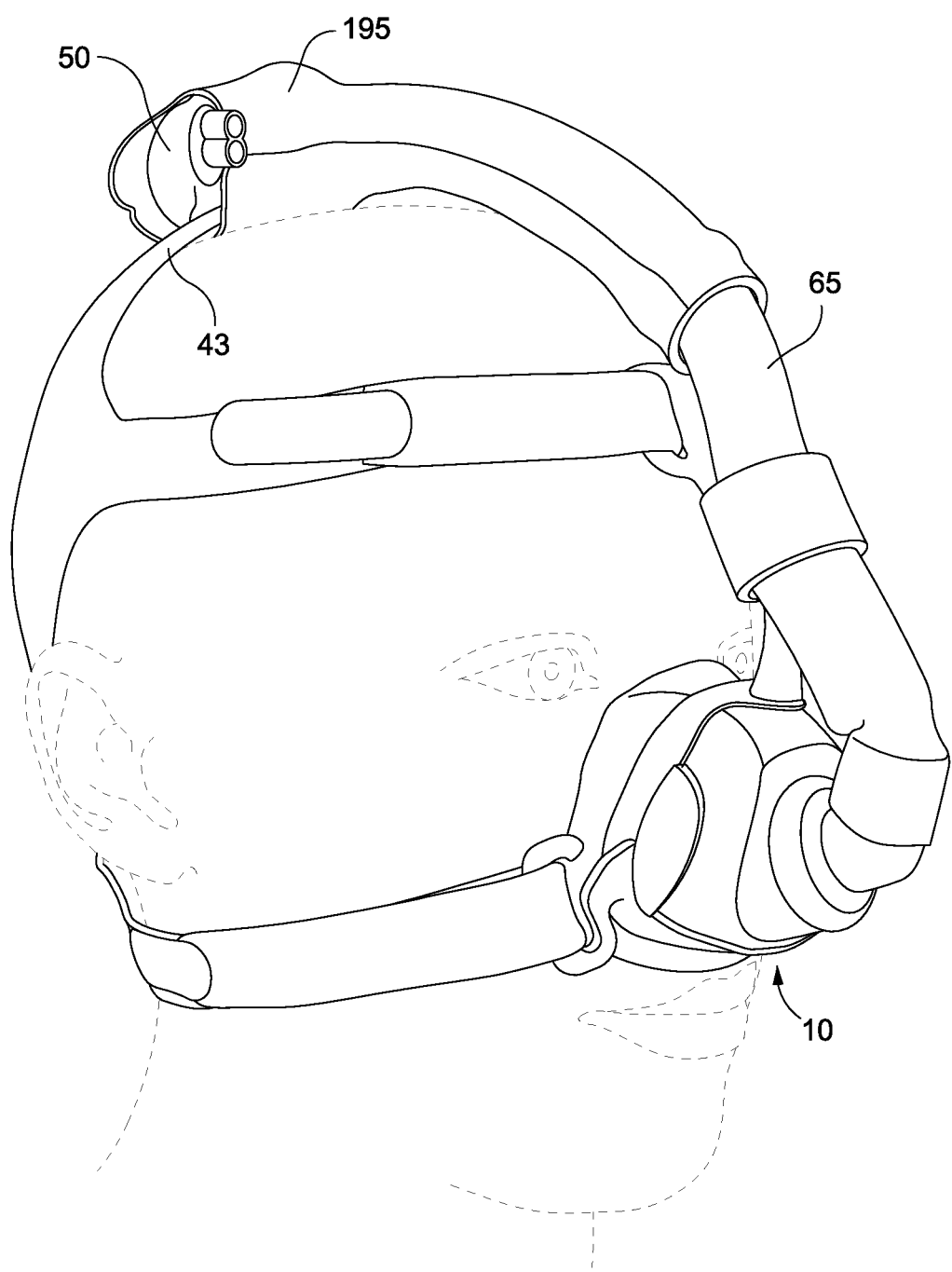
Figure 64:
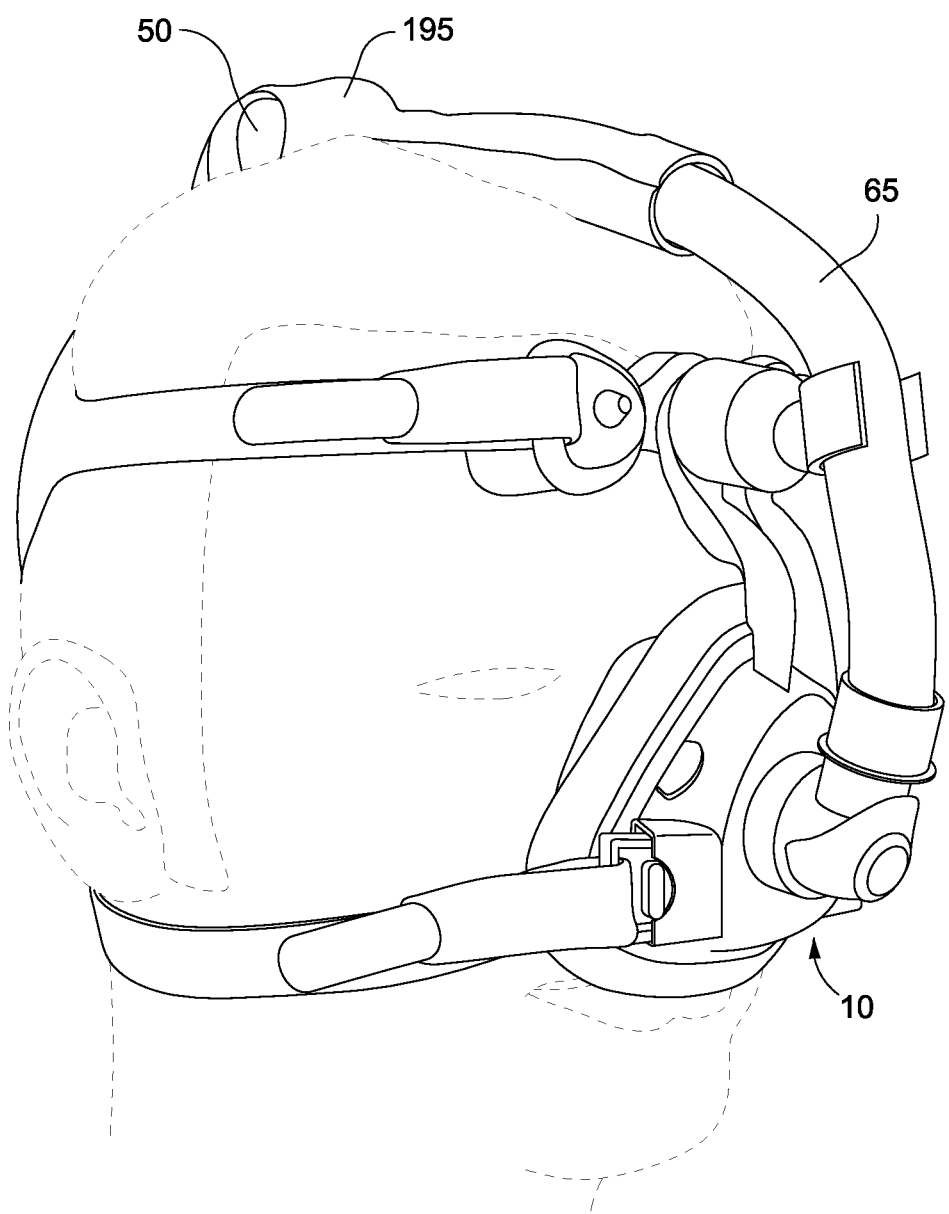
FIGS. 64 and 65 show alternative views of a headworn PAP system according to certain embodiments.
Figure 65:
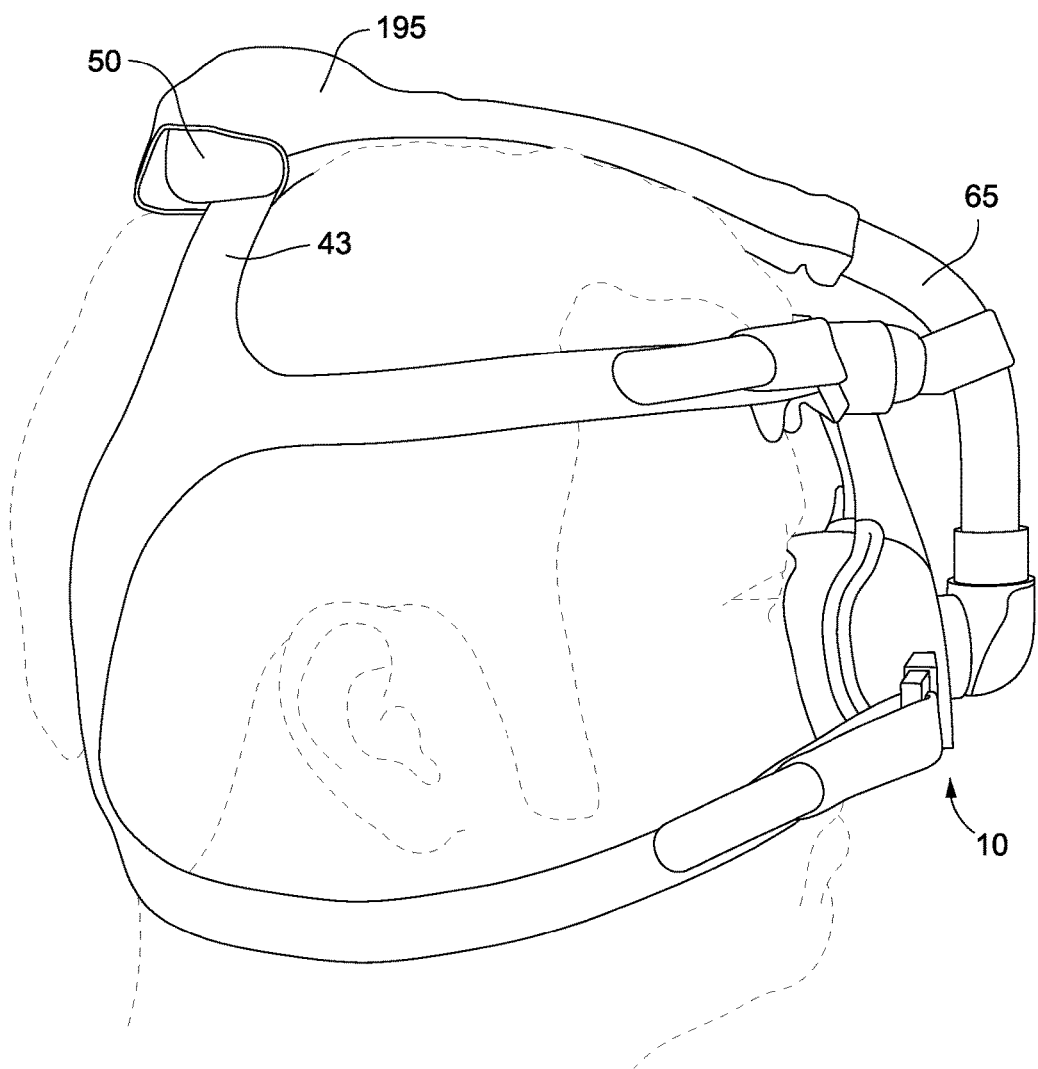
Figure 66:
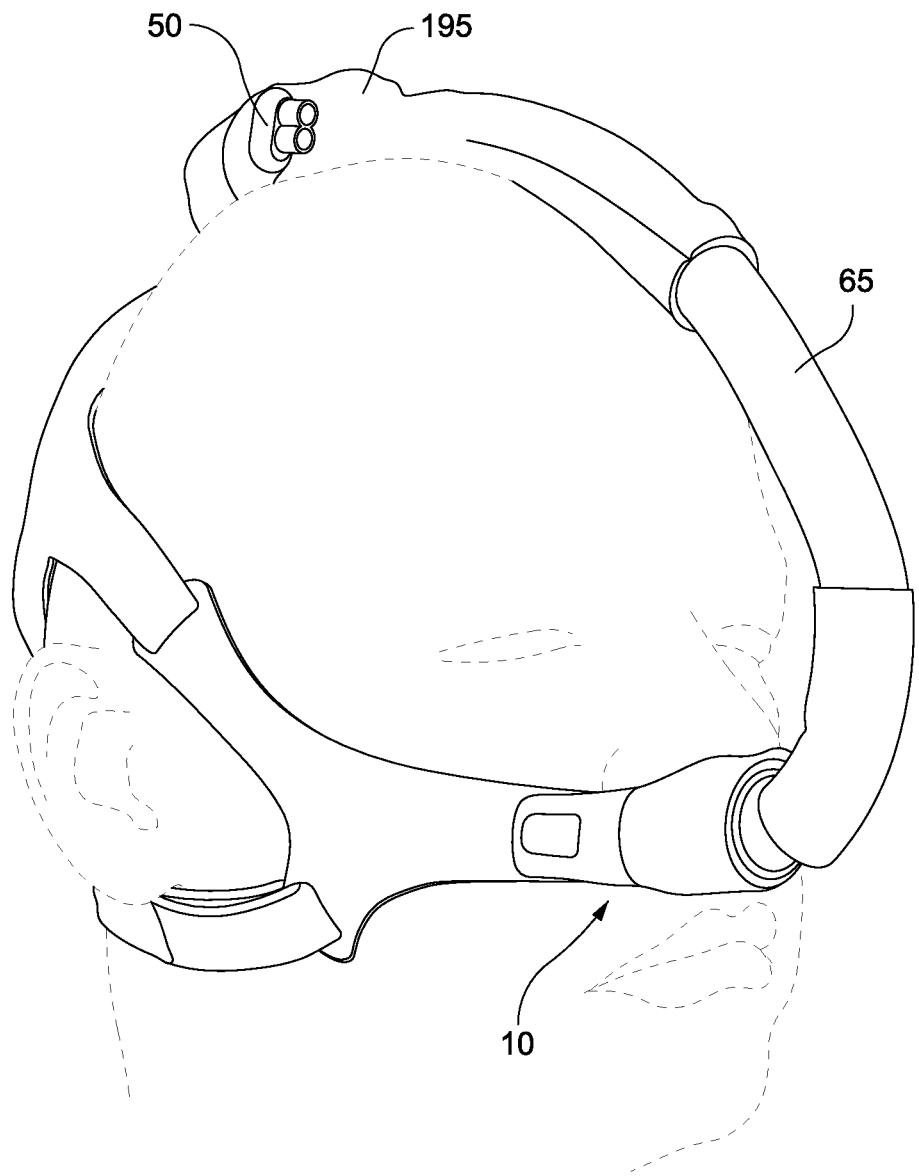
FIGS. 66 and 67 show alternative views of a headworn PAP system according to certain embodiments.
Figure 67:
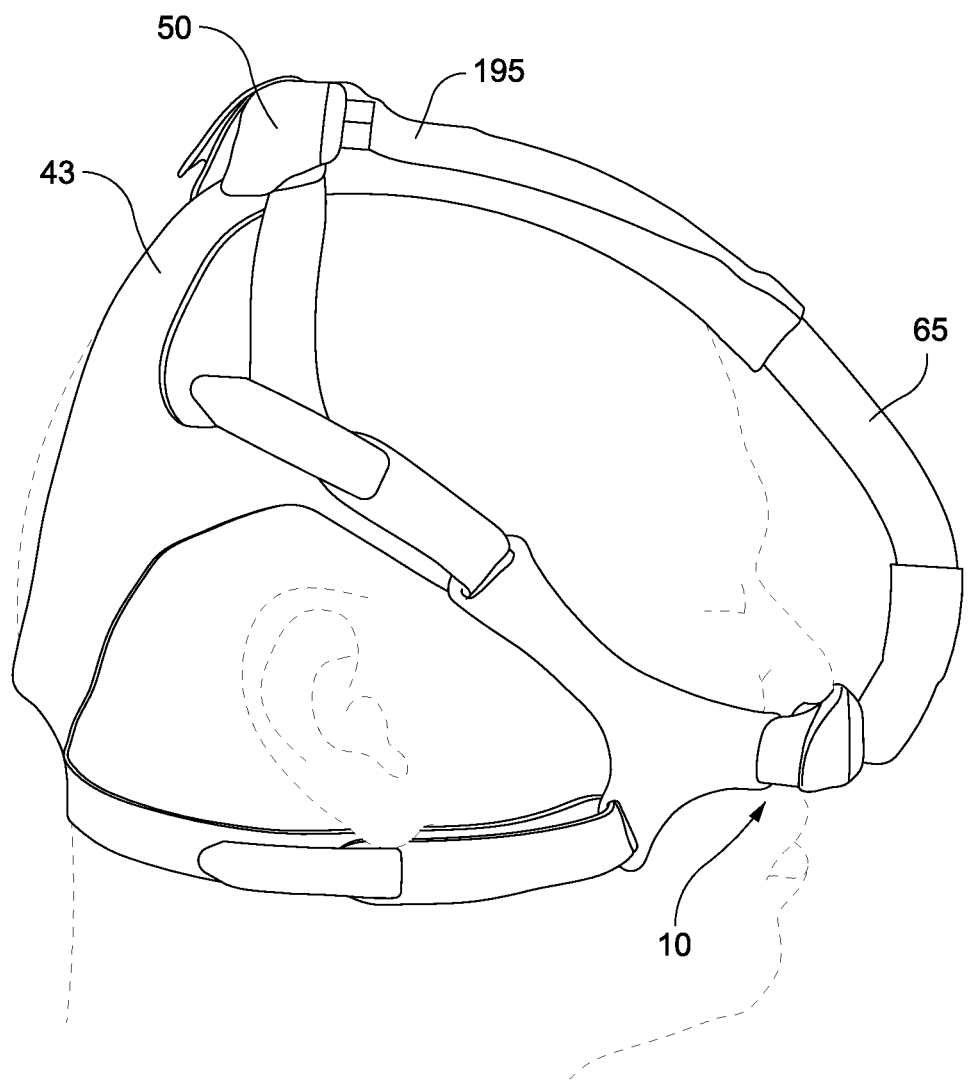

In FIGS. 42A, 43 and 52, the blower 2150 is supported by an article of clothing, such as a shirt (e.g., T-shirt) including a blower support structure (e.g., pocket) along the front of the shirt.

Figure 44:
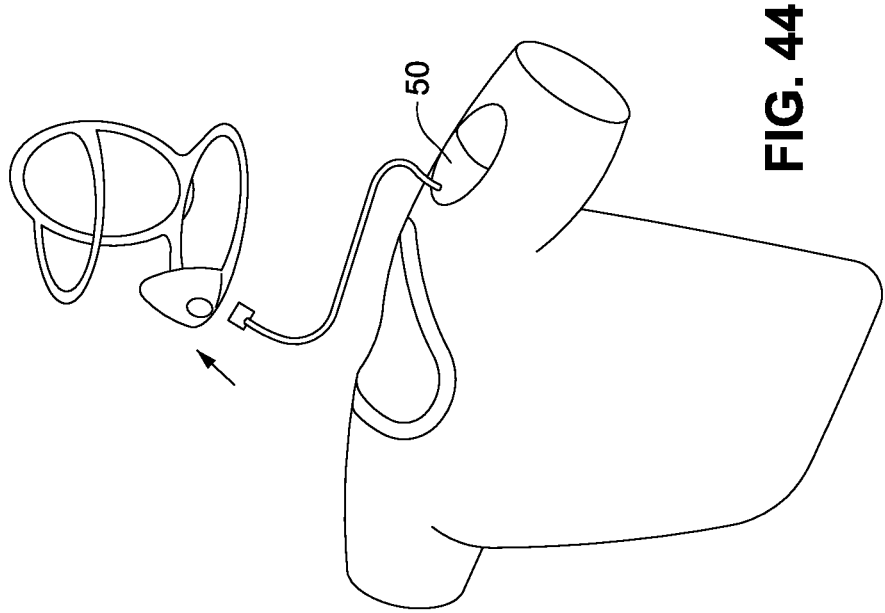
FIG. 44 shows a wearable blower according to certain embodiments.

In FIG. 44, the blower 2150 is supported by a shirt (e.g., T-shirt) including a blower support structure (e.g., pocket) along the shoulder of the shirt.

Figure 50:
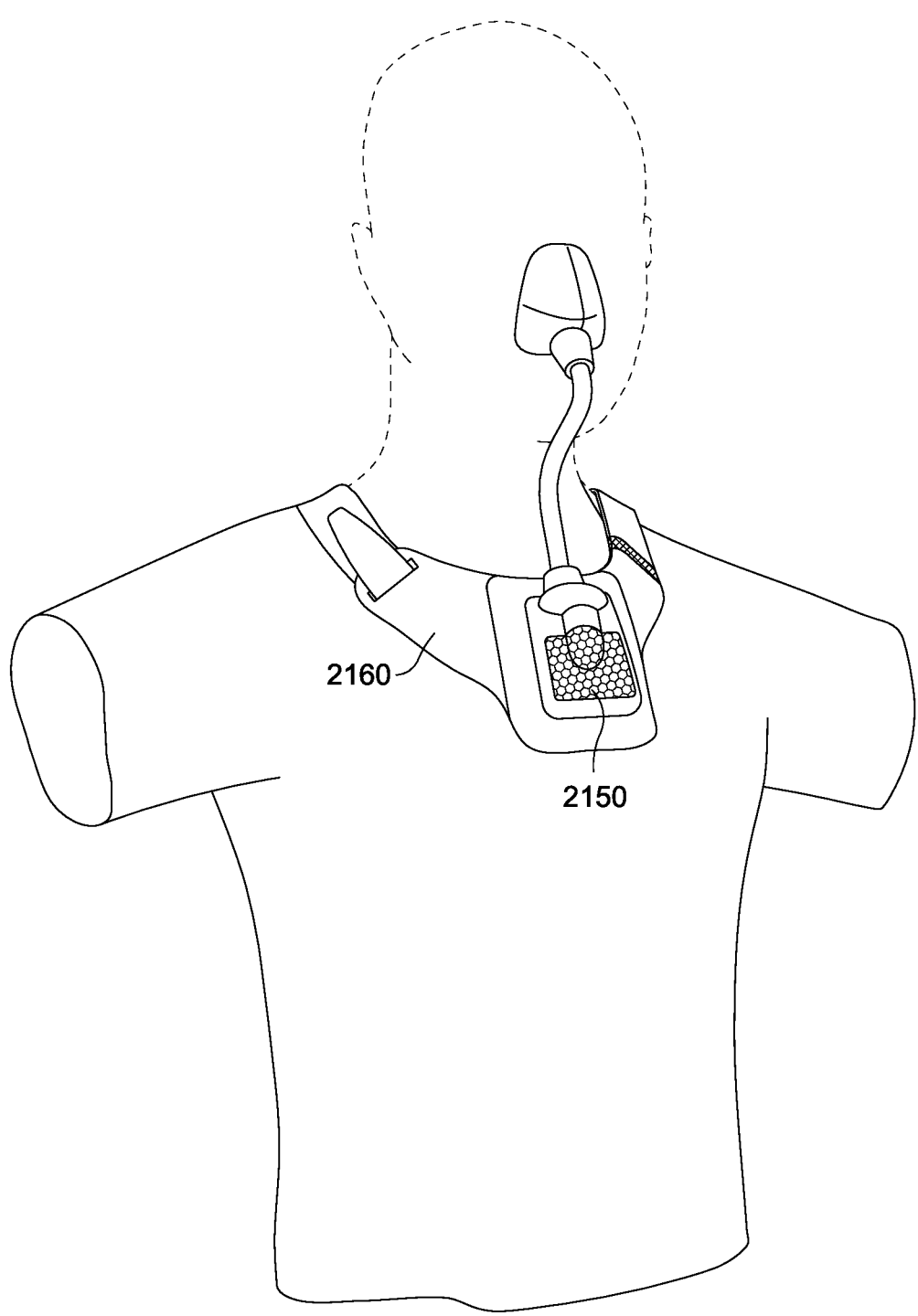
FIG. 50 shows a wearable blower according to certain embodiments.
Figure 51:
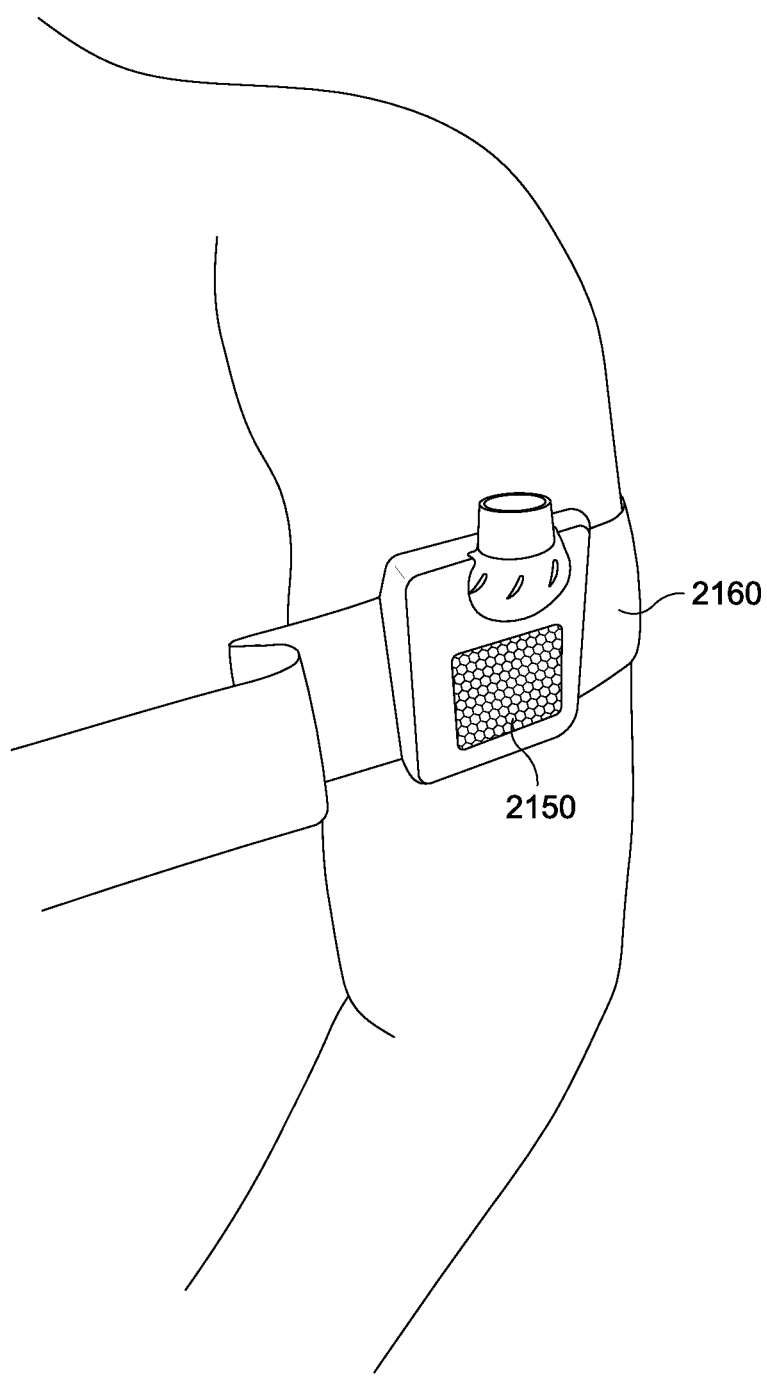
FIG. 51 shows a wearable blower according to certain embodiments.

FIGS. 50 and 51 show blowers 2150 supported by a strap or band arrangement 2160. In FIG. 50, the strap wraps around the patient's neck, e.g., collar style. In FIG. 51 the strap wraps around the patient's arm.

In the following, further embodiments are explained with the help of subsequent examples.

The invention claimed is:

1. A positive airway pressure (PAP) system adapted for treatment of respiratory disease or sleep disordered breathing comprising:
    a headgear adapted for engaging a patient's head;
    a patient interface adapted to be secured to and sealed against a portion of the patient's face, in use, by the headgear; and
    a flow generator adapted to be connected to the patient interface, and wherein the flow generator is adapted to be secured by a portion of the headgear to the patient's head,
    wherein the flow generator comprises a blower adapted to provide pressurised breathable gas to a patient through the patient interface and the blower is at least partially vibrationally isolated from the patient's head by at least one foam layer mounted within the flow generator to secure the blower, the at least one foam layer being adapted to reduce the amount of transmitted vibration received by the patient,
    wherein the flow generator comprises a mounting structure limiting an extent of a compression of the at least one foam layer due to the weight of the blower, the mounting structure including at least one protrusion extending from an interior surface of the flow generator toward the blower, and
    wherein the at least one protrusion is more rigid than the at least one foam layer.

2. The PAP system according to claim 1, wherein the PAP system is portable.

3. The PAP system according to claim 1, wherein the at least one foam layer has a spring constant sufficient to limit or reduce the vibration generated by vibration of the blower, in use.

4. The PAP system according to claim 3, wherein the spring constant is within a range of about 400-1,800 N/m.

5. The PAP system according to claim 3, wherein the spring constant is within a range of about 600-1,200 N/m.

6. The PAP system according to claim 1, wherein the at least one foam layer has a maximum spring constant sufficient to limit or reduce the vibration generated by vibration of the blower caused by the weight of the blower, in use.

7. The PAP system according to claim 6, wherein the maximum spring constant is about 9,800 N/m.

8. The PAP system according to claim 1, wherein the headgear comprises a receiving portion adapted to mate with the flow generator and the receiving portion comprises at least one cushion.

9. The PAP system according to claim 8, wherein the receiving portion comprises a cradle to receive the flow generator.

10. The PAP system according to claim 1, further comprising at least one cushion adapted to be mounted between the patient's head and an underside of the flow generator.

11. The PAP system according to claim 10, further comprising means for mounting the at least one cushion between the patient's head and the underside of the flow generator.

12. The PAP system according to claim 1, further comprising hook and loop fasteners, wherein said hook and loop fasteners secure the flow generator to a portion of the headgear.

13. The PAP system according to claim 1, further comprising means for securing the flow generator to a portion of the headgear.

14. The PAP system according to claim 1, wherein the at least one foam layer encapsulates the blower within the flow generator.

15. The PAP system according to claim 1, wherein the at least one protrusion extends upwardly from a lower surface of the flow generator towards the blower.

16. The PAP system according to claim 1, wherein the at least one protrusion includes four protrusions.

17. The PAP system according to claim 1, wherein the at least one protrusion is configured to limit or reduce vibration.

18. The PAP system according to claim 1, wherein the at least one protrusion is adapted to receive the blower and mate with the external shape of the blower.

19. The PAP system according to claim 1, wherein the at least one protrusion is flexible.

20. The PAP system according to claim 1, wherein the interior surface from which the at least one protrusion extends is a lower interior surface, and wherein the at least one protrusion is shorter than the distance between the blower and the lower interior surface of the flow generator.

21. The PAP system according to claim 1, wherein the at least one foam layer seals the interior of the flow generator.

22. The PAP system according to claim 1, wherein the flow generator comprises an outlet and an inlet, and wherein the flow generator is sealed with elastomer except for the outlet and the inlet.

23. The PAP system according to claim 1, wherein the headgear includes rigid portions adapted to prevent unintended movement of the flow generator.

24. The PAP system according to claim 1, wherein the flow generator comprises a single stage axial blower and a controller.

25. The PAP system according to claim 1, further comprising a layer of elastomer overmoulded to an interior wall of the flow generator.

26. The PAP system according to claim 1, wherein the at least one protrusion and the at least one foam layer are made of different materials.

27. A positive airway pressure (PAP) system adapted for treatment of respiratory disease or sleep disordered breathing comprising:
  a headgear adapted for engaging a patient's head;
  a patient interface adapted to be secured to and sealed against a portion of the patient's face, in use, by the headgear; and
  a flow generator adapted to be connected to the patient interface, and wherein the flow generator is adapted to be secured by a portion of the headgear to the patient's head,
  wherein the flow generator comprises a blower adapted to provide pressurised breathable gas to a patient through the patient interface and the blower is at least partially vibrationally isolated from the patient's head by at least one dampening means adapted to reduce the amount of transmitted vibration received by the patient, the at least one dampening means comprising at least one foam layer mounted within the flow generator to secure the blower,
  wherein the flow generator comprises a mounting structure limiting an extent of a compression of the at least one foam layer due to the weight of the blower, the mounting structure including at least one protrusion extending from an interior surface of the flow generator toward the blower, and
  wherein the at least one protrusion is more rigid than the at least one foam layer.

28. A positive airway pressure (PAP) system adapted for treatment of respiratory disease or sleep disordered breathing comprising:
  a headgear adapted for engaging a patient's head;
  a patient interface adapted to be secured to and sealed against a portion of the patient's face, in use, by the headgear; and
  a flow generator adapted to be connected to the patient interface, and wherein the flow generator is adapted to be secured by a portion of the headgear to the patient's head, the flow generator comprising:
    a blower adapted to provide pressurised breathable gas to a patient through the patient interface;
    compressible foam configured to a) support the blower and b) dampen and/or reduce vibration generated by the blower such that the blower is at least partially vibrationally isolated from the patient's head by the compressible foam; and
    at least one protrusion extending from an interior surface of the flow generator toward the blower to support the blower, the at least one protrusion being positioned to limit an extent of compression of the compressible foam due to the weight of the blower, wherein the at least one protrusion is more rigid than the compressible foam.

29. The PAP system of claim 28, wherein the at least one protrusion forms a cradle configured to receive the blower.

30. The PAP system of claim 29, wherein a distance by which the at least one protrusion extends from the interior surface of the flow generator is less than a thickness of the compressible foam supporting the blower.

* * * * *